United States Patent
Zhang et al.

(10) Patent No.: US 12,312,357 B2
(45) Date of Patent: May 27, 2025

(54) PRMT5 INHIBITING COMPOUNDS AND USES THEREOF

(71) Applicant: ANTENGENE DISCOVERY LIMITED, Shanghai (CN)

(72) Inventors: Ming Zhang, Shanghai (CN); Ya Kong, Shanghai (CN); Lulu Jiang, Shanghai (CN); Bin Jiang, Shanghai (CN); Guoqiang Dai, Shanghai (CN); Yulong He, Shanghai (CN); Bing Hou, Shanghai (CN); Bo Shan, Shanghai (CN); Jay Mei, Shanghai (CN)

(73) Assignee: ANTENGENE DISCOVERY LIMITED, Shanghai (CN)

( * ) Notice: Subject to any disclaimer, the term of this patent is extended or adjusted under 35 U.S.C. 154(b) by 0 days.

(21) Appl. No.: 18/589,461

(22) Filed: Feb. 28, 2024

(65) Prior Publication Data

US 2024/0262835 A1 Aug. 8, 2024

Related U.S. Application Data

(63) Continuation of application No. PCT/CN2024/072763, filed on Jan. 17, 2024.

(30) Foreign Application Priority Data

Jan. 18, 2023 (WO) ................ PCT/CN2023/072921
May 10, 2023 (WO) ................ PCT/CN2023/093297
Jan. 11, 2024 (WO) ................ PCT/CN2024/071750

(51) Int. Cl.
C07D 487/04 (2006.01)
A61K 31/4985 (2006.01)
A61K 31/506 (2006.01)
C07D 471/14 (2006.01)
C07D 519/00 (2006.01)

(52) U.S. Cl.
CPC ........ *C07D 487/04* (2013.01); *A61K 31/4985* (2013.01); *A61K 31/506* (2013.01); *C07D 471/14* (2013.01); *C07D 519/00* (2013.01)

(58) Field of Classification Search
CPC .. C07D 487/04; C07D 471/14; C07D 519/00; A61K 31/506
See application file for complete search history.

(56) References Cited

U.S. PATENT DOCUMENTS

2024/0376126 A1* 11/2024 Wang ................ A61K 31/437

FOREIGN PATENT DOCUMENTS

| CN | 114126614 A | 3/2022 | |
|---|---|---|---|
| WO | 2016199943 A1 | 12/2016 | |
| WO | 2018127195 A1 | 7/2018 | |
| WO | 2022115377 A1 | 6/2022 | |
| WO | 2022132914 A1 | 6/2022 | |
| WO | 2022169948 A1 | 8/2022 | |
| WO | 2023246873 A1 | 12/2023 | |
| WO | 2024002263 A1 | 1/2024 | |
| WO | 2024002376 A1 | 1/2024 | |
| WO | 2024002377 A1 | 1/2024 | |
| WO | 2024012308 A1 | 1/2024 | |
| WO | 2024027370 A1 | 2/2024 | |
| WO | 2024032572 A1 | 2/2024 | |
| WO | 2024037459 A1 | 2/2024 | |
| WO | WO-2024067433 A1 * | 4/2024 | ........... C07D 471/14 |

OTHER PUBLICATIONS

DeWitt S, Czarnik AW, Jacques V. Deuterium-Enabled Chiral Switching (DECS) Yields Chirally Pure Drugs from Chemically Interconverting Racemates. ACS Med Chem Lett. Mar. 5, 2020;11(10):1789-1792. doi: 10.1021/acsmedchemlett.0c00052. (Year: 2020).*

Yan Fang et al "Pharmacokinetic Advantage and Clinical Development of Deuterated Drugs", Chinese Journal of ClinicalPharmacology, vol. 36, No. 16, pp. 2558-2563, XP055931460. Aug. 31, 2020.

Alvin D N Vaz et al "Deuteration of Drugs for Pharmacokintic Enhancement: considerations Essential for Success", pp. 1-27, XP055139528, Sep. 11, 2014.

The International Search Report of the PCT Application No. PCT/CN2024/072762 mailed on Apr. 3, 2024.

The Extended European Search Report of the European Application No. 24711458.0 mailed on Dec. 9, 2024.

* cited by examiner

*Primary Examiner* — Clinton A Brooks
*Assistant Examiner* — Josmalen M. Ramos-Lewis
(74) *Attorney, Agent, or Firm* — Jun He Law Offices P.C.; James J. Zhu

(57) ABSTRACT

The present application provides novel PRMT5 and/or MTA-cooperative PRMT5 inhibiting compounds, or pharmaceutically acceptable salts thereof. The present application also provides pharmaceutical compositions comprising one or more of the compounds, or pharmaceutically acceptable salts thereof as an active ingredient, and the use of the compounds, or pharmaceutically acceptable salts thereof in the treatment of diseases or disorders, including cancers.

3 Claims, 2 Drawing Sheets

PRMT5 INHIBITING COMPOUNDS AND USES THEREOF

FIELD OF THE DISCLOSURE

The present application relates to novel compounds, or pharmaceutically acceptable salts thereof, which are inhibitors of PRMT5, in particular, MTA-cooperative inhibitors of PRMT5. The present application also relates to pharmaceutical compositions comprising the compounds, or pharmaceutically acceptable salts thereof, and to the use of the compounds or pharmaceutically acceptable salts thereof in the treatment of diseases or disorders, including cancers.

BACKGROUND OF THE DISCLOSURE

Epigenetic alterations are key mediators driving and maintaining the malignant phenotype of tumors. Changes in DNA methylation, histone acetylation and methylation, non-coding RNAs, and post-translational modifications are all epigenetic drivers of cancer development, independent of changes in DNA sequence. Arginine methylation is an important class of post-translational modifications that affect cell growth and proliferation, apoptosis, angiogenesis and metastasis by regulating transcription and post-transcriptional RNA processing. PRMT (protein arginine methyltransferase) family enzymes serve as "writers" of PTM (Post-translational modifications) catalyzing methylation.

PRMT5 is a type II PRMT catalyzing ω-$N^G$-monomethylarginine (MMA) and ω-$N^G$, $N^G$-symmetric dimethylarginine (sDMA). The modifications elicit a steric effect and change hydrogen bonding interaction of the methylated side chain, in turn altering molecular characteristics and function of the modified protein. PRMT5 also forms a complex with MEP50 (methylosome protein 50), which is required for substrate recognition and orientation and is also required for PRMT5-catalyzed histone 2A and histone 4 methyltransferase activity.

The gene encoding methylthioadenosine phosphorylase (MTAP) is ubiquitously expressed in normal tissues. However, homozygous deletion of MTAP occurs frequently in cancer due to its proximity to CDKN2A, one of the most commonly deleted tumor suppressor genes. For example, MTAP is deleted in 40% of glioblastomas; 25% of melanomas, urothelial carcinomas, and pancreatic adenocarcinomas; and 15% of non-small cell lung carcinomas (NSCLC). MTAP is required for the methionine salvage pathway, and homozygous gene deletion causes MTAP-deleted (MTAP-del) cells to accumulate methylthioadenosine (MTA). Accumulation of MTA in cells with MTAP deletion causes a partial inhibition of the methylation activity of PRMT5, which in turn reduces the level of symmetric arginine dimethylation of the whole proteome, and thus an increased sensitivity of cells to modulation of the methylosome activity. Therapeutic targeting of PRMT5 in homozygous MTAP-deleted cancers constitute a promising strategy of selective killing of genetically defined cancer cells. Hence, inhibition of PRMT5 activity merits further investigation as a potential therapy for MTAP-deleted tumors.

SUMMARY OF THE DISCLOSURE

In one aspect, the present disclosure provides a compound of Formula (I):

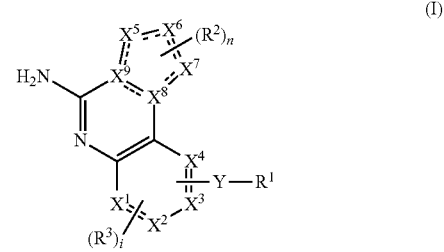

or a pharmaceutically acceptable salt, or a deuterated derivative thereof, wherein each of $X^1$, $X^2$, $X^3$, $X^4$, $X^5$, $X^6$, $X^7$, $X^8$, and $X^9$ is independently selected from C, CH or N, provided that at least one of $X^8$ and $X^9$ is N;

each ═ is independently a single bond or a double bond;

Y is selected from cycloalkyl, heterocyclyl, aryl, heteroaryl or —C(O)—, wherein the cycloalkyl, heterocyclyl, aryl, and heteroaryl are optionally substituted with one or more $R^a$;

$R^a$ is selected from the group consisting of hydrogen, deuterium, hydroxyl, halogen, cyano, oxo, alkyl, alkenyl, alkynyl, heteroalkyl, heteroalkenyl, heteroalkynyl, and haloalkyl;

$R^1$ is selected from cycloalkyl, heterocyclyl, aryl, heteroaryl or —$N(R^b)_2$, wherein the cycloalkyl, heterocyclyl, aryl, and heteroaryl are optionally substituted with one or more $R^c$;

each $R^b$ is independently selected from the group consisting of hydrogen, deuterium, alkyl, alkenyl, alkynyl, heteroalkyl, heteroalkenyl, heteroalkynyl, cycloalkyl, heterocyclyl, aryl and heteroaryl, wherein the alkyl, alkenyl, alkynyl, heteroalkyl, heteroalkenyl, heteroalkynyl, cycloalkyl, heterocyclyl, aryl and heteroaryl are optionally substituted with one or more $R^d$; or two $R^b$ together with the nitrogen atom to which they are attached form a heterocyclyl optionally substituted with one or more $R^c$;

each $R^c$ is independently selected from the group consisting of deuterium, cyano, halogen, hydroxyl, oxo, alkyl, alkenyl, alkynyl, heteroalkyl, heteroalkenyl, heteroalkynyl, cycloalkyl, heterocyclyl, aryl, heteroaryl and $OR^d$, wherein the alkyl, alkenyl, alkynyl, heteroalkyl, heteroalkenyl, heteroalkynyl, cycloalkyl, heterocyclyl, aryl and heteroaryl are optionally substituted with one or more groups independently selected from oxo, cyano, halogen, hydroxyl, alkyl, or haloalkyl;

$R^d$ is selected from the group consisting of hydrogen, deuterium, hydroxyl, halogen, cyano, oxo, alkoxyl, alkyl, haloalkyl, haloalkoxyl, cycloalkyl, heterocyclyl, aryl and heteroaryl, wherein the alkyl, haloalkyl, cycloalkyl, heterocyclyl, aryl and heteroaryl are optionally substituted with one or more groups independently selected from deuterium, oxo, cyano, halogen, hydroxyl, alkoxyl, alkyl, haloalkyl, haloalkoxyl;

each of $R^2$ and $R^3$ is independently selected from the group consisting of hydrogen, deuterium, cyano, halogen, hydroxyl, amino, oxo, alkyl, alkenyl, alkynyl, heteroalkyl, heteroalkenyl and heteroalkynyl, wherein the alkyl, alkenyl, alkynyl, heteroalkyl, heteroalkenyl and heteroalkynyl are optionally substituted with one or more groups independently selected from cyano, halogen, hydroxyl or amino;

n is 0, 1, 2, or 3; and i is 0, 1, 2 or 3.

In another aspect, the present disclosure provides a pharmaceutical composition, comprising a therapeutically effective amount of the compound of Formula (I) or a pharmaceutically acceptable salt thereof, and a pharmaceutically acceptable excipient.

In a further aspect, the present disclosure provides a method for inhibiting PRMT5 activity in a subject in need thereof, comprising administering an effective amount of the compound of Formula (I) or a pharmaceutically acceptable salt thereof or the pharmaceutical composition comprising the same to the subject.

In a further aspect, the present disclosure provides a method for treating cancer in a subject in need thereof, comprising administering an effective amount of the compound of Formula (I) or a pharmaceutically acceptable salt thereof or the pharmaceutical composition comprising the same to the subject.

DETAILED DESCRIPTION OF THE DISCLOSURE

Figure 1A:
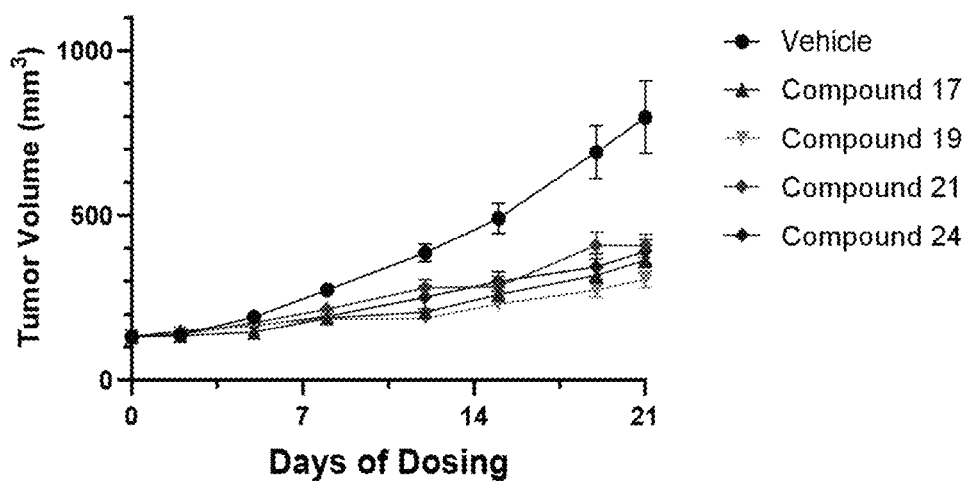
FIGS. 1A and 1B show the in vivo efficacy of exemplary compounds in human colon cancer cell line HCT 116 (MTAP KO).

Reference will now be made in detail to certain embodiments of the present disclosure, examples of which are illustrated in the accompanying structures and formulas. While the present disclosure will be described in conjunction with the enumerated embodiments, it will be understood that they are not intended to limit the present disclosure to those embodiments. On the contrary, the present disclosure is intended to cover all alternatives, modifications, and equivalents, which may be included within the scope of the present disclosure as defined by the claims. One skilled in the art will recognize many methods and materials similar or equivalent to those described herein, which could be used in the practice of the present disclosure. The present disclosure is in no way limited to the methods and materials described. In the event that one or more of the incorporated references and similar materials differs from or contradicts this application, including but not limited to defined terms, term usage, described techniques, or the like, the present disclosure controls. All references, patents, patent applications cited in the present disclosure are hereby incorporated by reference in their entireties.

It is appreciated that certain features of the present disclosure, which are, for clarity, described in the context of separate embodiments, can also be provided in combination in a single embodiment. Conversely, various features of the present disclosure, which are, for brevity, described in the context of a single embodiment, can also be provided separately or in any suitable sub-combination. It must be noted that, as used in the specification and the appended claims, the singular forms "a," "an," and "the" include plural forms of the same unless the context clearly dictates otherwise. Thus, for example, reference to "a compound" includes a plurality of compounds.

Definitions

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Organic Chemistry, Thomas Sorrell, 2$^{nd}$ Edition, University Science Books, Sausalito, 2006; Smith and March March's Advanced Organic Chemistry, 6$^{th}$ Edition, John Wiley & Sons, Inc., New York, 2007; Larock, Comprehensive Organic Transformations, 3$^{rd}$ Edition, VCH Publishers, Inc., New York, 2018; Carruthers, Some Modern Methods of Organic Synthesis, 4$^{th}$ Edition, Cambridge University Press, Cambridge, 2004; the entire contents of each of which are incorporated herein by reference.

At various places in the present disclosure, linking substituents are described. Where the structure clearly requires a linking group, the Markush variables listed for that group are understood to be linking groups. For example, if the structure requires a linking group and the Markush group definition for that variable lists "alkyl", then it is understood that the "alkyl" represents a linking alkylene group.

When a bond is shown as a dash line, then such bond may be absent or present in a single bond form.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., $R^1$) occurs more than one time in any constituent or formula for a compound, its definition at each occurrence is independent of its definition at every other occurrence. Thus, for example, if a group is shown to be substituted with 0-2 $R^i$ moieties, then the group may optionally be substituted with up to two $R^i$ moieties and $R^i$ at each occurrence is selected independently from the definition of $R^i$. Also, combinations of substituents and/or variables are permissible, but only if such combinations result in stable compounds.

As used herein, the term "$C_{i-j}$" indicates a range of the carbon atoms numbers, wherein i and j are integers and the range of the carbon atoms numbers includes the endpoints (i.e. i and j) and each integer point in between, and wherein j is greater than i. For examples, $C_{1-6}$ indicates a range of one to six carbon atoms, including one carbon atom, two carbon atoms, three carbon atoms, four carbon atoms, five carbon atoms and six carbon atoms. In some embodiments, the term "$C_{1-12}$" indicates 1 to 12, particularly 1 to 10, particularly 1 to 8, particularly 1 to 6, particularly 1 to 5, particularly 1 to 4, particularly 1 to 3 or particularly 1 to 2 carbon atoms.

As used herein, the term "alkyl", whether as part of another term or used independently, refers to a saturated linear or branched-chain hydrocarbon radical, which may be optionally substituted independently with one or more substituents described below. The term "$C_{i\text{-}j}$ alkyl" refers to an alkyl having i to j carbon atoms. In some embodiments, alkyl groups contain 1 to 12 carbon atoms. In some embodiments, alkyl groups contain 1 to 11 carbon atoms. In some embodiments, alkyl groups contain 1 to 10 carbon atoms. In some embodiments, alkyl groups contain 1 to 9 carbon atoms. In some embodiments, alkyl groups contain 1 to 8 carbon atoms, 1 to 7 carbon atoms, 1 to 6 carbon atoms, 1 to 5 carbon atoms, 1 to 4 carbon atoms, 1 to 3 carbon atoms, or 1 to 2 carbon atoms. Examples of "$C_{1\text{-}10}$ alkyl" include, but are not limited to, methyl, ethyl, propyl, butyl, pentyl, hexyl, heptyl, octyl, nonyl, and decyl. Examples of "$C_{1\text{-}6}$ alkyl" are methyl, ethyl, propyl, isopropyl, n-butyl, i-butyl, s-butyl, t-butyl, n-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, and the like.

The alkyl groups can be further substituted by substituents which independently replace one or more hydrogen atoms on one or more carbons of the alkyl groups. Examples of such substituents can include, but are not limited to, acyl, alkyl, alkenyl, alkynyl, halogen, hydroxyl, alkoxyl, haloalkyl, haloalkoxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonate, sulfamoyl, sulfonamido, nitro, trifluoromethyl, cyano, nitro, azido, heterocyclyl, alkylaryl, or an aromatic or heteroaromatic moiety. Alkenyl, alkynyl, cycloalkyl, heterocyclyl, aryl and heteroaryl groups as described below may also be similarly substituted.

As used herein, the term "alkenyl", whether as part of another term or used independently, refers to linear or branched-chain hydrocarbon radical having at least one carbon-carbon double bond, which may be optionally substituted independently with one or more substituents described herein, and includes radicals having "cis" and "trans" orientations, or alternatively, "E" and "Z" orientations. In some embodiments, alkenyl groups contain 2 to 12 carbon atoms. In some embodiments, alkenyl groups contain 2 to 11 carbon atoms. In some embodiments, alkenyl groups contain 2 to 11 carbon atoms, 2 to 10 carbon atoms, 2 to 9 carbon atoms, 2 to 8 carbon atoms, 2 to 7 carbon atoms, 2 to 6 carbon atoms, 2 to 5 carbon atoms, 2 to 4 carbon atoms, 2 to 3 carbon atoms, and in some embodiments, alkenyl groups contain 2 carbon atoms. Examples of alkenyl group include, but are not limited to, ethylenyl (or vinyl), propenyl, butenyl, pentenyl, 1-methyl-2 buten-1-yl, 5-hexenyl, and the like.

As used herein, the term "alkynyl", whether as part of another term or used independently, refers to a linear or branched hydrocarbon radical having at least one carbon-carbon triple bond, which may be optionally substituted independently with one or more substituents described herein. In some embodiments, alkynyl groups contain 2 to 12 carbon atoms. In some embodiments, alkynyl groups contain 2 to 11 carbon atoms. In some embodiments, alkynyl groups contain 2 to 11 carbon atoms, 2 to 10 carbon atoms, 2 to 9 carbon atoms, 2 to 8 carbon atoms, 2 to 7 carbon atoms, 2 to 6 carbon atoms, 2 to 5 carbon atoms, 2 to 4 carbon atoms, 2 to 3 carbon atoms, and in some embodiments, alkynyl groups contain 2 carbon atoms. Examples of alkynyl group include, but are not limited to, ethynyl, 1-propynyl, 2-propynyl, and the like.

As used herein, the term "alkoxy" or "alkoxyl", whether as part of another term or used independently, refers to an alkyl group, as previously defined, attached to the parent molecule through an oxygen atom. The term "$C_{i\text{-}j}$ alkoxyl" means that the alkyl moiety of the alkoxy group has i to j carbon atoms. In some embodiments, alkoxy groups contain 1 to 12 carbon atoms. In some embodiments, alkoxy groups contain 1 to 11 carbon atoms. In some embodiments, alkoxy groups contain 1 to 10 carbon atoms. In some embodiments, alkoxy groups contain 1 to 9 carbon atoms. In some embodiments, alkoxy groups contain 1 to 8 carbon atoms, 1 to 7 carbon atoms, 1 to 6 carbon atoms, 1 to 5 carbon atoms, 1 to 4 carbon atoms, 1 to 3 carbon atoms, or 1 to 2 carbon atoms. Examples of "$C_{1\text{-}6}$ alkoxyl" include, but are not limited to, methoxy, ethoxy, propoxy (e.g. n-propoxy and isopropoxy), t-butoxy, neopentoxy, n-hexoxy, and the like.

As used herein, the term "amino" refers to —NH$_2$.

As used herein, the term "aryl", whether as part of another term or used independently, refers to monocyclic and polycyclic ring systems having a total of 5 to 20 ring members, wherein at least one ring in the system is aromatic and wherein each ring in the system contains 3 to 12 ring members. Examples of "aryl" include, but are not limited to, phenyl, naphthyl, anthracenyl and the like, which may bear one or more substituents. Also included within the scope of the term "aryl", as it is used herein, is a group in which an aromatic ring is fused to one or more additional rings. In the case of polycyclic ring system, only one of the rings needs to be aromatic (e.g., 2,3-dihydro-1H-indene), although all of the rings may be aromatic (e.g., naphthalene). The second ring can also be fused or bridged. Examples of polycyclic aryl include, but are not limited to, indanyl, indenyl, dihydronaphthyl, tetrahydronaphthyl, dihydroindene and the like. Aryl groups can be substituted at one or more ring positions with substituents as described above.

As used herein, the term "cycloalkyl", whether as part of another term or used independently, refer to a monovalent non-aromatic, saturated or partially unsaturated monocyclic and polycyclic ring system, in which all the ring atoms are carbon and which contains at least three ring forming carbon atoms. In some embodiments, the cycloalkyl may contain 3 to 12 ring forming carbon atoms, 3 to 11 ring forming carbon atoms, 3 to 10 ring forming carbon atoms, 3 to 9 ring forming carbon atoms, 3 to 8 ring forming carbon atoms, 3 to 7 ring forming carbon atoms, 3 to 6 ring forming carbon atoms, 3 to 5 ring forming carbon atoms, 3 to 4 ring forming carbon atoms, 4 to 12 ring forming carbon atoms, 4 to 11 ring forming carbon atoms, 4 to 10 ring forming carbon atoms, 4 to 9 ring forming carbon atoms, 4 to 8 ring forming carbon atoms, 4 to 7 ring forming carbon atoms, 4 to 6 ring forming carbon atoms, 4 to 5 ring forming carbon atoms. Cycloalkyl groups may be saturated or partially unsaturated. Cycloalkyl groups may be substituted. In some embodiments, the cycloalkyl group may be a saturated cyclic alkyl group. In some embodiments, the cycloalkyl group may be a partially unsaturated cyclic alkyl group that contains at least one double bond or triple bond in its ring system.

In some embodiments, the cycloalkyl group may be monocyclic or polycyclic. Examples of monocyclic cycloalkyl group include, but are not limited to, cyclopropyl, cyclobutyl, cyclopentyl, 1-cyclopent-1-enyl, 1-cyclopent-2- enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl and cyclododecyl.

In some embodiments, the cycloalkyl group may be saturated or partially unsaturated polycyclic (e.g., bicyclic and tricyclic) carbocyclic ring system, which can be arranged as a fused-, spiro- or bridged-ring system. As used herein, the term "fused-ring" refers to a ring system having two rings sharing two adjacent atoms, the term "spiro-ring" refers to a ring systems having two rings connected through one single common atom, and the term "bridged-ring" refers to a ring system with two rings sharing three or more atoms. Examples of fused cycloalkyl include, but are not limited to, decahydronaphthyl, icosahydrobenzopyrenyl, tetradecahydroanthracenyl, dodecahydroacenaphthyl, dodecahydrofluorenyl and the like. Examples of spiro cycloalkyl include, but are not limited to, spiro[5.5]undecanyl, spiro[3.6]-decanyl, and the like. Examples of bridged cycloalkyl include, but are not limited to bicyclo[1.1.1]pentenyl, bicyclo[2.2.1]heptenyl, bicyclo[2.2.1]heptanyl, bicyclo[2.2.2]octanyl, bicyclo[3.3.1]nonanyl, bicyclo[3.3.3]undecanyl, adamantyl and the like.

As used herein, the term "carboxyl" refers to —C(O)OH.

As used herein, the term "cyano" refers to —CN.

As used herein, the term "halogen" refers to an atom selected from fluorine (or fluoro), chlorine (or chloro), bromine (or bromo) and iodine (or iodo).

As used herein, the term "haloalkyl", whether as part of another term or used independently, refers to an alkyl group having one or more halogen substituents. Examples of haloalkyl group include, but are not limited to, trifluoromethyl (—$CF_3$), pentafluoroethyl (—$C_2F_5$), difluoromethyl (—$CHF_2$), trichloromethyl (—$CCl_3$), dichloromethyl (—$CHCl_2$), pentachloroethyl (—$C_2Cl_5$), and the like.

As used herein, the term "haloalkoxy" or "haloalkoxyl", refers to an haloalkyl group, as previously defined, attached to the parent molecule through an oxygen atom. Examples of haloalkoxy group include, but are not limited to, trifluoromethoxy (—$OCF_3$), pentafluoroethoxy (—$OC_2F_5$), difluoromethoxy (—$OCHF_2$), trichloromethoxy (—$OCCl_3$), dichloromethoxy (—$OCHCl_2$), pentachloroethoxy (—$OC_2Cl_5$), and the like.

As used herein, the term "heteroatom" refers to nitrogen (N), oxygen (O), sulfur (S), and includes any oxidized form of nitrogen or sulfur, and any quaternized form of a basic nitrogen (including N-oxides).

As used herein, the term "heteroalkyl", "heteroalkenyl", or "heteroalkynyl", whether as part of another term or used independently, refers to an alkyl, alkenyl, or alkynyl group containing one or more heteroatoms. As a result, the term "hetero-$C_{i-j}$ alkyl", "hetero-$C_{i-j}$ alkenyl", or "hetero-$C_{i-j}$ alkynyl", whether as part of another term or used independently, refers to a $C_{i-j}$ alkyl, $C_{i-j}$ alkenyl, or $C_{i-j}$ alkynyl containing one or more heteroatoms. For example, the term "hetero-$C_{1-6}$ alkyl", whether as part of another term or used independently, refers to a $C_{1-6}$ alkyl containing one or more heteroatoms.

As used herein, the term "heteroaryl", whether as part of another term or used independently, refers to an aryl group having, in addition to carbon atoms, one or more heteroatoms such as oxygen, sulfur, nitrogen, phosphorus and the like. The heteroaryl group can be monocyclic. Examples of monocyclic heteroaryl include, but are not limited to, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, benzofuranyl and pteridinyl. The heteroaryl group also includes polycyclic groups. Examples of polycyclic heteroaryl include, but are not limited to, indolyl, isoindolyl, benzothienyl, benzofuranyl, dihydrobenzofuranyl, furopyridinyl, dihydrofuropyridinyl, benzo[1,3]dioxolyl, dibenzofuranyl, indazolyl, benzimidazolyl, benzthiazolyl, quinolyl, isoquinolyl, dihydroquinolinyl, dihydroisoquinolinyl, tetrahydroquinolinyl, tetrahydroisoquinolinyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, chromanyl, isochromanyl, pyrrolopyridine, dihydropyrrolopyridine, and the like.

As used herein, the term "heterocyclyl" refers to a saturated or partially unsaturated carbocyclyl group in which one or more ring atoms are heteroatoms independently selected from oxygen, sulfur, nitrogen, phosphorus, and the like, the remaining ring atoms being carbon, wherein one or more ring atoms may be optionally substituted independently with one or more substituents. In some embodiments, the heterocyclyl is a saturated heterocyclyl. In some embodiments, the heterocyclyl is a partially unsaturated heterocyclyl having one or more double or triple bonds in its ring system. In some embodiments, the heterocyclyl may contains any oxidized form of carbon, nitrogen or sulfur, and any quaternized form of a basic nitrogen. The heterocyclyl radical may be carbon linked or nitrogen linked where such is possible. In some embodiments, the heterocycle is carbon linked. In some embodiments, the heterocycle is nitrogen linked. For example, a group derived from pyrrolidine may be pyrrolidin-1-yl (nitrogen linked) or pyrrolidin-3-yl (carbon linked).

Heterocyclyl group may be monocyclic. Examples of monocyclic heterocyclyl include, but are not limited to oxetanyl, tetrahydrofuryl, tetrahydropyranyl, tetrahydrothienyl, azetidinyl, pyrrolidinyl, piperidyl, piperazinyl, morpholinyl, pyrrolidinyl, and the like.

Heterocyclyl group may be polycyclic, including the fused-, spiro- and bridged-ring systems. The fused heterocyclyl group includes radicals wherein a monocyclic heterocyclyl is fused with a saturated or partially unsaturated carbocyclic or heterocyclic ring. Examples of fused heterocyclyl include, but are not limited to, phenyl fused-ring or pyridinyl fused-ring, such as decahydroquinolinyl, decahydroisoquinolinyl, decahydroquinoxalinyl, decahydroquinolizinyl, decahydroquinazolinyl, octahydroazaindolizinyl, decahydropteridinyl, octahydrochromenyl, octahydroisochromenyl groups, and the like. Examples of spiro heterocyclyl include, but are not limited to, 5-aza-spiro[2.4]heptanyl, 6-aza-spiro[2.5]octanyl, 6-aza-spiro[3.4]octanyl, 2-oxa-6-aza-spiro[3.3]heptanyl, 2-oxa-6-aza-spiro[3.4]octanyl, 6-aza-spiro[3.5]nonanyl, 7-aza-spiro[3.5]nonanyl, 1-oxa-7-aza-spiro[3.5]nonanyl and the like. Examples of bridged heterocyclyl include, but are not limited to, 8-aza-bicyclo[3,2,1]octanyl, 1-aza-bicyclo[2,2,2]octanyl, 2-aza-bicyclo[2,2,1]heptanyl, 1,4-diazabicyclo[2,2,2]octanyl, and the like.

As used herein, the term "hydroxyl" or "hydroxy" refers to —OH.

As used herein, the term "partially unsaturated" refers to a radical that includes at least one double or triple bond. The term "partially unsaturated" is intended to encompass rings having multiple sites of unsaturation, but is not intended to include aromatic (i.e., fully unsaturated) moieties.

As used herein, the term "substituted", whether preceded by the term "optionally" or not, means that one or more hydrogens of the designated moiety are replaced with a suitable substituent. It will be understood that "substitution" or "substituted with" includes the implicit proviso that such substitution is in accordance with permitted valence of the substituted atom and that the substitution results in a stable or chemically feasible compound, e.g., which does not spontaneously undergo transformation such as by rearrangement, cyclization, elimination, etc. Unless otherwise indicated, an "optionally substituted" group may have a suitable substituent at each substitutable position of the group, and when more than one position in any given structure may be substituted with more than one substituent selected from a specified group, the substituent may be either the same or different at every position. It will be understood by those skilled in the art that substituents can themselves be substituted, if appropriate. Unless specifically stated as "unsubstituted", references to chemical moieties herein are understood to include substituted variants. For example, reference to an "aryl" group or moiety implicitly includes both substituted and unsubstituted variants.

Compounds

The present disclosure provides novel compounds, or pharmaceutically acceptable salts thereof, synthetic methods for making the compounds, pharmaceutical compositions containing them and various uses of the disclosed compounds.

In some embodiments, the present disclosure provides a compound of Formula (I):

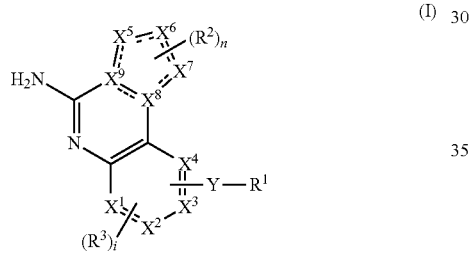

or a pharmaceutically acceptable salt, or a deuteride derivative thereof,
wherein
each of $X^1$, $X^2$, $X^3$, $X^4$, $X^5$, $X^6$, $X^7$, $X^8$, and $X^9$ is independently selected from C, CH or N, provided that at least one of $X^8$ and $X^9$ is N;
each ═ is independently a single bond or a double bond;
Y is selected from cycloalkyl, heterocyclyl, aryl, heteroaryl or —C(O)—, wherein the cycloalkyl, heterocyclyl, aryl, and heteroaryl are optionally substituted with one or more $R^a$;
  $R^a$ is selected from the group consisting of hydrogen, deuterium, hydroxyl, halogen, cyano, oxo, alkyl, alkenyl, alkynyl, heteroalkyl, heteroalkenyl, heteroalkynyl, and haloalkyl;
$R^1$ is selected from cycloalkyl, heterocyclyl, aryl, heteroaryl or —N($R^b$)$_2$, wherein the cycloalkyl, heterocyclyl, aryl, and heteroaryl are optionally substituted with one or more $R^c$;
  each $R^b$ is independently selected from the group consisting of hydrogen, deuterium, alkyl, alkenyl, alkynyl, heteroalkyl, heteroalkenyl, heteroalkynyl, cycloalkyl, heterocyclyl, aryl and heteroaryl, wherein the alkyl, alkenyl, alkynyl, heteroalkyl, heteroalkenyl, heteroalkynyl, cycloalkyl, heterocyclyl, aryl and heteroaryl are optionally substituted with one or more $R^d$; or two $R^b$ together with the nitrogen atom to which they are attached form a heterocyclyl optionally substituted with one or more $R^c$;

each $R^c$ is independently selected from the group consisting of deuterium, cyano, halogen, hydroxyl, oxo, alkyl, alkenyl, alkynyl, heteroalkyl, heteroalkenyl, heteroalkynyl, cycloalkyl, heterocyclyl, aryl, heteroaryl and $OR^d$, wherein the alkyl, alkenyl, alkynyl, heteroalkyl, heteroalkenyl, heteroalkynyl, cycloalkyl, heterocyclyl, aryl and heteroaryl are optionally substituted with one or more groups independently selected from oxo, cyano, halogen, hydroxyl, alkyl, or haloalkyl;

$R^d$ is selected from the group consisting of hydrogen, deuterium, hydroxyl, halogen, cyano, oxo, alkoxyl, alkyl, haloalkyl, haloalkoxyl, cycloalkyl, heterocyclyl, aryl and heteroaryl, wherein the alkyl, haloalkyl, cycloalkyl, heterocyclyl, aryl and heteroaryl are optionally substituted with one or more groups independently selected from oxo, cyano, halogen, hydroxyl, alkoxyl, alkyl, haloalkyl, haloalkoxyl;

each of $R^2$ and $R^3$ is independently selected from the group consisting of hydrogen, deuterium, cyano, halogen, hydroxyl, amino, oxo, alkyl, alkenyl, alkynyl, heteroalkyl, heteroalkenyl and heteroalkynyl, wherein the alkyl, alkenyl, alkynyl, heteroalkyl, heteroalkenyl and heteroalkynyl are optionally substituted with one or more groups independently selected from deuterium, cyano, halogen, hydroxyl or amino;

n is 0, 1, 2, or 3; and i is 0, 1, 2 or 3.

In some embodiments, one of $X^5$, $X^6$ and $X^7$ is N, and the other two are C or CH.

In some embodiments, $X^8$ is N and $X^9$ is C or CH.

In some embodiments, $X^5$ and $X^7$ are C or CH, and $X^6$ is N.

In some embodiments, $X^5$ and $X^7$ are C or CH, $X^6$ is N, $X^8$ is N and $X^9$ is C or CH.

In some embodiments,

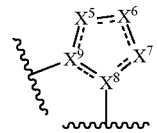

moiety is

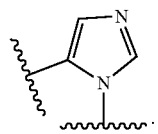

In some embodiments, $X^5$ and $X^6$ are C or CH and $X^7$ is N.

In some embodiments, $X^5$ and $X^6$ are C or CH, $X^7$ is N, $X^8$ is N and $X^9$ is C or CH.

In some embodiments,

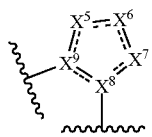

moiety is

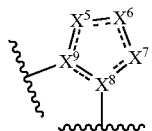

In some embodiments, $X^8$ is C or CH and $X^9$ is N.

In some embodiments, $X^5$ and $X^7$ are C or CH, $X^6$ is N, $X^8$ is C or CH and $X^9$ is N.

In some embodiments,

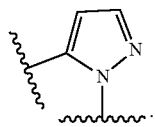

moiety is

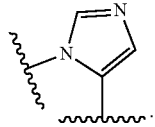

In some embodiments, $X^5$ and $X^6$ are each C or CH, $X^7$ is N, $X^8$ is C or CH and $X^9$ is N.

In some embodiments,

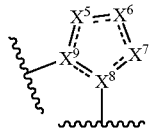

moiety is or

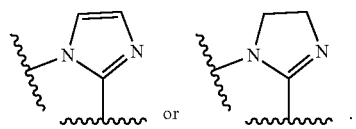 [SMILES: *c1nccn1* ; *C1=NCCN1*]

In some embodiments, $X^5$ is N, $X^6$ and $X^7$ are C or CH, $X^8$ is C or CH and $X^9$ is N.

In some embodiments,

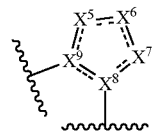

moiety is

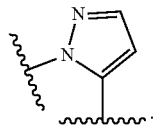 [SMILES: *c1ccnn1*]

In some embodiments, each $R^2$ is independently selected from hydrogen, cyano, halogen, amino, oxo, or alkyl optionally substituted with one or more groups independently selected from cyano, halogen or hydroxyl.

In some embodiments, $R^2$ is hydrogen.

In some embodiments, $R^2$ is alkyl. In certain embodiments, $R^2$ is $C_{1-6}$ alkyl, $C_{1-5}$ alkyl, $C_{1-4}$ alkyl, or $C_{1-3}$ alkyl. In certain embodiments, $R^2$ is methyl.

In some embodiments,

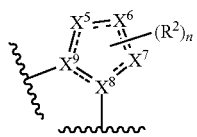

is selected from the group consisting of:

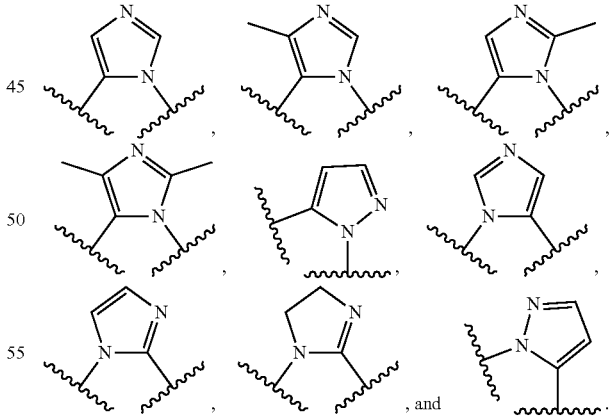

In some embodiments, $X^1$, $X^2$, $X^3$, and $X^4$ are C or CH.

In some embodiments, $X^1$ is N, and $X^2$, $X^3$ and $X^4$ are C or CH.

In some embodiments, $X^2$ is N, and $X^1$, $X^3$ and $X^4$ are C or CH.

In some embodiments, $X^4$ is N, and $X^1$, $X^2$ and $X^3$ are C or CH.

In some embodiments, the moiety is selected from the group consisting of:

[structures shown]

and

In some embodiments, R³ is hydrogen.

In some embodiments, R³ is halogen. In certain embodiments, R³ is F.

In some embodiments, Y is —C(O)—.

In some embodiments, Y is —C(O)— and R¹ is —N(R$^b$)$_2$.

In some embodiments, Y is —C(O)— and R¹ is —N(R$^b$)$_2$, each R$^b$ is independently selected from hydrogen, deuterium, alkyl, or heteroaryl, wherein the alkyl and heteroaryl are optionally substituted with one or more R$^d$, and each R$^d$ is independently selected from hydrogen, deuterium, hydroxyl, halogen, cyano, oxo, alkoxyl, alkyl, haloalkyl, haloalkoxyl or heteroaryl optionally substituted with one or more groups independently selected from oxo, cyano, halogen, hydroxyl, alkyl, alkoxyl, haloalkyl or haloalkoxyl. In certain embodiments, each R$^b$ is independently selected from hydrogen, deuterium, $C_{1-6}$ alkyl, or 5- to 10-membered heteroaryl, wherein the alkyl and heteroaryl are optionally substituted with one or more R$^d$, and each R$^d$ is independently selected from hydrogen, deuterium, hydroxyl, halogen, cyano, oxo, $C_{1-6}$ alkoxyl, $C_{1-6}$ alkyl, $C_{1-6}$ haloalkyl, $C_{1-6}$ haloalkoxyl or 5- to 10-membered heteroaryl optionally substituted with one or more groups independently selected from oxo, cyano, halogen, hydroxyl, $C_{1-6}$ alkyl, $C_{1-6}$ alkoxyl, $C_{1-6}$ haloalkyl or $C_{1-6}$ haloalkoxyl.

In certain embodiments, Y is —C(O)— and R¹ is —N(R$^b$)$_2$, each R$^b$ is independently selected from deuterium, alkyl, -alkyl-heteroaryl, heteroaryl or -heteroaryl-heteroaryl, wherein the alkyl and heteroaryl are optionally substituted with one or more groups independently selected from deuterium, hydroxyl, halogen, cyano, oxo, alkyl, alkoxyl, haloalkyl or haloalkoxyl. In certain embodiments, each R$^b$ is independently selected from deuterium, $C_{1-6}$ alkyl, —$C_{1-6}$ alkyl-(5- to 10-membered heteroaryl), $C_{5-10}$ aryl, 5- to 10-membered heteroaryl or -(5- to 10-membered heteroaryl)-(5- to 10-membered heteroaryl), wherein the alkyl, aryl and heteroaryl are optionally substituted with one or more groups independently selected from deuterium, hydroxyl, halogen, cyano, oxo, $C_{1-6}$ alkyl, $C_{1-6}$ alkoxyl, $C_{1-6}$ haloalkyl or $C_{1-6}$ haloalkoxyl. In certain embodiments, the heteroaryl in -alkyl-heteroaryl, heteroaryl and -heteroaryl-heteroaryl is selected from

[structures shown]

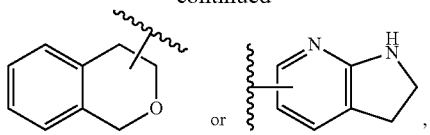 or 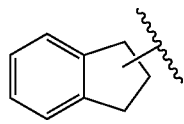, each of which is optionally substituted with one or more groups independently selected from deuterium, hydroxyl, halogen, cyano, oxo, alkyl, alkoxyl, haloalkyl or haloalkoxyl. In certain embodiments, the aryl is

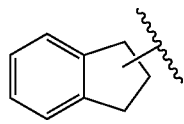

optionally substituted with one or more groups independently selected from deuterium, hydroxyl, halogen, cyano, oxo, alkyl, alkoxyl, haloalkyl or haloalkoxyl.

In some embodiments, Y is —C(O)— and $R^1$ is —N($R^b$)$_2$, wherein one $R^b$ is alkyl, and the other $R^b$ is -heteroaryl-heteroaryl, wherein the alkyl and heteroaryl are optionally substituted with one or more groups independently selected from deuterium, hydroxyl, halogen, cyano, oxo, alkyl, alkoxyl, haloalkyl or haloalkoxyl. In certain embodiments, one $R^b$ is $C_{1-6}$ alkyl, and the other $R^b$ is -(5- to 10-membered heteroaryl)-(5- to 10-membered heteroaryl), wherein the alkyl and heteroaryl are optionally substituted with one or more groups independently selected from deuterium, hydroxyl, halogen, cyano, oxo, $C_{1-6}$ alkyl, $C_{1-6}$ alkoxyl, $C_{1-6}$ haloalkyl or $C_{1-6}$ haloalkoxyl. In certain embodiments, one $R^b$ is methyl optionally substituted with one or more deuterium, and the other $R^b$ is

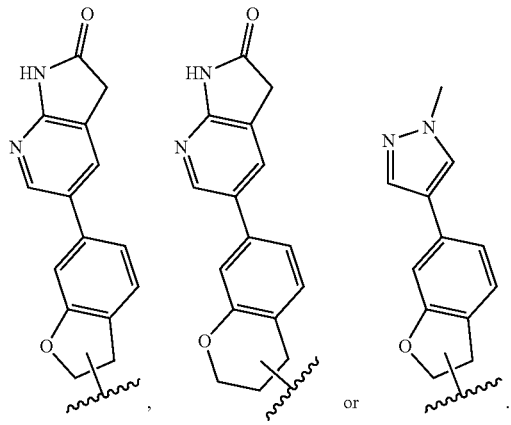

In some embodiments, Y is —C(O)— and $R^1$ is —N($R^b$)$_2$, wherein each $R^b$ is independently -alkyl-heteroaryl, wherein the alkyl and heteroaryl are optionally substituted with one or more groups independently selected from deuterium, hydroxyl, halogen, cyano, oxo, alkyl, alkoxyl, haloalkyl or haloalkoxyl. In certain embodiments, each $R^b$ is independently —$C_{1-6}$ alkyl-(5- to 10-membered heteroaryl), wherein the alkyl and heteroaryl are optionally substituted with one or more groups independently selected from deuterium, hydroxyl, halogen, cyano, oxo, $C_{1-6}$ alkyl, $C_{1-6}$ alkoxyl, $C_{1-6}$ haloalkyl or $C_{1-6}$ haloalkoxyl. In certain embodiments, one $R^b$ is

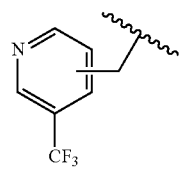

and the other $R^b$ is

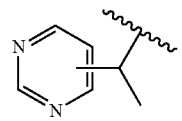.

In some embodiments, Y is —C(O)— and $R^1$ is —N($R^b$)$_2$, wherein one $R^b$ is alkyl, and the other $R^b$ is aryl or heteroaryl, wherein the alkyl, aryl and heteroaryl are optionally substituted with one or more groups independently selected from deuterium, hydroxyl, halogen, cyano, oxo, alkyl, alkoxyl, haloalkyl or haloalkoxyl. In certain embodiments, one $R^b$ is $C_{1-6}$ alkyl, and the other $R^b$ is $C_{5-10}$ aryl or 5- to 10-membered heteroaryl, wherein the alkyl, aryl and heteroaryl are optionally substituted with one or more groups independently selected from deuterium, hydroxyl, halogen, cyano, oxo, $C_{1-6}$ alkyl, $C_{1-6}$ alkoxyl, $C_{1-6}$ haloalkyl or $C_{1-6}$ haloalkoxyl.

In certain embodiments, Y is —C(O)— and $R^1$ is —N($R^b$)$_2$, wherein one $R^b$ is methyl optionally substituted with one or more deuterium, and the other $R^b$ is

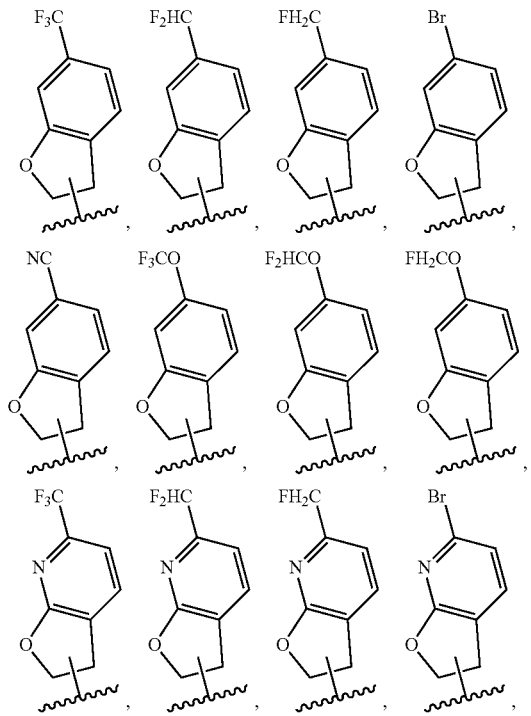

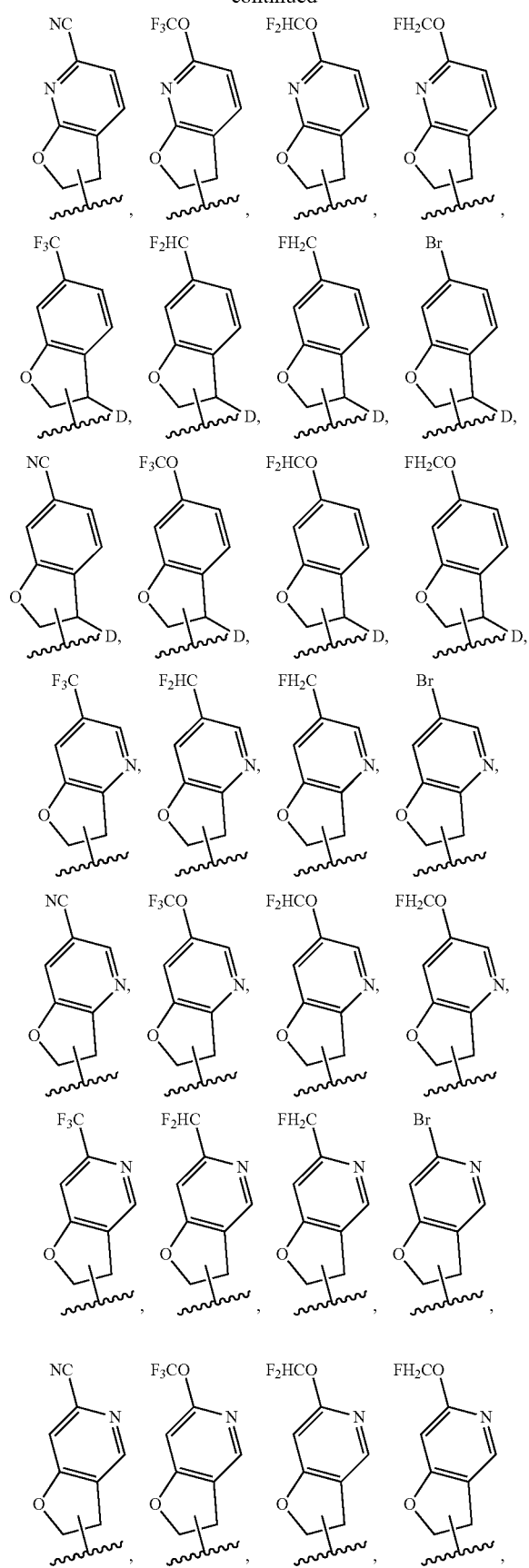
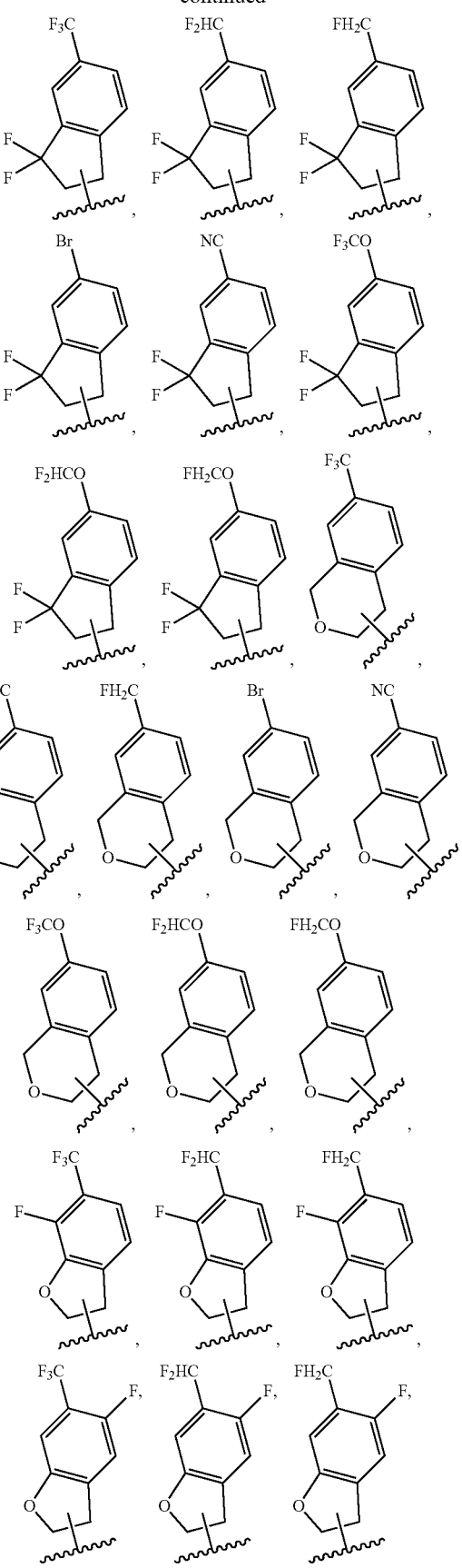

19

-continued

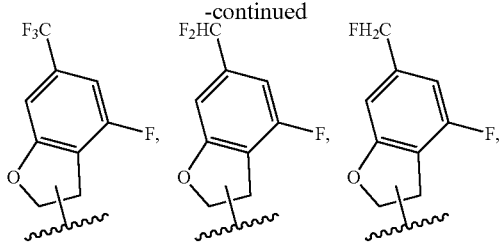

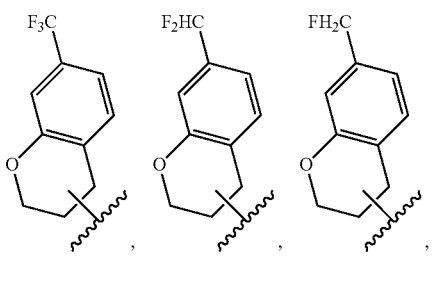

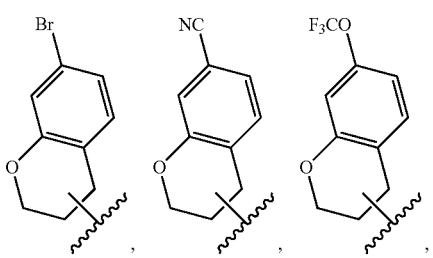

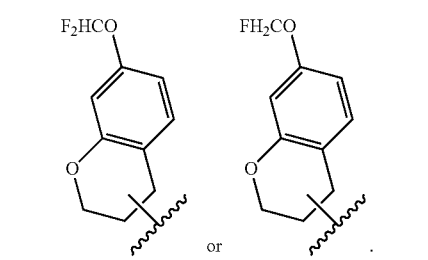

or

In some embodiments, Y is —C(O)— and $R^1$ is —N($R^b$)$_2$, wherein two $R^b$ together with the nitrogen atom to which they are attached form a heterocyclyl optionally substituted with one or more $R^c$. In certain embodiments, two $R^b$ together with the nitrogen atom to which they are attached form a 5- to 10-membered heterocyclyl optionally substituted with one or more $R^c$. In certain embodiments, two $R^b$ together with the nitrogen atom to which they are attached form a piperidinyl optionally substituted with one or more $R^c$. In certain embodiments, each $R^c$ is independently selected from alkyl or heteroaryl optionally substituted with one or more groups independently selected from oxo, cyano, halogen, hydroxyl, alkyl or haloalkyl. In certain embodiments, each $R^c$ is independently selected from $C_{1-6}$ alkyl or $C_{5-10}$ heteroaryl optionally substituted with one or more groups independently selected from oxo, cyano, halogen, hydroxyl, $C_{1-6}$ alkyl or $C_{1-6}$ haloalkyl.

20

In certain embodiments, Y is —C(O)— and $R^1$ is —N($R^b$)$_2$, wherein two $R^b$ together with the nitrogen atom to which they are attached form a piperidinyl optionally substituted with one or more $R^c$ independently selected from the group consisting of:

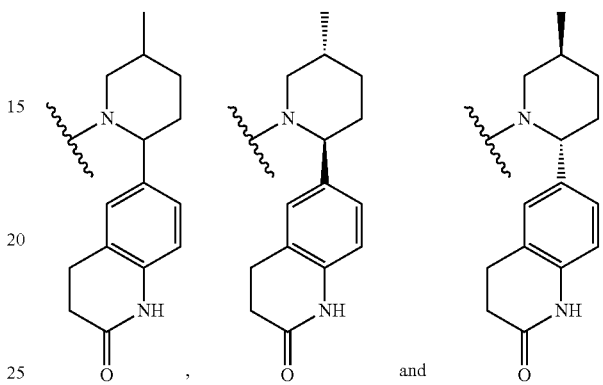

and

In some embodiments, Y is heteroaryl optionally substituted with one or more groups independently selected from halogen, cyano, alkyl, alkenyl or alkynyl. In certain embodiments, Y is 5- to 10-membered heteroaryl optionally substituted with one or more groups independently selected from halogen, cyano, $C_{1-6}$ alkyl, $C_{2-6}$ alkenyl or $C_{2-6}$ alkynyl.

In certain embodiments, Y is pyrazolyl optionally substituted with one or more groups independently selected from halogen, cyano, hydroxyl, or alkyl. In certain embodiments, Y is pyrazolyl optionally substituted with one or more groups independently selected from halogen, cyano, hydroxyl, or $C_{1-6}$ alkyl.

In certain embodiments, Y is

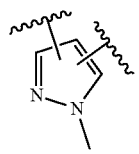

In some embodiments, $R^1$ is aryl optionally substituted with one or more $R^c$. In certain embodiments, $R^1$ is $C_{6-12}$ aryl optionally substituted with one or more $R^c$.

In certain embodiments, $R^1$ is phenyl or naphthalinyl optionally substituted with one or more $R^c$.

In certain embodiments, each $R^c$ is independently selected from cyano, halogen, hydroxyl, alkyl, or $OR^d$, wherein $R^d$ is selected from alkyl, haloalkyl, or cycloalkyl. In certain embodiments, each $R^c$ is independently selected from cyano, halogen, hydroxyl, $C_{1-6}$ alkyl, or $OR^d$, wherein $R^d$ is selected from $C_{1-6}$ alkyl, $C_{1-6}$ haloalkyl, or $C_{3-6}$ cycloalkyl.

Exemplary compounds of the present disclosure are set forth below.
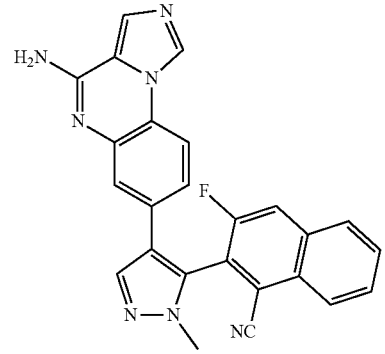
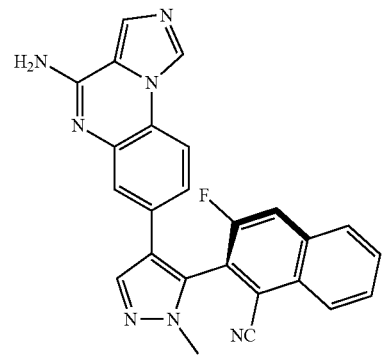
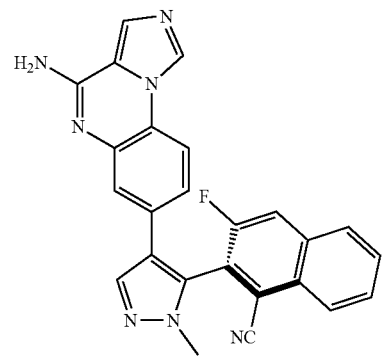
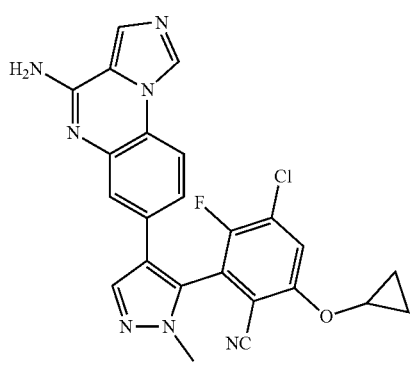
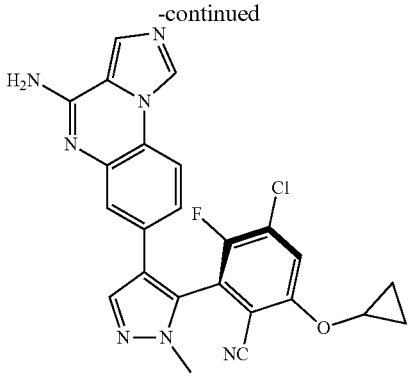
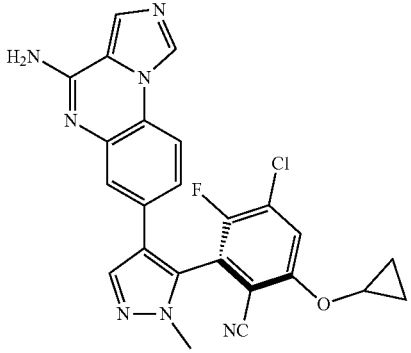
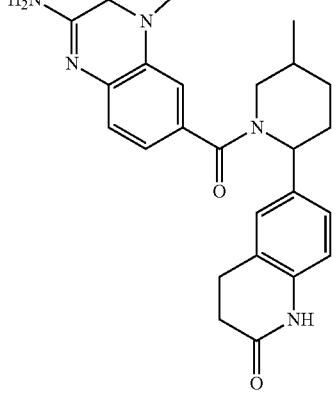
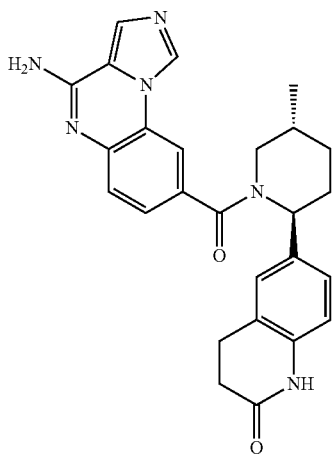

-continued
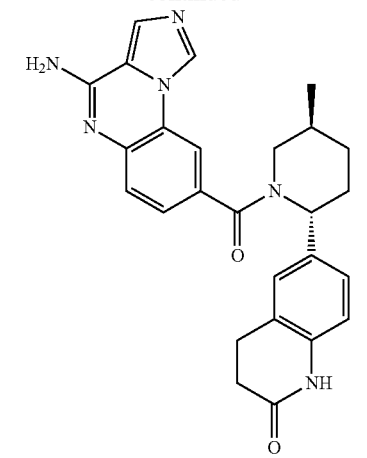
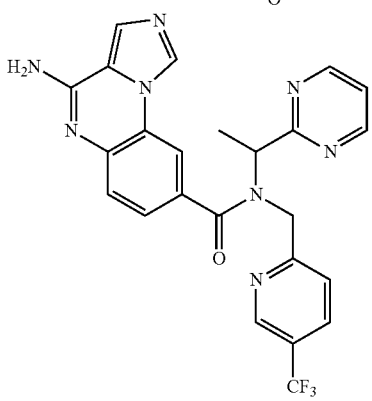
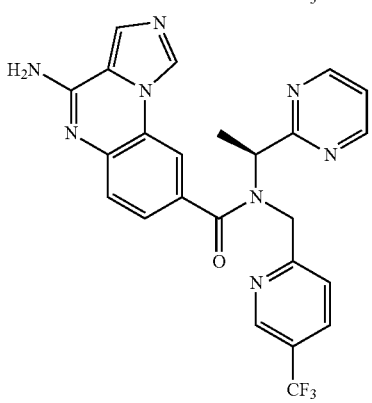
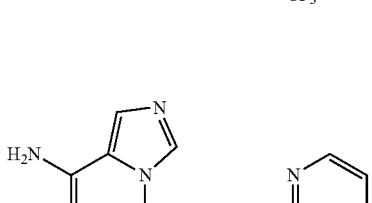
-continued
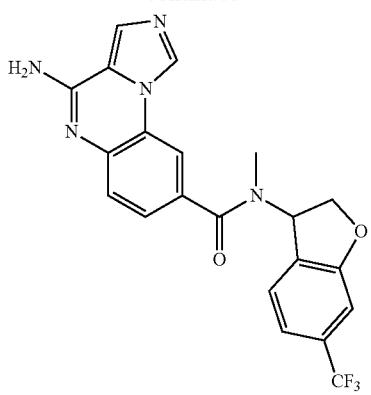
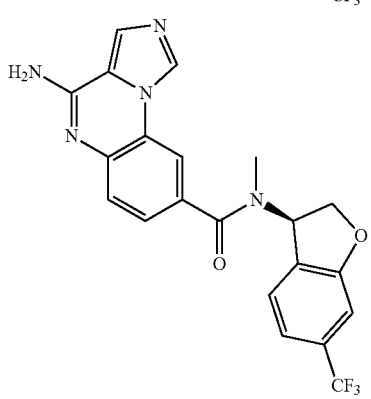
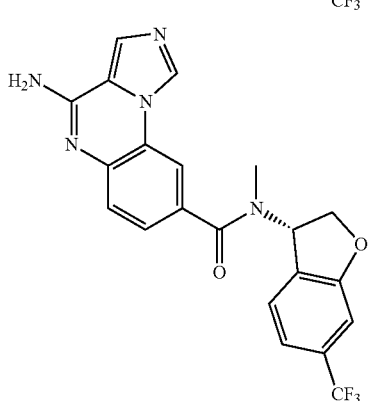
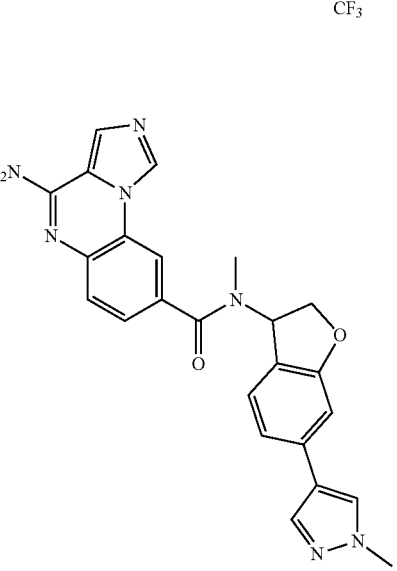

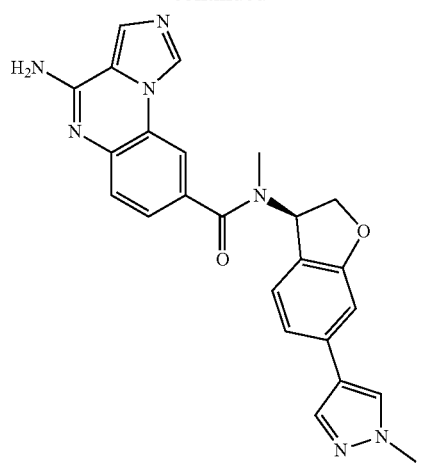
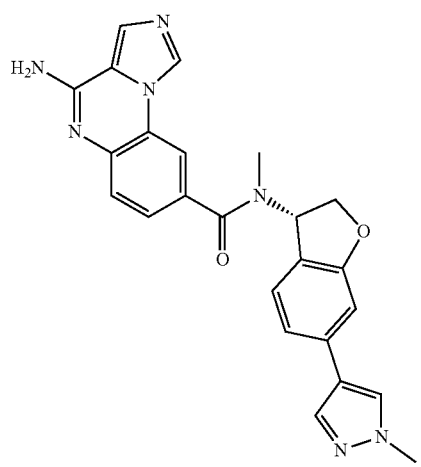
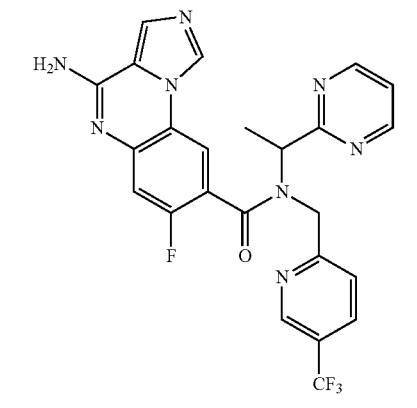
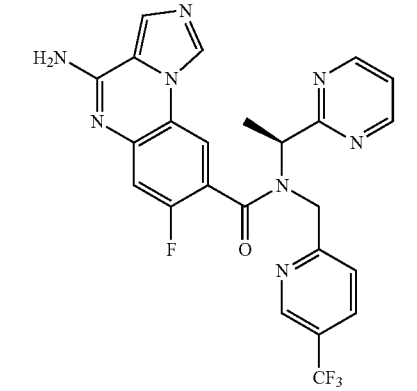
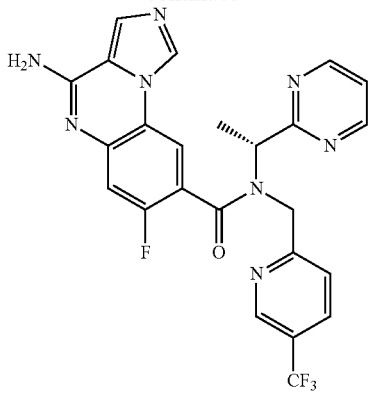
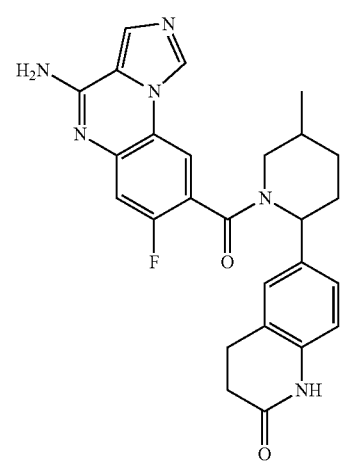
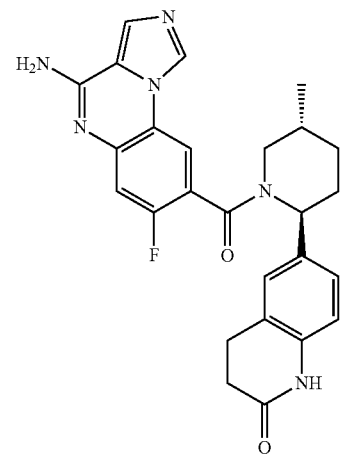

27
-continued
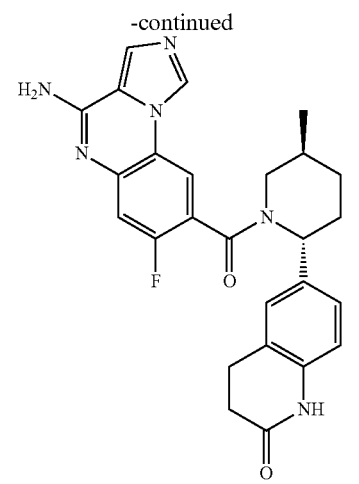
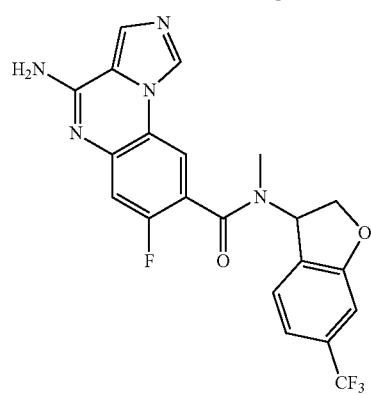
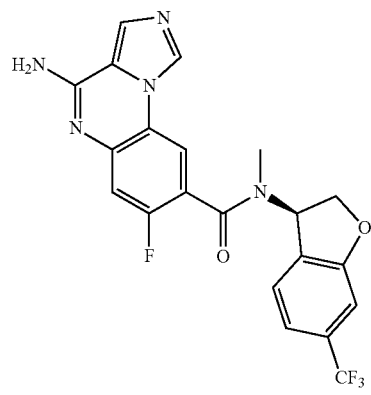
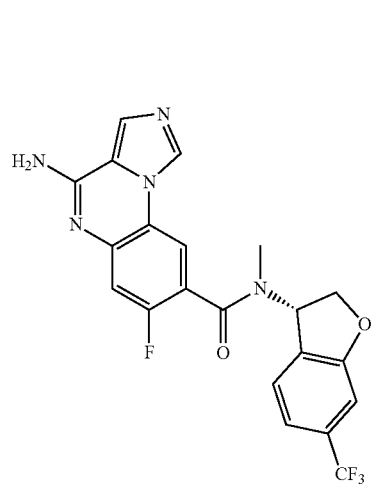
28
-continued
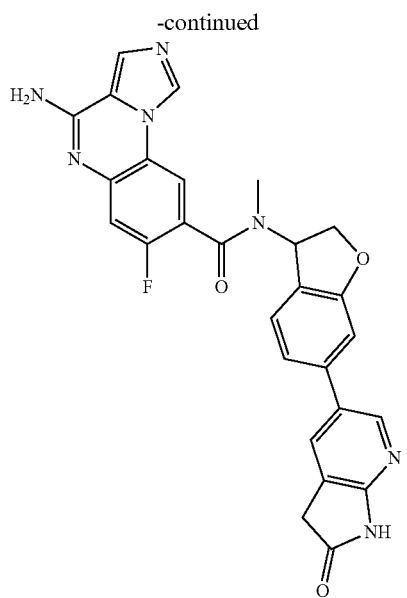
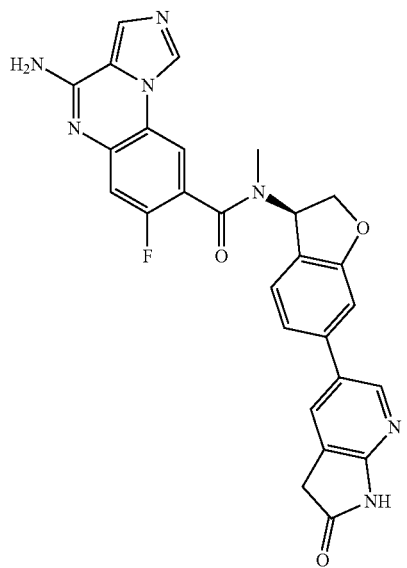
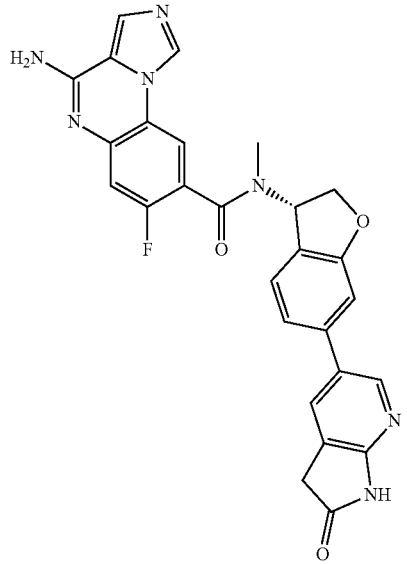

-continued
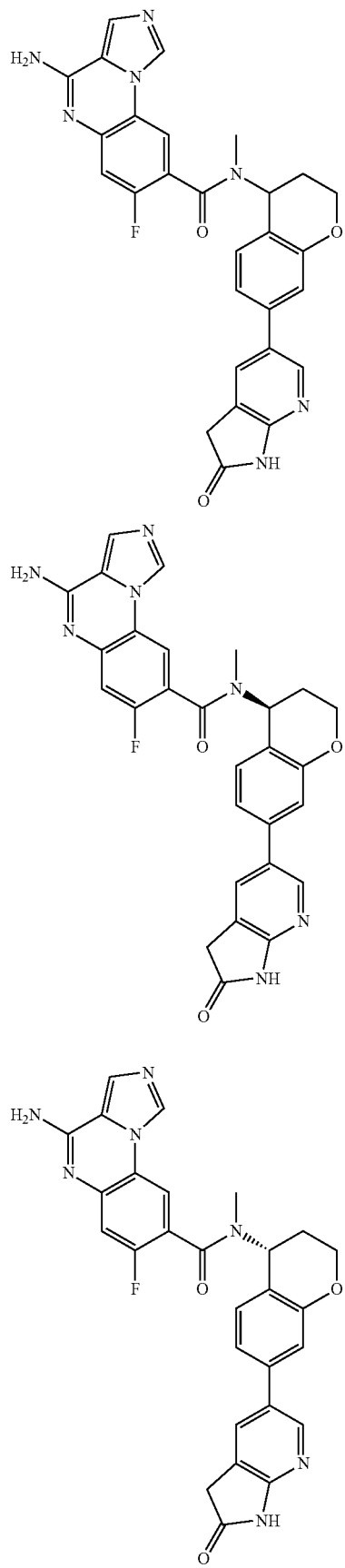
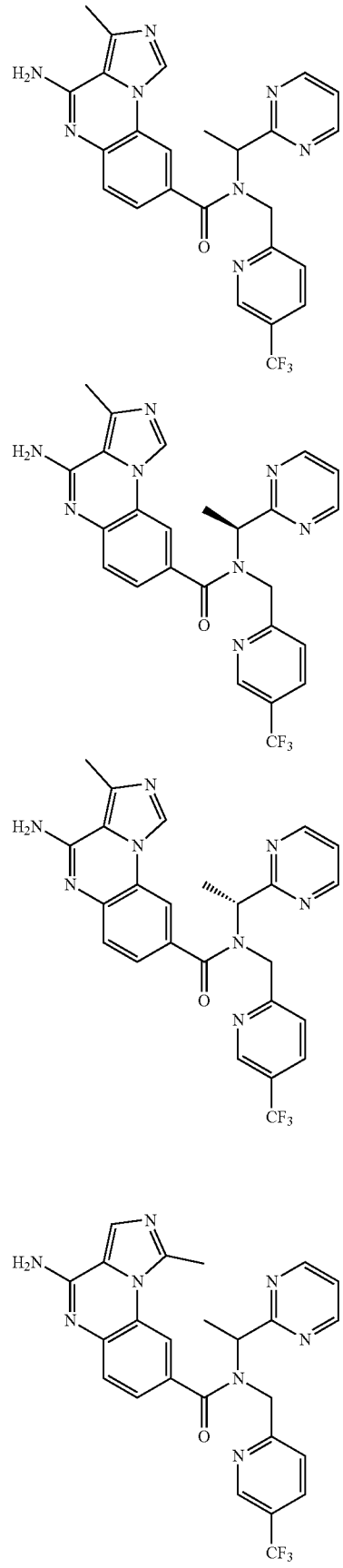

-continued
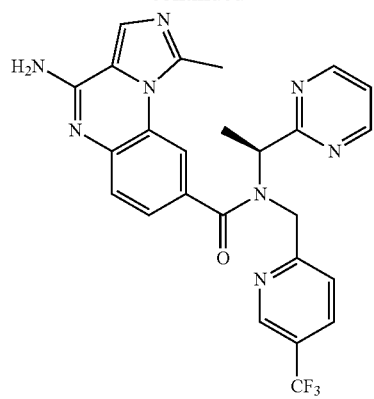
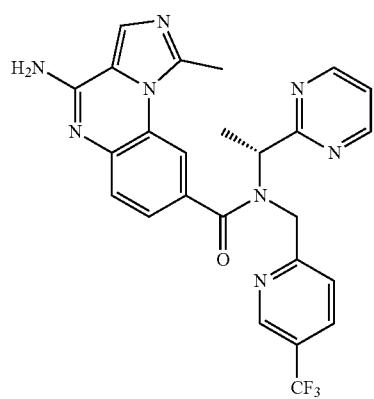
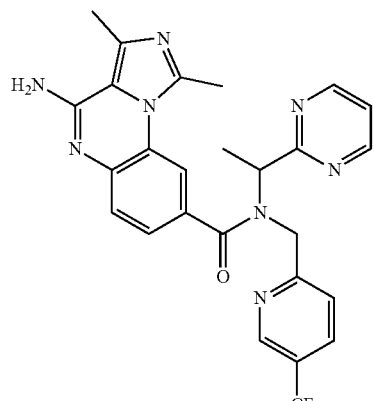
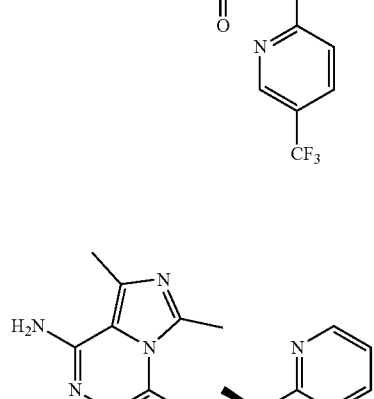
-continued
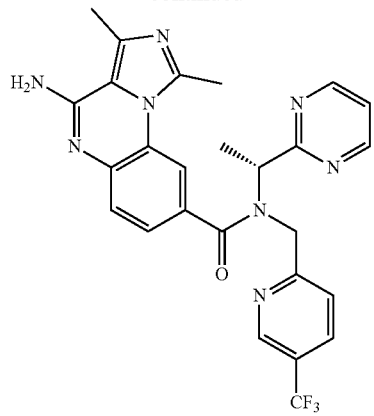
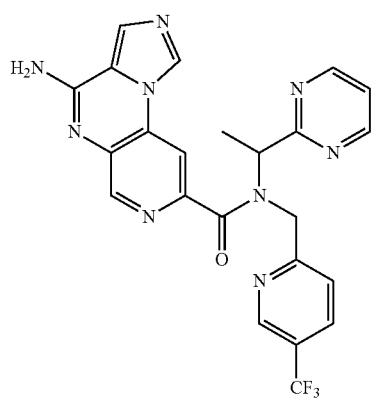
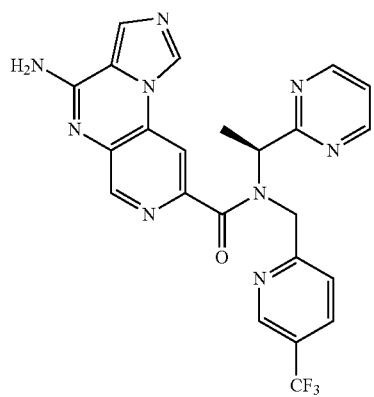
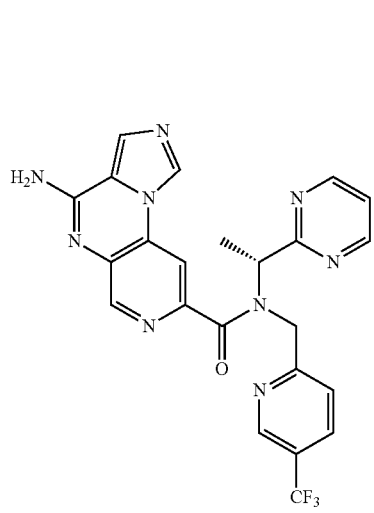

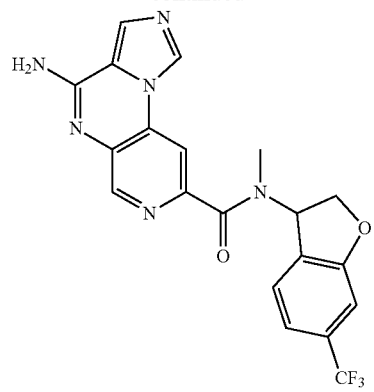
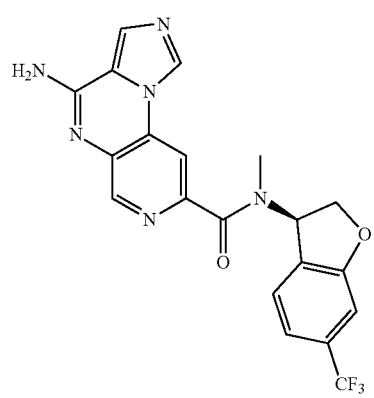
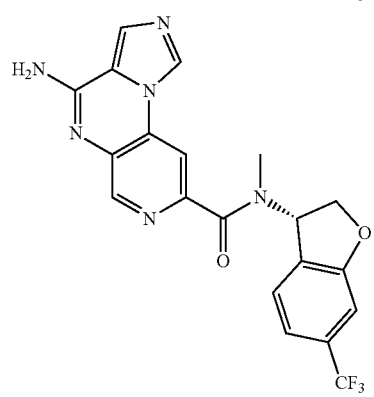
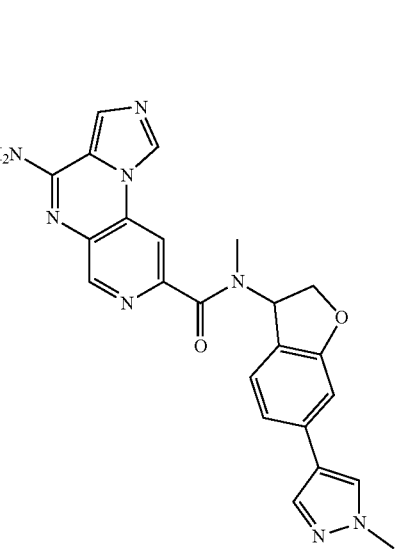
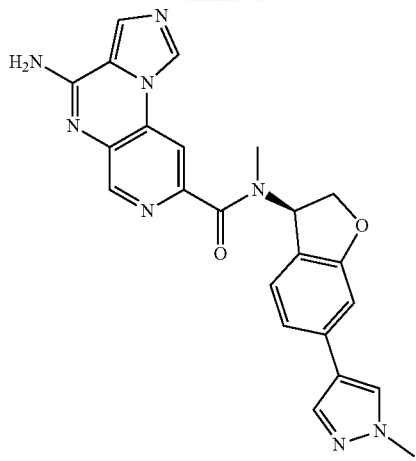
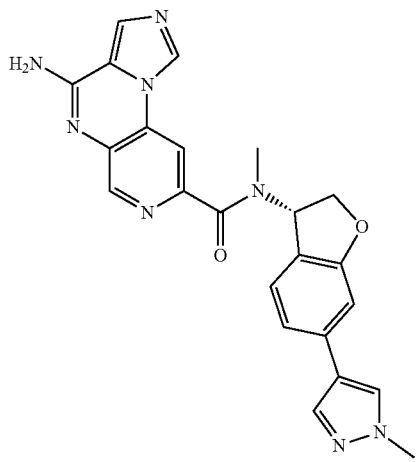
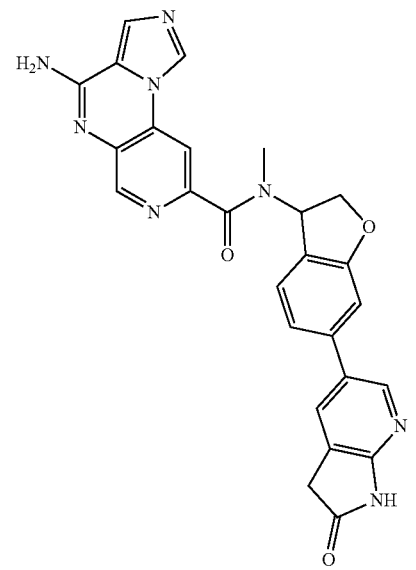

-continued
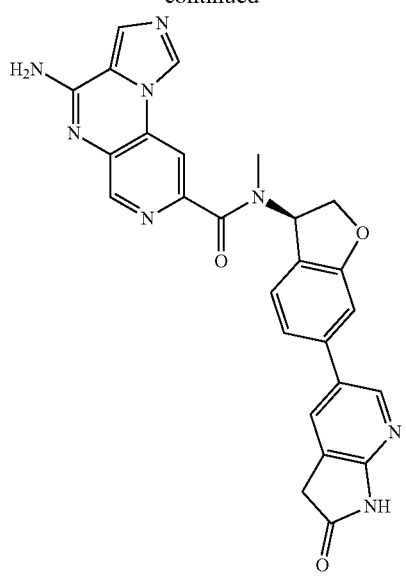
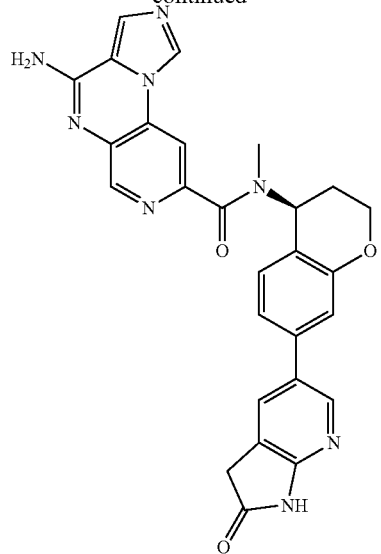
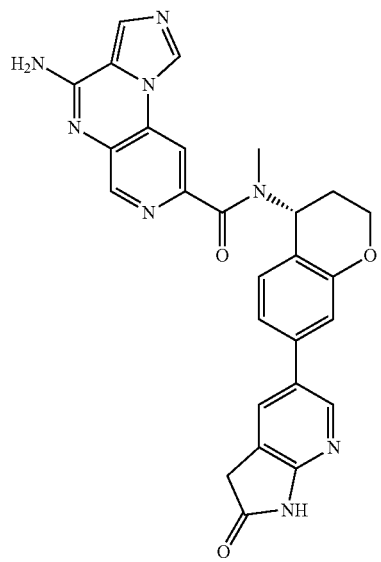
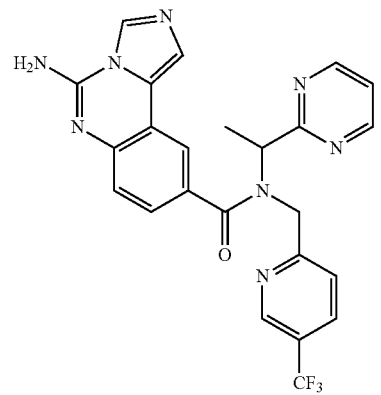

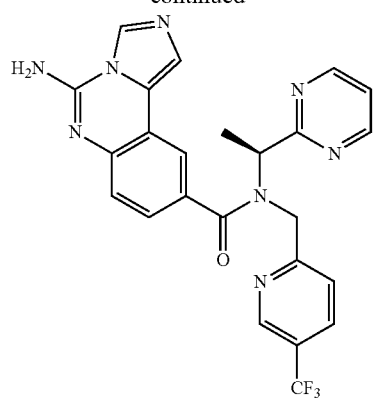
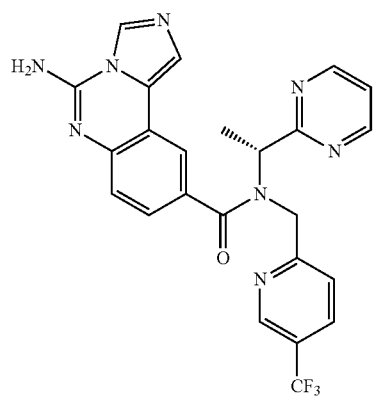
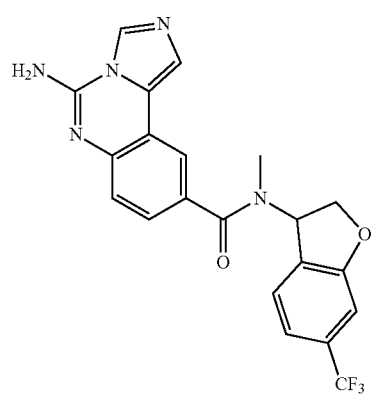

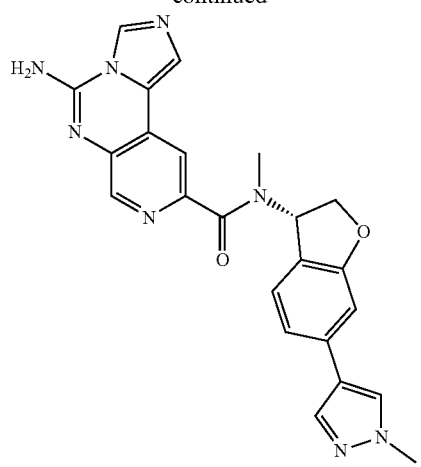
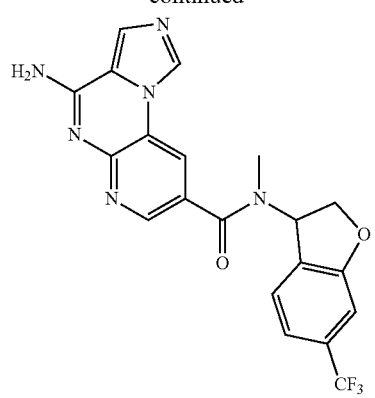
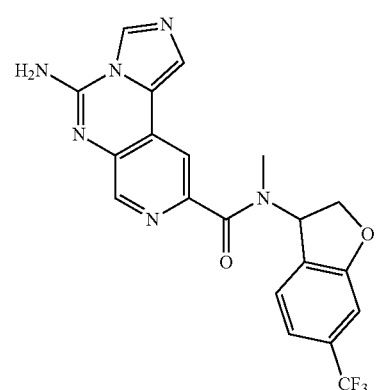
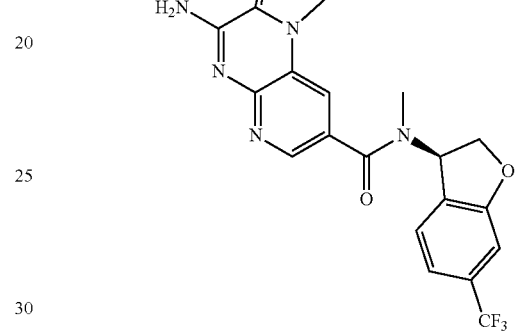
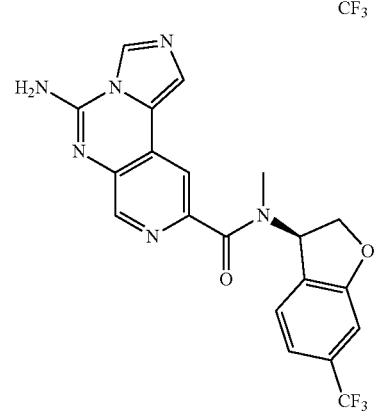
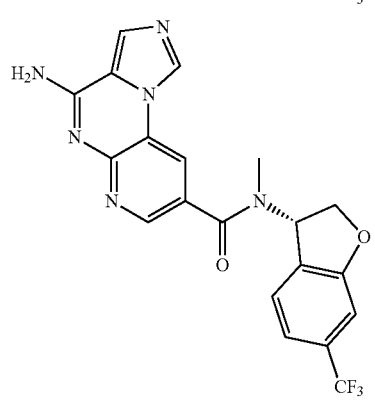
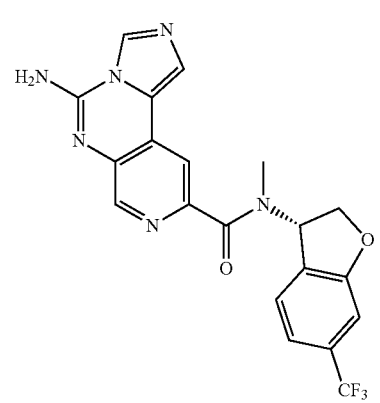
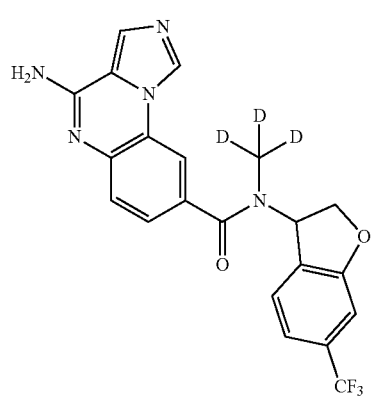

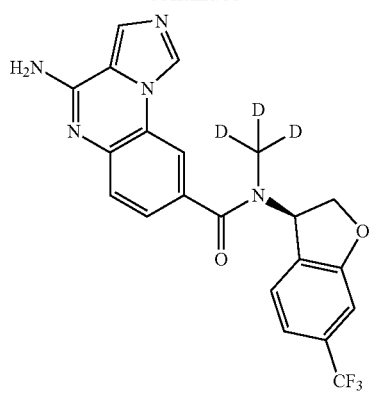
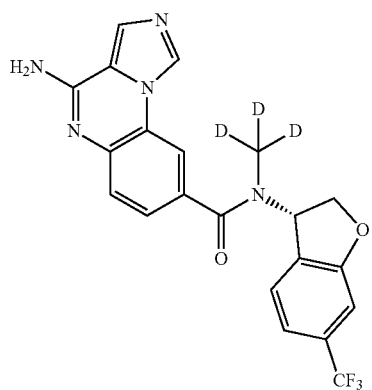
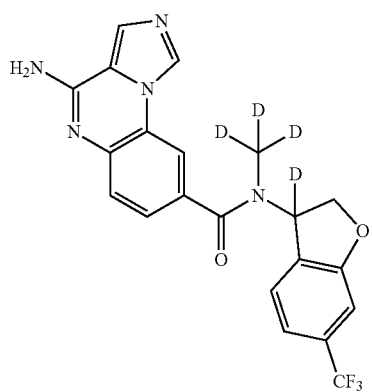
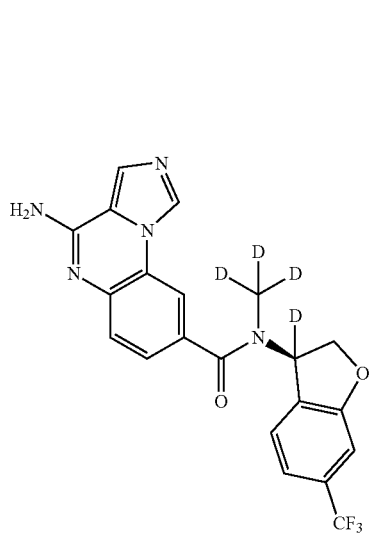
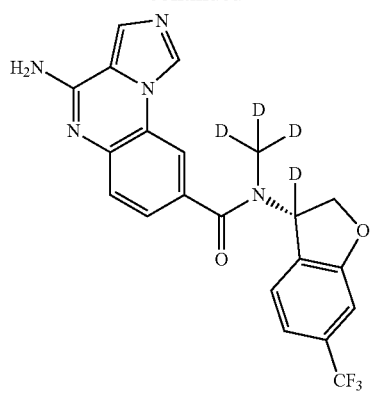
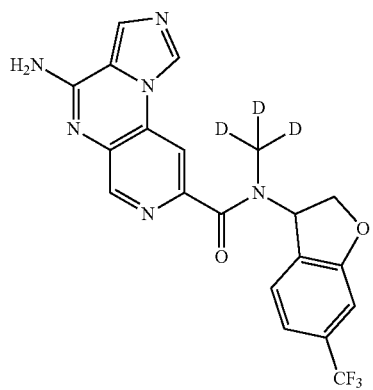
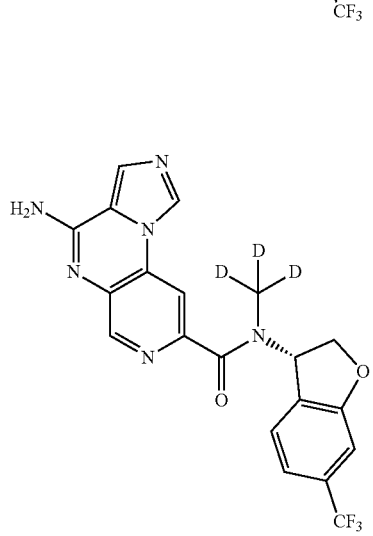
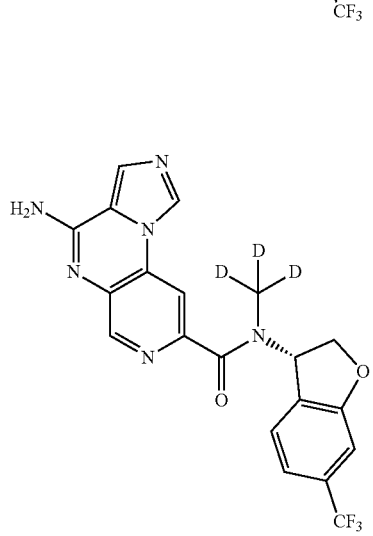

-continued
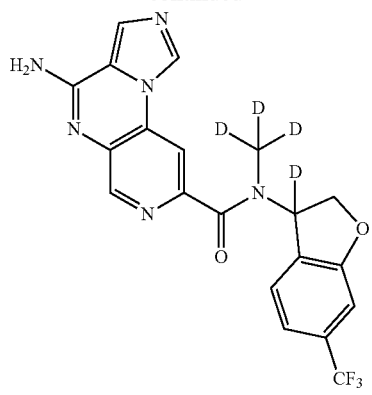
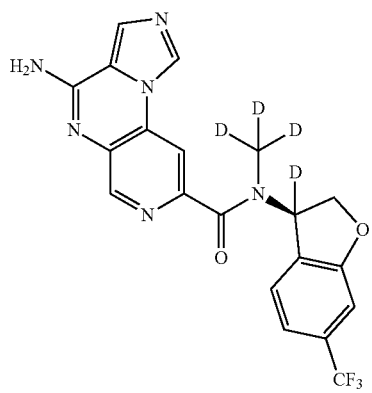
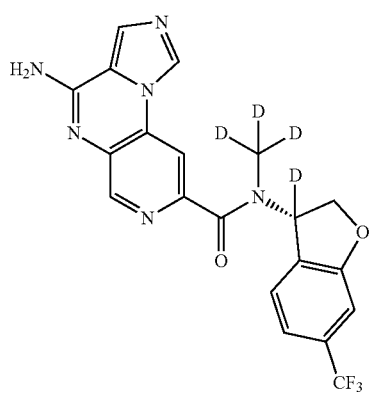
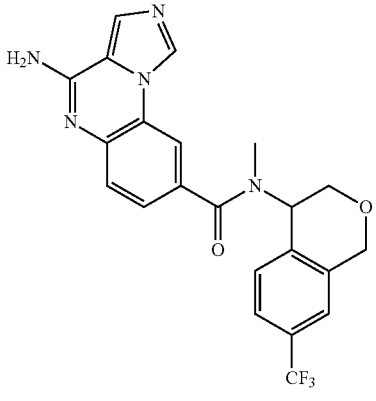
-continued
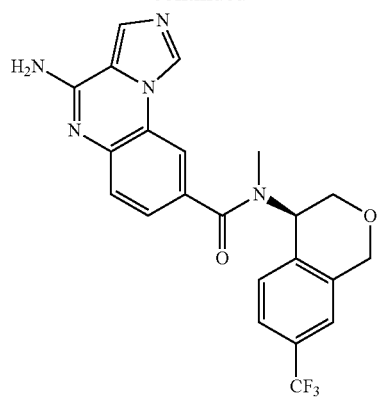
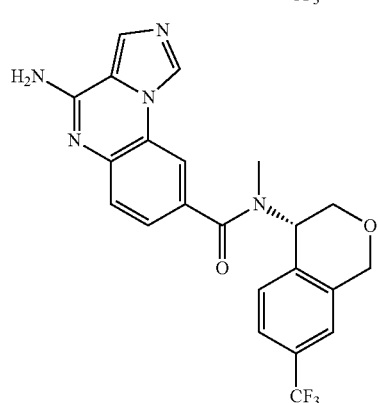
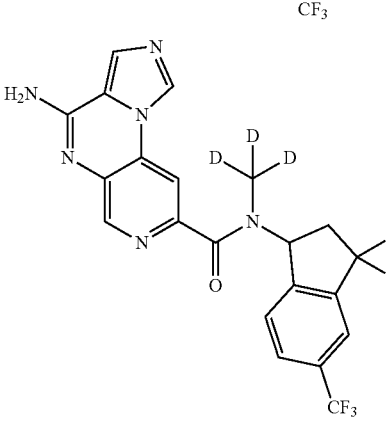
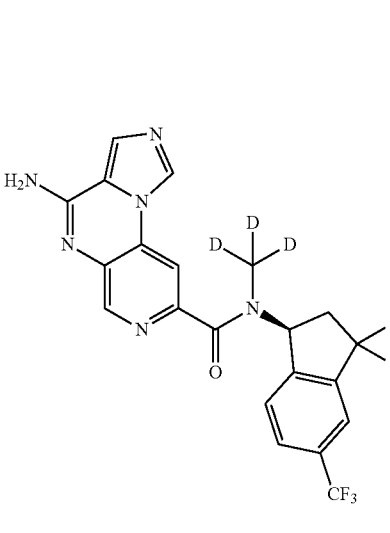

-continued
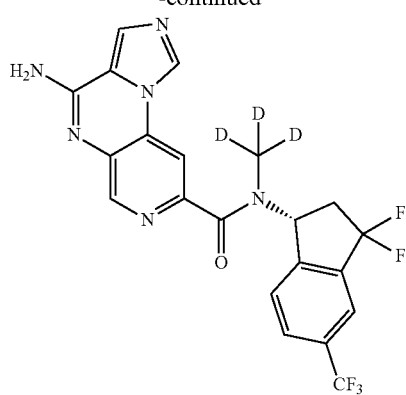
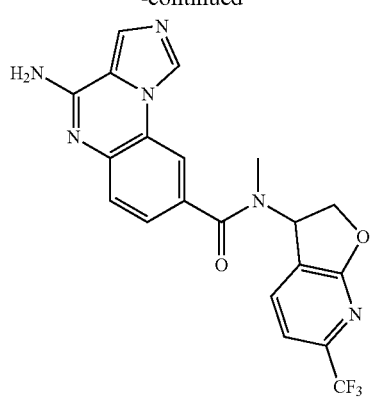
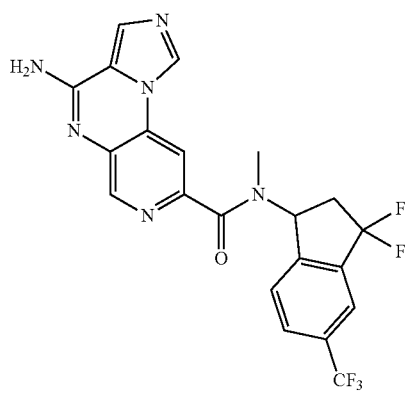
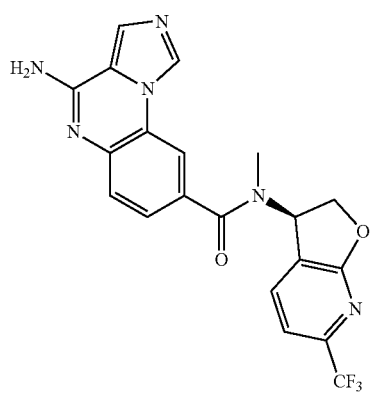
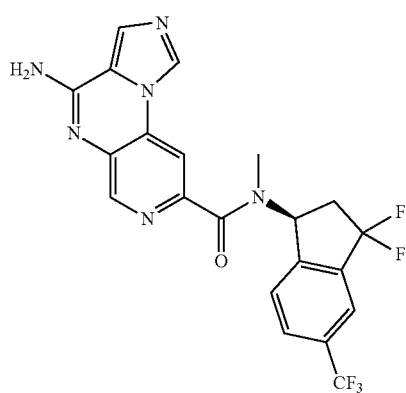
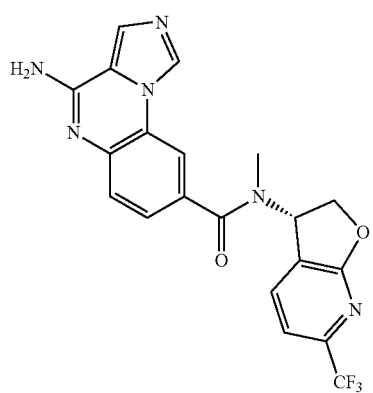
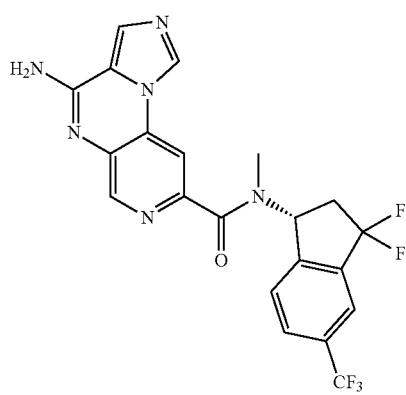
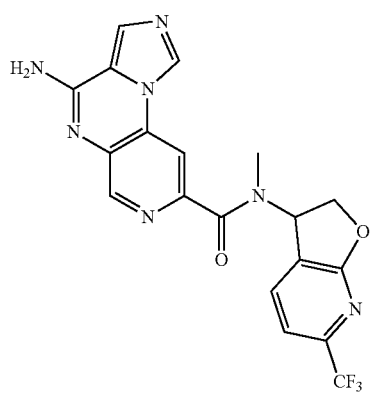

-continued
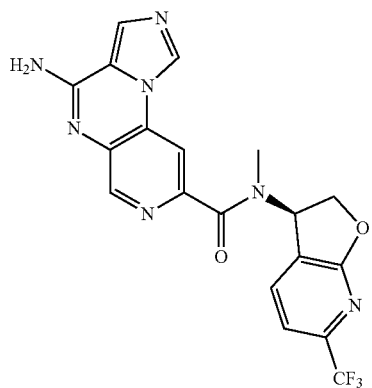
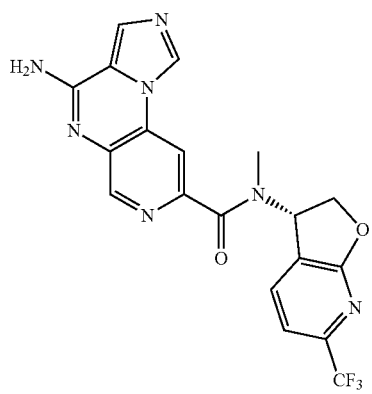
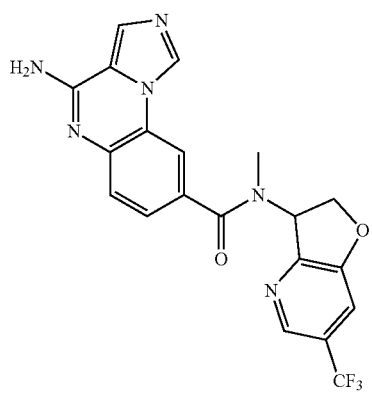
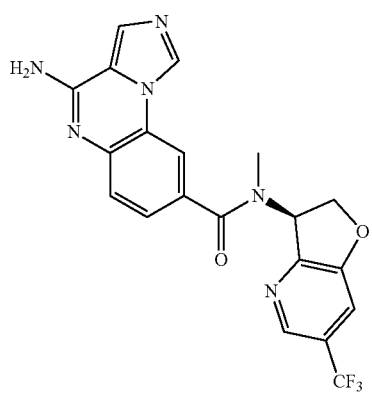
-continued
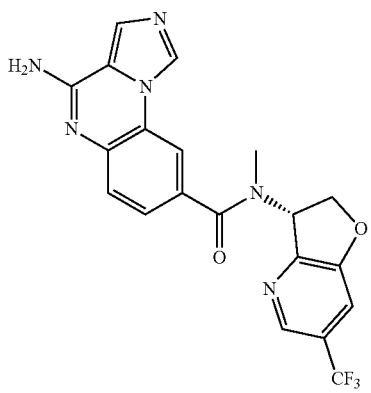
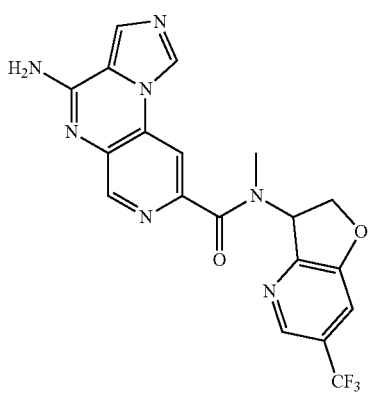
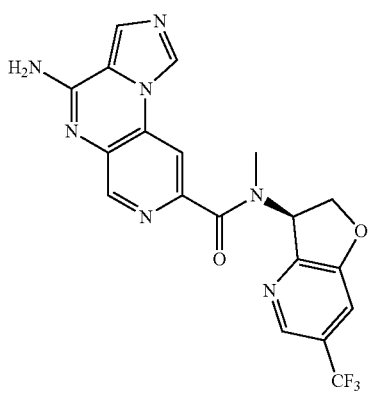
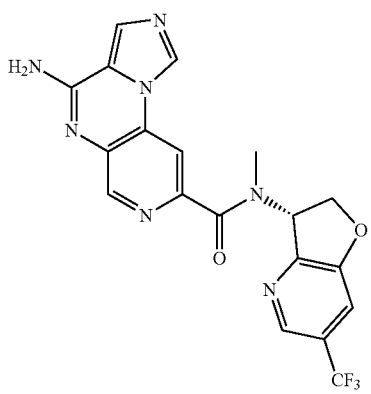

-continued
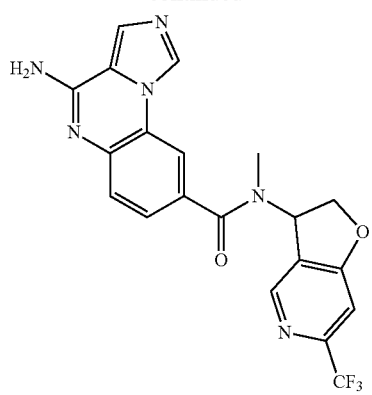
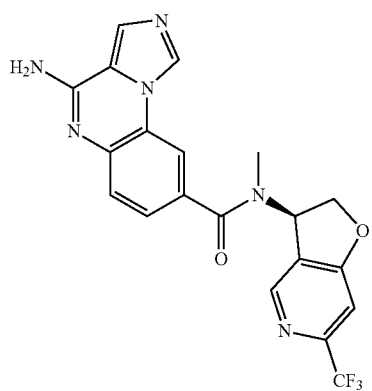
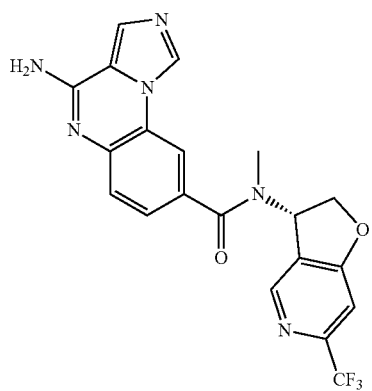
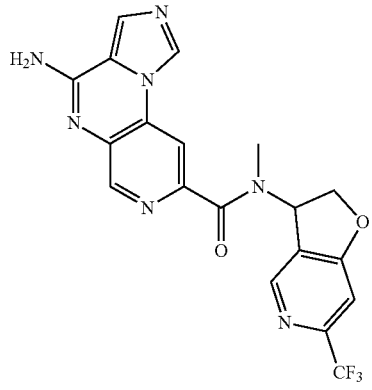
-continued
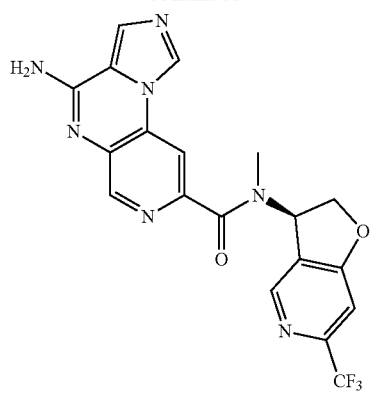
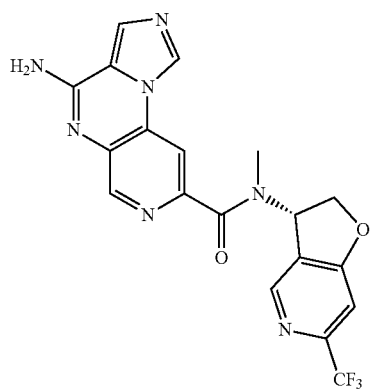
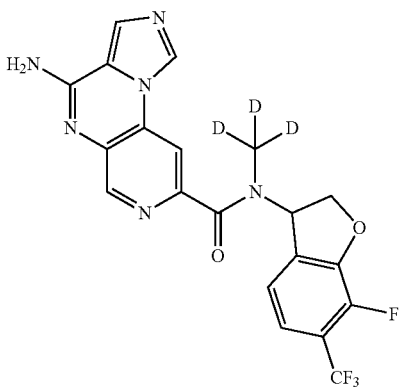
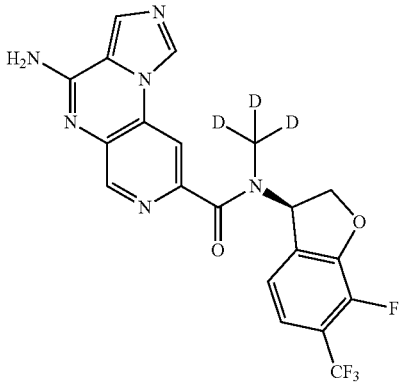

51
-continued
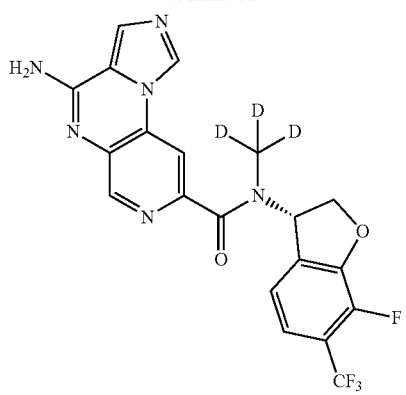
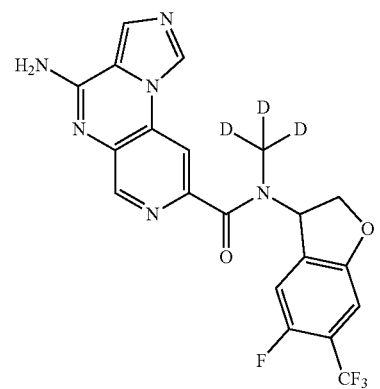
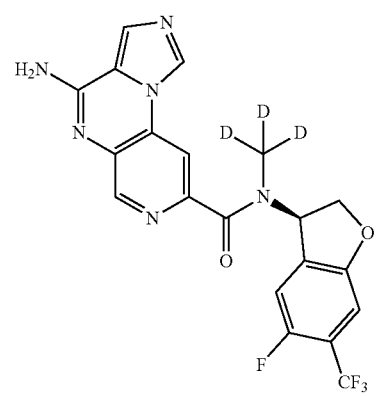
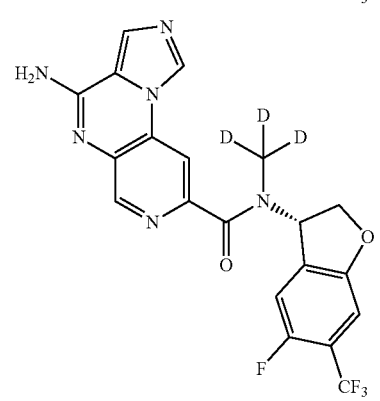
52
-continued
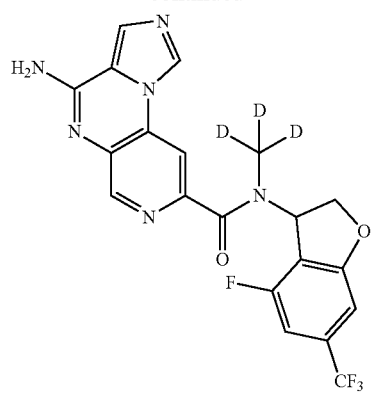
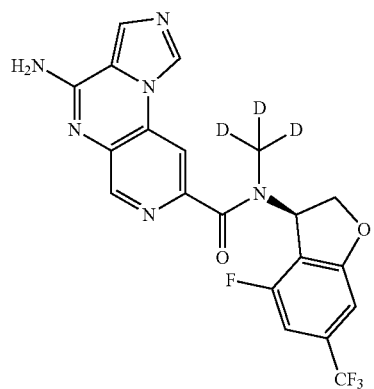
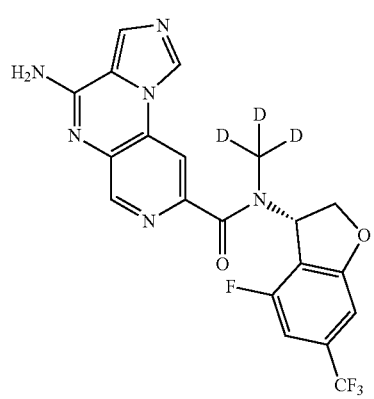
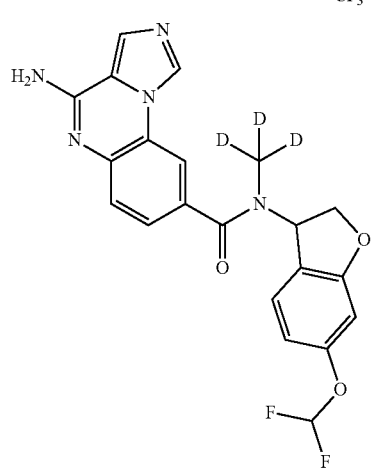

-continued

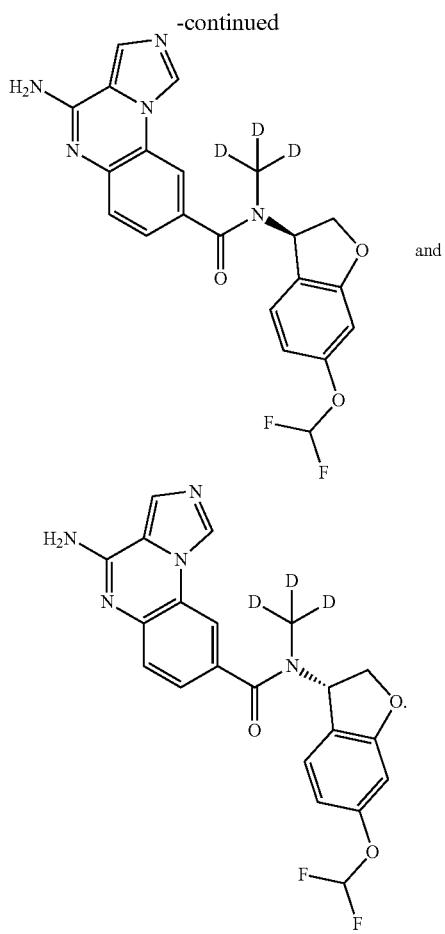

and

Compounds provided herein are described with reference to both generic formulae and specific compounds. In addition, the compounds of the present disclosure may exist in a number of different forms or derivatives, including but not limited to, stereoisomers, racemic mixtures, regioisomers, tautomers, salts, prodrugs, soft drugs, active metabolic derivatives (active metabolites), solvated forms, different crystal forms or polymorphs, all within the scope of the present disclosure.

The compounds of present disclosure can comprise one or more asymmetric centers, and thus can exist in various stereoisomeric forms, e.g., enantiomers and/or diastereomers. Thus, the compounds of present disclosure and compositions thereof may be in the form of an individual enantiomer, diastereomer or geometric isomer, or may be in the form of a mixture of stereoisomers. In certain embodiments, the compounds of the present disclosure are enantiopure compounds. In certain embodiments, mixtures of enantiomers or diastereomers are provided.

The term "enantiomer" refers to two stereoisomers of a compound which are non-superimposable mirror images of one another. The term "diastereomer" refers to a pair of optical isomers which are not mirror images of one another. Diastereomers have different physical properties, e.g. melting points, boiling points, spectral properties, and reactivities.

Furthermore, certain compounds, as described herein may have one or more double bonds that can exist as either the Z or E isomer, unless otherwise indicated. The present disclosure additionally encompasses the compounds as individual isomers substantially free of other isomers and alternatively, as mixtures of various isomers, e.g., racemic mixtures of enantiomers. In addition to the above-mentioned compounds per se, this disclosure also encompasses compositions comprising one or more compounds.

As used herein, the term "isomers" includes any and all geometric isomers and stereoisomers. For example, "isomers" include cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, a stereoisomer may, in some embodiments, be provided substantially free of one or more corresponding stereoisomers, and may also be referred to as "stereochemically enriched".

Where a particular enantiomer is preferred, it may, in some embodiments be provided substantially free of the opposite enantiomer, and may also be referred to as "optically enriched". "Optically enriched", as used herein, means that the compound is made up of a significantly greater proportion of one enantiomer. In certain embodiments, the compound is made up of at least about 90% by weight of a preferred enantiomer. In other embodiments, the compound is made up of at least about 95%, 98%, or 99% by weight of a preferred enantiomer. Preferred enantiomers may be isolated from racemic mixtures by any method known to those skilled in the art, including chiral high performance liquid chromatography (HPLC) and the formation and crystallization of chiral salts or prepared by asymmetric syntheses. See, for example, Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, NY, 1962); Wilen, S. H. Tables of Resolving Agents and Optical Resolutions p. 268 (E. L. Eliel, Ed., Univ. of Notre Dame Press, Notre Dame, IN 1972).

The compounds of the present disclosure may also exist in different tautomeric forms, and all such forms are embraced within the scope of the present disclosure. The term "tautomer" or "tautomeric form" refers to structural isomers of different energies which are interconvertible via a low energy barrier. The presence and concentrations of the isomeric forms will depend on the environment the compound is found in and may be different depending upon, for example, whether the compound is a solid or is in an organic or aqueous solution. By way of examples, proton tautomers (also known as prototropic tautomers) include interconversions via migration of a proton, such as keto-enol, amide-imidic acid, lactam-lactim, imine-enamine isomerizations and annular forms where a proton can occupy two or more positions of a heterocyclic system. Valence tautomers include interconversions by reorganization of some of the bonding electrons. Tautomers can be in equilibrium or sterically locked into one form by appropriate substitution. Compounds of the present disclosure identified by name or structure as one particular tautomeric form are intended to include other tautomeric forms unless otherwise specified.

As used herein, the term "prodrug" refers to compounds or pharmaceutically acceptable salts thereof which, when metabolized under physiological conditions or when converted by solvolysis, yield the desired active compound. Prodrugs include, without limitation, esters, amides, carbamates, carbonates, ureides, solvates, or hydrates of the active compound. Typically, the prodrug is inactive, or less active than the active compound, but may provide one or more advantageous handling, administration, and/or metabolic properties. For example, some prodrugs are esters of the active compound; during metabolism, the ester group is cleaved to yield the active drug. Also, some prodrugs are activated enzymatically to yield the active compound, or a compound which, upon further chemical reaction, yields the active compound. Prodrugs may proceed from prodrug form to active form in a single step or may have one or more intermediate forms which may themselves have activity or may be inactive. Preparation and use of prodrugs are discussed in T. Higuchi and V. Stella, "Pro-drugs as Novel Delivery Systems", Vol. 14 of the A.C.S. Symposium Series, in Bioreversible Carriers in Drug Design, ed. Edward B. Roche, American Pharmaceutical Association and Pergamon Press, 1987; in Prodrugs: Challenges and Rewards, ed. V. Stella, R. Borchardt, M. Hageman, R. Oliyai, H. Maag, J. Tilley, Springer-Verlag New York, 2007, all of which are hereby incorporated by reference in their entireties.

As used herein, the term "soft drug" refers to compounds that exert a pharmacological effect but break down to inactive metabolites degradants so that the activity is of limited time. See, for example, "Soft drugs: Principles and methods for the design of safe drugs", Nicholas Bodor, Medicinal Research Reviews, Vol. 4, No. 4, 449-469, 1984, which is hereby incorporated by reference in its entirety.

As used herein, the term "metabolite", e.g., active metabolite overlaps with prodrug as described above. Thus, such metabolites are pharmacologically active compounds or compounds that further metabolize to pharmacologically active compounds that are derivatives resulting from metabolic process in the body of a subject. For example, such metabolites may result from oxidation, reduction, hydrolysis, amidation, deamidation, esterification, deesterification, enzymatic cleavage, and the like, of the administered compound or salt or prodrug. Of these, active metabolites are such pharmacologically active derivative compounds. For prodrugs, the prodrug compound is generally inactive or of lower activity than the metabolic product. For active metabolites, the parent compound may be either an active compound or may be an inactive prodrug.

Prodrugs and active metabolites may be identified using routine techniques known in the art. See, e.g., Bertolini et al., 1997, J Med Chem 40:2011-2016; Shan et al., J Pharm Sci 86:756-757; Bagshawe, 1995, *Drug Dev Res* 34:220-230.

As used herein, the term "active intermediate" refers to an intermediate compound in the synthetic process, which exhibits the same or essentially the same biological activity as the final synthesized compound.

Compounds of the present disclosure can be formulated as or be in the form of pharmaceutically acceptable salts. Unless specified to the contrary, a compound provided herein includes pharmaceutically acceptable salts of such compound.

As used herein, the term "pharmaceutically acceptable" indicates that the substance or composition is compatible chemically and/or toxicologically, with the other ingredients comprising a formulation, and/or the subjects being treated therewith.

As used herein, the term "pharmaceutically acceptable salt", unless otherwise indicated, includes salts that retain the biological effectiveness of the free acids and bases of the specified compound and that are not biologically or otherwise undesirable. Contemplated pharmaceutically acceptable salt forms include, but are not limited to, mono, bis, tris, tetrakis, and so on. Pharmaceutically acceptable salts are non-toxic in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug.

Pharmaceutically acceptable salts include acid addition salts such as those containing sulfate, chloride, hydrochloride, fumarate, maleate, phosphate, sulfamate, acetate, citrate, lactate, tartrate, methanesulfonate, ethanesulfonate, benzenesulfonate, p-toluenesulfonate, cyclohexylsulfamate and quinate. Pharmaceutically acceptable salts can be obtained from acids such as hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, fumaric acid, and quinic acid.

Pharmaceutically acceptable salts also include basic addition salts such as those containing benzathine, chloroprocaine, choline, diethanolamine, ethanolamine, t-butylamine, ethylenediamine, meglumine, procaine, aluminum, calcium, lithium, magnesium, potassium, sodium, ammonium, alkylamine, and zinc, when acidic functional groups, such as carboxylic acid or phenol are present. For example, see Remington's Pharmaceutical Sciences, 19$^{th}$ ed., Mack Publishing Co., Easton, PA, Vol. 2, p. 1457, 1995; "Handbook of Pharmaceutical Salts: Properties, Selection, and Use" by Stahl and Wermuth, Wiley-VCH, Weinheim, Germany, 2002. Such salts can be prepared using the appropriate corresponding bases.

Pharmaceutically acceptable salts can be prepared by standard techniques. For example, the free-base form of a compound can be dissolved in a suitable solvent, such as an aqueous or aqueous-alcohol solution containing the appropriate acid and then isolated by evaporating the solution. Thus, if the particular compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

Similarly, if the particular compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as L-glycine, L-lysine, and L-arginine, ammonia, primary, secondary, and tertiary amines, and cyclic amines, such as hydroxyethylpyrrolidine, piperidine, morpholine or piperazine, and inorganic salts derived from sodium, calcium, potassium, magnesium, manganese, iron, copper, zinc, aluminum and lithium.

It is also to be understood that the compounds of present disclosure can exist in unsolvated forms, solvated forms (e.g., hydrated forms), and solid forms (e.g., crystal or polymorphic forms), and the present disclosure is intended to encompass all such forms.

As used herein, the term "solvate" or "solvated form" refers to solvent addition forms that contain either stoichiometric or non-stoichiometric amounts of solvent. Some compounds have a tendency to trap a fixed molar ratio of solvent molecules in the crystalline solid state, thus forming a solvate. If the solvent is water, then the solvate formed is a hydrate; and if the solvent is alcohol, then the solvate formed is an alcoholate. Hydrates are formed by the combination of one or more molecules of water with one molecule of the substance in which the water retains its molecular state as $H_2O$. Examples of solvents that form solvates include, but are not limited to, water, isopropanol, ethanol, methanol, DMSO, ethyl acetate, acetic acid, and ethanolamine.

As used herein, the terms "crystal form", "crystalline form", "polymorphic forms" and "polymorphs" can be used interchangeably, and mean crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The compounds of the present disclosure also include all isotopic forms thereof. "Isotopic form" of a compound indicates that atom(s) in the compound is substituted by isotope(s) of such atom(s). Isotopes of an atom include atoms having the same atomic number but different mass numbers. Examples of an isotope which can be incorporated into the compounds of the present disclosure include isotopes of hydrogen, carbon, nitrogen, oxygen, phosphorous, sulfur, fluorine, chlorine, bromide or iodine, such as but not limited to $^{1}H$, $^{2}H$, $^{3}H$, $^{11}C$, $^{12}C$, $^{13}C$, $^{14}C$, $^{14}N$, $^{15}N$, $^{16}O$, $^{17}O$, $^{18}O$, $^{31}P$, $^{32}P$, $^{32}S$, $^{33}S$, $^{34}S$, $^{36}S$, $^{17}F$, $^{18}F$, $^{19}F$, $^{35}Cl$, $^{37}Cl$, $^{79}Br$, $^{81}Br$, $^{124}I$, $^{127}I$ and $^{131}I$. In some embodiments, hydrogen in the compounds provided herein includes protium, deuterium and tritium. In some embodiments, carbon in the compounds provided herein includes $^{12}C$ and $^{13}C$.

Synthesis of Compounds

Synthesis of the compounds provided herein, including pharmaceutically acceptable salts thereof, are illustrated in the synthetic schemes in the examples. The compounds provided herein can be prepared using any known organic synthesis techniques and can be synthesized according to any of numerous possible synthetic routes, and thus these schemes are illustrative only and are not meant to limit other possible methods that can be used to prepare the compounds provided herein. Additionally, the steps in the Schemes are for better illustration and can be changed as appropriate. The embodiments of the compounds in examples were synthesized for the purposes of research and potentially submission to regulatory agencies.

The reactions for preparing compounds of the present disclosure can be carried out in suitable solvents, which can be readily selected by one skilled in the art of organic synthesis. Suitable solvents can be substantially non-reactive with the starting materials (reactants), the intermediates, or products at the temperatures at which the reactions are carried out, e.g. temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected by one skilled in the art.

Preparation of compounds of the present disclosure can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, Protective Groups in Organic Synthesis, 3rd Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g. $^{1}H$ or $^{13}C$), infrared spectroscopy, spectrophotometry (e.g. UV-visible), mass spectrometry, or by chromatographic methods such as high performance liquid chromatography (HPLC), liquid chromatography-mass spectroscopy (LCMS), or thin layer chromatography (TLC). Compounds can be purified by one skilled in the art by a variety of methods, including high performance liquid chromatography (HPLC) ("Preparative LC-MS Purification: Improved Compound Specific Method Optimization" Karl F. Blom, Brian Glass, Richard Sparks, Andrew P. Combs J. Combi. Chem. 2004, 6(6), 874-883, which is incorporated herein by reference in its entirety), and normal phase silica chromatography.

The structures of the compounds in the examples are characterized by nuclear magnetic resonance (NMR) or/and liquid chromatography-mass spectrometry (LC-MS). NMR chemical shift (δ) is given in the unit of $10^{-6}$ (ppm). $^{1}H$-NMR spectra is recorded in $CDCl_3$, $CD_3OD$ or DMSO-$d_6$ solutions (reported in ppm) on a Bruker instrument (400 MHz or 500 MHz), using tetramethylsilane (TMS) as the reference standard (0.0 ppm).

Unless otherwise specified, the reactions of the present disclosure were typically done under a positive pressure of nitrogen or argon or with a drying tube in anhydrous solvents, and the reaction flasks were typically fitted with rubber septa for the introduction of substrates and reagents via syringe. Glassware was oven dried and/or heat dried.

Uses of Compounds

In one aspect, the present disclosure provides compounds of Formula (I) or pharmaceutically acceptable salts thereof, which show PRMT5 inhibitory activity.

As used herein, the term "PRMT5" refers to Protein Arginine N-Methyl Transferase 5 (PRMT5) enzyme.

As used herein, the term "PRMT5 inhibitor" refers to any compound capable of inhibiting the production, level, activity, expression or presence of PRMT5. The term "MTA-cooperative PRMT5 inhibitor" refers to any compound capable of inhibiting the production, level, activity, expression or presence of PRMT5 in the presence of bound MTA, in vitro or in vivo, in the cells with elevated levels of MTA.

In some embodiments, the compounds of Formula (I) or pharmaceutically acceptable salts thereof are PRMT5 inhibitors. In some embodiments, the compounds of Formula (I) or pharmaceutically acceptable salts thereof show PRMT5 inhibitory activity with an $IC_{50}$ when tested in an assay according to the assays described herein of less than 5000 nM, less than 4000 nM, less than 3000 nM, less than 2000 nM, less than 1000 nM, less than 900 nM, less than 800 nM, less than 700 nM, less than 600 nM, less than 500 nM, less than 400 nM, less than 300 nM, less than 200 nM, less than 150 nM, less than 120 nM, less than 100 nM, less than 90 nM, less than 80 nM, less than 70 nM, less than 60 nM, less than 50 nM, less than 40 nM, less than 30 nM, or less than 20 nM.

In some embodiments, the compounds of Formula (I) or pharmaceutically acceptable salts thereof show selective MTA-cooperative PRMT5 inhibitory activity, for example in at least one assay described herein (e.g., biochemical or cellular), with an $IC_{50}$ for inhibiting PRMT5 in the absence of bound MTA at least 1000 fold higher, at least 500 fold higher, at least 400 fold higher, at least 300 fold higher, at least 200 fold higher, at least 100 fold higher, at least 90 fold higher, at least 80 fold higher, at least 70 fold higher, at least 60 fold higher, at least 50 fold higher, at least 40 fold higher, at least 30 fold higher, at least 20 fold higher, at least 10 fold higher, at least 5 fold higher, at least 2 fold higher, or at least 1.5 fold higher, than the $IC_{50}$ for inhibiting PRMT5 in the presence of bound MTA.

As a result of their PRMT5 inhibitory activity and/or MTA-cooperative PRMT5 inhibitory activity, the compounds of Formula (I) or a pharmaceutically acceptable salt thereof are useful in a method of inhibiting PRMT5 in a cell, comprising contacting a cell with an effective amount of the compound or composition described herein to inhibit PRMT5 in the cell. In certain embodiments, the cell is a cancer cell. In certain embodiments, the cancer is MTAP-associated cancer. In certain embodiments, the method comprises administering an effective amount of the compound or composition described herein to a subject in need thereof.

In some embodiments, the compounds of Formula (I) or a pharmaceutically acceptable salt thereof are useful in therapy, for example in the treatment of PRMT5-associated diseases or disorders including cancers.

As used herein, the term "therapy" is intended to have its normal meaning of dealing with a disease in order to entirely or partially relieve one, some or all of its symptoms, or to correct or compensate for the underlying pathology. The term "therapy" also includes "prophylaxis" unless there are specific indications to the contrary. The terms "therapeutic" and "therapeutically" should be interpreted in a corresponding manner.

As used herein, the term "prophylaxis" is intended to have its normal meaning and includes primary prophylaxis to prevent the development of the disease and secondary prophylaxis whereby the disease has already developed and the patient is temporarily or permanently protected against exacerbation or worsening of the disease or the development of new symptoms associated with the disease.

The term "treatment", "treat" or "treating" is used synonymously with "therapy". Similarly the term "treat" can be regarded as "applying therapy" where "therapy" is as defined herein.

Therefore, in one aspect, there is provided a compound of Formula (I) or a pharmaceutically acceptable salt thereof, for use in therapy.

In some embodiments, there is provided a compound of Formula (I) or a pharmaceutically acceptable salt thereof, for use in the treatment of PRMT5-associated diseases or disorders.

As used herein, the term "PRMT5-associated diseases or disorders" refers to any disease or disorder or other pathological condition in which PRMT5 is known to play a role.

In some embodiments, the PRMT5-associated diseases or disorders is associated with MTAP deficiency and MTA accumulation. In some embodiments, the disease or disorder is a cancer. As used herein, the term "cancer" is intended to encompass both non-metastatic cancer and metastatic cancer. In this context, treating cancer involves treatment of both primary tumors and tumor metastases.

In some embodiments, the cancers include, but are not limited to, Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Biliary tract: gall bladder carcinoma, ampullary carcinoma, cholangiocarcinoma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial wcarcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma.

In some embodiments, the cancer is a MTAP-associated cancer. In some embodiments, the MTAP-associated cancer is liver cancer, breast cancer, skin cancer, bladder cancer, pancreatic cancer, or head and neck cancer.

In some embodiments, the liver cancer can be hepatocellular cancer (HCC) or malignant hepatoma.

In some embodiments, the breast cancer can be a lobular carcinoma in situ (LCIS), a ductal carcinoma in situ (DCIS), an invasive ductal carcinoma (IDC), inflammatory breast cancer, Paget disease of the nipple, Phyllodes tumor, Angiosarcoma, adenoid cystic carcinoma, low-grade adenosquamous carcinoma, medullary carcinoma, mucinous carcinoma, papillary carcinoma, tubular carcinoma, metaplastic carcinoma, micropapary carcinoma, mixed carcinoma, or another breast cancer, including but not limited to triple negative, HER positive, estrogen receptor positive, progesterone receptor positive, HER and estrogen receptor positive, HER and progesterone receptor positive, estrogen and progesterone receptor positive, and HER and estrogen and progesterone receptor positive.

In some embodiments, the skin cancer can be squamous cell carcinoma (SCO), keratoacanthoma (KA), melanoma, basal cell carcinoma (BCC)).

In some embodiments, the pancreatic cancer can be pancreatic adenocarcinoma.

In some embodiments, there is provided a compound of Formula (I) or a pharmaceutically acceptable salt thereof, for use as a medicament.

In some embodiments, there is provided a compound of Formula (I) or a pharmaceutically acceptable salt thereof, for use in the manufacture of a medicament for the treatment of diseases or disorders. In some embodiments, the diseases or disorders is a cancer.

In some embodiments, the compounds disclosed herein show desirable metabolic stability, including hepatic metabolic stability (HMS) and liver microsome metabolic stability (LMS). In some embodiments, the compounds disclosed herein show desirable hepatic metabolic stability with a half-life time no less than 50 min, 75 min, 80 min or 100 min in mammalian (e.g., human, mouse, rat, dog, monkey) hepatocyte. In some embodiments, the compounds disclosed herein show desirable liver microsome metabolic stability with a half-life time no less than 50 min, 75 min, 80 min or 100 min in mammalian (e.g., human, mouse, rat, dog, monkey) liver microsome.

In some embodiments, the compounds disclosed herein show desirable gastrointestinal absorption or intestinal absorption. In some embodiments, the compounds disclosed herein show $P_{app}$ (e.g., $P_{app(A-B)}$ or $P_{app(B-A)}$) between $5 \times 10^{-8}$ cm/s and $5 \times 10^{-5}$ cm/s, between $1 \times 10^{-6}$ cm/s and $5 \times 10^{-5}$ cm/s or between $5 \times 10^{-6}$ cm/s and $2 \times 10^{-5}$ cm/s, measured by Caco-2 model as exemplified in Examples. In some embodiments, the compounds disclosed herein display efflux ratio about 1.5, about 1.6, about 1.7, about 1.8, about 1.9 or about 2.0, measured by Caco-2 model as exemplified in Examples.

In some embodiments, the compounds disclosed herein show desirable hERG potassium ion channel inhibitory activity. In some embodiments, the compounds disclosed herein display low hERG potassium ion channel inhibitory activity with $IC_{50}$ no less than 10 M, 11 M, 12 M, 13 M, 15 M or 20 M.

In some embodiments, the compounds disclosed herein are capable of in vivo brain penetration. In some embodiments, the compounds of the present disclosure show a brain to plasma concentration (B/P) ratio of greater than about 0.1, greater than about 0.15, greater than about 0.2, greater than about 0.25, greater than about 0.3, greater than about 0.35, greater than about 0.4, greater than about 0.45, greater than about 0.5, as exemplified in Examples.

In some embodiments, the compounds disclosed herein show desirable pharmacokinetics properties, including drug exposure, clearance, plasma protein binding, etc. In some embodiments, the compounds disclosed herein display high drug exposure, low clearance and/or preferable fraction of unbound.

Pharmaceutical Compositions

The present disclosure provides pharmaceutical compositions comprising one or more compound of the present disclosure, or a pharmaceutically acceptable salt thereof. In some embodiments, the pharmaceutical composition comprises one or more compounds of the present disclosure, or a pharmaceutically acceptable salt thereof, and at least one pharmaceutical acceptable excipient.

A "pharmaceutical composition", as used herein, is a formulation containing the compounds of the present disclosure in a form suitable for administration to a subject. In some embodiments, the pharmaceutical composition is in bulk or in unit dosage form. The unit dosage form is any of a variety of forms, including, for example, tablets, capsules, pills, powders, granules, sachets, cachets, lozenges, suspensions, emulsions, solutions, syrups, aerosols (as a solid or in a liquid medium), spray, ointment, paste, cream, lotion, gel, patch, inhalant, or suppository. The quantity of active ingredient (e.g., a formulation of the disclosed compound or salt, hydrate, solvate or isomer thereof) in a unit dose of composition is a therapeutically effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In some embodiments, the compound of the present disclosure is mixed under sterile conditions with a pharmaceutically acceptable excipient, and with any preservatives, buffers or propellants that are required.

As used herein, the term "pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

As used herein, the term "therapeutically effective amount" refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

In some embodiments, the pharmaceutical compositions can be formulated so that a dosage of between 0.01-1000 mg/kg body weight/day, for example, 0.01-900 mg/kg body weight/day, 0.01-800 mg/kg body weight/day, 0.05-700 mg/kg body weight/day, 0.05-600 mg/kg body weight/day, 0.05-500 mg/kg body weight/day, 0.1-500 mg/kg body weight/day, 0.1-400 mg/kg body weight/day, 0.1-300 mg/kg body weight/day, 0.1-200 mg/kg body weight/day, 0.1-100 mg/kg body weight/day, 0.1-80 mg/kg body weight/day, 1-100 mg/kg body weight/day or 1-80 mg/kg body weight/day of the compounds of the present disclosure, or a pharmaceutically acceptable salt thereof, can be administered. In certain embodiments, the dose of the compounds can be administered once per day or divided into subdoses and administered in multiple doses, e.g., twice, three times, or four times per day.

In some embodiments, the pharmaceutical compositions comprise one or more compounds of the present disclosure, or a pharmaceutically acceptable salt thereof, as a first active ingredient, and further comprise a second active ingredient. The second active ingredient can be any anti-tumor agent known in the art, for example, other anti-cancer agents, anti-tumor agents, anti-allergic agents, anti-nausea agents, pain relievers, cytoprotective agents, and combinations thereof.

Therefore, in some embodiments, there is provided pharmaceutical composition comprising a compound of Formula (I) or a pharmaceutically acceptable salt thereof, or a pharmaceutically acceptable salt thereof, and at least one additional anti-tumor agent. In some embodiments, there is one additional anti-tumor agent. In some embodiments, there are two additional anti-tumor agents. In some embodiments, there are three or more additional anti-tumor agents.

In some embodiments, the amount of additional anti-tumor agent present in the composition of the present disclosure can be no more than the amount that would normally be administered in a composition comprising that anti-tumor agent as the only active agent. In certain embodiments, the amount of the additional anti-tumor agent in the composition of the present disclosure will range from about 50% to 100% of the amount normally present in a composition comprising that anti-tumor agent as the only therapeutically active agent.

Therefore, in another aspect, there is provided a compound of Formula (I) or a pharmaceutically acceptable salt thereof in combination with one or more anti-tumor agents listed above.

In some embodiments, the additional anti-tumor agent is selected from the group consisting of doxorubicin, irinotecan, topotecan, etoposide, mitomycin, bendamustine, chlorambucil, cyclophosphamide, ifosfamide, carmustine, melphalan and bleomycin.

As used herein, the term "combination" refers to simultaneous, separate or sequential administration. In some embodiments, "combination" refers to simultaneous administration. In some embodiments, "combination" refers to separate administration. In some embodiments, "combination" refers to sequential administration. Where the administration is sequential or separate, the delay in administering the second component should not be such as to lose the beneficial effect of the combination.

In a further aspect, there is provided a pharmaceutical composition comprising a compound of Formula (I) or a pharmaceutically acceptable salt thereof in combination with one or more anti-tumor agents listed above, in association with a pharmaceutically acceptable excipient.

In a further aspect, there is provided a kit comprising a compound of Formula (I) or a pharmaceutically acceptable salt thereof in combination with one or more anti-tumor agents listed above.

In a further aspect, there is provided a kit comprising:
  (a) a compound of Formula (I) or a pharmaceutically acceptable salt thereof in a first unit dosage form;
  (b) a second therapeutic agent such as an anti-tumor agent in a second unit dosage form; and
  (c) container for containing the first and second unit dosage forms.

Methods for Treatment

In a further aspect, there is provided a method of treating diseases or disorders in a subject in need thereof, which comprises administering to the subject a therapeutically effective amount of a compound of Formula (I) or a pharmaceutically acceptable salt thereof, or a pharmaceutical composition of the present disclosure, owning to the PRMT5 inhibitory activity and/or MTA-cooperative PRMT5 inhibitory activity of the compounds of the present disclosure.

In some embodiments, the disease or disorder is cancer. In some embodiments, the cancer includes, for example, Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Biliary tract: gall bladder carcinoma, ampullary carcinoma, cholangiocarcinoma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial wcarcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma.

In some embodiments, the cancer includes, for example, diffuse large B-cell lymphoma, chronic lymphocytic leukaemia, acute myeloid leukaemia, mantle cell lymphomas, gastro-intestinal cancer, gastric cancer, vascular cancer, biliary carcinomas, pancreatic cancer, colorectal cancer, esophageal cancer, hepatocellular cancer, melanoma, myeloma, oral cancer, ovarian cancer, small cell lung cancer, non-small cell lung cancer, myeloma, prostate cancer, bladder cancer, brain cancer, breast cancer, bone marrow cancer, cervical cancer, spleen cancer, glioblastoma, head and neck squamous cell carcinoma.

In some embodiments, the cancer is head and neck squamous cell carcinoma, including but not limited to, lip carcinoma, oral cavity carcinoma, oropharynx carcinoma, hypopharynx carcinoma, glottic larynx carcinoma, supraglottic larynx carcinoma, ethmoid sinus carcinoma, maxillary sinus carcinoma, and occult primary carcinoma.

In some embodiments, the cancer is leukemia, including but not limited to, lymphatic leukemia, lymphocytic leukemia, chronic lymphocytic leukemia, small lymphocytic lymphoma, diffuse large B-cell lymphoma, acute myeloid leukemia, lymphoblastic leukemia, follicular lymphoma, lymphoid malignancies of T-cell or B-cell origin, myelogenous leukemia, granulocytic leukemia, polycythemia vera, erythremia.

In some embodiments, the cancer is hepatocellular carcinoma, breast cancer, skin cancer, bladder cancer, liver cancer, pancreatic cancer, or head and neck cancer. In some embodiments, the cancer is a MTAP-associated cancer.

In some embodiments, the cancer is metastatic cancer. In some embodiments, the metastatic cancer comprises metastases of the central nervous system. In some embodiments, the metastases of the central nervous system comprise brain metastases. In some embodiments, the metastases of the central nervous system comprise leptomeningeal metastases. "Leptomeningeal metastases" occur when cancer spreads to the meninges, the layers of tissue that cover the brain and the spinal cord. Metastases can spread to the meninges through the blood or they can travel from brain metastases, carried by the cerebrospinal fluid (CSF) that flows through the meninges.

As used herein, the term "subject in need thereof" is a subject having a disease or disorder (e.g., cancer), or a subject having an increased risk of developing disease or disorder (e.g., cancer) relative to the population at large. In the case of cancer, a subject in need thereof can have a precancerous condition. A "subject" includes a warm-blooded animal. In some embodiments, the warm-blooded animal is a mammal, e.g. human.

In this context, the term "therapeutically effective amount" refers to an amount of a compound of Formula (I) or a pharmaceutically acceptable salt thereof which is effective to provide "therapy" in a subject, or to "treat" a disease or disorder in a subject. In the case of cancer, the therapeutically effective amount may cause any of the changes observable or measurable in a subject as described in the definition of "therapy", "treatment" and "prophylaxis" above. For example, the effective amount can reduce the number of cancer or tumor cells; reduce the overall tumor size; inhibit or stop tumor cell infiltration into peripheral organs including, for example, the soft tissue and bone; inhibit and stop tumor metastasis; inhibit and stop tumor growth; relieve to some extent one or more of the symptoms associated with the cancer; reduce morbidity and mortality; improve quality of life; or a combination of such effects. For cancer therapy, efficacy in-vivo can, for example, be measured by assessing the duration of survival, time to disease progression (TTP), the response rates (RR), duration of response, and/or quality of life. As recognized by those skilled in the art, effective amounts may vary depending on route of administration, excipient usage, and co-usage with other agents. For example, where a combination therapy is used, the amount of the compound of Formula (I) or a pharmaceutically acceptable salt thereof described in this specification and the amount of the other pharmaceutically active agent(s) are, when combined, jointly effective to treat a targeted disorder in the animal patient. In this context, the combined amounts are in a "therapeutically effective amount" if they are, when combined, sufficient to decrease the symptoms of a disease or disorder as described above.

In generally, "therapeutically effective amount" may be determined by one skilled in the art by, for example, starting with the dosage range described in this specification for the compound of Formula (I) or a pharmaceutically acceptable salt thereof and an approved or otherwise published dosage range(s) of the other pharmaceutically active compound(s).

The method of treating diseases or disorders described in this specification may be used as a monotherapy. As used herein, the term "monotherapy" refers to the administration of a single active or therapeutic compound to a subject in need thereof. In some embodiments, monotherapy will involve administration of a therapeutically effective amount of one of the compounds of the present disclosure, or a pharmaceutically acceptable salt thereof, to a subject in need of such treatment.

Depending upon the particular diseases or conditions to be treated, the method of treating diseases or disorders described in this specification may involve, in addition to administration of the compound of the present disclosure, one or more additional therapies, for example, conventional surgery, radiotherapy, chemotherapy, immunotherapy, or a combination of such additional therapies. As used herein, the term "combination therapy" refers to the administration of a combination of multiple active compounds.

The additional therapies, such as additional anti-tumor agents, may be administered separately from the compounds of the present disclosure, as part of a multiple dosage regimen. Alternatively, these additional therapies may be part of a single dosage form, mixed with the compounds of the present disclosure in a single composition.

In some embodiments, the compounds of the present disclosure may be administered simultaneously, sequentially or separately to treatment with the conventional surgery, radiotherapy, chemotherapy or immunotherapy.

Radiotherapy may include one or more of the following categories of therapy: (i) external radiation therapy using electromagnetic radiation, and intraoperative radiation therapy using electromagnetic radiation; (ii) internal radiation therapy or brachytherapy; including interstitial radiation therapy or intraluminal radiation therapy; or (iii) systemic radiation therapy, including but not limited to iodine 131 and strontium 89.

Chemotherapy may include those known in the art, for example, antineoplastic agents, antiangiogenic agents, immunotherapies, efficacy enhancers, and the like.

Examples of the antineoplastic agents include, but are not limited to, DNA alkylating agents (for example cisplatin, oxaliplatin, carboplatin, cyclophosphamide, nitrogen mustards like ifosfamide, bendamustine, melphalan, chlorambucil, busulphan, temozolamide and nitrosoureas like carmustine); antimetabolites (for example gemcitabine and antifolates such as fluoropyrimidines like 5-fluorouracil and tegafur, raltitrexed, methotrexate, cytosine arabinoside, and hydroxyurea); anti-tumor antibiotics (for example anthracyclines like adriamycin, bleomycin, doxorubicin, liposomal doxorubicin, pirarubicin, daunomycin, valrubicin, epirubicin, idarubicin, mitomycin, dactinomycin, amrubicin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, irinotecan, topotecan and camptothecin); inhibitors of DNA repair mechanisms such as CHK kinase; DNA-dependent protein kinase inhibitors; inhibitors of poly (ADP-ribose) polymerase (PARP inhibitors, including Olaparib, Rucaparib, Niraparib, Talazoparib, Pamiparib and Fluzoparib); and Hsp90 inhibitors such as tanespimycin and retaspimycin, inhibitors of ATR kinase (such as AZD6738); and inhibitors of WEE 1 kinase (such as AZD1775/MK-1775).

Examples of antiangiogenic agents include those that inhibit the effects of vascular endothelial growth factor, such as but not limited to, the anti-vascular endothelial cell growth factor antibody bevacizumab, a VEGF receptor tyrosine kinase inhibitor such as vandetanib (ZD6474), sorafenib, vatalanib (PTK787), sunitinib (SU11248), axitinib (AG-013736), pazopanib (GW 786034) and cediranib (AZD2171); compounds such as those disclosed in International Patent Applications WO 97/22596, WO 97/30035, WO 97/32856 and WO 98/13354; and compounds that work by other mechanisms (for example linomide, inhibitors of integrin αvβ3 function and angiostatin), or inhibitors of angiopoietins and their receptors (Tie-1 and Tie-2), inhibitors of PLGF, inhibitors of delta-like ligand (DLL-4).

Immunotherapy may include, for example, immune checkpoint modulator. Immune checkpoints are regulators of the immune system, and belong to immunoinhibitory pathway or immunostimulatory pathway, responsible for co-stimulatory or inhibitory interactions of T-cell responses, and regulate and maintain self-tolerance and physiological immune responses. Non-limiting immunoinhibitory checkpoint molecules found in the immunoinhibitory pathways can include LAG3 (CD223), A2AR, B7-H3 (CD276), B7-H4 (VTCN1), BTLA (CD272), BTLA, CD160, CTLA-4 (CD152), IDO1, IDO2, TDO, KIR, LAIR-1, NOX2, PD-1, PD-L1, PD-L2, TIM-3, VISTA, SIGLEC-7 (CD328), TIGIT, PVR (CD155), TGFβ, or SIGLEC9 (CD329), among others. Non-limiting immunostimulatory checkpoint molecules found in the immunostimulatory pathways can include CD2, CD3, CD7, CD16, CD27, CD30, CD70, CD83, CD28, CD80 (B7-1), CD86 (B7-2), CD40, CD40L (CD154), CD47, CD122, CD137, CD137L, OX40 (CD134), OX40L (CD252), NKG2C, 4-1BB, LIGHT, PVRIG, SLAMF7, HVEM, BAFFR, ICAM-1, 2B4, LFA-1, GITR, ICOS (CD278), or ICOSLG (CD275), among others.

Examples of efficacy enhancers include leucovorin.

Therefore, in one aspect, there is provided a method of treating diseases or disorders in a subject in need thereof, wherein the compound of Formula (I), Formula (Ia), Formula (Ia-1) or Formula (II), or a pharmaceutically acceptable salt thereof is administered simultaneously, separately or sequentially with a second therapy. In some embodiments, the method comprising administering a therapeutically effective amount of a second therapeutic agent prior to, concurrently with or subsequent to the administration of the compound of Formula (I) or a pharmaceutically acceptable salt thereof.

In some embodiments, the second therapy is chemotherapy or immunotherapy. In some embodiments, the second therapy is selected from the group consisting of a chemotherapeutic agent, an anti-tumor agent, a radiation therapy agent, an immunotherapy agent, an anti-angiogenesis agent, a targeted therapy agent, a cellular therapy agent, a gene therapy agent, a hormonal therapy agent, an antiviral agent, an antibiotic, an analgesics, an antioxidant, a metal chelator, and cytokines. In some embodiments, the second therapy is a BTK inhibitor, a BCR-ABL inhibitor, a JAK1 inhibitor, a JAK2 inhibitor, a JAK3 inhibitor, a PARP inhibitor, a MEK inhibitor, an ERK inhibitor or a RAF inhibitor.

In some embodiments, the second therapy is selected from the group consisting of a platinating agent, alkylating agent, antibiotic agent, antimetabolite, topoisomerase inhibiting agent (e.g., topoisomerase I inhibitor, topoisomerase II inhibitor), antimicrotubule agent, hormonal agent, antiangiogenic agent, differentiation inducing agents, cell growth arrest inducing agent, apoptosis inducing agent, cytotoxic agent, and immunotherapeutic agent.

In another aspect, there is provided a method of treating diseases or disorders in a subject in need thereof, wherein the compound of Formula (I) or a pharmaceutically acceptable salt thereof is administered simultaneously, separately or sequentially with one or more additional anti-tumor agents.

In some embodiments, the disease or disorder is cancer. In certain embodiments, the amounts of the compound of Formula (I) or a pharmaceutically acceptable salt thereof, and the one or more additional anti-tumor agents are jointly effective in producing an anti-cancer effect.

EXAMPLES

For the purpose of illustration, the following examples are included. However, it is to be understood that these examples do not limit the invention and are only meant to suggest a method of practicing the present disclosure. Persons skilled in the art will recognize that the chemical reactions described may be readily adapted to prepare a number of other compounds of the present disclosure, and alternative methods for preparing the compounds of the present disclosure are deemed to be within the scope of the present disclosure. For example, the synthesis of non-exemplified compounds according to the present disclosure may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the present disclosure.

Abbreviations

BPD: bis(pinacolato)diborane
DCM: dichloromethane
DEA: diethylamine
DIEA: diisopropylethylamine
DMA: dimethylacetamide
DMF: N,N-dimethylformamide
DMSO: dimethylsulfoxide DPPF: bis(diphenyphosphino)ferrocene
DPPP: 1,3-bis(diphenylphosphino)propane
FA: formic acid
HATU: hexafluorophosphate azabenzotriazole tetramethyl uronium
IPA: isopropyl alcohol
MTBE: methyl tert-butyl ether
NaHMDS: Sodium bis(trimethylsilyl)amide
NBS: N-bromosuccinimide
PE: petroleum ether
THE: tetrahydrofuran
TEA: triethylamine
TFA: trifluoroacetic acid Example 1: Synthesis of Compound 1

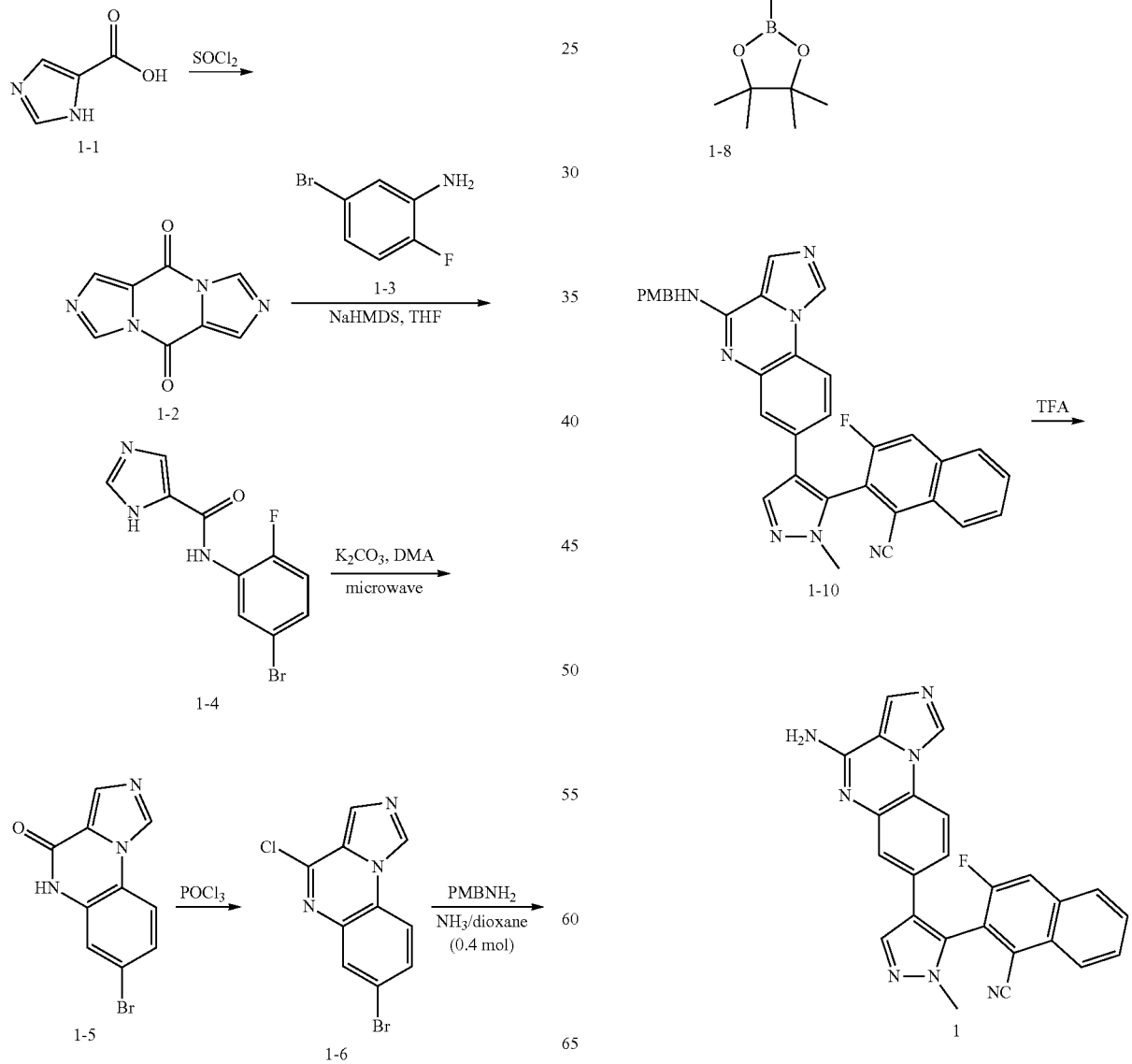

Step 1: Synthesis of Compound 1-2

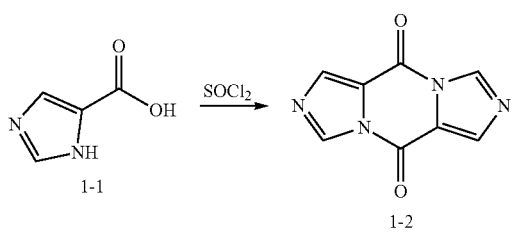

A mixture of compound 1-1 (5.00 g, 44.6 mmol) in SOCl₂ (50 mL) was stirred at 80° C. for 12 hrs. The reaction mixture was filtered, the solid was collected and dried under reduced pressure to give compound 1-2 (4.70 g, 25.0 mmol, 56% yield).

$^1$H NMR of compound 1-2: (400 MHz, DMSO-$d_6$) δ 8.87 (s, 2H), 8.24 (s, 2H).

Step 2: Synthesis of Compound 1-4

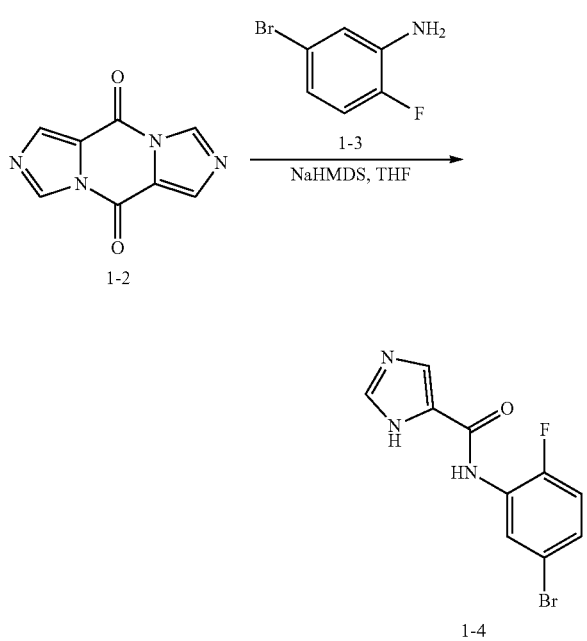

To a THF (10 mL) solution of compound 1-3 (2.00 g, 10.5 mmol, 2 eq) was added NaHMDS (1.00 M, 23.1 mL, 4.4 eq) at −10° C. The mixture was stirred at −10 to 0° C. for 1 hr. Then a THF (15 mL) solution of compound 1-2 (990 mg, 5.26 mmol) was added to the mixture and stirred at 25° C. for another 2 hrs. The pH of the reaction mixture was adjusted to 7 with AcOH. The resulting mixture was concentrated under reduced pressure to give a slurry. It was diluted with water (20 mL) and saturated NaHCO₃ (30 mL). The mixture was filtered. The solid was washed with PE (20 mL) and dried to give crude compound 1-4 (1.00 g, 3.52 mmol, 33% yield). LCMS (M+H)⁺: 283.8.

$^1$H NMR of compound 1-4: (400 MHz, DMSO-$d_6$) δ 12.73 (brs, 1H), 9.49 (s, 1H), 8.07 (t, J=8.8 Hz, 1H), 7.86-7.84 (m, 2H), 7.65-7.62 (m, 1H), 7.42 (d, J=8.8 Hz, 1H).

Step 3: Synthesis of Compound 1-5

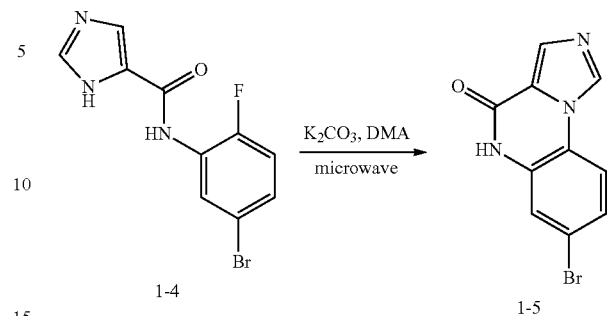

To a DMA (10 mL) solution of compound 1-4 (200 mg, 704 μmol) was added K₂CO₃ (195 mg, 1.41 mmol, 2.00 eq). The mixture was stirred at 140° C. for 10 hrs under microwave. The reaction mixture was diluted with water (10 mL), saturated NH₄Cl (10 mL) then filtered. The solid was washed with water (20 mL) and dried under reduced pressure to give compound 1-5 (50.0 mg, 189 μmol, 27% yield). LCMS (M+H)⁺: 263.9.

$^1$H NMR of compound 1-5: (400 MHz, DMSO-$d_6$) δ 11.48 (brs, 1H), 9.06 (s, 1H), 8.15 (s, 1H), 7.87 (s, 1H), 7.46 (d, 2H).

Step 4: Synthesis of Compound 1-6

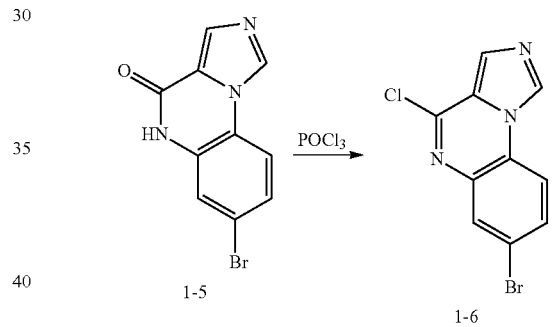

A mixture of compound 1-5 (320 mg, 1.21 mmol) in POCl₃ (5 mL) was stirred at 110° C. for 4 hrs. The reaction mixture was concentrated under reduced pressure to give a slurry. It was carefully diluted with iced water (10 mL) and the pH of the mixture was adjusted to 7-8 with saturated NaHCO₃. The resulting mixture was extracted with EtOAc (10 mL×3). The combined organic layer was washed with brine (15 mL×2), dried over Na₂SO₄, filtered and concentrated under reduced pressure to give crude compound 1-6 (300 mg). LCMS (M+H)⁺: 281.8.

Step 5: Synthesis of Compound 1-7

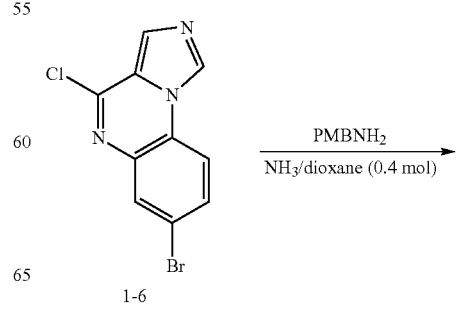

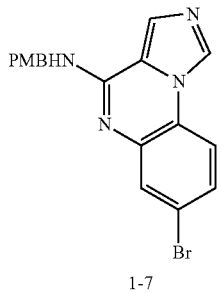

1-7

To a solution of compound 1-6 (200 mg) in 0.4 M NH$_3$/dioxane (6 mL) was added 4-methoxybenzylamine (PMBNH$_2$) (486 mg, 3.54 mmol, 458 μL). The mixture was stirred at 120° C. for 3 hrs. The reaction mixture was diluted with water (10 mL) and extracted with EtOAc (10 mL×3). The combined organic layers were washed with brine (15 mL×2), dried over Na$_2$SO$_4$, filtered and concentrated under reduced pressure to give the crude product. It was purified by column chromatography (SiO$_2$, PE/EtOAc=100/1 to 1/1) to give pure compound 1-7 (100 mg, 261 μmol, 37% yield). LCMS (M+H)$^+$: 383.0.

$^1$H NMR of compound 1-7: (400 MHz, CDCl$_3$) δ 8.56 (s, 1H), 7.89 (d, J=1.6 Hz, 1H), 7.65 (d, J=8.4 Hz, 2H), 7.41-7.36 (m, 3H), 6.93-6.91 (m, 2H), 4.84 (d, J=4.4 Hz, 2H), 3.82 (s, 3H).

Step 6: Synthesis of Compound 1-8

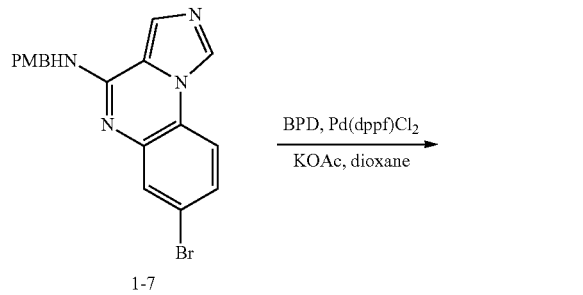

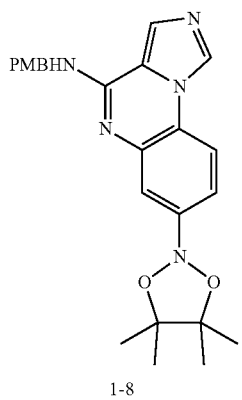

1-8

A mixture of compound 1-7 (80.0 mg, 209 μmol), BPD (79.5 mg, 313 μmol, 1.50 eq), Pd(dppf)Cl$_2$ (15.3 mg, 20.9 μmol, 0.100 eq) and KOAc (87.8 mg, 626 μmol, 3.00 eq) in dioxane (2 mL) was degassed and purged with N$_2$ for 3 times. The mixture was stirred at 90° C. for 12 hrs under N$_2$ atmosphere. The reaction mixture was filtered and concentrated under reduced pressure to give crude compound 1-8 (80.0 mg). LCMS (M+H)$^+$: 431.2.

Step 7: Synthesis of Compound 1-10

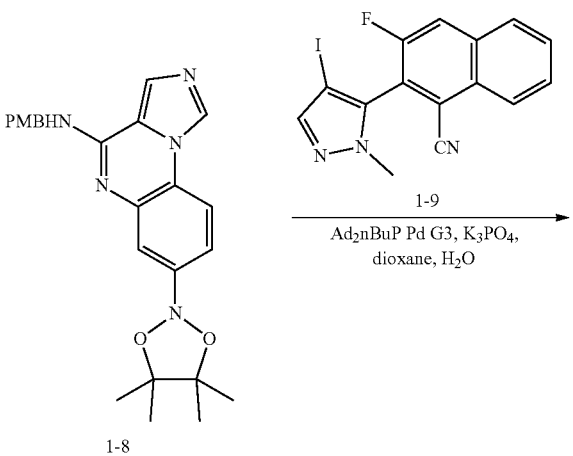

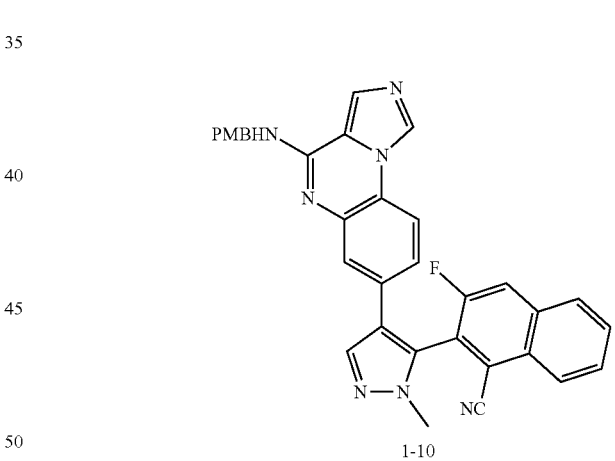

1-10

A mixture of compound 1-8 (80.0 mg), compound 1-9 (70.1 mg, 186 μmol, synthesized according to the known method: J. Med. Chem., 2022, 65, 1749-1766), cat-aCXium® A Pd G3 (CAS #1651823-59-4, 13.5 mg, 18.6 μmol) and K$_3$PO$_4$ (118 mg, 558 μmol) in dioxane (2 mL) and H$_2$O (0.4 mL) was degassed and purged with N$_2$ for 3 times, and then the mixture was stirred at 90° C. for 12 hrs under N$_2$ atmosphere. The reaction mixture was diluted with water (10 mL) and extracted with EtOAc (10 mL×3). The combined organic layer was washed with brine (15 mL×2), dried over Na$_2$SO$_4$, filtered and concentrated under reduced pressure to give crude product. It was purified by prep-TLC (SiO$_2$, PE:EA=1:1) to give pure compound 1-10 (50.0 mg, 90.3 μmol, 49% yield). LCMS (M+H)$^+$: 554.3.

Step 8: Synthesis of Compound 1

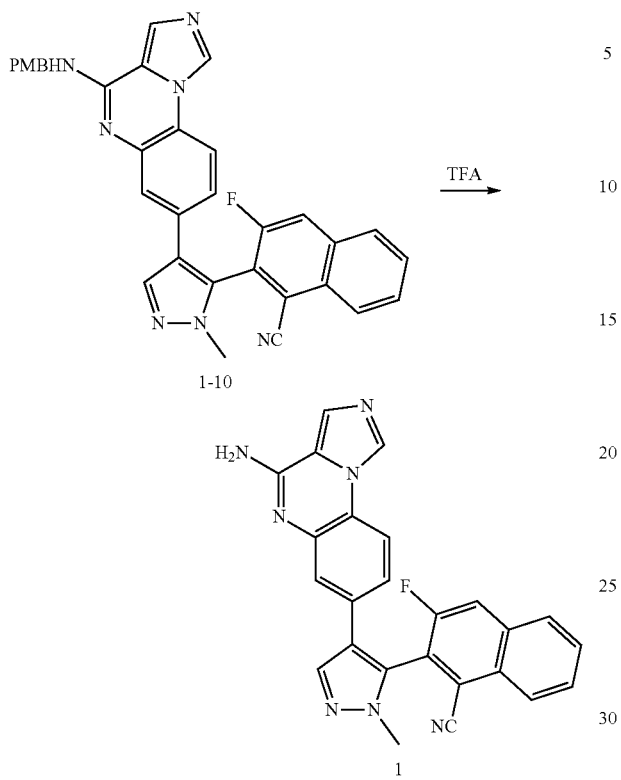

A mixture of compound 1-10 (25.0 mg, 45.2 μmol) in TFA (2 mL) was stirred at 110° C. for 5 hrs under microwave. The reaction mixture was concentrated under reduced pressure, the residue was dissolved in MeOH (5 mL), the pH of the solution was adjusted to 7-8 with $K_2CO_3$ solid. The resulting mixture was filtered. The filtrate was concentrated under reduced pressure to give the crude product. It was purified by prep-HPLC (column: Waters Xbridge 150×25 mm, 5 μm; mobile phase: [solvent A: 5/10000 ammonium hydroxide/water; solvent B: MeCN]; gradient: 26-56% B, 9 min) to give compound 1 (5.03 mg, 11.3 μmol, 25% yield, 97% purity). LCMS (M+H)$^+$: 434.2.

$^1$H NMR of compound 1: (400 MHz, CDCl$_3$) δ 8.53 (s, 1H), 8.20-8.18 (m, 2H), 7.98 (d, J=8.8 Hz, 2H), 7.91 (s, 1H), 7.71-7.64 (m, 3H), 7.40 (s, 1H), 7.14 (d, J=7.6 Hz, 1H), 3.86 (s, 3H).

Example 2: Synthesis of Compound 2

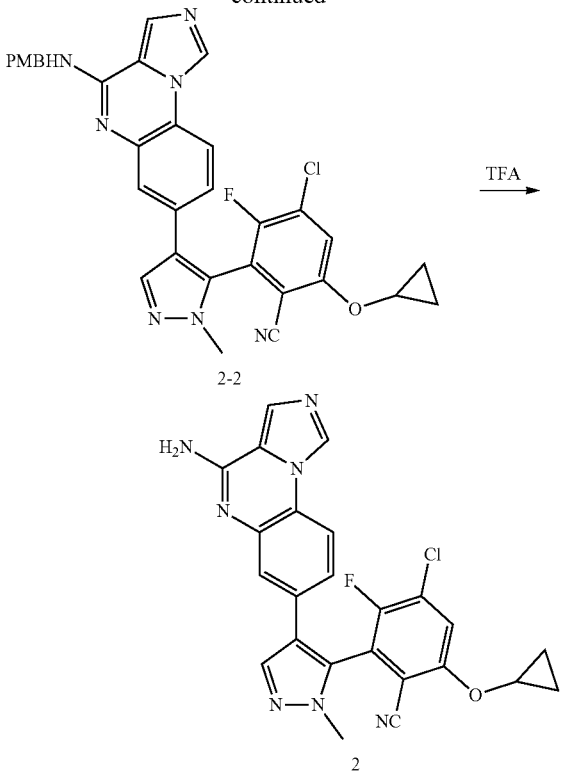

Step 1: Synthesis of Compound 2-1

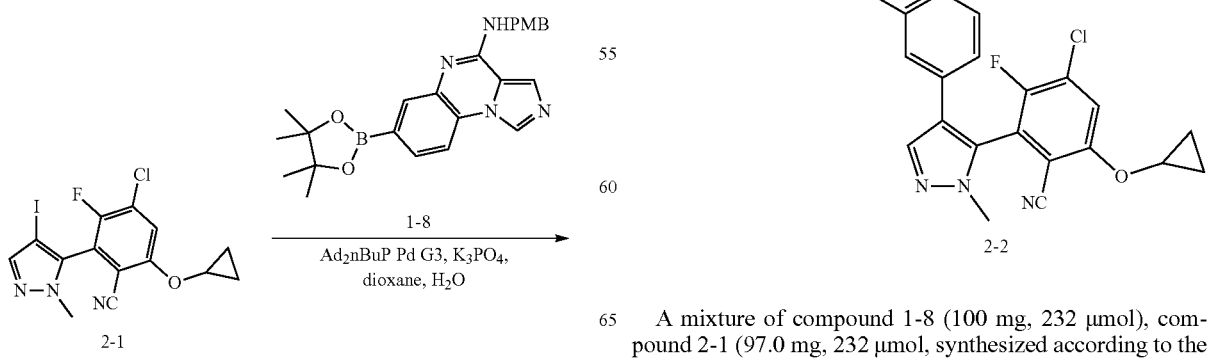

A mixture of compound 1-8 (100 mg, 232 μmol), compound 2-1 (97.0 mg, 232 μmol, synthesized according to the known method: J. Med. Chem. 2022, 65, 1749-1766), cataCXium® A Pd G3 (CAS #1651823-59-4, 16.9 mg, 23.2 μmol, 0.100 eq), K₃PO₄ (148 mg, 697 μmol, 3.00 eq) in dioxane (2.5 mL) and H₂O (0.5 mL) was degassed and purged with N₂ for 3 times. The mixture was stirred at 90° C. for 5 hrs under N₂ atmosphere. The residue was diluted with H₂O (20 mL) and extracted with DCM (20 mL×2). The combined organic layer was washed with brine (15 mL), dried over Na₂SO₄ and filtered. The filtrate was concentrated under reduced pressure. The crude product was purified by prep-TLC (SiO₂, EtOAc) to give compound 2-2 (55.0 mg, 77.8 μmol, 34% yield, 84% purity) as yellow solid. LC-MS (M+H)⁺: 594.2

Step 2: Synthesis of Compound 2

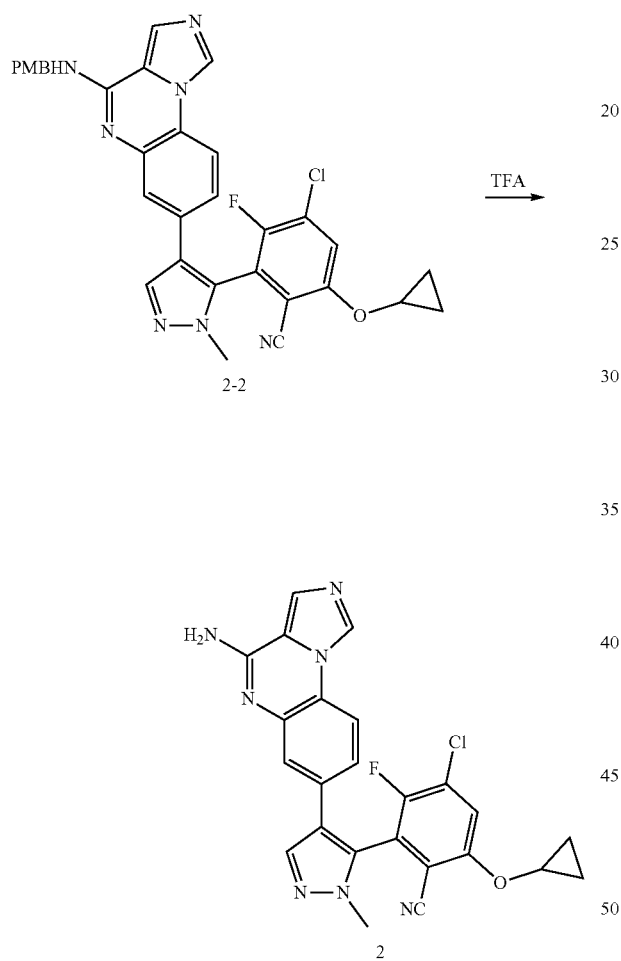

A mixture of compound 2-2 (45.0 mg, 75.8 μmol) in TFA (3 mL) was stirred at 100° C. for 2 hrs under microwave. The mixture was concentrated under reduced pressure. The crude was purified by prep-HPLC (column: Waters Xbridge 150× 25 mm, 5 μm; mobile phase: [solvent A: 5/10000 ammonium hydroxide/water; solvent B: MeCN]; gradient: 30-60% B, 9 min) to give compound 2 (10.66 mg, 22.0 μmol, 29% yield, 98% purity) as white solid. LC-MS (M+H)⁺: 474.1.

$^1$H NMR of Compound 2 (400 MHz, DMSO-$d_6$) δ 9.05 (s, 1H), 8.10 (d, J=8.4 Hz, 1H), 8.05 (s, 1H), 8.00 (d, J=8.4 Hz, 1H), 7.93 (s, 1H), 7.14 (s, 1H), 7.06 (d, J=8.8 Hz, 1H), 4.21-4.17 (m, 1H), 3.74 (s, 3H), 0.94-0.88 (m, 2H), 0.81-0.78 (m, 2H).

Example 3: Synthesis of Compound 3

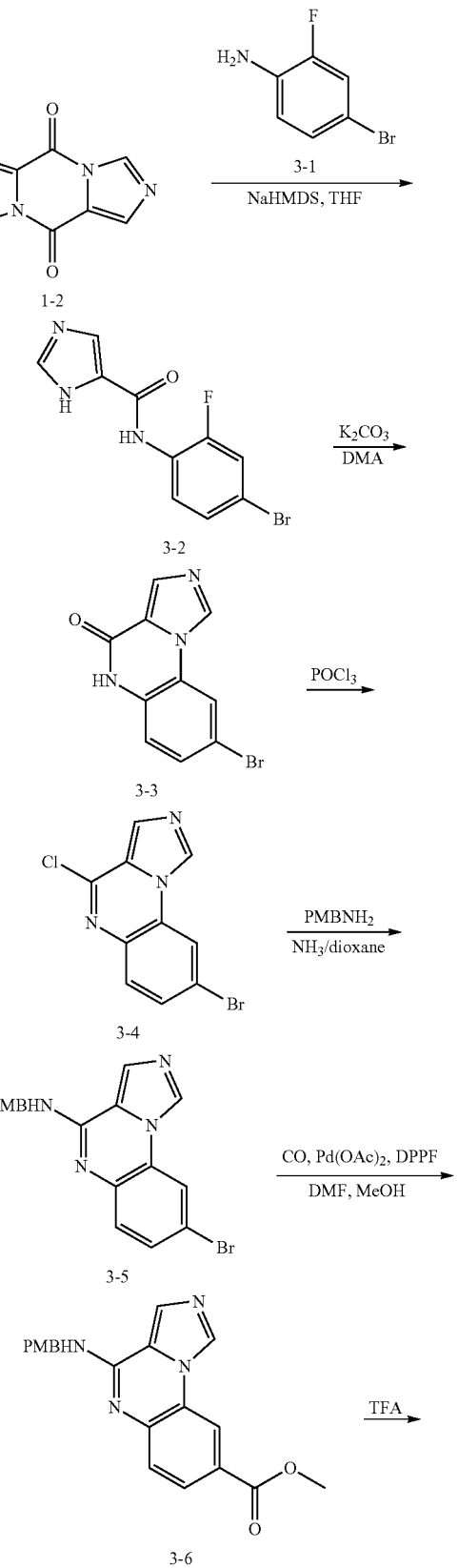

Step 1: Synthesis of Compound 3-2

In analogous to the synthesis of compound 1-4, compound 1-2 (990 mg, 5.26 mmol) was reacted with compound 3-1 (2.00 g, 10.52 mmol) to give compound 3-2 (1 g, 67% yield). LC-MS (M+H)$^+$: 283.8. [0200]$^1$H NMR of compound 3-2: (400 MHz, DMSO-d$_6$) δ 12.72 (br s, 1H), 9.48 (s, 1H), 8.08 (t, J=8.8 Hz, 1H), 7.85 (d, J=8.0 Hz, 2H), 7.64 (dd, J$_1$=12.4 Hz, J$_2$=2.0 Hz, 1H), 7.42 (d, J=8.8 Hz, 1H).

Step 2: Synthesis of Compound 3-3

In analogous to the synthesis of compound 1-5, compound 3-2 (800 mg, 2.82 mmol) was converted to compound 3-3 (400 mg, 1.21 mmol, 43% yield, 80% purity). LC-MS (M+H)$^+$: 263.9.

$^1$H NMR of compound 3-3: (400 MHz, DMSO-d$_6$) δ 9.08 (s, 1H), 8.50 (s, 1H), 7.86 (s, 1H), 7.53 (dd, J$_1$=8.4 Hz, J$_2$=1.6 Hz, 1H), 7.24 (d, J=8.8 Hz, 1H).

Step 3: Synthesis of Compound 3-4

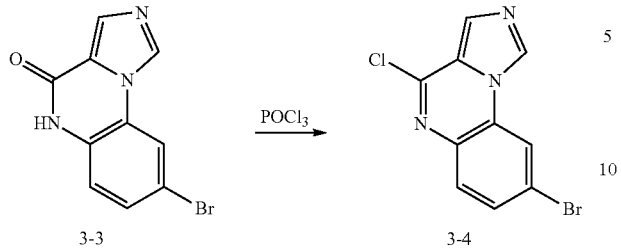

In analogous to the synthesis of compound 1-6, compound 3-3 (400 mg, 1.51 mmol) was converted to compound 3-4 (400 mg, 1.19 mmol, 79% yield, 84% purity). LC-MS (M+H)$^+$: 281.8.

Step 4: Synthesis of Compound 3-5

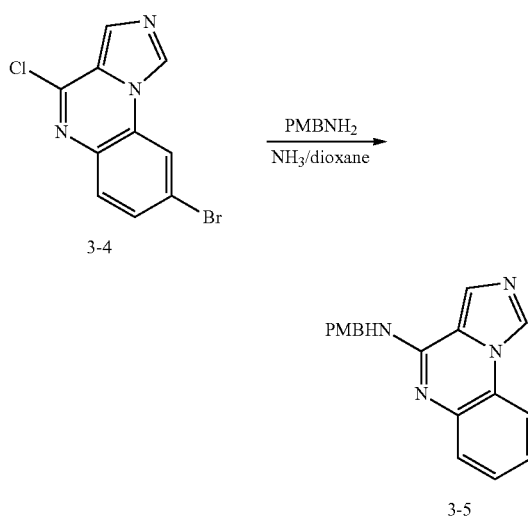

In analogous to the synthesis of compound 1-7, compound 3-4 (400 mg, 1.42 mmol) was converted to compound 3-5 (350 mg, 886 μmol, 63% yield, 97% purity). LC-MS (M+H)$^+$: 383.0.

$^1$H NMR of compound 3-5: (400 MHz, DMSO-d$_6$) δ 9.12 (s, 1H), 8.46 (d, J=2.0 Hz, 1H), 8.35 (t, J=5.6 Hz, 1H), 7.93 (s, 1H), 7.49-7.46 (m, 1H), 7.40 (d, J=8.8 Hz, 1H), 7.33 (d, J=8.8 Hz, 2H), 6.88 (d, J=8.8 Hz, 2H), 4.68 (d, J=5.6 Hz, 2H), 3.71 (s, 3H).

Step 5: Synthesis of Compound 3-6

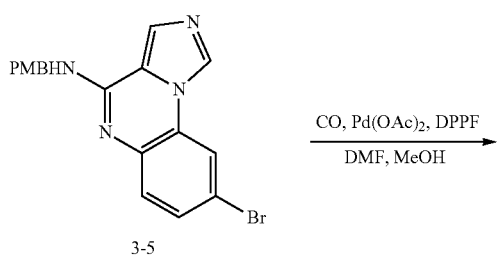

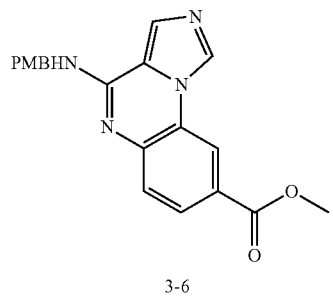

To a solution of compound 3-5 (350 mg, 913 μmol) in DMF (5 mL) and MeOH (5 mL) was added Pd(OAc)$_2$ (103 mg, 457 μmol, 0.500 eq), DPPF (253 mg, 457 μmol, 0.500 eq) and triethylamine (277 mg, 2.74 mmol, 381 μL, 3.00 eq). The mixture was stirred at 80° C. for 18 hrs under CO atmosphere (50 psi). It was filtered and the solid was washed with MeOH (20 mL). The combined filtrate was concentrated under reduced pressure. The residue was dissolved in EtOAc (50 mL) and the resulting solution was washed with water (30 mL×2). The organic layers were dried over Na$_2$SO$_4$, filtered and concentrated. The residue was purified by column chromatography (SiO$_2$, 100% PE to 2:1 PE/EtOAc) to give compound 3-6 (300 mg, 758 μmol, 83% yield, 92% purity). LC-MS (M+H)$^+$: 363.1.

$^1$H NMR of compound 3-6: (DMSO-d$_6$) δ 8.69 (br s, 1H), 8.49 (s, 1H), 8.07 (d, J=8.4 Hz, 1H), 7.73 (d, J=8.8 Hz, 1H), 7.62-7.45 (m, 1H), 7.38 (d, J=8.4 Hz, 2H), 6.92 (d, J=8.4 Hz, 2H), 4.87 (s, 2H), 3.99 (s, 3H), 3.82 (s, 3H)

Step 6: Synthesis of Compound 3-7

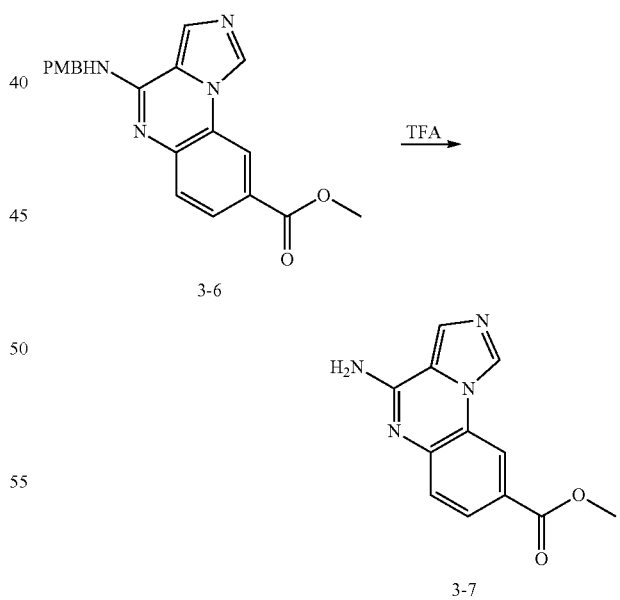

A mixture of compound 3-6 (250 mg, 688 μmol) in TFA (5 mL) was stirred at 110° C. for 2 hrs under microwave. The mixture was concentrated under reduced pressure to give crude compound 3-7 (160 mg) as a brown oil. LC-MS (M+H)$^+$: 243.1.

Step 7: Synthesis of Compound 3-8

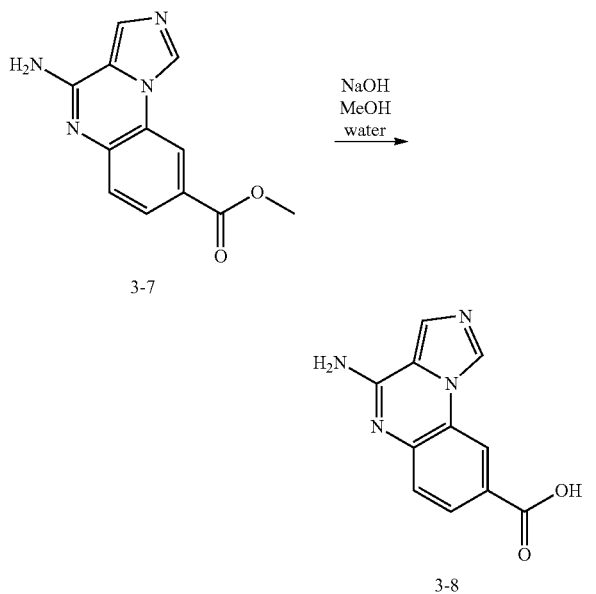

A mixture of compound 3-7 (160 mg, 660 μmol) and aqueous NaOH (1 M, 3.3 mL, 5.00 eq) in THF (5 mL) and MeOH (5 mL) was stirred at 70° C. for 3 hrs. The mixture was concentrated to remove organic solvents. The aqueous was acidified with 1.0 M HCl to pH=6.0~7.0. The resulting suspension was filtered and the solid was dried to give compound 3-8 (120 mg, 446 μmol, 68% yield, 85% purity). LC-MS (M+H)$^+$: 228.9.

Step 8: Synthesis of Compound 3-9

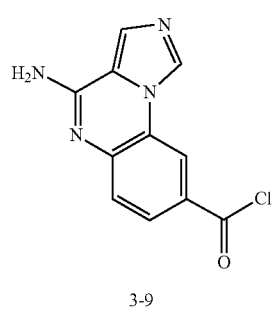

A toluene (2 mL) solution of compound 3-8 (50.0 mg) and SOCl$_2$ (130 mg, 1.10 mmol, 79.5 μL) was stirred at 110° C. for 2 hrs. The mixture was concentrated under reduced pressure to give the crude compound 3-9 (50.0 mg) as yellow solid, which was used in the next step directly.

Step 9: Synthesis of Compound 3

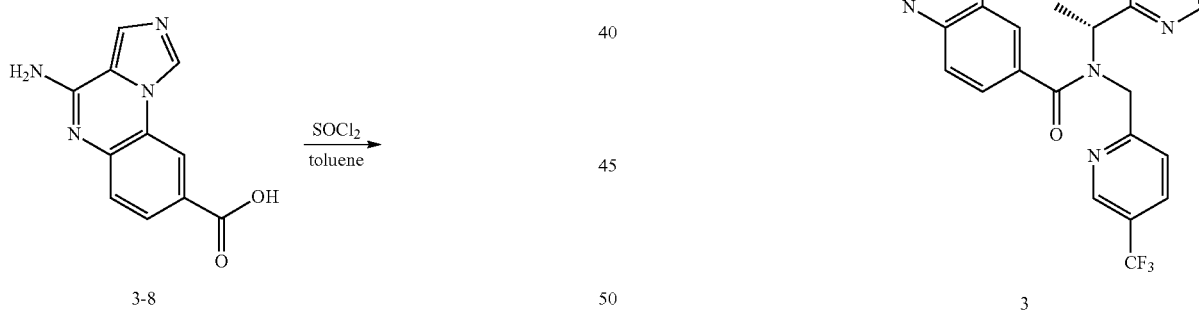

A mixture of compound 3-9 (50.0 mg, 203 μmol), compound 3-10 (45.8 mg, 162 μmol, synthesized according to the known method: WO2021163344A1) and DIEA (82.9 μL, 476 μmol) in DCM (2 mL) was stirred at 25° C. for 1 hr. The mixture was concentrated and purified by prep-HPLC (column: Waters Xbridge 150×25 mm, 5 μm; mobile phase: [solvent A: 5/10000 ammonium hydroxide/water; solvent B: MeCN]; gradient: 22-52% B, 9 min) to give compound 3 (14.95 mg, 29.3 μmol, 15% yield, 97% purity). LC-MS (M+H)$^+$: 493.2.

$^1$H NMR of compound 3: (400 MHz, DMSO-d$_6$) δ 9.14 (s, 1H), 8.43 (s, 1H), 8.79 (t, J=5.2 Hz, 2H), 8.38 (s, 1H), 8.05-8.12 (m, 1H), 7.91 (s, 1H), 7.55 (t, J=2.0 Hz, 2H), 7.48-7.38 (m, 4H), 5.44-5.42 (m, 1H), 4.92 (t, J=17.2 Hz, 1H), 4. (d, J=12.4 Hz, 1H), 1.62 (d, J=6.0 Hz, 3H).

Example 4: Synthesis of Compound 4

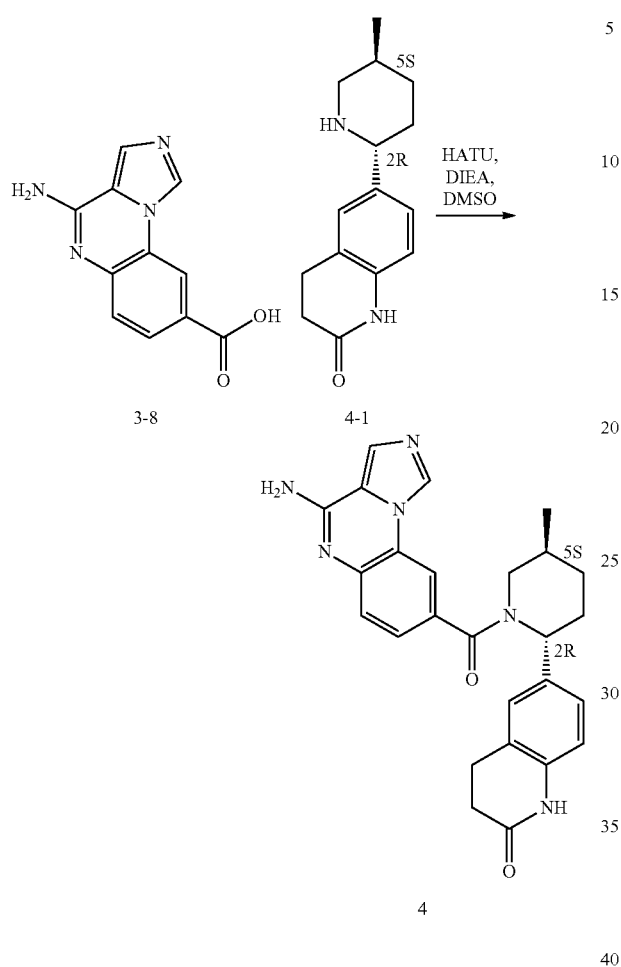

A DMSO (1 mL) solution of compound 3-8 (20.0 mg, 87.6 μmol), (2R, 5S) homochiral compound 4-1 containing 12% (2S, 5S) isomer as the major impurity (21.4 mg, 87.6 μmol, synthesized according to the known method: WO2022026892A1), HATU (50.0 mg, 131.5 μmol) and DIEA (34.0 mg, 263 μmol, 45.8 μL) was degassed and purged with N₂ for 3 times. The mixture was stirred at 25° C. for 2 hrs under N₂ atmosphere. The mixture was purified by prep-HPLC (column: Phenomenex luna C18 150×25 mm, 10 μm; mobile phase: [solvent A: water (0.1% FA), solvent B: MeCN]; gradient: 14-44% B, 10 min). Fractions containing product were concentrated. Saturated NaHCO₃ (5 mL) was added to the resulting residue. The mixture was extracted with DCM (20 mL×3). The combined organic layer was washed with water (15 mL) then concentrated under reduced pressure to give compound 4 (21.88 mg, 47.5 μmol, 57% yield). LC-MS (M+H)⁺: 455.2.

¹H NMR of compound 4: (400 MHz, DMSO-d₆) δ 10.07 (s, 1H), 9.16 (s, 1H), 8.24 (s, 1H), 8.13 (s, 1H), 7.44-7.34 (m 4H), 7.13 (s, 2H), 6.89 (d, J=8.8 Hz, 1H), 5.38-5.31 (m, 1H), 3.15-3.05 (m, 1H), 2.90-2.60 (m, 2H), 2.24-2.05 (m, 2H), 1.85-1.78 (m, 1H), 1.70-1.65 (m, 1H), 1.37-1.26 (m, 2H), 1.21-1.13 (m, 2H), 1.00 (d, J=6.0 Hz, 3H)

Analytical chiral SFC (Column: Chiralpak AS-3 50×4.6 mm, 3 μm; Mobile phase: [solvent A: CO₂, solvent B: 3:1 IPA/MeCN with 0.05% DEA]; Gradient: isocratic 50% B; Flow rate: 3 mL/min; Column Temp: 35° C.; Back Pressure: 100 Bar)

trans (2R, 5S) isomer: Rt=1.174 min (92%)

cis (2S, 5S) isomer: Rt=1.838 min (8%)

Example 5: Synthesis of Compound 5

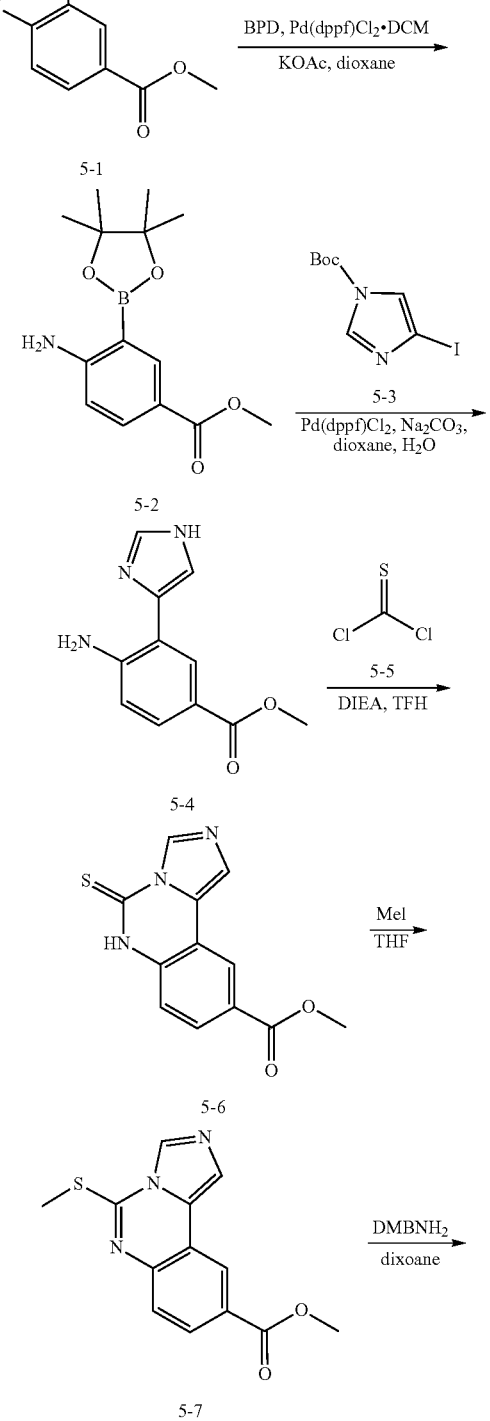

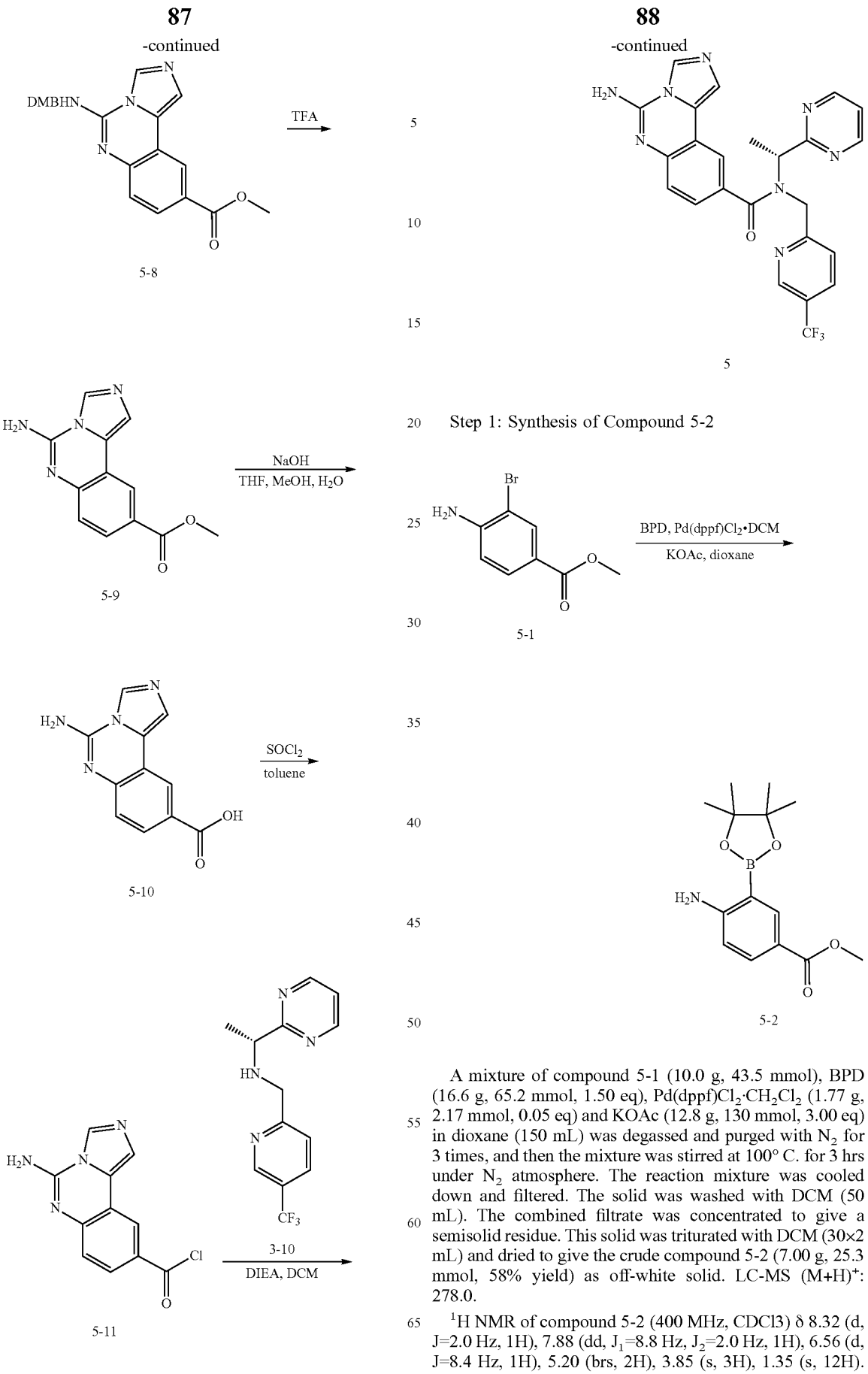

Step 1: Synthesis of Compound 5-2

A mixture of compound 5-1 (10.0 g, 43.5 mmol), BPD (16.6 g, 65.2 mmol, 1.50 eq), Pd(dppf)Cl$_2$·CH$_2$Cl$_2$ (1.77 g, 2.17 mmol, 0.05 eq) and KOAc (12.8 g, 130 mmol, 3.00 eq) in dioxane (150 mL) was degassed and purged with N$_2$ for 3 times, and then the mixture was stirred at 100° C. for 3 hrs under N$_2$ atmosphere. The reaction mixture was cooled down and filtered. The solid was washed with DCM (50 mL). The combined filtrate was concentrated to give a semisolid residue. This solid was triturated with DCM (30×2 mL) and dried to give the crude compound 5-2 (7.00 g, 25.3 mmol, 58% yield) as off-white solid. LC-MS (M+H)$^+$: 278.0.

$^1$H NMR of compound 5-2 (400 MHz, CDCl3) δ 8.32 (d, J=2.0 Hz, 1H), 7.88 (dd, J$_1$=8.8 Hz, J$_2$=2.0 Hz, 1H), 6.56 (d, J=8.4 Hz, 1H), 5.20 (brs, 2H), 3.85 (s, 3H), 1.35 (s, 12H).

Step 2: Synthesis of Compound 5-4

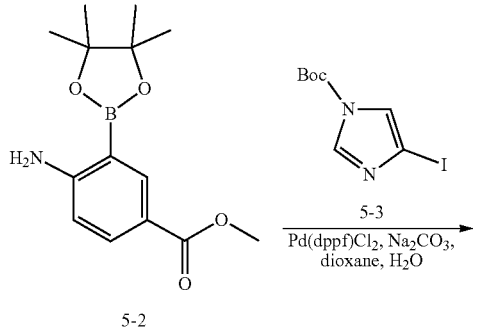

5-2

5-3
Pd(dppf)Cl₂, Na₂CO₃, dioxane, H₂O 5-4

-continued

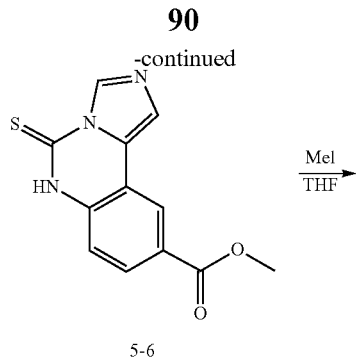

5-6

MeI
THF 5-7

A mixture of compound 5-2 (2.00 g, 7.22 mmol, 1.2 eq), compound 5-3 (1.68 g, 5.78 mmol), Na₂CO₃ (1.89 g, 17.9 mmol, 15.9 μL, 3 eq) and Pd(dppf)Cl₂·CH₂Cl₂ (583 mg, 714 μmol, 0.12 eq) in dioxane (30 mL) and water (6 mL) was degassed and purged with N₂ for 3 times. The mixture was stirred at 90° C. for 12 hrs under N₂ atmosphere. After cooling down, the reaction mixture was filtered. The solid was washed with EtOAc (50 mL), the filtrate was concentrated. The residue was purified by column chromatography (SiO₂, gradient: 100/1 PE/EtOAc to 100% EtOAc) to give compound 5-4 (800 mg, 3.68 mmol, 51% yield) as a yellow oil. LC-MS (M+H)⁺: 218.0.

¹H NMR of compound 5-4 (400 MHz, DMSO-d6) δ 12.36 (brs, 1H), 8.03 (s, 1H), 7.79 (s, 1H), 7.60-7.58 (m, 1H), 7.55-7.52 (m, 1H), 7.16 (s, 2H), 6.70 (d, J=8.8 Hz, 1H), 3.76 (s, 3H).

Step 3: Synthesis of Compound 5-7

To a THF (3 mL) solution of compound 5-4 (800 mg, 3.68 mmol) and thiophosgene (424 mg, 3.68 mmol, 282 μL) was added DIEA (2.38 g, 18.4 mmol, 3.21 mL, 5.00 eq) slowly at 0° C. The mixture was warmed up and stirred at 25° C. for 1 hr. MeI (628 mg, 4.40 mmol, 275 μL, 1.20 eq) was added and the mixture was stirred at 25° C. for another 1 hr. The reaction mixture was diluted with water (10 mL) and extracted with EtOAc (10 mL×3). The combined organic layer was washed with brine (15 mL×2), dried over Na₂SO₄, filtered and concentrated under reduced pressure to give a residue. The residue was purified by prep-TLC (SiO₂, PE:EA=1:1) to give compound 5-7 (200 mg, 732 μmol, 21% yield) as a brown solid. LC-MS (M+H)⁺: 274.0.

¹H NMR of compound 5-7 (400 MHz, CDCl₃) δ 8.65 (d, J=2.0 Hz, 1H), 8.27 (s, 1H), 8.18-8.14 (m, 1H), 7.91 (s, 1H), 7.81 (d, J=8.4 Hz, 1H), 4.00 (s, 3H), 2.88 (s, 3H).

Step 4: Synthesis of Compound 5-8

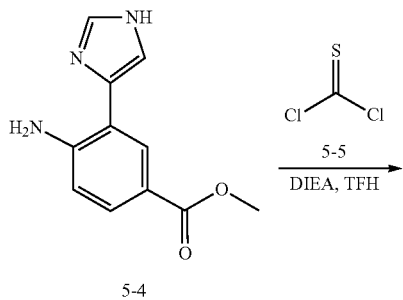

5-4

5-5
DIEA, TFH

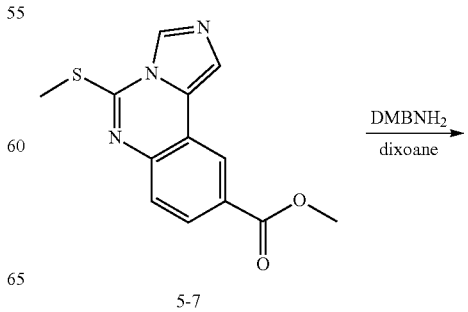

5-7

DMBNH₂
dixoane

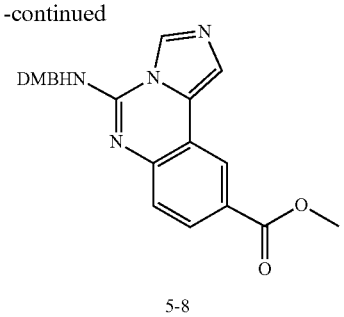

5-8

A dioxane (1 mL) solution of compound 5-7 (200 mg, 732 µmol) and 2,4-dimethoxybenzylamine (612 mg, 3.66 mmol, 550 µL, 5.00 eq) was stirred at 120° C. for 1 hr under N₂. The reaction mixture was diluted with EtOAc (10 mL) and washed with saturated NH₄Cl (30 mL). The organic layer was dried over Na₂SO₄, filtered and concentrated under reduced pressure to give a residue. The residue was purified by prep-TLC (SiO₂, 100% EA) to give compound 5-8 (100 mg, 255 µmol, 35% yield) as a yellow solid. LC-MS (M+H)⁺: 393.2.

¹H NMR of compound 5-8 (400 MHz, CDCl₃) δ 8.50-8.49 (m, 1H), 8.25 (s, 1H), 8.06-8.03 (m, 1H), 7.71 (s, 1H), 7.60 (d, J=8.4 Hz, 1H), 7.37 (d, J=8.4 Hz, 1H), 8.45-8.43 (m, 3H), 4.82 (s, 2H), 3.96 (s, 3H), 3.83 (s, 3H), 3.76 (s, 3H).

Step 5: Synthesis of Compound 5-9

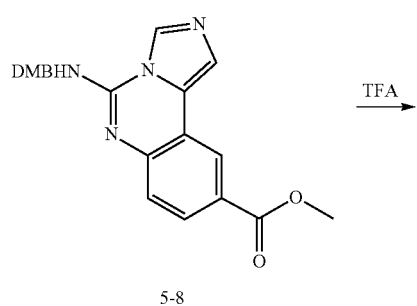

A TFA (2 mL) solution of compound 5-8 (120 mg, 306 µmol) was stirred at 70° C. for 12 hrs under N₂. The reaction mixture was concentrated to give the crude compound 5-9 (100 mg) as yellow solid. LC-MS (M+H)⁺: 243.1.

Step 6: Synthesis of Compound 5-10

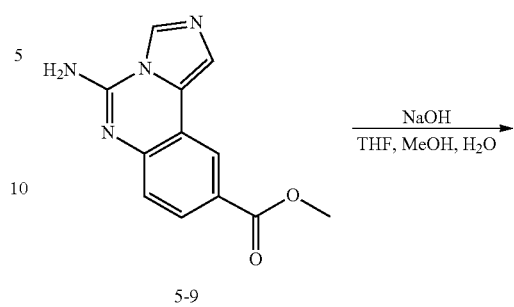

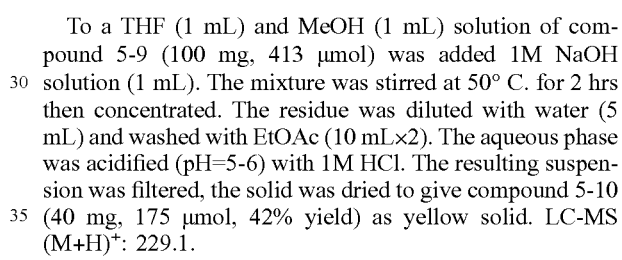

5-10

To a THF (1 mL) and MeOH (1 mL) solution of compound 5-9 (100 mg, 413 µmol) was added 1M NaOH solution (1 mL). The mixture was stirred at 50° C. for 2 hrs then concentrated. The residue was diluted with water (5 mL) and washed with EtOAc (10 mL×2). The aqueous phase was acidified (pH=5-6) with 1M HCl. The resulting suspension was filtered, the solid was dried to give compound 5-10 (40 mg, 175 µmol, 42% yield) as yellow solid. LC-MS (M+H)⁺: 229.1.

Step 7: Synthesis of Compound 5-11

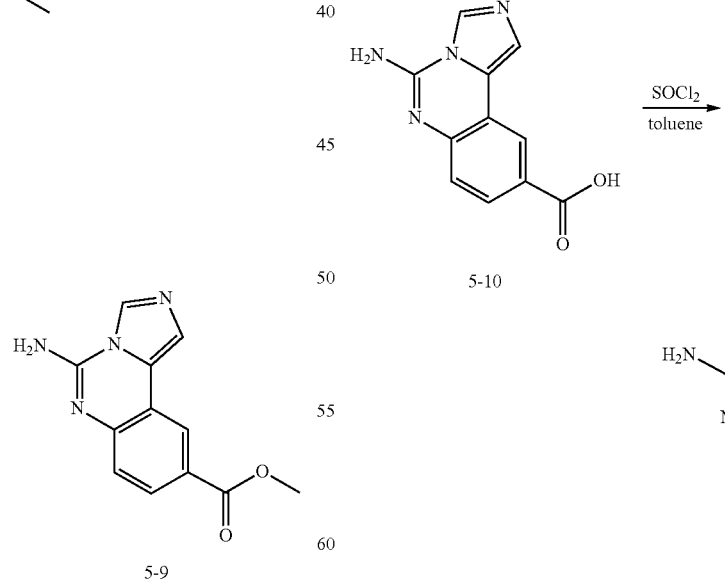

To a toluene (2 mL) solution of compound 5-10 (40 mg, 175 µmol) was added SOCl₂ (130 mg, 876 µmol, 63.7 µL, 5 eq). The mixture was stirred at 100° C. for 2 hrs under N₂ then concentrated under reduced pressure to give the crude compound 5-11 (40.0 mg) as yellow solid. It was used in the next step without further purification.

Step 8: Synthesis of Compound 5

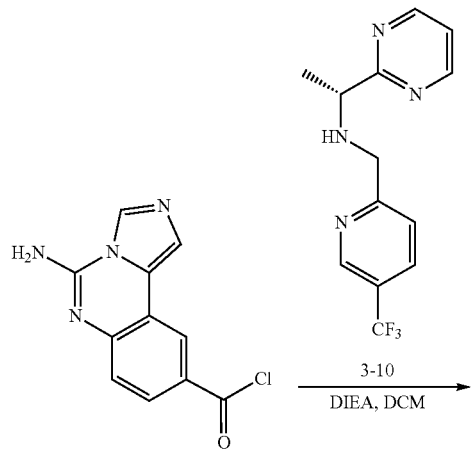

To a DCM (3 mL) solution of compound 3-10 (45.8 mg, 162 µmol) was added DIEA (62.9 mg, 487 µmol, 84.7 µL) and compound 5-11 (40.0 mg) dropwise at 0° C. The mixture was warmed up and stirred at 25° C. for 0.5 hr under $N_2$. The reaction mixture was concentrated to give a residue. The residue was purified by prep-HPLC (column: Waters Xbridge 150×25 mm, 5 µm; mobile phase: [solvent A: 5/10000 ammonium hydroxide/water; B: MeCN]; gradient: 25-55% B, 9 min) to give compound 5 (1.89 mg) as a white solid. LC-MS (M+H)+: 493.2.

$^1$H NMR of compound 5 (400 MHz, $CDCl_3$) δ 8.76-8.70 (m, 3H), 8.45 (s, 1H), 8.04 (s, 1H), 7.92-7.90 (m, 1H), 7.68-7.66 (m, 2H), 7.53-7.51 (m, 2H), 7.21 (t, J=5.2 Hz, 1H), 5.45-5.44 (m, 1H), 5.12-5.08 (m, 1H), 4.28-4.70 (m, 1H), 1.65 (d, J=6.4 Hz, 3H).

Analytical chiral SFC (Column: Chiralcel OJ-3 50×4.6 mm, 3 µm; Mobile phase [solvent A: $CO_2$, solvent B: 0.05% DEA-EtOH]; Gradient elution: 5-40% B; Flow rate: 3 mL/min; Column Temp: 35° C.; Back Pressure: 100 Bar) Rt=1.363 min (100% ee).

Example 6: Synthesis of Compound 6

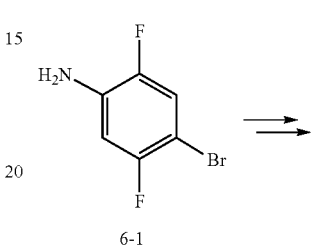

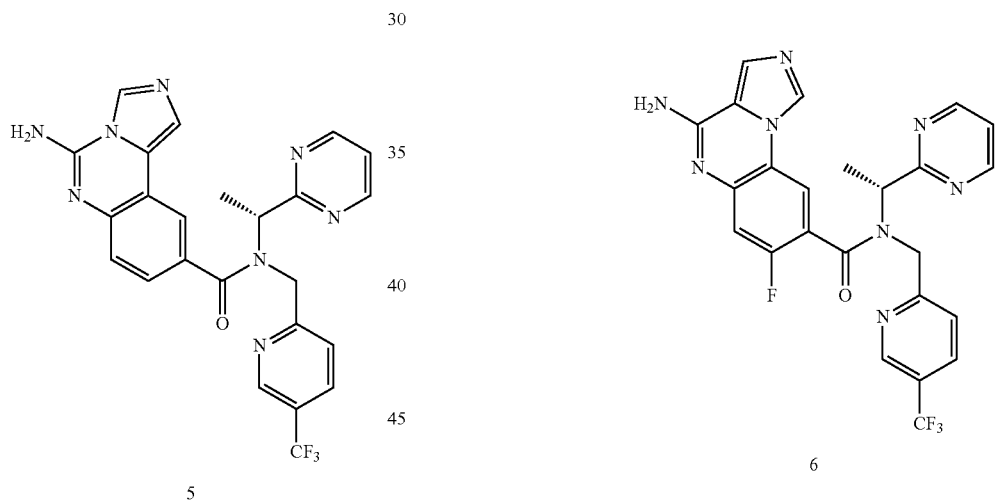

In analogous to the 9-step synthesis of compound 3, compound 6 (1.93 mg, 98% purity) was obtained as light yellow solid. LC-MS (M+H)+: 511.3.

$^1$H NMR of compound 6 (400 MHz, $CDCl_3$) δ 8.78-8.69 (m, 3H), 8.51 (s, 1H), 8.08-8.07 (m, 1H), 7.92-7.90 (m, 1H), 7.72 (s, 1H), 7.62-7.60 (m, 1H), 7.38-7.36 (m, 1H), 7.21-7.19 (m, 1H), 5.39-5.24 (m, 3H), 4.58 (brs, 1H), 1.68 (d, J=7.2 Hz, 3H).

Analytical chiral SFC (Column: Chiralpak AD-3 50×4.6 mm, 3 µm; Mobile phase [solvent A: $CO_2$; solvent B: 3:1 IPA/MeCN with 0.05% DEA]; Gradient: isocratic 60% B; Flow rate: 3 mL/min; Column Temp: 35° C.; Back Pressure: 100 Bar). Rt=0.979 min (100% ee).

Example 7: Synthesis of Compounds 7, 8 and 9
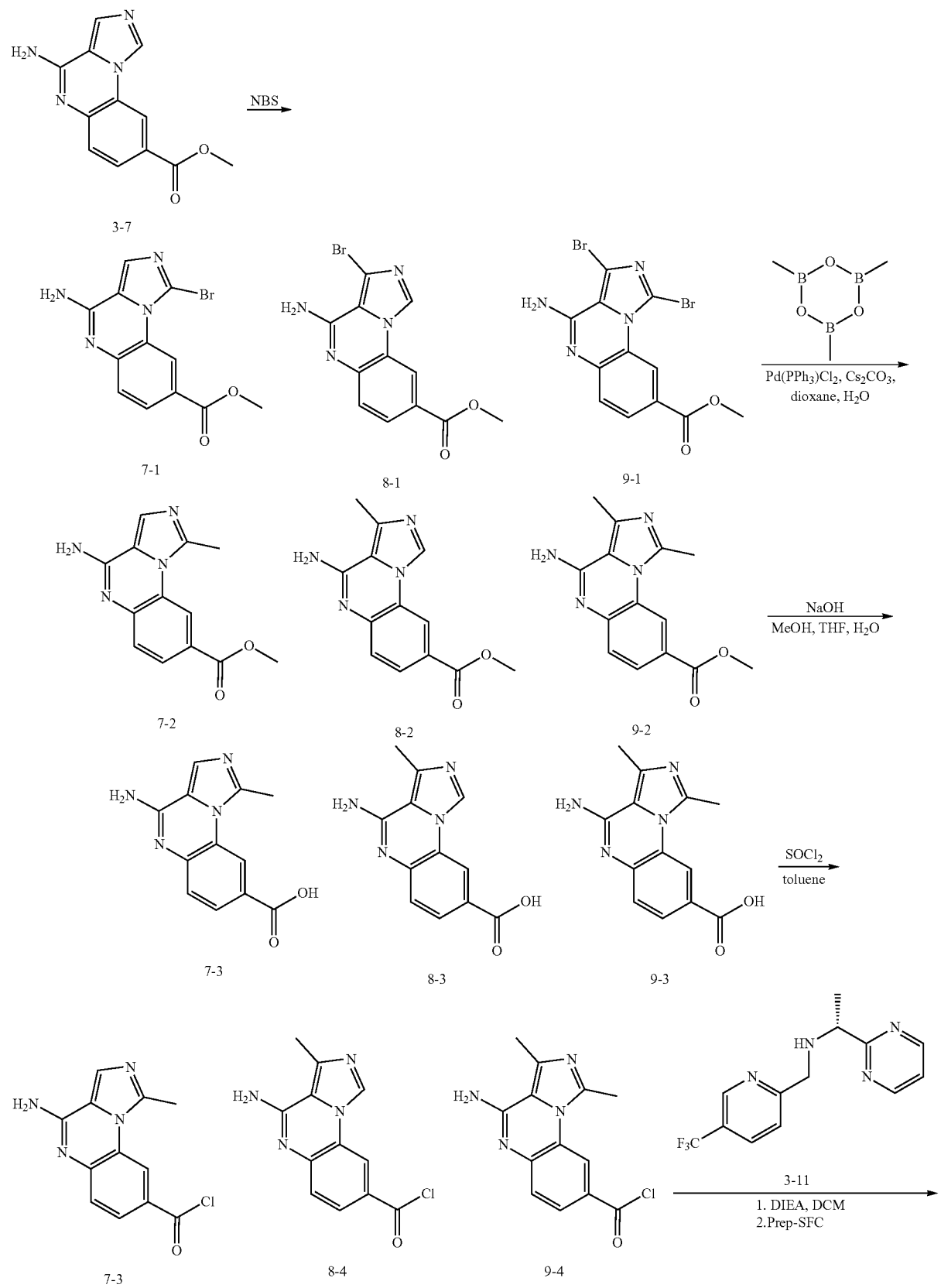

97 98
-continued
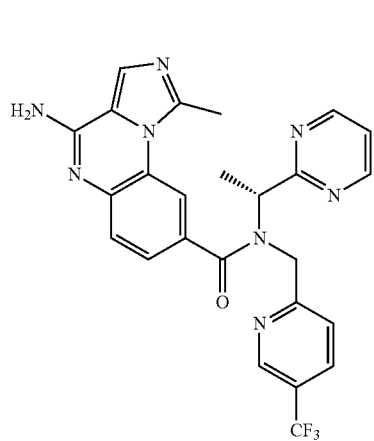
7
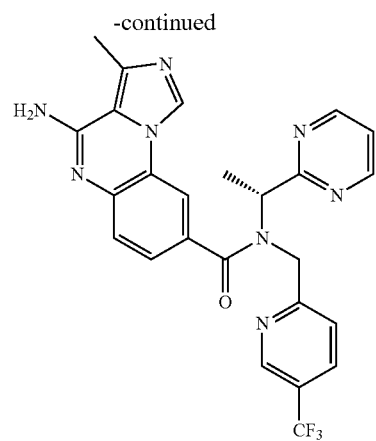
8
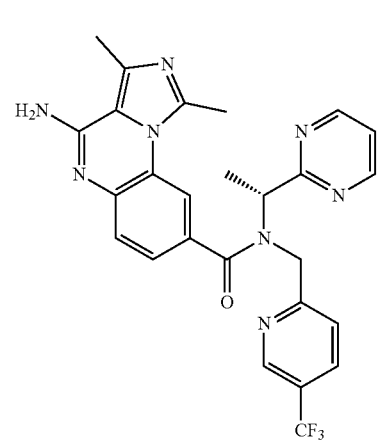
9
20
Step 1: Synthesis of Compounds 7-1, 8-1, 9-1
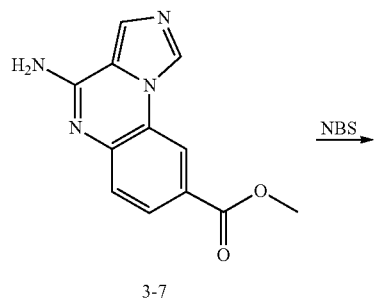
3-7
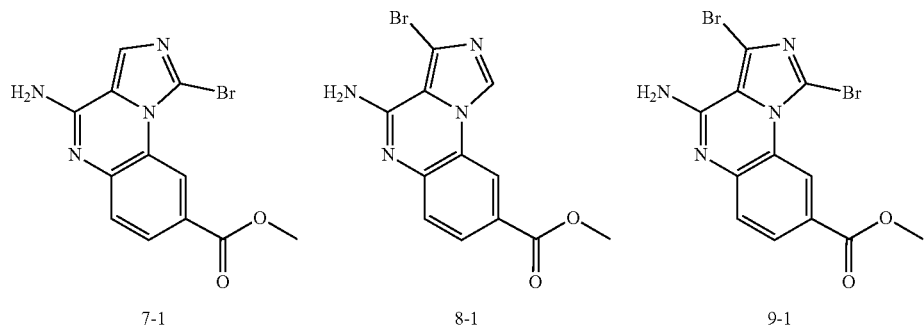
7-1    8-1    9-1

To a DMF (20 mL) solution of 3-7 TFA salt (500 mg) was added NBS (255 mg) at 0° C. The mixture was stirred at 0° C. for 2 hrs. Additional NBS (31.9 mg) was added and the mixture was stirred at 25° C. for additional 1 hr. The mixture was diluted with water (100 mL) and extracted with EtOAc (150 mL×3). The combined organic layer was concentrated under reduced pressure. The resulting residue was triturated with DCM (100 mL) then filtered. The yellow solid was collected as a mixture of compounds 7-1, 8-1 and 9-1 (400 mg).

LC-MS of the mixture:

Compounds 7-1 and 8-1 (M+H)$^+$: 321.0

Compound 9-1 (M+H)$^+$: 398.9

Step 2: Synthesis of Compounds 7-2, 8-2, 9-2

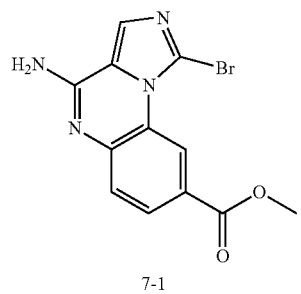

7-1

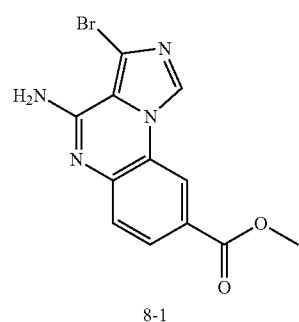

8-1

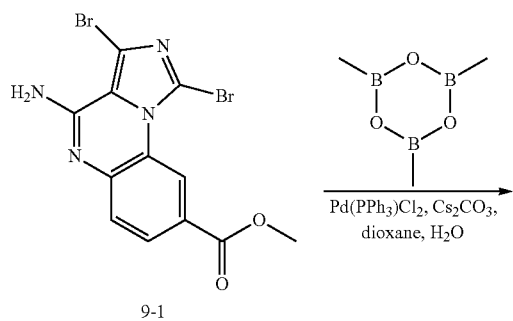

9-1

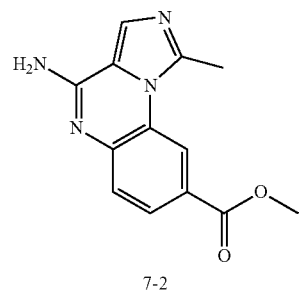

7-2

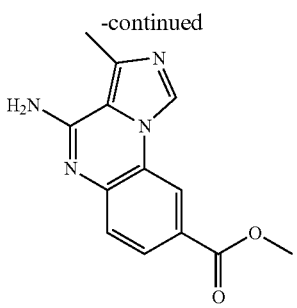

8-2

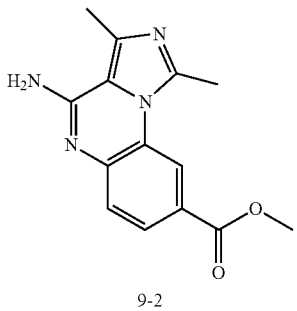 [SMILES: COC(=O)c1ccc2nc(N)c3c(C)nc(C)n3c2c1]

9-2

A dioxane (15 mL)-water (3 mL) solution of the mixture of compound 7-1, 8-1 and 9-1 (350 mg), 3.5 M trimethylboroxine in THF (3.11 mL), Cs$_2$CO$_3$ (1.07 g, 3.27 mmol) and Pd(PPh$_3$)$_2$Cl$_2$ (76.5 mg, 109 mmol) was degassed and purged with N$_2$ for 3 times. The mixture was heated at 120° C. for 4 hrs. The mixture was diluted with water (30 mL) and extracted with EtOAc (30 mL×3). The combined organic layer was washed with brine, dried over Na$_2$SO$_4$, filtered and concentrated. The resulting residue was triturated with DCM (20 mL) then filtered. The yellow solid was collected as a mixture of compounds 7-2, 8-2 and 9-2 (250 mg).

LC-MS of the Mixture:

Compounds 7-2 and 8-2 (M+H)$^+$: 257.1

Compound 9-2 (M+H)$^+$: 271.1.

Step 3: Synthesis of Compounds 7-3, 8-3, 9-3

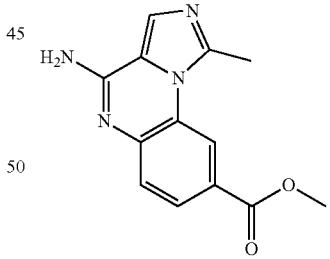

7-2

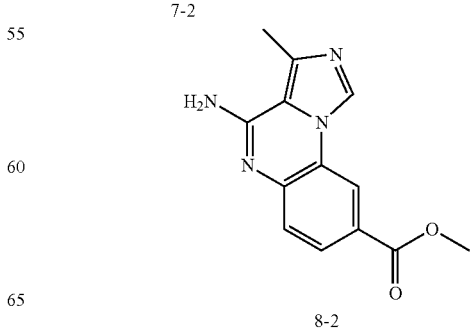

8-2

101
-continued

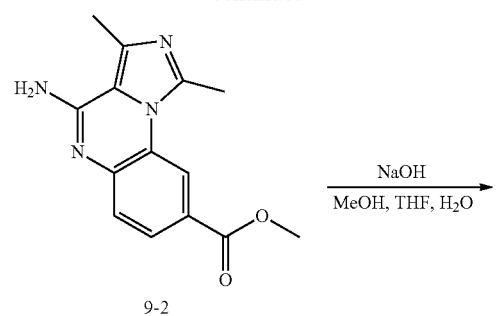

102
-continued

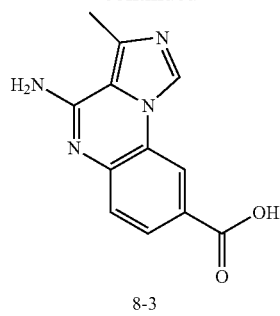

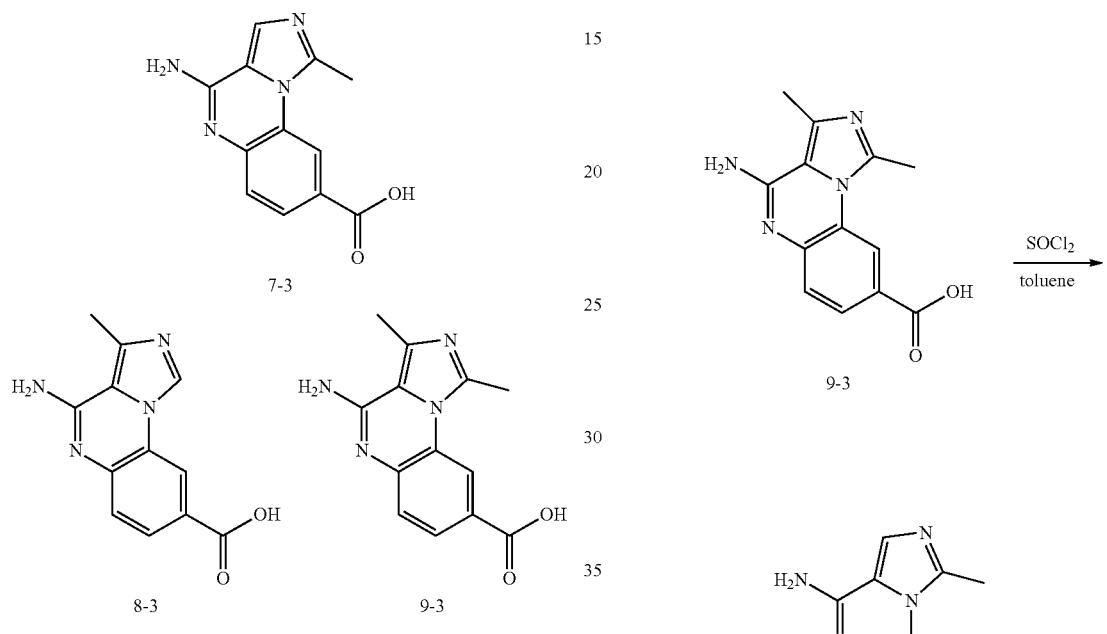

A THF (5 mL) and MeOH (5 mL) solution of the mixture of compounds 7-2, 8-2 and 9-2 (200 mg) and 1M NaOH (3.90 mL) was stirred at 70° C. for 2 hrs. The mixture was concentrated. The residue was diluted with water (10 mL) and washed with EtOAc (10 mL×2). The pH of the aqueous layer was adjusted to 6. The resulting suspension was filtered, and the brown solid was collected as a mixture of compounds 7-3, 8-3, 9-3 (130 mg).

LC-MS of the Mixture:

Compounds 7-3 and 8-3 (M+H)$^+$: 243.0

Compound 9-3 (M+H)$^+$: 257.0

Step 4: Synthesis of Compounds 7-4, 8-4, 9-4

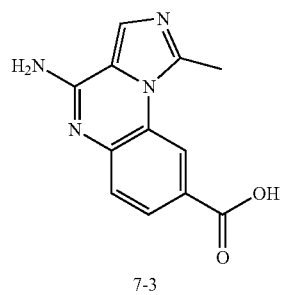

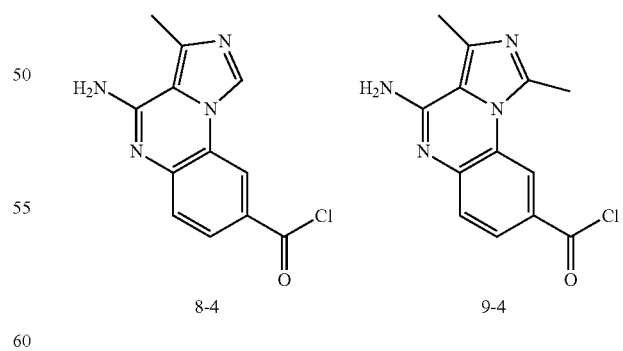

A toluene (5 mL) solution of the mixture of compounds 7-3, 8-3 and 9-3 (145 mg) and SOCl$_2$ (356 mg, 2.99 mmol, 217 µL) was stirred at 110° C. for 2 hrs. The mixture was concentrated to give a mixture of compounds 7-4, 8-4 and 9-4 (150 mg) as yellow solid, which was used in the next step directly.

Step 5: Synthesis of Compounds 7, 8, 9

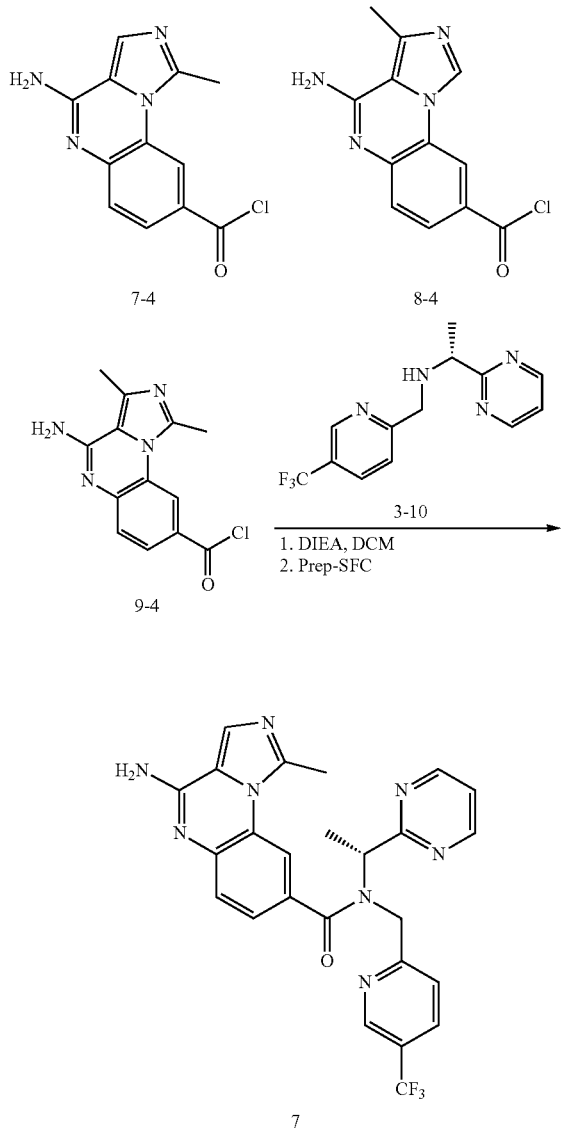

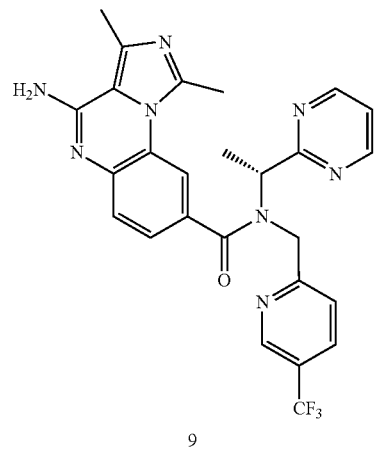 [SMILES: Cc1nc(C)n2c1c(N)nc1ccc(C(=O)N(Cc3ccc(C(F)(F)F)cn3)[C@H](C)c3ncccn3)cc12]

Compound 3-10 (126 mg, 445 μmol) was added to a DCM (5 mL) solution of the mixture of compounds 7-4, 8-4 and 9-4 (145 mg) and DIEA (215 mg, 1.67 mmol, 291 μL) at 0° C. The mixture was stirred at 25° C. for 1 hr. The mixture was concentrated and the resulting residue was purified by prep-HPLC (column: Phenomenex luna C18 150×25 mm, 10 μm; mobile phase: [solvent A: 0.1% FA in water; solvent B: MeCN]; gradient: 10-40% B, 10 min) to give a mixture of compounds 7, 8 and 9. This mixture was further separated by prep-chiral SFC (column: REGIS (R, R) WHELK-01, 250×25 mm, 10 μm; mobile phase [solvent A: $CO_2$, solvent B: 0.1% ammonium hydroxide in EtOH]; gradient: isocratic 55% B) to give pure compounds 7 and 9. The impure compound 8 was further purified by prep-HPLC (column: Waters xbridge 150×25 mm, 10 μm; mobile phase: [solvent A: 5/10000 ammonium hydroxide in water; solvent B: MeCN]; gradient: 25-55% B, 9 min).

Analytical chiral SFC method: (Column: Kromasil (S, S) Whelk-01, 50×4.6 mm, 3.5 μm; Mobile phase: [solvent A: $CO_2$; solvent B: 0.05% DEA in EtOH]; gradient: isocratic 60% B; Flow rate: 3 mL/min; Column Temp: 35° C.; Back Pressure: 100 Bar).

Compound 7 (3.36 mg, 6.53 μmol, 99% purity) was obtained as a yellow solid.

Analytical chiral SFC: Rt=1.007 min (100% ee)

LC-MS of Compound 7 (M+H)$^+$: 507.2.

$^1$H NMR of compound 7: (400 MHz, DMSO-$d_6$) δ 8.47 (s, 1H), 8.79 (t, J=5.2 Hz, 2H), 8.29 (br s, 1H), 8.10 (t, J=7.6 Hz, 1H), 7.79 (s, 1H), 7.55 (t, J=7.2 Hz, 2H), 7.51-7.44 (m, 1H), 7.41 (t, J=4.8 Hz, 1H), 7.29 (s, 2H), 5.47-5.32 (m, 1H), 4.90-4.88 (m, 1H), 4.58-4.55 (m, 1H), 2.89 (s, 3H), 1.60 (d, J=6.8 Hz, 3H).

Compound 8 (3.37 mg, 6.53 μmol, 98% purity) was obtained as a yellow solid.

Analytical chiral SFC: Rt=1.144 min (100% ee)

LC-MS of Compound 8 (M+H)$^+$: 507.4.

$^1$H NMR of compound 8: (400 MHz, DMSO-$d_6$) δ 9.01 (s, 1H), 8.87 (s, 1H), 8.78 (t, J=4.8 Hz, 2H), 8.30 (br s, 1H), 8.08 (d, J=10.4 Hz, 1H), 7.58 (d, J=6.4 Hz, 1H), 7.54-7.51 (m, 1H), 7.43-7.36 (m, 2H), 6.88 (s, 2H), 5.44-5.41 (m, 1H), 4.92 (d, J=16.8 Hz, 1H), 4.58-4.54 (m, 1H), 2.66 (s, 3H), 1.62 (d, J=5.6 Hz, 3H).

Compound 9 (2.58 mg, 4.92 μmol, 99% purity) was obtained as white solid.

Analytical chiral SFC: Rt=1.405 min (100% ee)

LC-MS of Compound 9 (M+H)⁺: 521.4.

$^1$H NMR of compound 9 (400 MHz, DMSO-$d_6$) δ 8.82 (s, 1H), 8.78 (t, J=4.8 Hz, 2H), 8.20 (br s, 1H), 8.10 (dd, $J_1$=8.4 Hz, $J_2$=2.4 Hz 1H), 7.56 (d, J=10.8 Hz, 1H), 7.53-7.43 (m, 2H), 7.40 (t, J=4.8 Hz, 1H), 6.76 (s, 2H), 5.46-5.41 (m, 1H), 4.89-4.85 (m, 1H), 4.60-4.54 (m, 1H), 2.81 (s, 3H), 2.58 (s, 3H), 1.62 (d, J=7.2 Hz, 3H).

Example 8: Synthesis of Compound 10

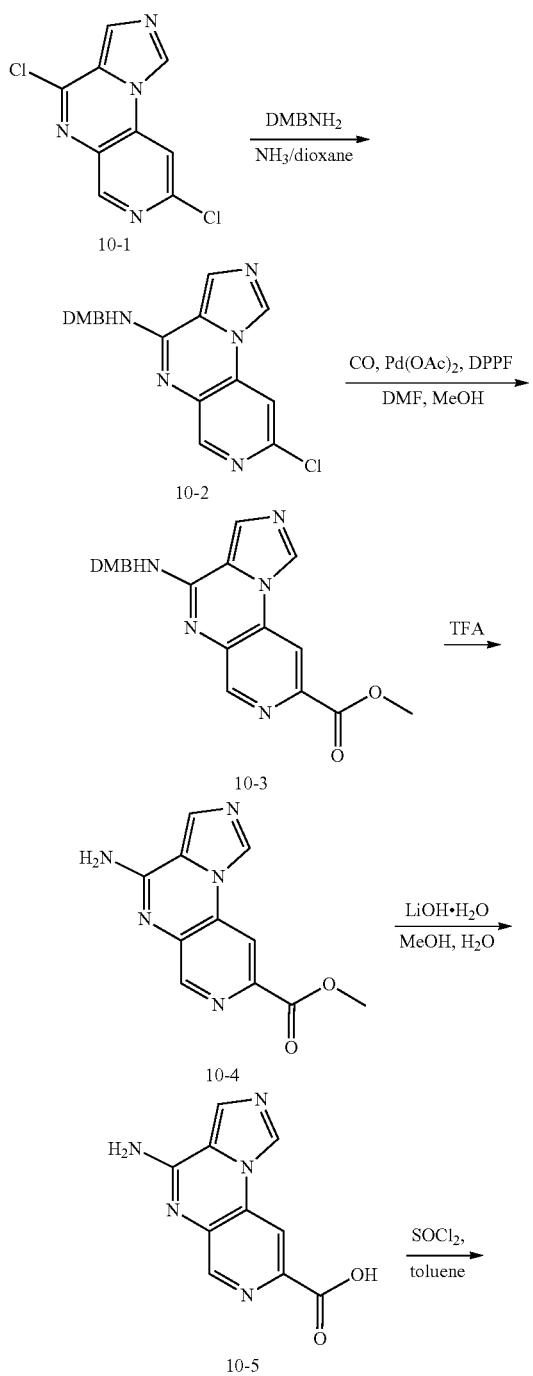

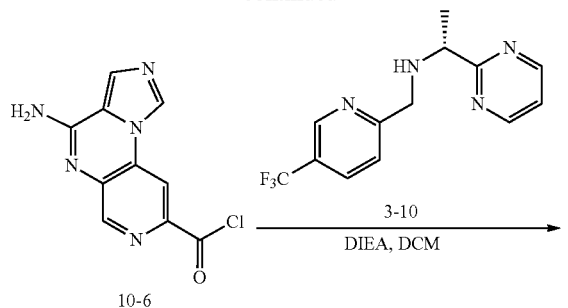

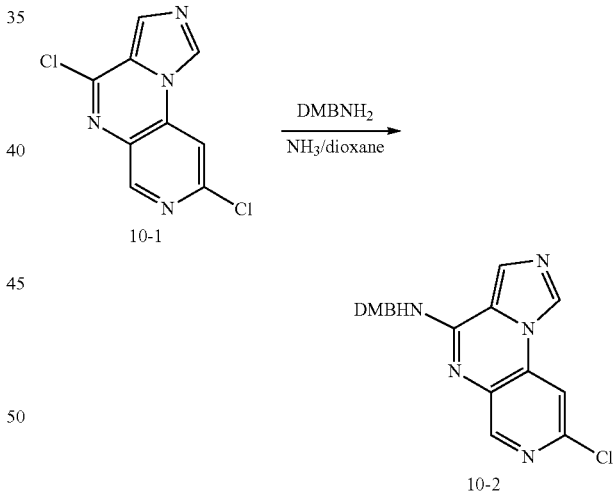

Step 1: Synthesis of Compound 10-2

To a 0.4 M NH$_3$/dioxane (20 mL) solution of compound 10-1 (1.07 g, 4.48 mmol, synthesized according to the known method: WO9945009A1) was added (2,4-dimethoxyphenyl)methanamine (898.06 mg, 5.37 mmol, 806.88 μL, 1.2 eq). The mixture was heated at 110° C. for 2 hrs then concentrated in vacuo. The residue was diluted with saturated NH$_4$Cl solution (30 mL) and the resulting suspension was extracted with DCM (25 mL×3). The combined organic layer was washed with brine (25 mL×2), dried over Na$_2$SO$_4$, filtered and concentrated in vacuo. The residue was purified by column chromatography (SiO$_2$, gradient from 4:1 PE/EtOAc to 100% EtOAc followed by 10:1 EtOAc/MeOH)

to give compound 10-2 (1.50 g, 4.06 mmol, 91% yield) as an off-white solid.

LC-MS (M+H)$^+$: 370.1.

$^1$H NMR of compound 10-2 (400 MHz, DMSO-d$_6$) δ 9.19 (s, 1H), 8.50 (s, 1H), 8.41-8.33 (m, 2H), 8.06 (s, 1H), 7.21 (d, J=8.4 Hz, 1H), 6.59 (d, J=2.4 Hz, 1H), 6.48 (dd, J=2.4, 8.4 Hz, 1H), 4.65 (d, J=5.6 Hz, 2H), 3.83 (s, 3H), 3.74 (s, 3H).

Step 2: Synthesis of Compound 10-3

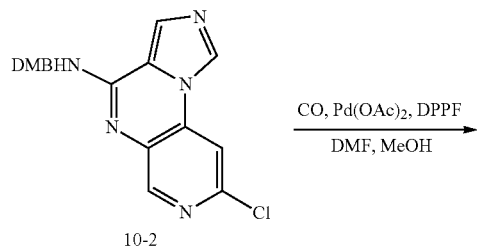

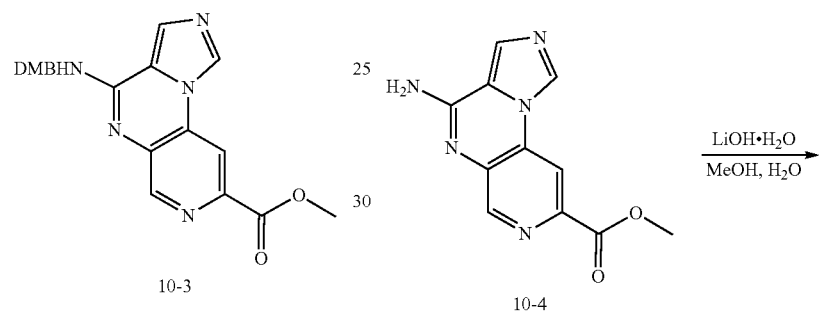

To a DMF (10 mL) and MeOH (10 mL) solution of compound 10-2 (0.8 g, 2.16 mmol) was added Pd(OAc)$_2$ (97.14 mg, 432.66 μmol, 0.2 eq), DPPP (178.45 mg, 432.66 μmol, 0.2 eq) and TEA (656.71 mg, 6.49 mmol, 903.31 μL, 3 eq). The mixture was heated at 80° C. for 16 hrs under CO atmosphere (50 psi). The reaction mixture was diluted with water (20 mL) and the resulting suspension was filtered. The solid was washed with water and dried in vacuo to give compound 10-3 (0.728 g, 1.85 mmol, 86% yield) as a red solid. LC-MS (M+H)$^+$: 394.1.

$^1$H NMR of compound 10-3 (400 MHz, DMSO-d$_6$) δ 9.38 (s, 1H), 8.82 (s, 1H), 8.74 (s, 1H), 8.62 (t, J=5.4 Hz, 1H), 8.10 (s, 1H), 7.22 (d, J=8.4 Hz, 1H), 6.60 (d, J=2.4 Hz, 1H), 6.48 (dd, J=2.4, 8.4 Hz, 1H), 4.70 (d, J=5.6 Hz, 2H), 3.91 (s, 3H), 3.83 (s, 3H), 3.74 (s, 3H).

Step 3: Synthesis of Compound 10-4

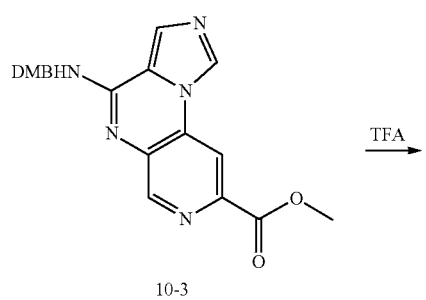

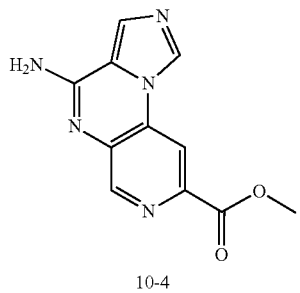

A TFA (4 mL) solution of compound 10-3 (0.080 g, 203.36 μmol) was heated at 75° C. for 30 minutes. The reaction mixture was concentrated in vacuo to give crude compound 10-4 (0.050 g) as a red solid. LC-MS (M+H)$^+$: 244.1.

Step 4: Synthesis of Compound 10-5

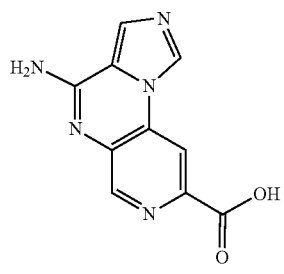

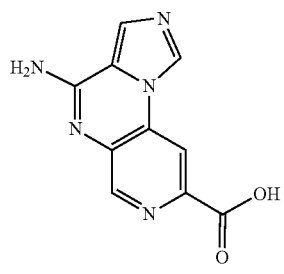

To a MeOH (4 mL) and water (1 mL) solution of compound 10-4 (0.050 g) was added LiOH H$_2$O (25.88 mg, 616.72 μmol). The reaction mixture was heated at 50° C. for 12 hrs. It was diluted with water (10 mL) and MTBE (10 mL). The pH of the aqueous phase was adjusted to 6 with 2M HCl and the resulting suspension was filtered. The solid was washed with water then dried in vacuo to give crude compound 10-5 (0.050 g) as a white solid. LC-MS (M+H)$^+$: 229.9.

Step 5: Synthesis of Compound 10-6

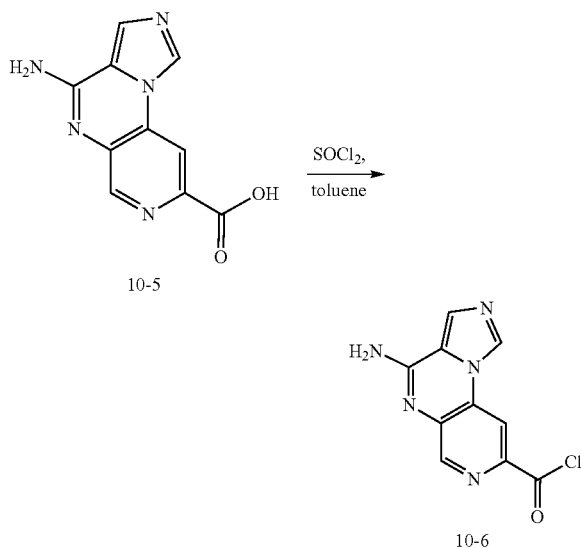

To a toluene (4 mL) solution of compound 10-5 (0.050 g) was added SOCl$_2$ (129.77 mg, 1.09 mmol, 79.22 μL). The reaction mixture was heated at 110° C. for 2 hrs. The reaction was concentrated in vacuo to give crude compound 10-6 (0.050 g) as a brown solid.

Step 6: Synthesis of Compound 10

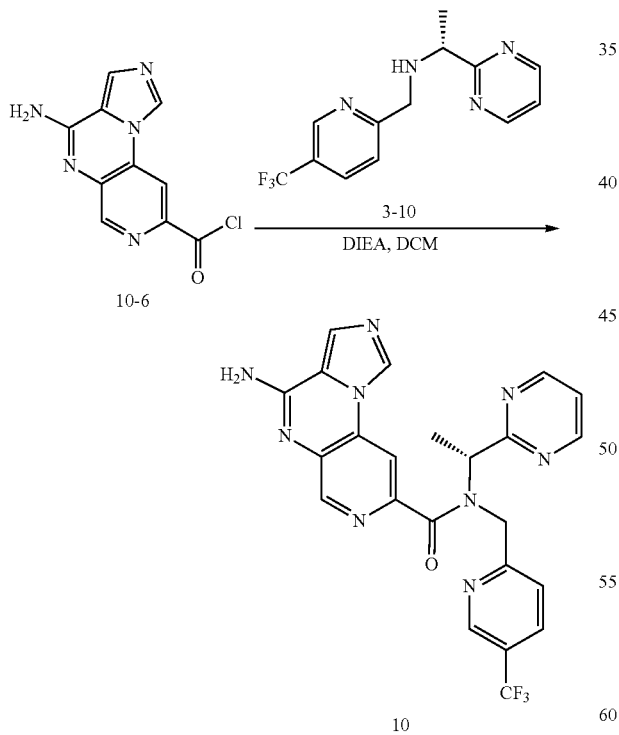

To a DCM (5 mL) solution of compound 3-10 (51.29 mg, 181.72 μmol) was added DIEA (78.28 mg, 605.72 μmol, 105.51 μL) and crude compound 10-6 (0.050 g). The mixture was stirred at 25° C. for 12 hrs. It was diluted with water (15 mL) and extracted with DCM (10 mL×3). The combined organic layer was washed with brine (10 mL×2), dried over Na$_2$SO$_4$, filtered and concentrated in vacuo. The residue was purified by prep-HPLC (column: Phenomenex luna C18 150×25 mm, 10 μm; mobile phase: [solvent A: 0.1% FA in water; solvent B: MeCN]; gradient: 18-48% B, 10 min) to give the FA salt of compound 10. The salt was dissolved in water (10 mL) and washed with DCM (10 mL). The pH of the aqueous layer was adjusted to 9 with saturated NaHCO$_3$ solution, then extracted with DCM (10 mL×3). The combined organic layer was washed with water (10 mL) and concentrated in vacuo to give free base of compound 10 (2 mg, 3.87 μmol, 95% purity) as a white solid.

LC-MS (M+H)$^+$: 494.1.

$^1$H NMR of compound 10 (400 MHz, CDCl$_3$) δ 8.87 (s, 1H), 8.74 (s, 1H), 8.67-8.64 (m, 2H), 8.37-8.30 (m, 1H), 7.87-7.84 (m, 1H), 7.78-7.74 (m, 1H), 7.60 (d, J=7.8 Hz, 1H), 7.14 (t, J=4.8 Hz, 1H), 6.18 (d, J=6.8 Hz, 1H), 5.48-5.37 (m, 2H), 5.26-5.16 (m, 1H), 4.62 (d, J=17.2 Hz, 1H), 3.77 (d, J=10.8 Hz, 1H), 1.81 (d, J=6.8 Hz, 3H).

Analytical chiral SFC (Column: Chiralpak IC-3, 50×4.6 mm, 3 μm; Mobile phase: [solvent A: CO$_2$; solvent B: 0.05% DEA in 3:1 IPA-MeCN]; Gradient: isocratic 50% B; Flow rate: 3 mL/min; Temp: 35° C.; Back Pressure: 100 Bar). Rt=1.484 min (97.73% ee)

Other compounds of the present disclosure are synthesized by similar methods as described above with modified conditions and different starting materials.

Example 9: Synthesis of Compound 11

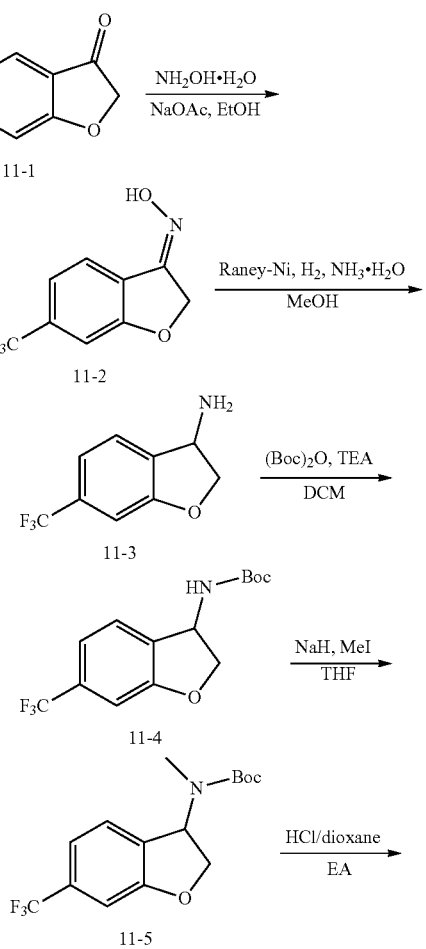

111
-continued

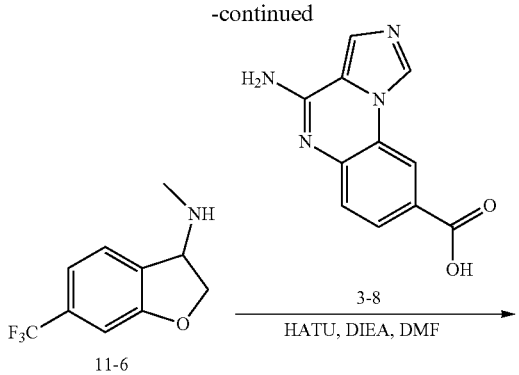

112

Step 2: Synthesis of Compound 11-3

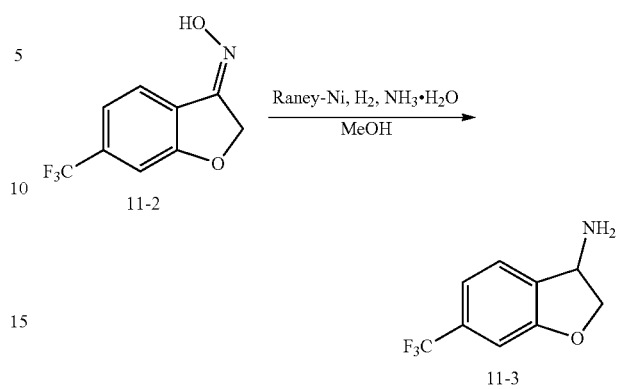

To a solution of compound 11-2 (1.08 g, 4.97 mmol) in MeOH (10 mL) and NH$_3$·H$_2$O (1 mL) was added Raney Nickel (0.216 g), the reaction was stirred for 12 h at 45° C. under H$_2$ atmosphere (50 psi). Then the reaction was warmed to 80° C. and stirred for 12 h. The reaction was filtered through of the celite and the filtrate was concentrated in vacuo. The crude was used directly next step. To afford compound 11-3 (0.9 g, crude) as a yellow solid. LCMS (M−14)$^+$: 189.1.

Step 3: Synthesis of Compound 11-4

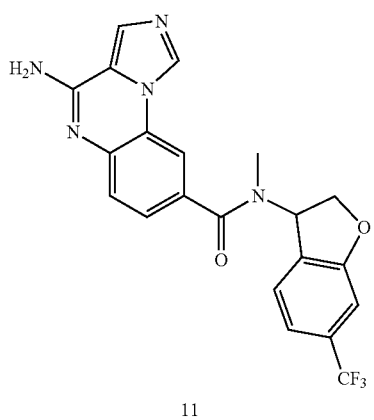

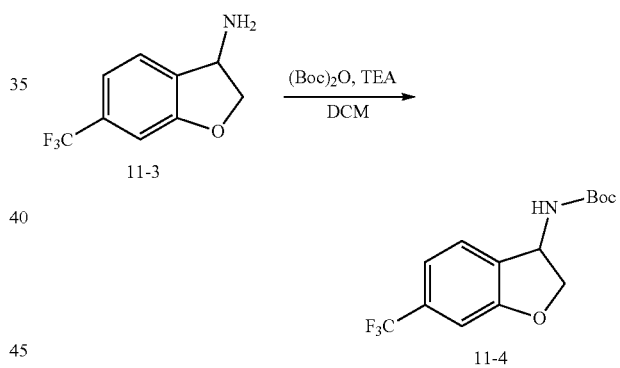

To a solution of compound 11-3 (0.9 g) and TEA (448.27 mg, 4.43 mmol, 616.60 μL) in DCM (20 mL) was added (Boc)$_2$O (966.83 mg, 4.43 mmol, 1.02 mL) under ice-bath at 0° C., then the reaction was warmed to 25° C. and stirred for 12 h. The reaction was concentrated in vacuo. The residue was purified by column chromatography (SiO$_2$, PE:EA=20:1-10:1). To afford compound 11-4 (0.7 g, 2.00 mmol) as a yellow solid. LCMS (M−55)$^+$: 248.1.

Step 4: Synthesis of Compound 11-5

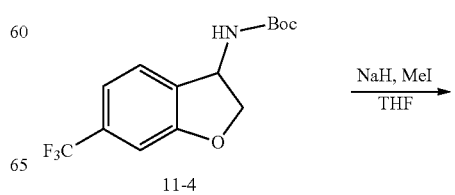

Step 1: Synthesis of Compound 11-2

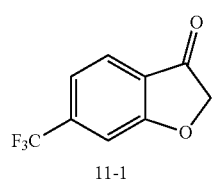

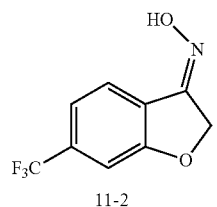

To a solution of compound 11-1 (1.25 g, 6.18 mmol) in EtOH (15 mL) was added NaOAc (1.52 g, 18.55 mmol, 3 eq) and hydroxylamine hydrochloride (1.29 g, 18.55 mmol), the reaction was stirred for 1 h at 25° C. The reaction was diluted with water (20 mL) and extracted with EtOAc (15 mL×3), the combined organic layers were washed with saturated NaCl solution (15 mL×2), dried over Na$_2$SO$_4$, filtered and concentrated in vacuo. The crude was used directly next step to afford compound 11-2 (1.2 g, crude) as a yellow solid.

Step 6: Synthesis of Compound 11

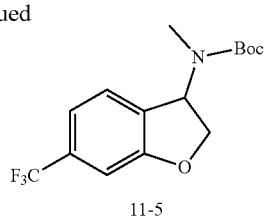

11-5

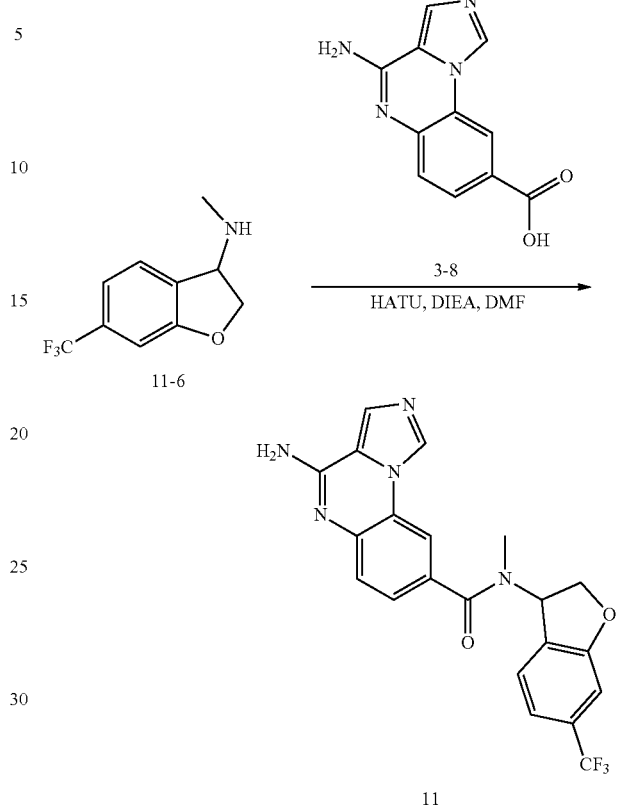

To a solution of compound 11-4 (0.7 g, 2.31 mmol) in THF (20 mL) was added NaH (184.65 mg, 4.62 mmol, 60% purity) under N$_2$ atmosphere at 0° C., the mixture was stirred for 15 minutes, then CH$_3$I (491.42 mg, 3.46 mmol, 215.53 μL) was added to the mixture. The reaction was stirred for 18 h at 25° C. The reaction was quenched by addition of MeOH (15 mL) under ice-bath, then the reaction was concentrated in vacuo. The residue was purified by column chromatography (SiO$_2$, PE:EA=20: 1-10:1). To afford compound 5 (0.62 g, 1.95 mmol, 85% yield) as a yellow oil. LC-MS: (M−55)$^+$: 262.1

Step 5: Synthesis of Compound 11-6

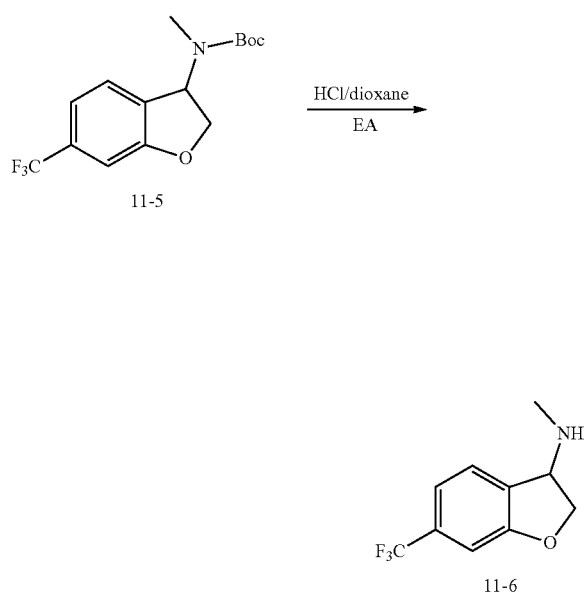

To a solution of compound 11-5 (0.62 g, 1.95 mmol) in EtOAc (10 mL) was added HCl/dioxane (4 M, 6.20 mL) at 25° C., the reaction was stirred for 12 h. The reaction was concentrated in vacuo. The crude was used directly next step to afford compound 11-6 (0.4 g, crude, HCl salt) as a white solid.

LC-MS: (M+H)$^+$: 218.1

H NMR: (400 MHz, DMSO-d6) δ 9.73-9.60 (m, 1H), 8.00-7.76 (m, 1H), 7.44-7.17 (m, 2H), 5.21-5.09 (m, 1H), 4.96-4.83 (m, 1H), 4.78-4.61 (m, 1H), 2.54 (s, 3H)

To a solution of 3-8 (0.040 g, 175.28 μmol) in DMF (4 mL) was added HATU (99.97 mg, 262.92 μmol) and DIEA (45.31 mg, 350.56 μmol, 61.06 μL), after stirring for 15 minutes, 11-6 (66.69 mg, 262.92 μmol, HCl salt) was added to the mixture, the reaction was stirred for 12 h at 25° C. The reaction was diluted with water (15 mL) and extracted with EtOAc (10 mL×3), the combined organic layers were washed with saturated NaCl solution (10 mL×2), dried over Na$_2$SO$_4$, filtered and concentrated in vacuo. The residue was purified by Prep-HPLC (column: Waters Xbridge 150×25 mm, 5 μm; mobile phase: [solvent A: 5/10000 ammonium hydroxide/water; solvent B: MeCN]; gradient: 27-57% B, 9 min) to afford Compound 11 (0.025 g, 58.43 μmol, 33% yield, 99.88% purity).

LC-MS: (M+H)$^+$: 428.2

H NMR: (400 MHz, DMSO-d6) δ 9.17 (s, 1H), 8.33 (s, 1H), 7.91 (s, 1H), 7.64 (d, J=7.6 Hz, 1H), 7.49-7.40 (m, 4H), 7.37-7.30 (m, 1H), 7.28-7.23 (m, 1H), 6.71-6.08 (m, 1H), 4.88-4.66 (m, 2H), 2.68 (s, 3H).

HPLC: 99.88% purity

Example 10: Synthesis of Compound 12

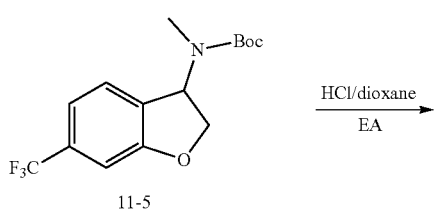

11-5

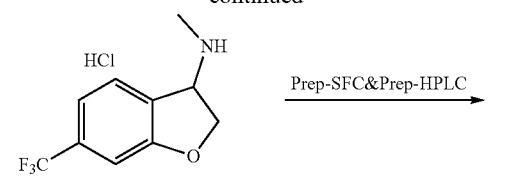

11-6

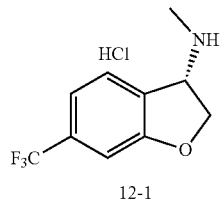

12-1

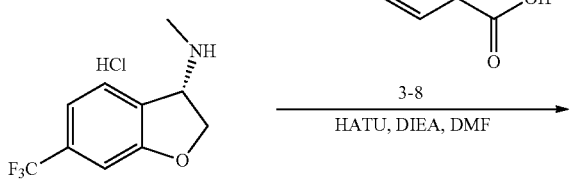

12-1

To a solution of compound 11-5 (1.80 g, 5.67 mmol) in DCM (20.0 mL) was added HCl/EtOAc (4 M, 20.0 mL). The mixture was stirred at 20° C. for 0.5 hr. The reaction mixture was concentrated under reduced pressure to give a residue. The compound was separated by SFC (column: DAICEL CHIRALPAK IG 250 mm*30 mm*5 um; mobile phase: [$CO_2$-MeOH (0.1% $NH_3H_2O$)]; B %: 20%, isocratic elution mode) to give compound 12-1 (crude, 700 mg, 2.77 mmol HCl salt) (Rt=0.791 min). Then the crude was purified by Prep-HPLC (column: Phenomenex luna C18 150×40 mm*15 μm; mobile phase: [solvent A: 0.1% HCl in water; solvent B: MeCN]; gradient: 5%-35% B over 10 min) to get compound 12-1 (280 mg, 1.29 mmol, 40% yield) (SFC: 100% ee) as white solid.

Step 2: Synthesis of Compound 12

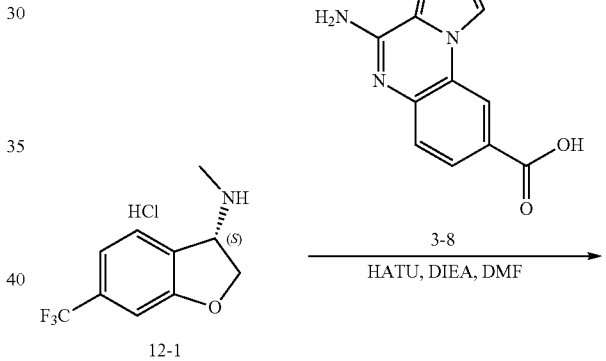

12

Step 1: Synthesis of Compound 12-1

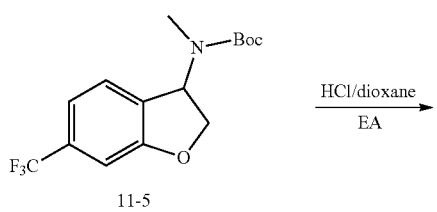

11-5

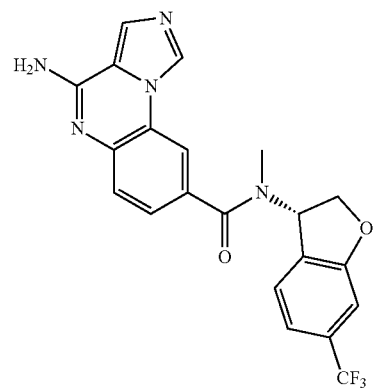

12

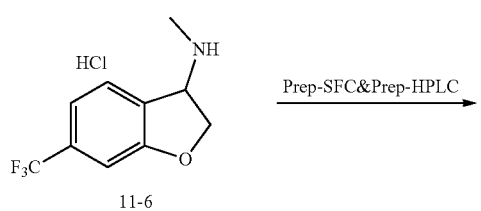

11-6

To a solution of compound 3-8 (0.080 g, 350.56 μmol) in DMF (2 mL) was added HATU (199.94 mg, 525.84 μmol) and DIEA (90.61 mg, 701.12 μmol, 122.12 μL), after stirring for 15 minutes, compound 12-1 (133.38 mg, 525.84 μmol, HCl salt) was added to the mixture, the reaction was stirred for 12 h at 25° C. The reaction was diluted with water (15 mL) and extracted with EtOAc (10 mL×3), the combined organic layers were washed with saturated NaCl solution (10 mL×2), dried over Na$_2$SO$_4$, filtered and concentrated in vacuo. The residue was purified by Prep-HPLC (column: Waters Xbridge 150×25 mm, 5 µm; mobile phase: [solvent A: 5/10000 ammonium hydroxide/water; solvent B: MeCN]; gradient: 27-57% B, 9 min) to afford compound 12 (0.070 g, 161.55 µmol, 46% yield, 99% purity).

H NMR: (400 MHz, DMSO-d$_6$) δ 9.18 (s, 1H), 8.35 (s, 1H), 7.91 (s, 1H), 7.63 (d, J=7.6 Hz, 1H), 7.50-7.42 (m, 4H), 7.38-7.30 (m, 1H), 7.28-7.23 (m, 1H), 6.81-5.89 (m, 1H), 4.94-4.62 (m, 2H), 2.68 (s, 3H).

LC-MS: (M+H)$^+$: 428.1.

HPLC: purity: 98.6% (220 nm).

Example 11: Synthesis of Compound 13

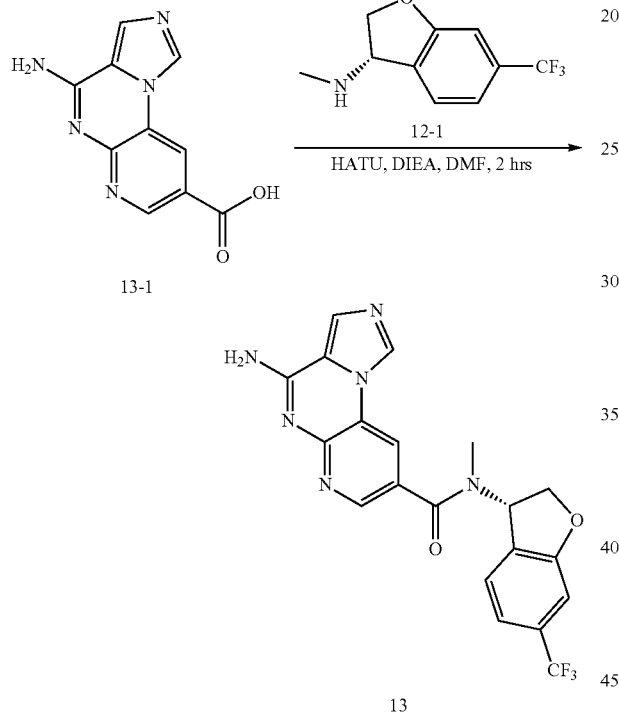

13

In analogous to the synthesis of compound 10-5, compound 13-1 was obtained. LC-MS (M+H)$^+$: 230.1. $^1$H NMR (400 MHz, DMSO-d$_6$) δ 13.25 (br s, 1H), 9.34 (s, 1H), 8.99 (d, J=1.8 Hz, 1H), 8.92 (s, 1H), 8.12 (br s, 2H), 7.98 (s, 1H).

To a solution of compound 13-1 (20.0 mg, 43.6 µmol) in DMF (2.00 mL) was added HATU (49.6 mg, 65.5 µmol), DIEA (22.5 mg, 87.2 µmol, 30.4 µL) and compound 12-1 (28.4 mg, 65.4 µmol), the mixture was stirred at 25° C. for 2 hrs. The mixture was diluted with water (20.0 mL), extracted with EtOAc (10.0 mL*3), the combined organic layers were washed with water (20.0 mL*4), dried over Na$_2$SO$_4$, filtered and concentrated under reduced pressure to give a residue. The crude was purified by prep-HPLC (column: Waters Xbridge 150×25 mm, 5 µm; mobile phase: [solvent A: 5/10000 ammonium hydroxide/water; solvent B: MeCN]; gradient: 24-54% B, 10 min) to get the desired product 13 (25.9 mg, 58.2 µmol, 67% yield, 96% purity).

H NMR: (400 MHz, DMSO-d$_6$) δ 9.22 (s, 1H), 8.71 (d, J=2.0 Hz, 1H), 8.60-8.59 (m, 1H), 7.95 (s, 1H), 7.90 (s, 2H), 7.66-7.64 (m, 1H), 7.34-7.32 (s, 1H), 7.26 (s, 1H), 6.39 (s, 1H), 4.85-4.72 (m, 2H), 2.72 (s, 3H).

LC-MS: (M+H)$^+$: 429.2.

Example 12: Synthesis of Compound 14

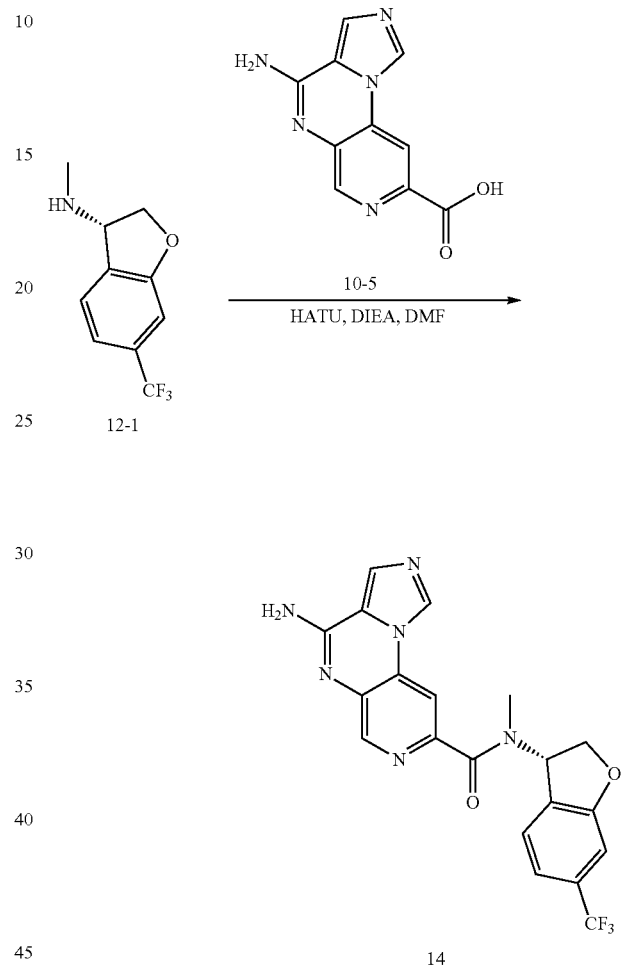

14

To a solution of compound 10-5 (30.0 mg, 131 µmol) and compound 12-1 (28.4 mg, 131 µmol) in DMF (0.5 mL) was added DIEA (50.8 mg, 393 µmol, 68.4 µL) and HATU (99.5 mg, 262 µmol), then the mixture was stirred at 25° C. for 2 hrs. The mixture was diluted with H$_2$O (20.0 mL) and extracted with EtOAc (20.0 mL*3), the combined organic phase was washed with brine (20.0 mL*2), dried over Na$_2$SO$_4$ and concentrated to give a residue. The residue was purified by Prep-HPLC (column: Waters Xbridge 150×25 mm, 5 µm; mobile phase: [solvent A: 5/10000 ammonium hydroxide/water; solvent B: MeCN]; gradient: 24-54% B, 10 min) Compound 14 (25.15 mg, 57.1 µmol, 44% yield, 97% purity).

H NMR: (400 MHz, DMSO-d$_6$) δ 9.32-9.30 (m, 1H), 8.70-8.65 (m, 1H), 8.56-8.51 (m, 1H), 7.99-7.98 (m, 1H), 7.76-7.72 (m, 3H), 7.34 (t, J=7.2 Hz, 1H), 7.28-7.25 (m, 1H), 6.46-6.02 (m, 2H), 4.89-4.68 (m, 2H), 2.76-2.69 (m, 3H).

LC-MS: (M+H)$^+$: 429.1.

Example 13: Synthesis of Compounds 15, 16, 19 and 20
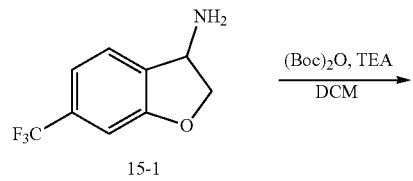
15-1
(Boc)₂O, TEA / DCM →
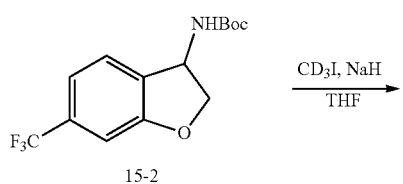
15-2
CD₃I, NaH / THF →
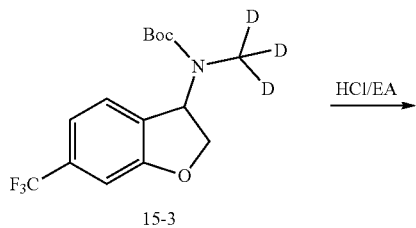
15-3
HCl/EA →
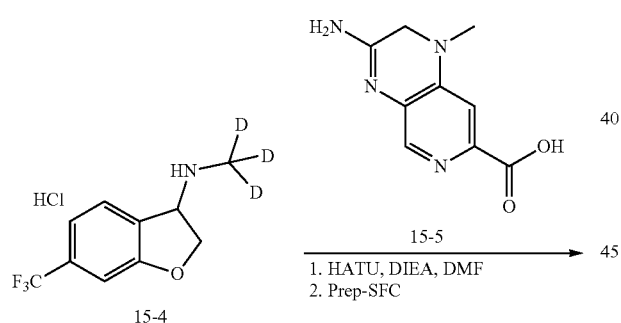
15-4
15-5
1. HATU, DIEA, DMF
2. Prep-SFC
→
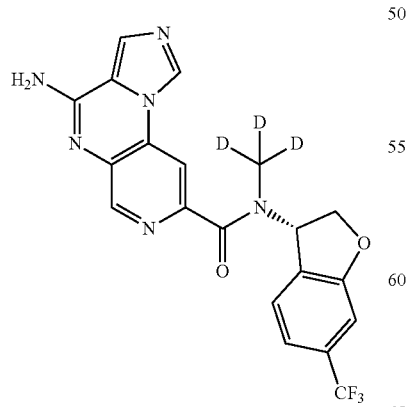
19
-continued
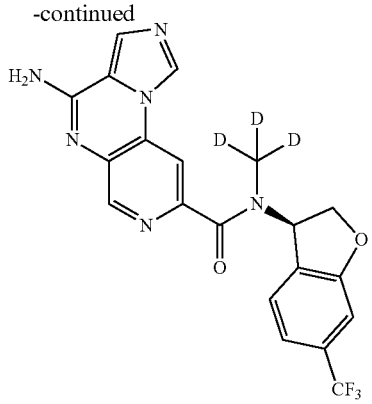
20
15-6
1. HATU, DIEA, DMF
2. Prep-SFC
→
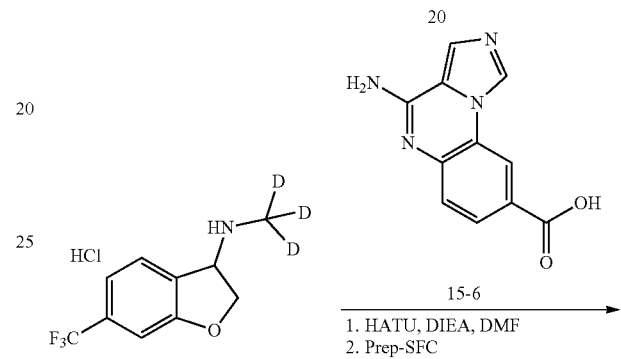
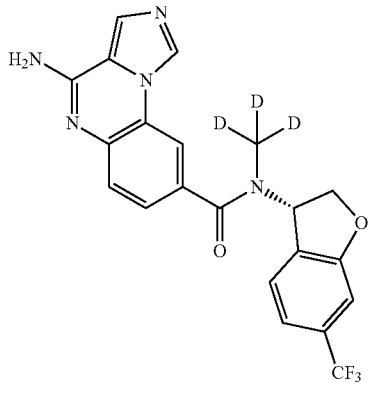
15
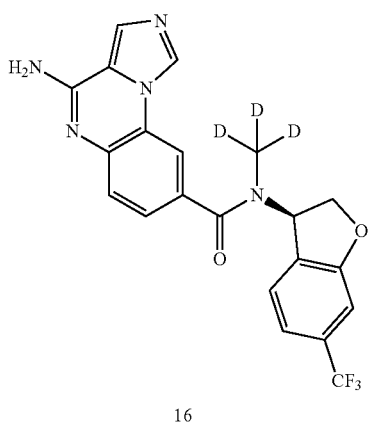
16

Step 1: Synthesis of Compound 15-2

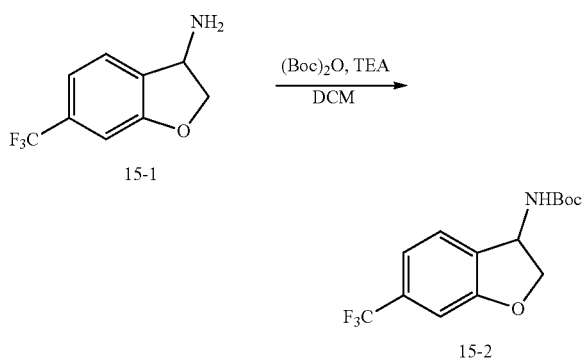

To a solution of compound 15-1 (300 mg, 1.20 mmol, 1.00 eq, FA) in DCM (5.00 mL) was added TEA (244 mg, 2.41 mmol, 335 μL, 2.00 eq) and Boc$_2$O (315 mg, 1.44 mmol, 332 μL, 1.20 eq). The mixture was stirred at 20° C. for 1 hrs. LC-MS showed compound 15-1 was consumed completely and one main peak with desired m/z was detected. The reaction mixture was diluted with water 10.0 mL and extracted with DCM 15.0 mL (5.00 mL*3). The combined organic layers were washed with brine 30.0 mL (15.0 mL*2), dried over Na$_2$SO$_4$, filtered and concentrated under reduced pressure to give a residue. The residue was purified by column chromatography (SiO$_2$, Petroleum ether/ Ethyl acetate=100/1 to 5/1, Plate 1, PE:EA=5:1, Rf=0.41). Compound 15-2 (300 mg, 989 μmol, 82.2% yield) was obtained as yellow solid.

H NMR: (400 MHz, CDCl$_3$) δ 7.45 (d, J=7.6 Hz, 1H), 7.21 (d, J=7.6 Hz, 1H), 7.08 (s, 1H), 5.43 (s, 1H), 4.88 (s, 1H), 4.77-4.73 (m, 1H), 4.42-4.38 (m, 1H), 1.47 (s, 9H).

Step 2: Synthesis of Compound 15-3

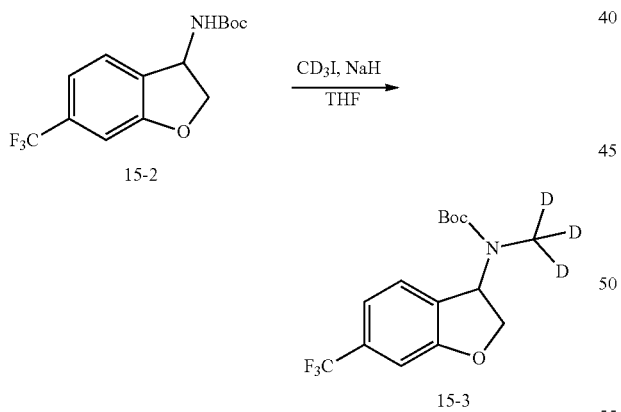

To a solution of compound 15-2 (300 mg, 989 μmol, 1.00 eq) in THF (100 mL) was added NaH (59.4 mg, 1.48 mmol, 60% purity, 1.50 eq) at 0° C., the mixture was stirred at 0° C. for 0.25 hr. Then trideuterio(iodo)methane (172 mg, 1.19 mmol, 73.9 μL, 1.20 eq) was added to the mixture. The mixture was stirred at 20° C. for another 0.25 hrs. LC-MS showed compound 15-2 was consumed completely and one main peak with desired m/z was detected. The reaction mixture was diluted with water 10.0 mL and extracted with EtOAc 30.0 mL (10.0 mL*3). The combined organic layers were washed with brine 30.0 mL (15.0 mL*2), dried over Na$_2$SO$_4$, filtered and concentrated under reduced pressure to give a residue. The residue was purified by column chromatography (SiO$_2$, Petroleum ether/Ethyl acetate=100/1 to 5/1, Plate 1, PE:EA=5:1, Rf=0.40). Compound 15-3 (250 mg, 780 μmol, 78.9% yield) was obtained as yellow oil.

H NMR: (400 MHz, CDCl$_3$) δ 7.35 (d, J=7.2 Hz, 1H), 7.20 (d, J=8.0 Hz, 1H), 7.08 (s, 1H), 6.12-5.84 (m, 1H), 4.71-4.66 (m, 1H), 4.45-4.43 (m, 1H), 1.50 (s, 9H).

Step 3: Synthesis of Compound 15-4

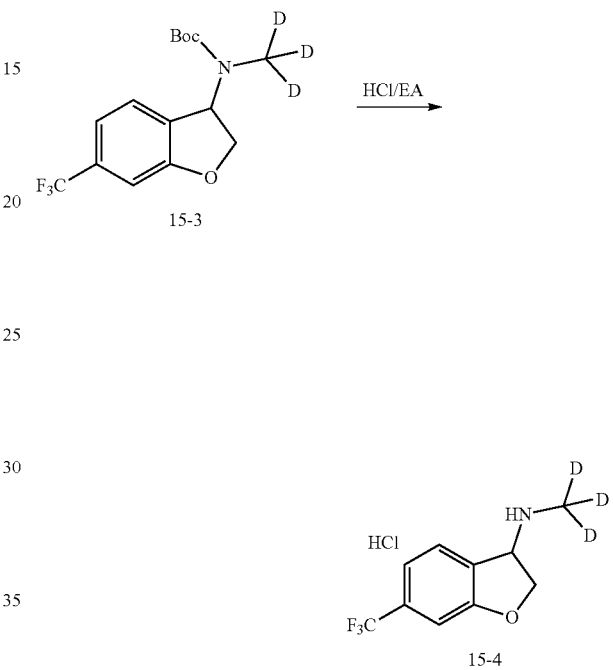

To a solution of compound 15-3 (250 mg, 780 μmol, 1.00 eq) in DCM (5.00 mL) was added HCl/EtOAc (2 M, 10.0 mL, 25.0 eq). The mixture was stirred at 20° C. for 2 hrs. LC-MS showed compound 15-3 was consumed completely and one main peak with desired m/z was detected. The reaction mixture was concentrated under reduced pressure to give a residue. The crude product compound 15-4 (180 mg, 701 μmol, 89.9% yield, HCl) as white solid was used into the next step without further purification.

Step 4: Synthesis of Compounds 19 and 20

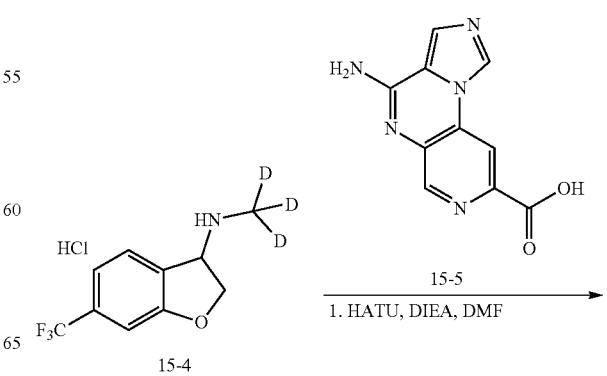

123
-continued

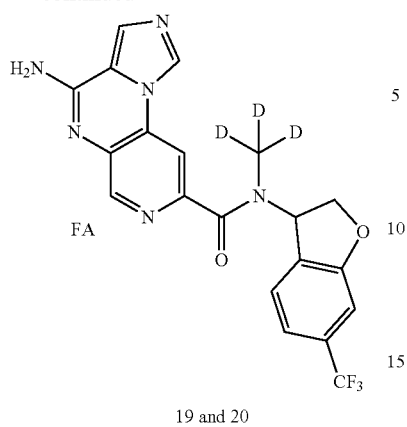

19 and 20

To a solution of compound 15-5 (40.0 mg, 175 μmol, 1.00 eq) and compound 15-4 (44.8 mg, 175 μmol, 1.00 eq, HCl) in DMF (3.00 mL) was added HATU (79.6 mg, 210 μmol, 1.20 eq) and DIEA (113 mg, 873 μmol, 5.00 eq). The mixture was stirred at 25° C. for 0.5 hrs. LC-MS showed compound 15-5 was consumed completely and one main peak with desired m/z was detected. The reaction mixture was diluted with (30.0 mL) and extracted with EtOAc 60.0 mL (20.0 mL*3). The combined organic layers were washed with brine 30.0 mL (15.0 mL*2), dried over $Na_2SO_4$, filtered and concentrated under reduced pressure to give a residue. The residue was purified by prep-HPLC (FA condition; column: Phenomenex luna C18 150*25 mm*10 um; mobile phase: [water (FA)-ACN]; gradient: 16%-46% B over 10 min). Mixture of Compounds 19 and 20 (30.0 mg, 63.0 μmol, 35.9% yield, FA) was obtained as white solid.

Step 5: Synthesis of Compounds 15 and 16

124
-continued

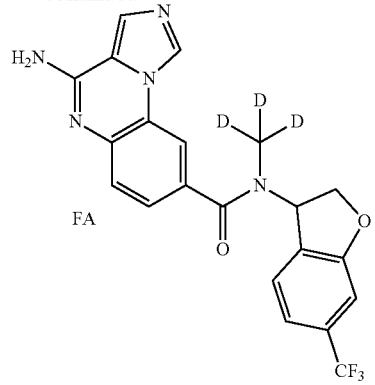

15 and 16

To a solution of compound 15-6 (40.0 mg, 175 μmol, 1.00 eq) and compound 15-4 (45.0 mg, 175 μmol, 1.00 eq, HCl) in DMF (3.00 mL) was added HATU (80.0 mg, 210 μmol, 1.20 eq) and DIEA (113 mg, 876 μmol, 5.00 eq). The mixture was stirred at 25° C. for 0.5 hrs. LC-MS showed compound 15-6 was consumed completely and one main peak with desired m/z was detected. The reaction mixture was diluted with (30.0 mL) and extracted with EtOAc 60.0 mL (20.0 mL*3). The combined organic layers were washed with brine 30.0 mL (15.0 mL*2), dried over $Na_2SO_4$, filtered and concentrated under reduced pressure to give a residue. The residue was purified by prep-HPLC (FA condition; column: Phenomenex luna C18 150*25 mm*10 um; mobile phase: [water (FA)-ACN]; gradient: 16%-46% B over 10 min). Mixture of Compounds 15 and 16 (30.0 mg, 63.0 μmol, 35.9% yield, FA) was obtained as yellow solid.

Step 6: Separation of Compounds 19 and 20

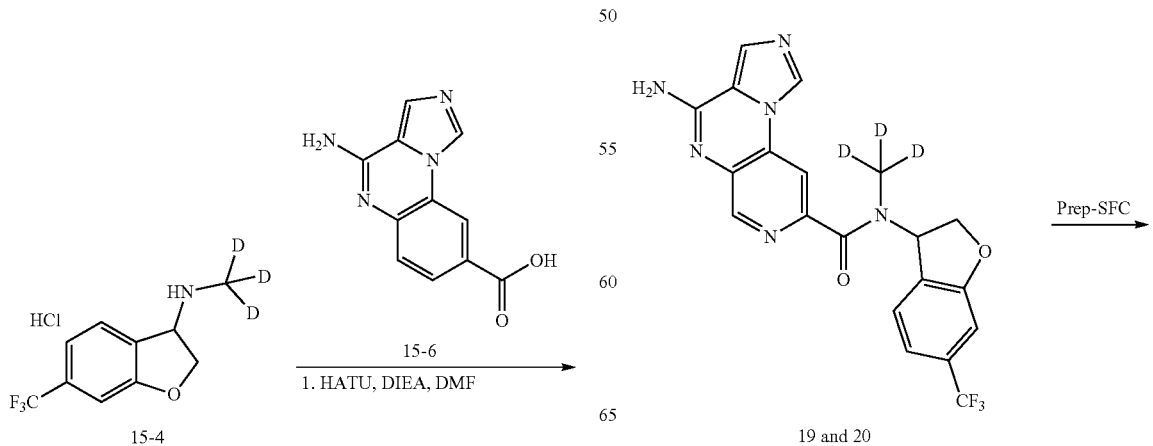

-continued

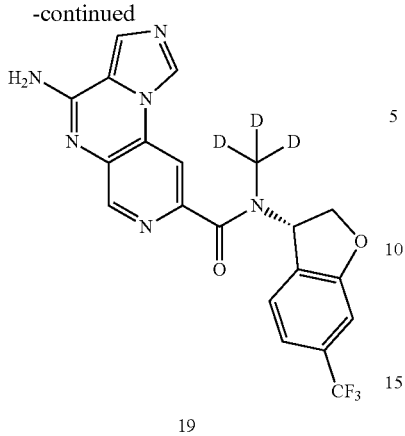

19

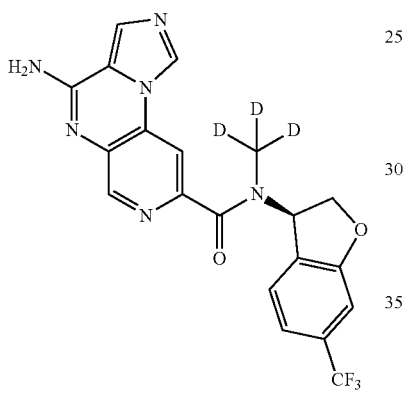

20

Step 7: Separation of Compounds 15 and 16

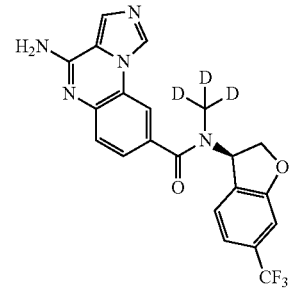

15 and 16

Prep-SFC

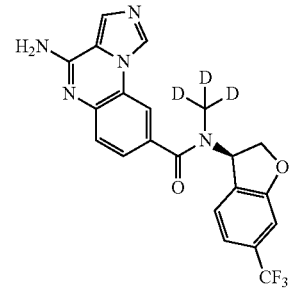

15                16

Mixture of Compounds 19 and 20 was separated by SFC (column: DAICEL CHIRALCEL OD (250 mm*30 mm, 10 um); mobile phase: [CO₂-EtOH]; B %: 45%, isocratic elution mode) to give Compound 20 (10.44 mg, 24.0 μmol, 28.6% yield, 99.12% purity) (Rt=1.969 min) and Compound 19 (7.61 mg, 17.6 μmol, 21.0% yield, 99.72% purity) (Rt=2.193 min). Compound 19 was purified by prep-HPLC (Neu condition; column: Waters Xbridge C18 150*50 mm*10 um; mobile phase: [water (NH₄HCO₃)-ACN]; gradient: 22%-52% B over 10 min). Compound 20 was purified by prep-HPLC (Neu condition; column: Waters Xbridge C18 150*50 mm*10 um; mobile phase: [water (NH₄HCO₃)-ACN]; gradient: 22%-52% B over 10 min). Compound 19 (7.61 mg, 17.6 μmol, 21.0% yield, 99.72% purity) was obtained. Compound 20 (10.44 mg, 24.0 μmol, 28.6% yield, 99.12% purity) was obtained.

H NMR of Compound 19 (400 MHz, DMSO-$d_6$) δ 9.34-9.30 (m, 1H), 8.71-8.64 (m, 1H), 8.56-8.51 (m, 1H), 7.99-7.98 (m, 1H), 7.76-7.56 (m, 3H), 7.37-7.25 (m, 2H), 6.46-6.02 (m, 1H), 4.85-4.69 (m, 2H).

H NMR of Compound 20 (400 MHz, DMSO-$d_6$) δ 9.33-9.30 (m, 1H), 8.71-8.65 (m, 1H), 8.58-8.51 (m, 1H), 8.01-7.98 (m, 1H), 7.80-7.55 (m, 3H), 7.36-7.25 (m, 2H), 6.45-6.02 (m, 1H), 4.89-4.68 (m, 2H).

Mixture of Compounds 15 and 16 was separated by SFC (column: DAICEL CHIRALCEL OJ (250 mm*30 mm, 10 um); mobile phase: [CO₂-EtOH (0.1% NH₃H₂O)]; B %: 35%, isocratic elution mode) to give Compound 16 (8.71 mg, 19.1 μmol, 30.3% yield, 94.14% purity) (Rt=1.837 min) and Compound 15 (5.92 mg, 13.6 μmol, 21.6% yield, 99.06% purity) (Rt=2.051 min). The Peak 1 was purified by prep-HPLC (Neu condition; column: Waters Xbridge C18 150*50 mm*10 um; mobile phase: [water (NH₄HCO₃)-ACN]; gradient: 24%-54% B over 10 min). The Peak 2 was purified by prep-HPLC (Neu condition; column: Waters Xbridge C18 150*50 mm*10 um; mobile phase: [water (NH₄HCO₃)-ACN]; gradient: 24%-54% B over 10 min). Compound 15 (5.92 mg, 13.6 μmol, 21.6% yield, 99.06% purity) was obtained. Compound 16 (8.71 mg, 19.1 μmol, 30.3% yield, 94.14% purity) was obtained.

H NMR of Compound 15 (400 MHz, DMSO-$d_6$) δ 9.18 (s, 1H), 8.33 (s, 1H), 7.91 (s, 1H), 7.65-7.63 (m, 1H), 7.48-7.45 (m, 4H), 7.34-7.32 (m, 1H), 7.26 (s, 1H), 6.42-5.67 (m, 1H), 4.84-4.69 (m, 2H).

H NMR Compound 16 (400 MHz, DMSO-$d_6$) δ 9.18 (s, 1H), 8.33 (s, 1H), 7.91 (s, 1H), 7.65-7.63 (m, 1H), 7.48-7.45 (m, 4H), 7.34-7.26 (m, 2H), 6.65-6.34 (m, 1H), 4.83-4.69 (m, 2H).

Example 15: Synthesis of Compounds 17, 18, 21 and 22
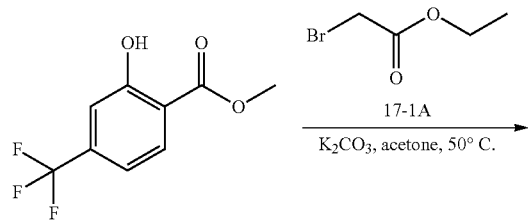
17-1
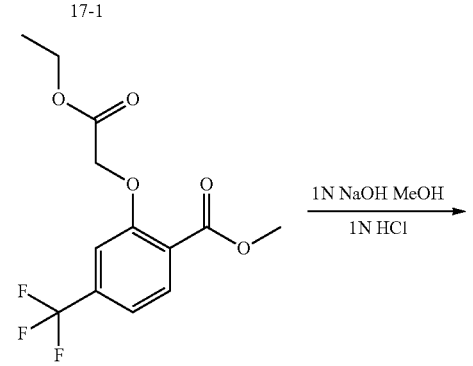
17-2
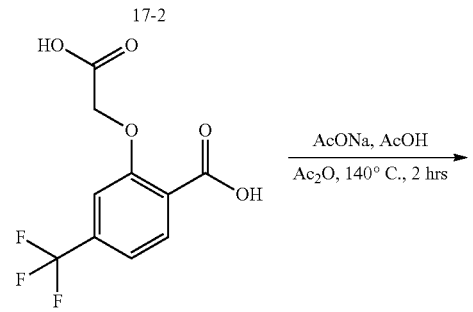
17-3
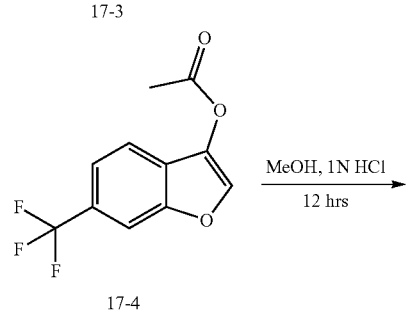
17-4
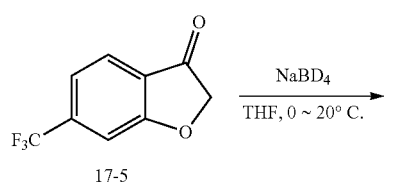
17-5
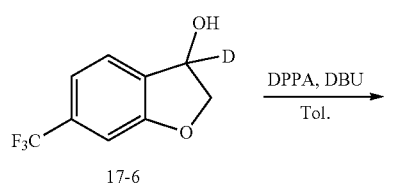
17-6
-continued
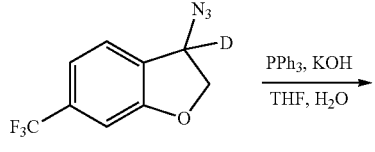
17-7
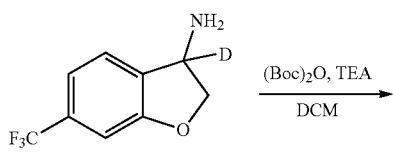
17-8
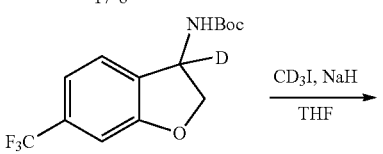
17-9
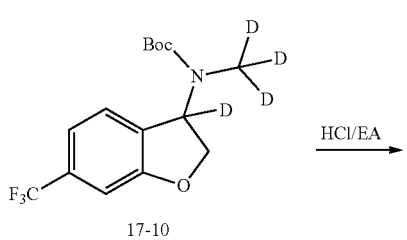
17-10
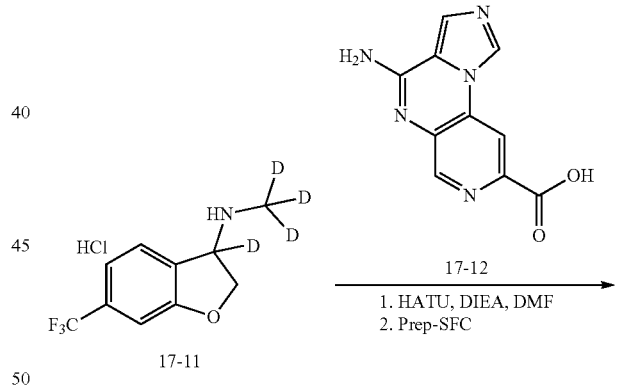
17-11     17-12
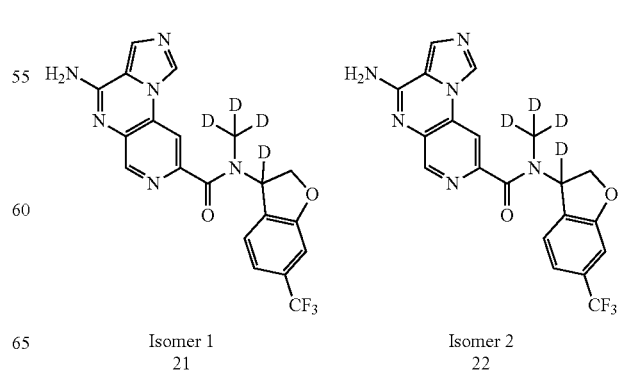
Isomer 1
21
Isomer 2
22

-continued

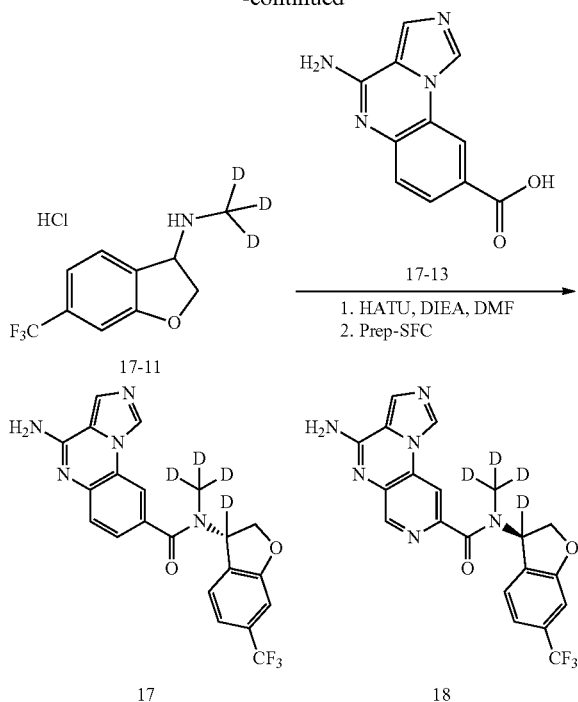

Step 1: Synthesis of Compound 17-2

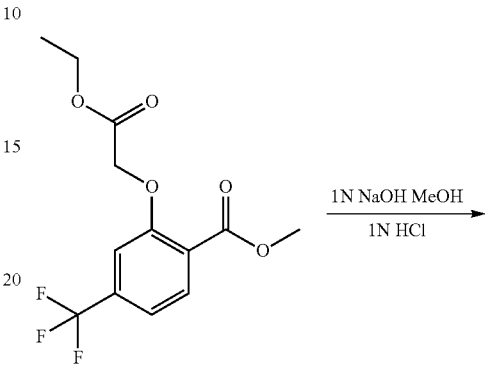

acetate=100/1 to 3/1, Plate 1, PE:EA=3:1, Rf=0.43). Compound 17-2 (135 g, 441 mmol, 97.1% yield) was obtained as colorless oil.

H NMR: (400 MHz, CDCl$_3$) δ 7.92 (d, J=8.0 Hz, 1H), 7.33-7.31 (m, 1H), 7.10 (s, 1H), 4.76 (s, 2H), 4.29 (q, J=14.4 Hz, 2H), 3.94 (s, 3H), 1.30 (t, J=7.2 Hz, 3H).

Step 2: Synthesis of Compound 17-3

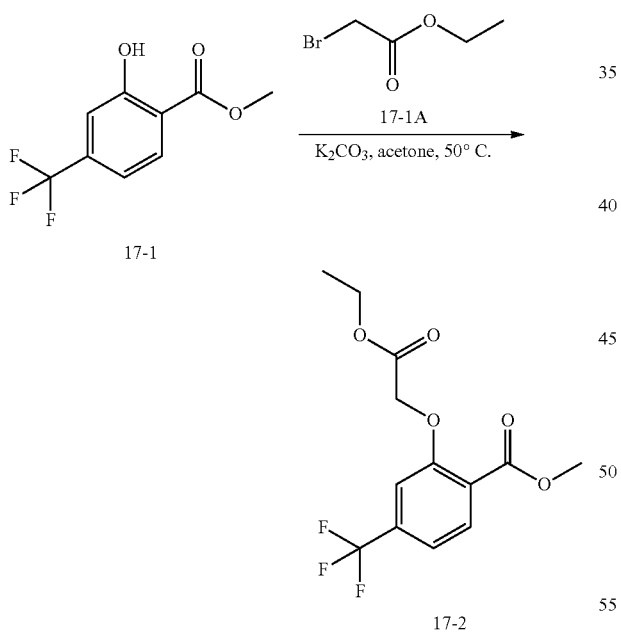

To a solution of compound 17-2 (135 g, 441 mmol, 1.00 eq) in MeOH (200 mL) was added NaOH (4 M, 355 mL, 3.00 eq). The mixture was stirred at 20° C. for 2 hrs. LC-MS showed compound 17-2 was consumed completely and one main peak with desired m/z was detected. The reaction mixture was concentrated under reduced pressure to give a residue. The aqueous phase was acidified to pH=3 with 1M HCl, the appeared solid was filtered and dried to give a residue. The crude product compound 17-3 (100 g, 379 mmol, 85.9% yield) as white solid was used into the next step without further purification.

Step 3: Synthesis of Compound 17-4

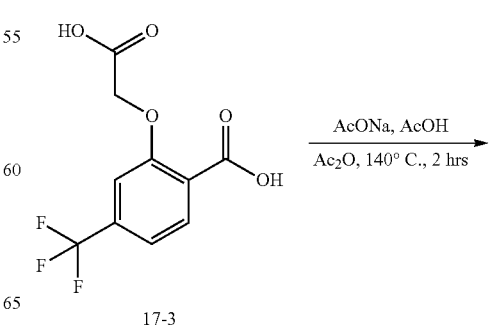

To a solution of compound 17-1 (100 g, 454 mmol, 1.00 eq) in acetone (500 mL) was added K$_2$CO$_3$ (89.2 g, 645 mmol, 1.42 eq) and compound 17-1A (114 g, 681 mmol, 1.50 eq). The mixture was stirred at 60° C. for 12 hrs. TLC (PE:EtOAc=3:1) indicated compound 17-1 was consumed, and one major new spot with larger polarity was detected. The reaction mixture was filtered and concentrated under reduced pressure to give a residue. The residue was purified by column chromatography (SiO$_2$, Petroleum ether/Ethyl -continued

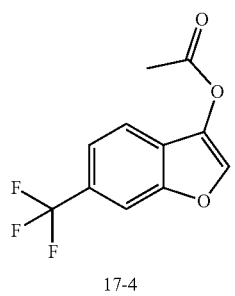

17-4

To a solution of compound 17-3 (100 g, 379 mmol, 1.00 eq) in Ac₂O (400 mL) was added AcOH (83.1 g, 1.38 μmol, 79.2 mL, 3.65 eq) and NaOAc (34.7 g, 422 mmol, 1.12 eq). The mixture was stirred at 140° C. for 2 hrs. LC-MS showed compound 17-3 was consumed completely and one main peak with desired m/z was detected. The reaction mixture was diluted with water 1000 mL and extracted with EtOAc 1500 mL (500 mL*3). The combined organic layers were washed with brine 2000 mL (1000 mL*2), dried over Na₂SO₄, filtered and concentrated under reduced pressure to give a residue. The crude product compound 17-4 (77.0 g, 315 mmol, 83.2% yield) as yellow solid was used into the next step without further purification.

H NMR: (400 MHz, CDCl₃) δ 8.17 (s, 1H), 7.76 (s, 1H), 7.68 (d, J=8.0 Hz, 1H), 7.54 (d, J=8.0 Hz, 1H), 2.41 (s, 3H).

Step 4: Synthesis of Compound 17-5

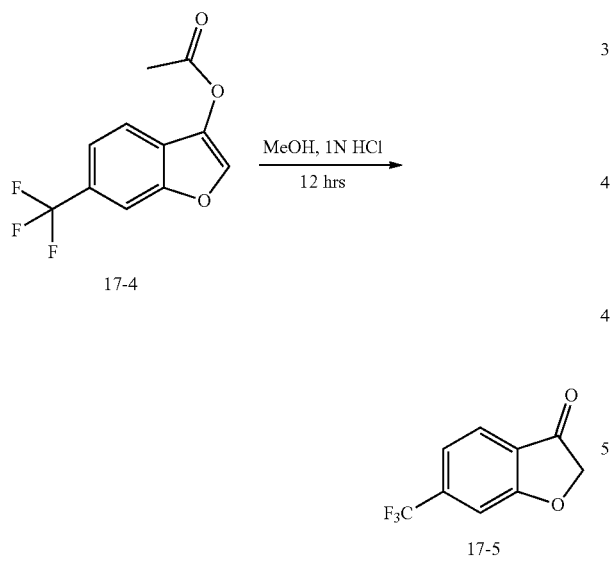

To a solution of compound 17-4 (77.0 g, 315 mmol, 1.00 eq) in MeOH (500 mL) and H₂O (250 mL) was added HCl (1 M, 88.2 mL, 0.28 eq). The mixture was stirred at 100° C. for 12 hrs. LC-MS showed compound 17-4 was consumed completely and one main peak with desired m/z was detected. The reaction mixture was concentrated under reduced pressure to give a residue. Compound 17-5 (50.0 g, 173 mmol, 70% purity, 55.0% yield) was obtained as red solid.

H NMR: (400 MHz, CDCl₃) δ 7.80 (d, J=8.0 Hz, 1H), 7.43 (s, 1H), 7.35 (d, J=8.0 Hz, 1H), 4.73 (s, 2H).

Step 5: Synthesis of Compound 17-6

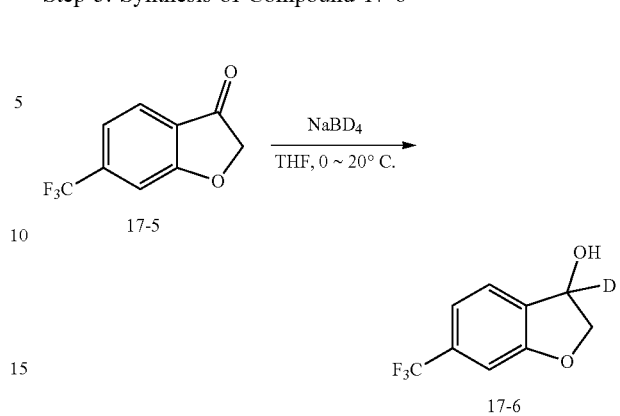

To a solution of compound 17-5 (5.00 g, 24.7 mmol, 1.00 eq) in MeOH (50.0 mL) was added NaBD₄ (1.03 g, 27.2 mmol, 1.10 eq) at 0° C. The mixture was stirred at 25° C. for 1 hr. LC-MS showed compound 17-5 was consumed completely and one main peak with desired m/z was detected. The reaction mixture was concentrated under reduced pressure to give a residue. The residue was purified by prep-HPLC (FA condition; column: Phenomenex luna C18 (250*70 mm, 10 um); mobile phase: [water (FA)-ACN]; gradient: 25%-55% B over 22 min). Compound 17-6 (3.00 g, 14.6 mmol, 59.1% yield) was obtained as light yellow solid.

H NMR: (400 MHz, CDCl₃) δ 7.53 (d, J=7.6 Hz, 1H), 7.24-7.22 (m, 1H), 7.14 (s, 1H), 4.66-4.51 (m, 2H).

Step 6: Synthesis of Compound 17-7

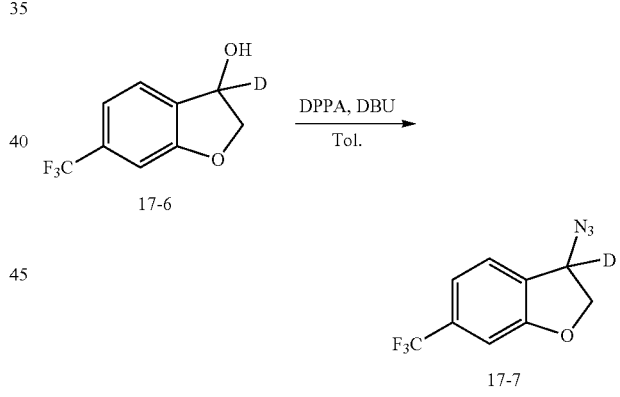

To a solution of compound 17-6 (3.00 g, 14.6 mmol, 1.00 eq) in toluene (45.0 mL) under N₂ were added DPPA (4.43 g, 16.1 mmol, 3.47 mL, 1.10 eq) and a solution of DBU (2.45 g, 16.1 mmol, 2.42 mL, 1.10 eq) in toluene (5.00 mL) dropwise at 0° C. over a period of 30 min. The mixture was stirred at 25° C. for 12 hrs. TLC (PE:EtOAc=5:1) indicated compound 17-6 was consumed, and one major new spot with lower polarity was detected. The reaction mixture was diluted with water 100 mL and extracted with EtOAc 300 mL (100 mL*3). The combined organic layers were washed with brine 300 mL (150 mL*2), dried over Na₂SO₄, filtered and concentrated under reduced pressure to give a residue. The residue was purified by column chromatography (SiO₂, Petroleum ether/Ethyl acetate=100/1 to 5/1, PE:EtOAc=5:1, Rf=0.43). Compound 17-7 (2.00 g, 8.69 mmol, 59.4% yield) was obtained as yellow oil.

H NMR: (400 MHz, CDCl₃) δ 7.52 (d, J=8.0 Hz, 1H), 7.28-7.26 (m, 1H), 7.17 (s, 1H), 4.67-4.56 (m, 2H).

Step 7: Synthesis of Compound 17-8

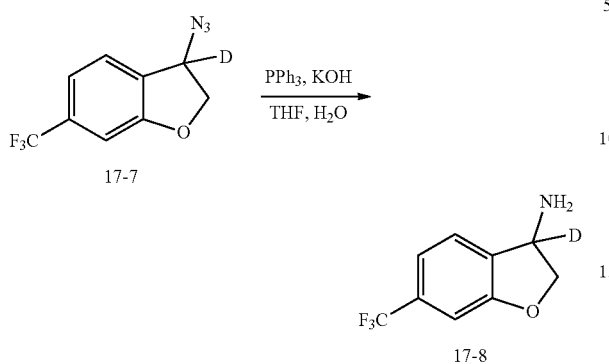

To a solution of compound 17-7 (2.00 g, 8.69 mmol, 1.00 eq) in THF (20.0 mL) under N₂ were added PPh₃ (3.42 g, 13.0 mmol, 1.50 eq) and stirred at 20° C. for 1 hrs. Then a solution of KOH (1.22 g, 21.7 mmol, 2.50 eq) in H₂O (5.00 mL) was added and stirred at 20° C. for another 12 hrs. LC-MS showed compound 17-7 was consumed completely and one main peak with desired m/z was detected. The reaction mixture was diluted with water 10.0 mL and extracted with EtOAc 30.0 mL (10.0 mL*3). The combined organic layers were washed with brine 30.0 mL (15.0 mL*2), dried over Na₂SO₄, filtered and concentrated under reduced pressure to give a residue. The residue was purified by column chromatography (SiO₂, Petroleum ether/Ethyl acetate=100/1 to 0/1, Plate 1, PE:EtOAc=0:1, Rf=0.11). Compound 17-8 (1.00 g, 4.90 mmol, 56.4% yield) was obtained as white solid.

Step 8: Synthesis of Compound 17-9

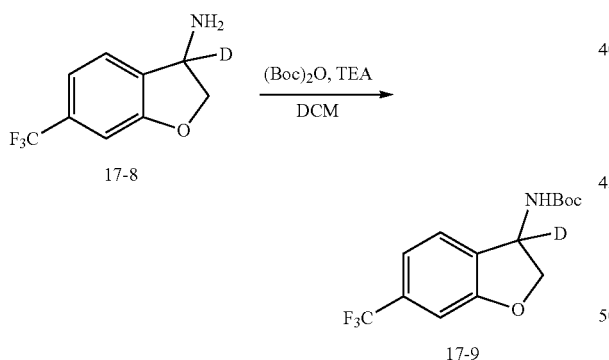

To a solution of compound 17-8 (1.00 g, 4.90 mmol, 1.00 eq) in DCM (20.0 mL) was added TEA (0.993 g, 9.80 mmol, 2.00 eq) and Boc₂O (1.28 g, 5.88 mmol, 1.20 eq). The mixture was stirred at 25° C. for 0.5 hrs. LC-MS showed compound 17-8 was consumed completely and one main peak with desired m/z was detected. The reaction mixture was concentrated under reduced pressure to give a residue. The residue was purified by column chromatography (SiO₂, Petroleum ether/Ethyl acetate=100/1 to 5/1, Plate 1, PE:EA=5:1, Rf=0.41). Compound 17-9 (1.00 g, 3.29 mmol, 67.1% yield) was obtained as white solid.

H NMR: (400 MHz, CDCl₃) δ 7.45 (d, J=7.6 Hz, 1H), 7.20 (d, J=7.6 Hz, 1H), 7.08 (s, 1H), 4.88 (brs, 1H), 4.75 (d, J=10.4 Hz, 1H), 4.40 (d, J=10.0 Hz, 1H), 1.47 (s, 9H).

Step 9: Synthesis of Compound 17-10

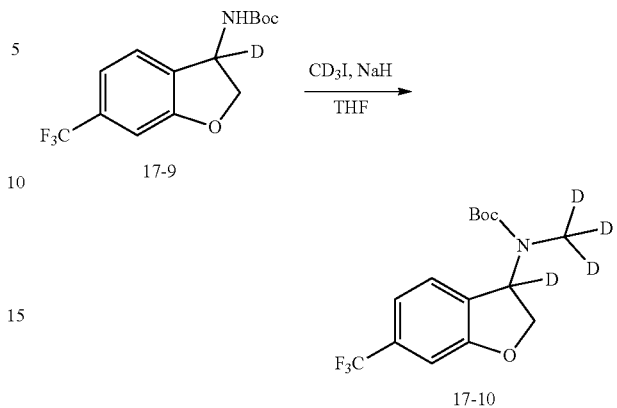

To a solution of compound 17-9 (1.00 g, 3.29 mmol, 1.00 eq) in THF (100 mL) was added NaH (197 mg, 4.93 mmol, 60% purity, 1.50 eq) at 0° C., the mixture was stirred at 0° C. for 0.5 hr. Then CD₃I (476 mg, 3.29 mmol, 205 μL, 1.00 eq) was added to the mixture. The mixture was stirred at 25° C. for another 1 hr. LC-MS showed compound 17-9 was consumed completely and one main peak with desired m/z was detected. The reaction mixture was diluted with water 100 mL and extracted with EA 300 mL (100 mL*3). The combined organic layers were washed with brine 300 mL (150 mL*2), dried over Na₂SO₄, filtered and concentrated under reduced pressure to give a residue. The residue was purified by column chromatography (SiO₂, Petroleum ether/ Ethyl acetate=100/1 to 5/1, PE:EtOAc=5:1, Rf=0.40). Compound 17-10 (550 mg, 1.71 mmol, 52.1% yield) was obtained as colorless oil.

H NMR: (400 MHz, CDCl₃) δ 7.34 (d, J=6.8 Hz, 1H), 7.20 (d, J=8.0 Hz, 1H), 7.08 (s, 1H), 4.68 (d, J=10.0 Hz, 1H), 4.44 (d, J=10.0 Hz, 1H), 1.50 (s, 9H).

Step 10: Synthesis of Compound 17-11

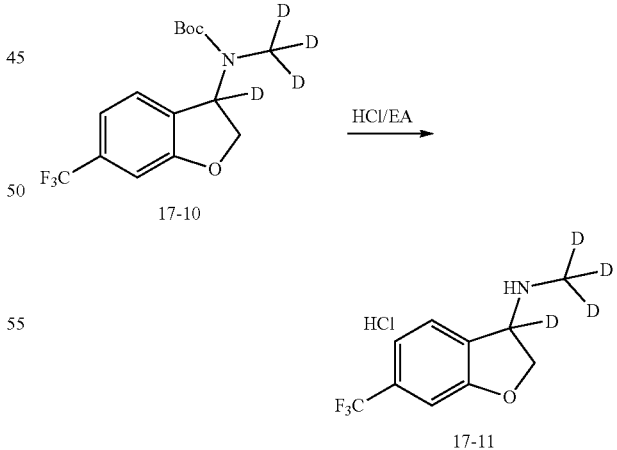

To a solution of compound 17-10 (550 mg, 1.71 mmol, 1.00 eq) in DCM (5.00 mL) was added HCl/EtOAc (2 M, 20.0 mL, 25.0 eq). The mixture was stirred at 20° C. for 1 hr. LC-MS showed compound 17-10 was consumed completely and one main peak with desired m/z was detected. The reaction mixture was concentrated under reduced pressure to give a residue. The crude product compound 17-11 (400 mg, 1.55 mmol, 90.7% yield, HCl) as white solid was used into the next step without further purification.

Step 11: Synthesis of Compounds 21 and 22

Step 12: Synthesis of Compounds 17 and 18

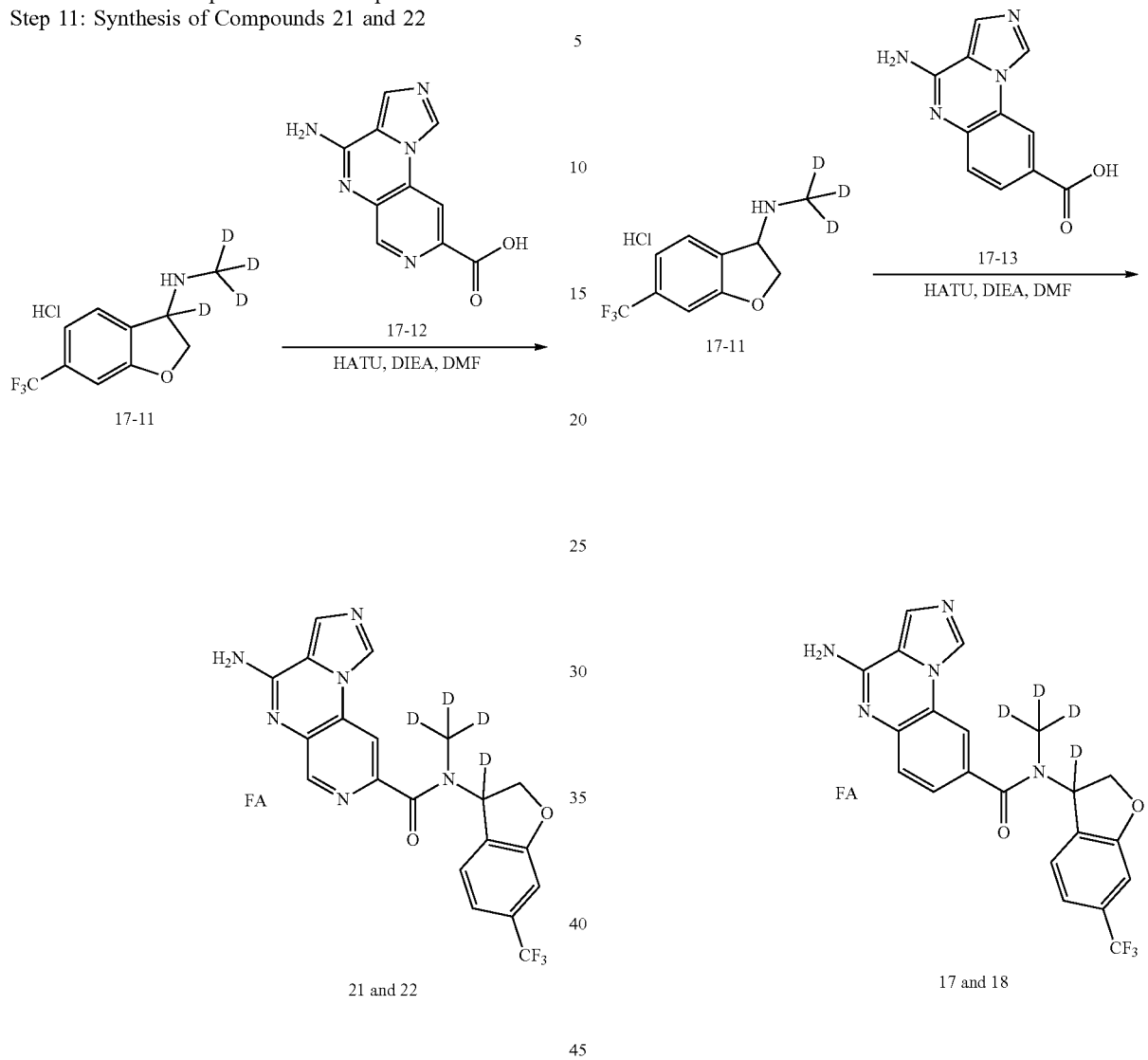

To a solution of compound 17-12 (80.0 mg, 349 µmol, 1.00 eq) and compound 17-11 (89.9 mg, 349 µmol, 1.00 eq, HCl) in DMF (3.00 mL) was added HATU (159 mg, 419 µmol, 1.20 eq) and DIEA (226 mg, 1.75 mmol, 5.00 eq). The mixture was stirred at 25° C. for 0.5 hrs. LC-MS showed compound 17-12 was consumed completely and one main peak with desired m/z was detected. The reaction mixture was diluted with (30.0 mL) and extracted with EtOAc 60.0 mL (20.0 mL*3). The combined organic layers were washed with brine 30.0 mL (15.0 mL*2), dried over $Na_2SO_4$, filtered and concentrated under reduced pressure to give a residue. The residue was purified by prep-HPLC (FA condition; column: Phenomenex luna C18 150*25 mm*10 um; mobile phase: [water (FA)-ACN]; gradient: 28%-58% B over 10 min). Mixture of Compounds 21 and 22 (60.0 mg, 125 µmol, 35.9% yield, FA) was obtained as white solid.

To a solution of compound 17-13 (80.0 mg, 351 µmol, 1.00 eq) and compound 17-11 (90.3 mg, 351 µmol, 1.00 eq, HCl) in DMF (3.00 mL) was added HATU (160 mg, 421 µmol, 1.20 eq) and DIEA (227 mg, 1.75 mmol, 5.00 eq). The mixture was stirred at 25° C. for 0.5 hrs. LC-MS showed compound 17-13 was consumed completely and one main peak with desired m/z was detected. The reaction mixture was diluted with (30.0 mL) and extracted with EtOAc 60.0 mL (20.0 mL*3). The combined organic layers were washed with brine 30.0 mL (15.0 mL*2), dried over $Na_2SO_4$, filtered and concentrated under reduced pressure to give a residue. The residue was purified by prep-HPLC (FA condition; column: Phenomenex luna C18 150*25 mm*10 um; mobile phase: [water (FA)-ACN]; gradient: 18%-48% B over 10 min). Mixture of Compounds 17 and 18 (60.0 mg, 126 µmol, 35.9% yield, FA) was obtained as white solid.

Step 13: Separation of Compounds 21 and 22

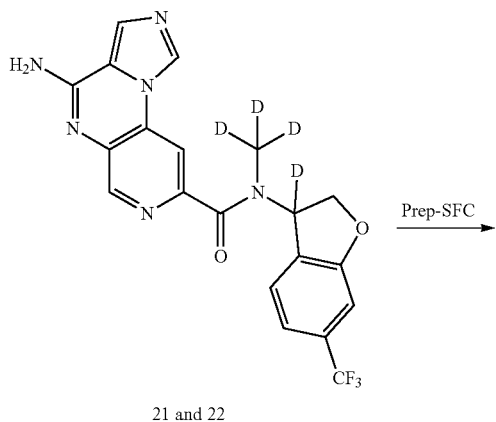

21 and 22

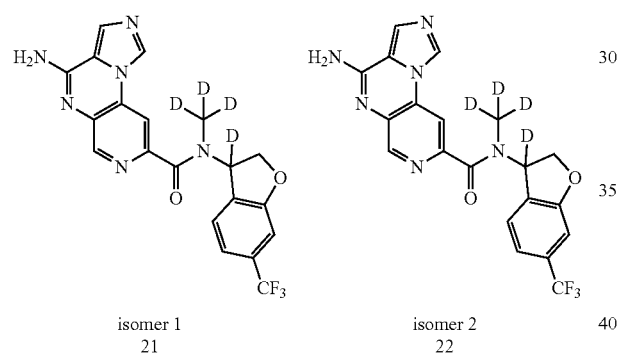

isomer 1  isomer 2
21        22

Mixture of Compounds 21 and 22 was separated by SFC (column: DAICEL CHIRALCEL OD (250 mm*30 mm, 10 um); mobile phase: [CO$_2$-EtOH]; B %: 45%, isocratic elution mode) to give Compound 21 (22.02 mg, 50.7 µmol, 40.4% yield, 99.51% purity) (Rt=1.972 min) and Compound 22 (19.47 mg, 44.2 µmol, 35.2% yield, 98.15% purity) (Rt=2.213 min). Compound 21 was purified by prep-HPLC (Base condition; column: Waters Xbridge C18 150*25 mm*5 um; mobile phase: [water (ammonia hydroxide v/v)-ACN]; gradient: 27%-57% B over 10 min). Compound 22 was purified by prep-HPLC (Base condition; column: Waters Xbridge C18 150*25 mm*5 um; mobile phase: [water (ammonia hydroxide v/v)-ACN]; gradient: 27%-57% B over 10 min). Compound 21 (22.02 mg, 50.7 µmol, 40.4% yield, 99.51% purity) was obtained. Compound 22 (19.47 mg, 44.2 µmol, 35.2% yield, 98.15% purity) was obtained.

H NMR of Compound 21 (400 MHz, DMSO-d$_6$) δ 9.32-9.30 (m, 1H), 8.70-8.65 (m, 1H), 8.56-8.50 (m, 1H), 7.99-7.98 (m, 1H), 7.76-7.56 (m, 3H), 7.36-7.25 (m, 2H), 4.88-4.68 (m, 2H).

H NMR of Compound 22 (400 MHz, DMSO-d$_6$) δ 9.32-9.30 (m, 1H), 8.70-8.65 (m, 1H), 8.56-8.51 (m, 1H), 7.99-7.98 (m, 1H), 7.76-7.56 (m, 3H), 7.35-7.25 (m, 2H), 4.88-4.68 (m, 2H).

Step 14: Separation of Compounds 17 and 18

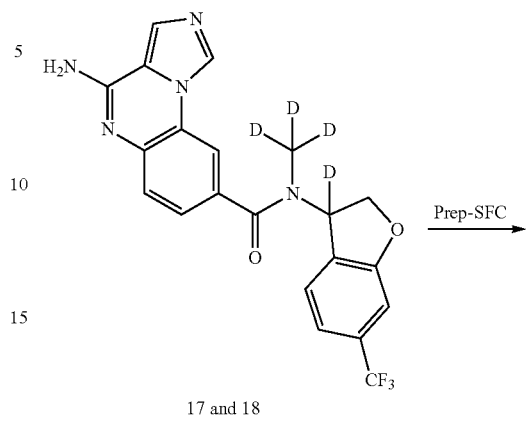

17 and 18

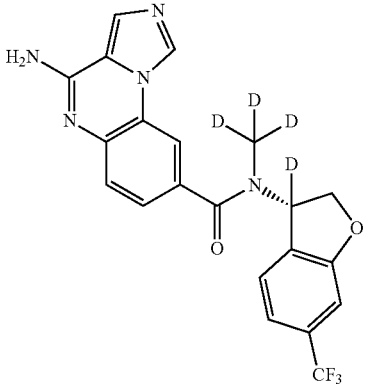

17

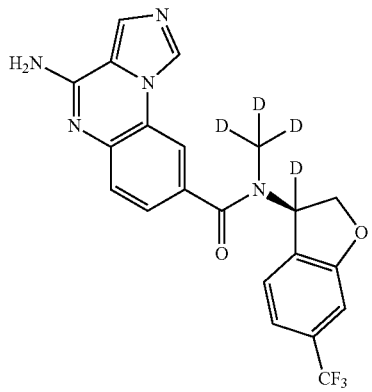

18

Mixture of Compounds 17 and 18 was separated by SFC (column: DAICEL CHIRALCEL OJ (250 mm*30 mm, 10 um); mobile phase: [CO$_2$-EtOH (0.1% NH$_3$H$_2$O)]; B %: 35%, isocratic elution mode) to give Compound 17 (18.98 mg, 43.6 µmol, 34.7% yield, 99.07% purity) (Rt=1.852 min) and Compound 18 (25.69 mg, 58.8 µmol, 46.8% yield, 98.77% purity) (Rt=2.050 min). Compound 17 was purified by prep-HPLC (Neu condition; column: Waters Xbridge C18 150*50 mm*10 um; mobile phase: [water (NH$_4$HCO$_3$)-ACN]; gradient: 24%-54% B over 10 min). Compound 18 was purified by prep-HPLC (Neu condition; column: Waters Xbridge C18 150*50 mm*10 um; mobile phase: [water (NH$_4$HCO$_3$)-ACN]; gradient: 24%-54% B over 10 min). Compound 17 (18.98 mg, 43.6 µmol, 34.7% yield, 99.07% purity) was obtained. Compound 18 (25.69 mg, 58.8 µmol, 46.8% yield, 98.77% purity) was obtained.

H NMR of Compound 17 (400 MHz, DMSO-d$_6$) δ 9.18 (s, 1H), 8.33 (s, 1H), 7.91 (s, 1H), 7.65-7.63 (m, 1H), 7.50-7.45 (m, 4H), 7.35-7.26 (m, 2H), 4.84-4.70 (m, 2H).

H NMR of Compound 18 (400 MHz, DMSO-d$_6$) δ 9.18 (s, 1H), 8.33 (s, 1H), 7.91 (s, 1H), 7.65-7.63 (m, 1H), 7.48-7.45 (m, 4H), 7.34-7.26 (m, 2H), 4.85-4.70 (m, 2H).

Example 16: Synthesis of Compound 23

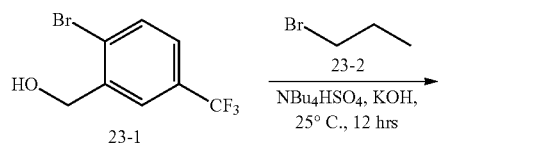
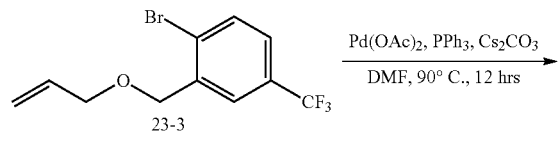
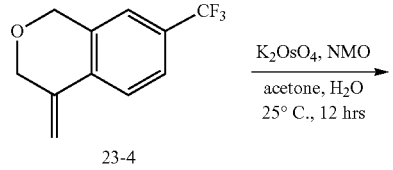
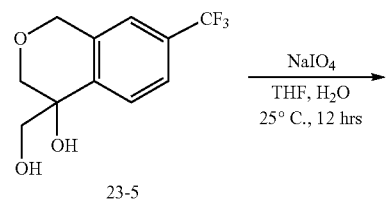
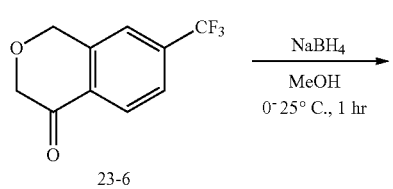
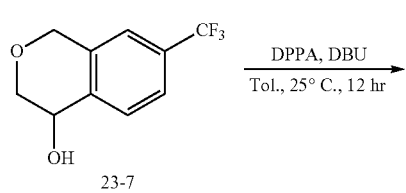
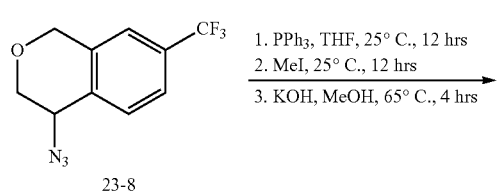
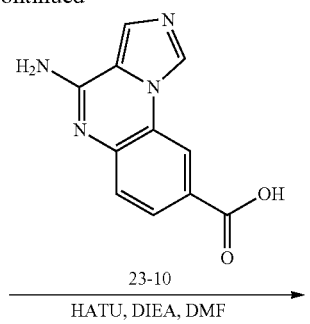
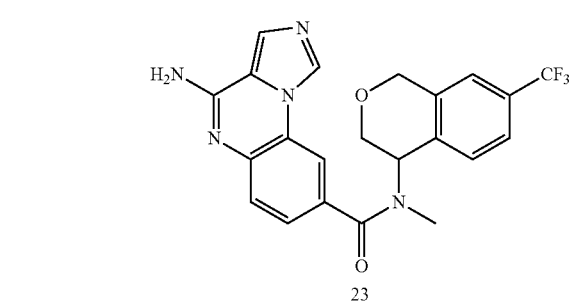

Step 1: Synthesis of Compound 23-3

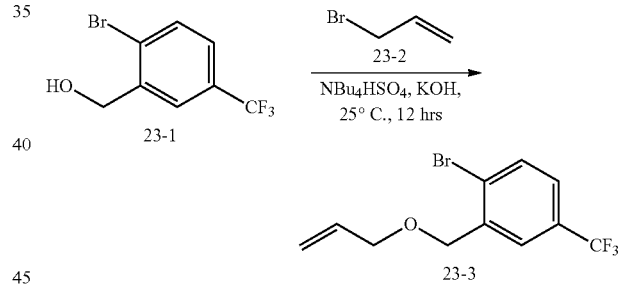

To a solution of compound 23-1 (10.0 g, 39.1 mmol, 1.00 eq) in DCM (120 mL) was added compound 23-2 (4.74 g, 39.1 mmol, 1.00 eq), hydrogen sulfate; tetrabutylammonium (2.00 g, 5.88 mmol, 0.150 eq) and KOH (4.18 g, 74.5 mmol, 1.90 eq). The mixture was stirred at 25° C. for 2 hrs. TLC (Plate 1, PE:EtOAc=10:1) indicated compound 23-1 was consumed, and one major new spot with lower polarity was detected. The reaction mixture was diluted with water 200 mL and extracted with DCM 300 mL (100 mL*3). The combined organic layers were washed with brine 300 mL (150 mL*2), dried over Na$_2$SO$_4$, filtered and concentrated under reduced pressure to give a residue. The residue was purified by column chromatography (SiO$_2$, Petroleum ether/Ethyl acetate=100/1 to 5/1, Plate 1, PE:EA=10:1, Rf=0.60). Compound 23-3 (10.0 g, 33.9 mmol, 86.7% yield) was obtained as colorless oil.

H NMR: (400 MHz, CDCl$_3$) δ 7.80 (d, J=1.2 Hz, 1H), 7.66 (d, J=8.4 Hz, 1H), 7.42-7.40 (m, 1H), 6.04-5.96 (m, 1H), 5.40-5.26 (m, 2H), 4.60 (s, 2H), 4.17-4.15 (m, 2H).

Step 2: Synthesis of Compound 23-4

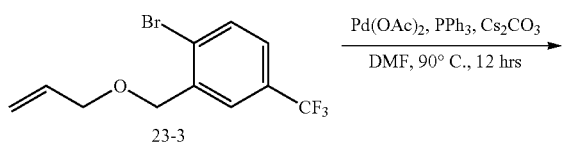

A mixture of compound 23-3 (10.0 g, 33.9 mmol, 1.00 eq), Pd(OAc)$_2$ (1.14 g, 5.08 mmol, 0.150 eq), PPh$_3$ (4.00 g, 15.3 mmol, 0.450 eq) and Cs$_2$CO$_3$ (13.3 g, 40.7 mmol, 1.20 eq) in DMF (200 mL) was degassed and purged with N$_2$ for 3 times, and then the mixture was stirred at 90° C. for 12 hrs under N$_2$ atmosphere. TLC (Plate 1, PE:EtOAc=10:1) indicated compound 23-3 was consumed, and one major new spot with larger polarity was detected. The reaction mixture was filtered and the filterate was diluted with water 200 mL and extracted with EtOAc 600 mL (200 mL*3). The combined organic layers were washed with brine 300 mL (150 mL*2), dried over Na$_2$SO$_4$, filtered and concentrated under reduced pressure to give a residue. The residue was purified by column chromatography (SiO$_2$, Petroleum ether/Ethyl acetate=100/1 to 5/1, Plate 1, PE:EA=10:1, Rf=0.43). Compound 23-4 (6.00 g, 28.0 mmol, 82.7% yield) was obtained as yellow oil.

H NMR: (400 MHz, CDCl$_3$) δ 7.79 (d, J=8.4 Hz, 1H), 7.49 (d, J=8.0 Hz, 1H), 7.31 (s, 1H), 5.73 (s, 1H), 5.16 (s, 1H), 4.85 (s, 2H), 4.48 (s, 2H).

Step 3: Synthesis of Compound 23-5

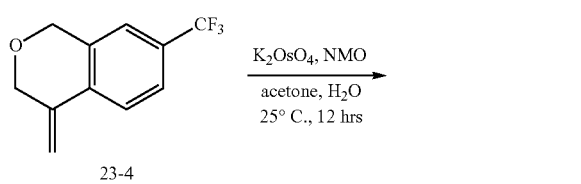

To a solution of compound 23-4 (6.00 g, 28.0 mmol, 1.00 eq) in acetone (60.0 mL) and H$_2$O (12.0 mL) was added K$_2$O$_5$O$_4$·2H$_2$O (1.03 g, 2.80 mmol, 0.100 eq) and NMO (11.5 g, 98.1 mmol, 10.4 mL, 3.50 eq) and then degassed and purged with N$_2$ for 3 times, and then the mixture was stirred at 25° C. for 12 hrs under N$_2$ atmosphere. TLC (PE: EtOAc=3:1) indicated compound 23-4 was consumed, and one major new spot with larger polarity was detected. The reaction mixture was quenched by Na$_2$SO$_3$ (Sat.) 100 mL and then extracted with EtOAc 600 mL (200 mL*3). The combined organic layers were washed with brine 300 mL (150 mL*2), dried over Na$_2$SO$_4$, filtered and concentrated under reduced pressure to give a residue. The residue was purified by column chromatography (SiO$_2$, Petroleum ether/Ethyl acetate=100/1 to 5/1, PE: EtOAc=3:1, Rf=0.27). Compound 23-5 (4.00 g, 16.2 mmol, 57.7% yield) was obtained as white solid.

H NMR: (400 MHz, CDCl$_3$) δ 7.72 (d, J=8.4 Hz, 1H), 7.55 (d, J=8.0 Hz, 1H), 7.28 (s, 1H), 4.83 (s, 2H), 4.17 (d, J=11.2 Hz, 1H), 3.90 (d, J=11.2 Hz, 1H), 3.71-3.62 (m, 2H), 2.95 (s, 1H), 2.35 (brs, 1H).

Step 4: Synthesis of Compound 23-6

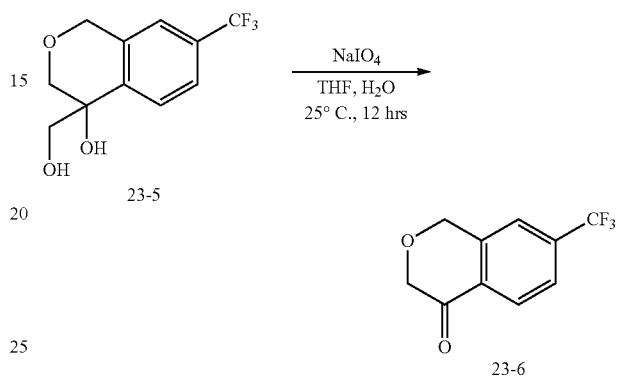

To a solution of compound 23-5 (4.00 g, 16.2 mmol, 1.00 eq) in THF (90.0 mL) was added NaIO$_4$ (14.7 g, 68.5 mmol, 3.80 mL, 3.40 eq) and H$_2$O (3.00 mL), then degassed and purged with N$_2$ for 3 times, and then the mixture was stirred at 25° C. for 12 hrs under N$_2$ atmosphere. TLC (PE: EtOAc=3:1) indicated compound 23-5 was consumed, and one major new spot with lower polarity was detected. LC-MS showed compound 23-5 was consumed completely and one main peak with desired m/z was detected. The reaction mixture was filtered and washed with EtOAc 100 mL*2, then the filtrate was washed with NaHCO$_3$ (Sat.) 200 mL and brine 200 mL, dried over Na$_2$SO$_4$, filtered and concentrated under reduced pressure to give a residue. The residue was purified by column chromatography (SiO$_2$, Petroleum ether/Ethyl acetate=100/1 to 5/1, PE:EA=3:1, Rf=0.48). Compound 23-6 (3.00 g, 13.9 mmol, 86.0% yield) was obtained as white solid.

H NMR: (400 MHz, CDCl$_3$) δ 8.17 (d, J=8.0 Hz, 1H), 7.69 (d, J=8.0 Hz, 1H), 7.52 (s, 1H), 4.96 (s, 2H), 4.43 (s, 2H).

Step 5: Synthesis of Compound 23-7

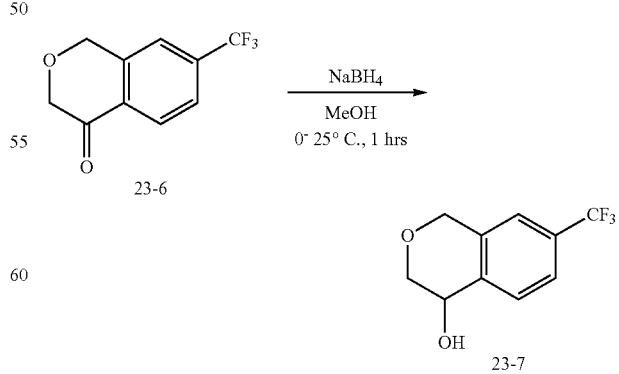

To a solution of compound 23-6 (3.00 g, 13.9 mmol, 1.00 eq) in MeOH (50.0 mL) was added NaBH$_4$ (683 mg, 18.0 mmol, 1.30 eq) in portions at 0° C., then the mixture was stirred at 25° C. for 1 hr. TLC (PE:EtOAc=3:1) indicated compound 23-6 was consumed, and one major new spot with larger polarity was detected. The reaction mixture was filtered concentrated under reduced pressure to remove MeOH. Then diluted with brine 50.0 mL, extracted with DCM 100 mL (50.0 mL*2), the organic layers were dried over Na₂SO₄, filtered and concentrated under reduced pressure to give a residue. Compound 23-7 (3.00 g, 13.8 mmol, 99.1% yield) was obtained as colorless oil.

H NMR: (400 MHz, CDCl₃) δ 7.61-7.54 (m, 2H), 7.30 (s, 1H), 4.87-4.71 (m, 2H), 4.63-4.61 (m, 1H), 4.13-4.09 (m, 1H), 3.94-3.90 (m, 1H), 2.38-2.36 (m, 1H).

Step 6: Synthesis of Compound 23-8

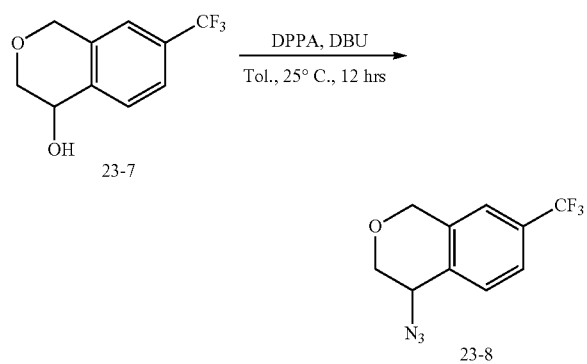

To a solution of compound 23-7 (1.50 g, 6.87 mmol, 1.00 eq) in toluene (15.0 mL) under N₂ was added DPPA (1.39 g, 5.04 mmol, 1.09 mL, 1.10 eq) and a solution of DBU (768 mg, 5.04 mmol, 760 µL, 1.10 eq) in toluene (3.00 mL) dropwise at 0° C. over a period of 30 min. The mixture was stirred at 25° C. for 12 hrs. TLC (Plate 1, PE:EtOAc=3:1) indicated compound 23-7 was consumed, and one major new spot with lower polarity was detected. The reaction mixture was diluted with water 50.0 mL and extracted with EtOAc 150 mL (50.0 mL*3). The combined organic layers were washed with brine 300 mL (150 mL*2), dried over Na₂SO₄, filtered and concentrated under reduced pressure to give a residue. The residue was purified by column chromatography (SiO₂, Petroleum ether/Ethyl acetate=100/1 to 5/1, Plate 1, PE:EtOAc=3:1, Rf=0.48). Compound 23-8 (500 mg, 2.06 mmol, 29.9% yield) was obtained as colorless oil.

H NMR: (400 MHz, CDCl₃) δ 7.59 (d, J=8.0 Hz, 1H), 7.52 (d, J=8.4 Hz, 1H), 7.37 (s, 1H), 4.93 (d, J=15.2 Hz, 1H), 4.77 (d, J=15.6 Hz, 1H), 4.27-4.21 (m, 2H), 4.03-3.99 (m, 1H).

Step 7: Synthesis of Compound 23-9

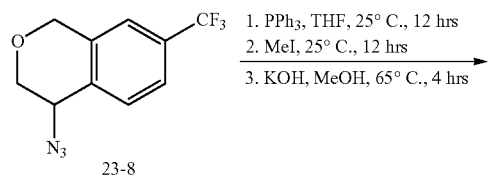

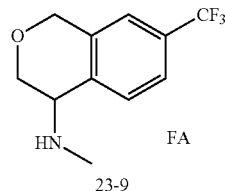

To a solution of PPh₃ (647 mg, 2.46 mmol, 2.00 eq) in THF (5.00 mL) was added and a solution of compound 23-8 (300 mg, 1.23 mmol, 1.00 eq) in THF (3.00 mL). The mixture was stirred at 25° C. for 4 hrs. Then MeI (117 mg, 1.23 mmol, 1.00 eq) was added to the mixture and stirred at 25° C. for 12 hrs. The appeared solid was filtered and washed with THF (10.0 mL) and MeOH (10.0 mL). The filtercake was suspended in MeOH (3.00 mL) and then KOH (102 mg, 1.81 mmol, 2.20 eq) was added to the mixture. The resulting mixture was stirred at 65° C. for 4 hrs. LC-MS showed compound 23-8 was consumed completely and one main peak with desired m/z was detected. The reaction mixture was concentrated under reduced pressure to give a residue. The residue was purified by prep-HPLC (FA condition; column: Phenomenex luna C18 150*25 mm*10 um; mobile phase: [water (FA)-ACN]; gradient: 0%-30% B over 10 min). Compound 23-9 (80.0 mg, 289 µmol, 23.5% yield, FA) was obtained as colorless oil.

H NMR: (400 MHz, CDCl₃) δ 7.70 (d, J=7.6 Hz, 1H), 7.57 (d, J=8.0 Hz, 1H), 7.36 (s, 1H), 4.98 (d, J=16.0 Hz, 1H), 4.77 (d, J=15.6 Hz, 1H), 4.53 (d, J=12.8 Hz, 1H), 4.11 (s, 1H), 3.88-3.84 (m, 1H), 2.59 (s, 3H).

Step 8: Synthesis of Compound 23

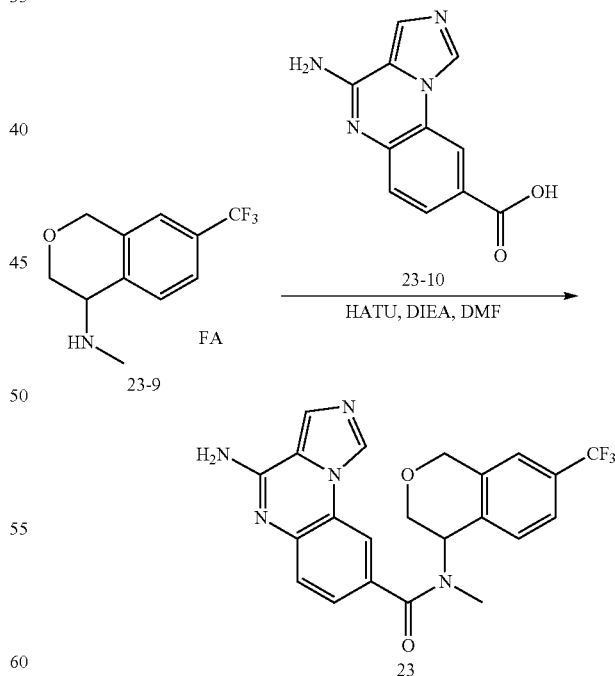

To a solution of compound 23-10 (30.0 mg, 131 µmol, 1.00 eq) and compound 23-9 (36.5 mg, 131 µmol, 1.00 eq, FA) in DMF (3.00 mL) was added HATU (60.0 mg, 158 µmol, 1.20 eq) and DIEA (85.0 mg, 657 µmol, 5.00 eq). The mixture was stirred at 25° C. for 0.5 hrs. LC-MS showed compound 23-10 was consumed completely and one main peak with desired m/z was detected. The reaction mixture was diluted with (30.0 mL) and extracted with EtOAc 60.0 mL (20.0 mL*3). The combined organic layers were washed with brine 30.0 mL (15.0 mL*2), dried over $Na_2SO_4$, filtered and concentrated under reduced pressure to give a residue. The residue was purified by prep-HPLC (Neu condition; column: Waters Xbridge C18 150*50 mm*10 um; mobile phase: [water ($NH_4HCO_3$)-ACN]; gradient: 22%-52% B over 10 min). Compound 23 (15.74 mg, 35.0 μmol, 26.6% yield, 98.11% purity) was obtained as white solid.

H NMR: (400 MHz, DMSO-$d_6$) δ 9.21-9.17 (m, 1H), 8.40-8.35 (m, 1H), 7.91 (s, 1H), 7.71-7.43 (m, 7H), 5.78 (brs, 1H), 4.93-4.67 (m, 2H), 4.17-4.08 (m, 2H), 2.75 (s, 3H).

Example 17: Synthesis of Compounds 24 and 25

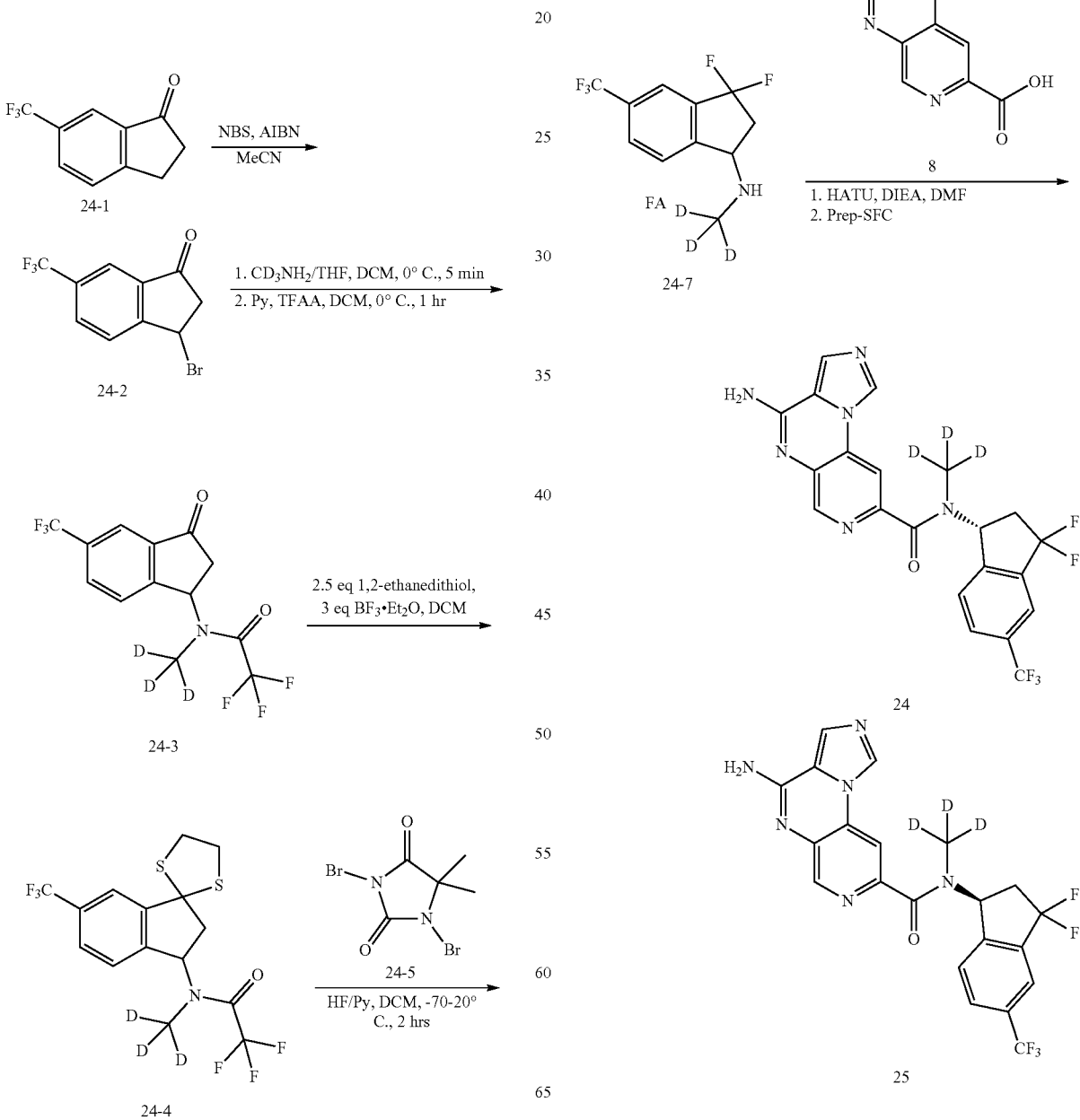

Step 1: Synthesis of Compound 24-2

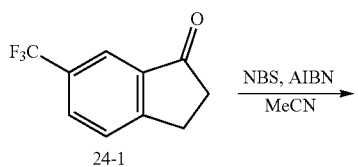

To a solution of compound 24-1 (5.00 g, 25.0 mmol, 1.00 eq) in MeCN (50.0 mL) was added AIBN (410 mg, 2.50 mmol, 0.100 eq) and NBS (4.45 g, 25.0 mmol, 1.00 eq). The mixture was stirred at 70° C. for 2 hrs. LC-MS showed compound 24-1 was consumed completely and one main peak with desired m/z was detected. The reaction mixture was cooled to 20° C., then filtered and concentrated under reduced pressure to give a residue. The residue was purified by column chromatography (SiO$_2$, Petroleum ether/Ethyl acetate=100/1 to 5/1, PE:EtOAc=3:1, Rf=0.40). Compound 24-2 (5.00 g, 17.8 mmol, 71.2% yield) was obtained as yellow oil.

H NMR: (400 MHz, CDCl$_3$) δ 8.04 (s, 1H), 7.97-7.95 (m, 1H), 7.87-7.85 (m, 1H), 5.63-5.60 (m, 1H), 3.48-3.42 (m, 1H), 3.15-3.10 (m, 1H).

Step 2: Synthesis of Compound 24-3

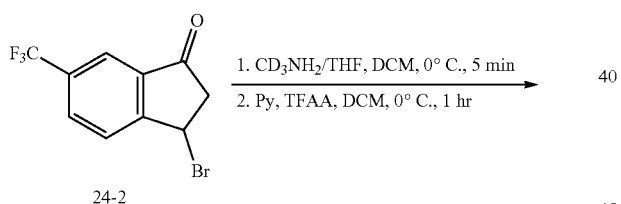

To a solution of compound 24-2 (5.00 g, 17.8 mmol, 1.00 eq) in DCM (50.0 mL) was added CD$_3$NH$_2$·HCl (3.79 g, 53.4 mmol, 3.00 eq). The mixture was stirred at 20° C. for 5 mins. Then Py (2.84 g, 35.6 mmol, 2.00 eq) was added to the mixture, followed by a solution of TFAA (5.64 g, 26.7 mmol, 1.50 eq) in DCM (20.0 mL) was added to the mixture at 0° C. and stirred at 0° C. for another 0.5 hrs. LC-MS showed compound 24-2 was consumed completely and one main peak with desired m/z was detected. The reaction mixture was concentrated under reduced pressure to give a residue. The residue was purified by column chromatography (SiO$_2$, Petroleum ether/Ethyl acetate=100/1 to 5/1, PE:EtOAc=3:1, Rf=0.40). Compound 24-3 (2.00 g, 6.10 mmol, 34.2% yield) was obtained as yellow oil.

H NMR: (400 MHz, CDCl$_3$) δ 8.13-8.11 (m, 1H), 8.02-7.96 (m, 1H), 7.69-7.62 (m, 1H), 6.40-6.37 (m, 0.6H), 5.84-5.81 (m, 0.3H), 3.25-3.17 (m, 1H), 2.81-2.67 (m, 1H).

Step 3: Synthesis of Compound 24-4

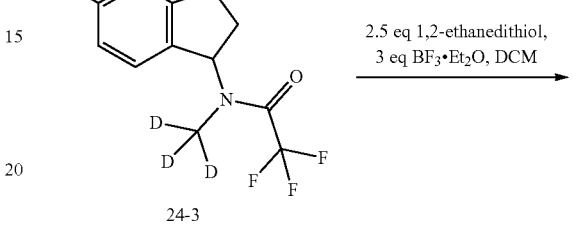

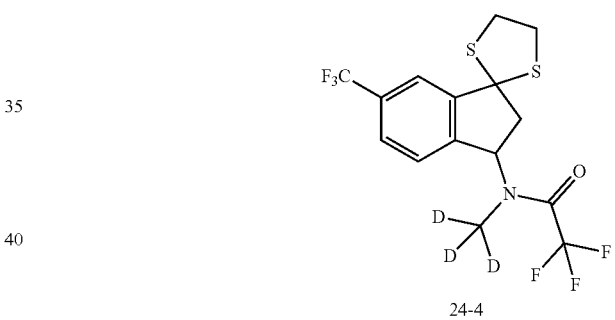

To a solution of compound 24-3 (2.00 g, 6.10 mmol, 1.00 eq) and 1,2-ethanedithiol (1.81 g, 19.2 mmol, 3.15 eq) in DCM (50.0 mL) was added BF$_3$·Et$_2$O (2.59 g, 18.3 mmol, 2.25 mL, 3.00 eq) at −15° C. The mixture was stirred at −15° C. for 2 hrs and warmed to 20° C. and stirred for another 2 hrs. LC-MS showed compound 24-3 was consumed completely and one main peak with desired m/z was detected. The reaction mixture was quenched by NaHCO$_3$ (Sat.) 100 mL and extracted with DCM 300 mL (100 mL*3). The combined organic layers were washed with brine 300 mL (150 mL*2), dried over Na$_2$SO$_4$, filtered and concentrated under reduced pressure to give a residue. The residue was purified by column chromatography (SiO$_2$, Petroleum ether/Ethyl acetate=100/1 to 5/1, PE:EtOAc=5:1, Rf=0.37). Compound 24-4 (2.00 g, 4.95 mmol, 81.1% yield) was obtained as yellow oil.

H NMR: (400 MHz, DMSO-d$_6$) δ 7.90-7.89 (m, 1H), 7.63-7.58 (m, 1H), 7.24-7.17 (m, 1H), 6.28-6.24 (m, 0.6H), 5.67-5.64 (m, 0.4H), 3.68-3.57 (m, 3H), 3.46-3.40 (m, 1H), 3.18-3.09 (m, 1H), 2.82-2.67 (m, 1H).

Step 4: Synthesis of Compound 24-6

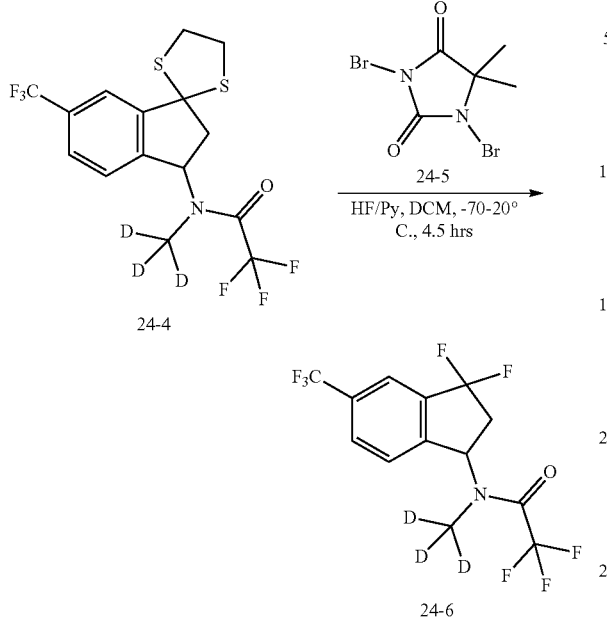

To a solution of HF/Pyridine (5.60 g, 39.6 mmol, 5.09 mL, 70.0% purity, 8.00 eq) in DCM (60.0 mL) was added compound 24-5 (5.66 g, 19.8 mmol, 4.00 eq) in DCM (20.0 mL) at −70° C. under N₂. The mixture was stirred at −70° C. for 30 min under N₂. Then a solution of compound 24-4 (2.00 g, 4.95 mmol, 1.00 eq) in DCM (20.0 mL) was added to the mixture. The mixture was stirred at −70° C. for further 1 hr and at 20° C. for another 3 hrs. TLC (Petroleum ether:Ethyl acetate=3:1, R$_f$(P1)=0.800) showed the starting material was consumed completely and there was a new spot with lower polarity. The reaction mixture was quenched by addition sat. aq. NaHCO₃ (50.0 mL) at 0° C., and then extracted with DCM 100 mL (50.0 mL*2). The combined organic layers were dried over anhydrous Na₂SO₄, filtered and concentrated under reduced pressure to give a residue. The residue was purified by prep-TLC (Petroleum ether: Ethyl acetate=3:1, R$_f$(P1)=0.800). Compound 24-6 (600 mg, 1.71 mmol, 34.6% yield) was obtained as yellow oil, confirmed by H NMR and F NMR.

H NMR: (400 MHz, CDCl₃) δ 7.94-7.93 (m, 1H), 7.89-7.84 (m, 1H), 7.47-7.41 (m, 1H), 6.36-6.31 (m, 0.6H), 5.74-5.70 (m, 0.3H), 3.20-3.08 (m, 1H), 2.74-2.53 (m, 1H).

Step 5: Synthesis of Compound 24-7

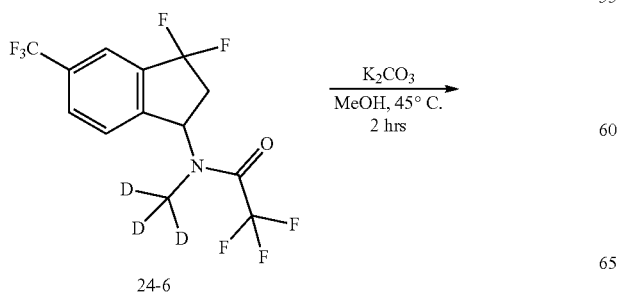

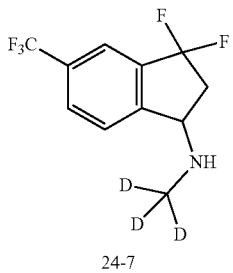

To a solution of compound 24-6 (300 mg, 857 μmol, 1.00 eq) in MeOH (5.00 mL) was added K₂CO₃ (355 mg, 2.57 mmol, 3.00 eq). Then the mixture was stirred at 45° C. for 2 hrs. LC-MS showed there was desired mass. The mixture was concentrated under reduced pressure to give a residue. The residue was purified by prep-HPLC (FA condition, column: Phenomenex luna C18 150*25.0 mm*10.0 um; mobile phase: [water (FA)-ACN]; gradient: 6.00%-26.0% B over 10 min). Then the mixture was concentrated under reduced pressure to give the product. Compound 24-7 (160 mg, 533 μmol, 62.2% yield, FA) was obtained as a yellow solid, confirmed by H NMR and F NMR.

H NMR: (400 MHz, CDCl₃) δ 8.18 (s, 1H), 7.90-7.84 (m, 3H), 4.87-4.82 (m, 1H), 3.15-3.03 (m, 1H), 2.86-2.75 (m, 1H).

Step 6: Synthesis of Compound 24-9

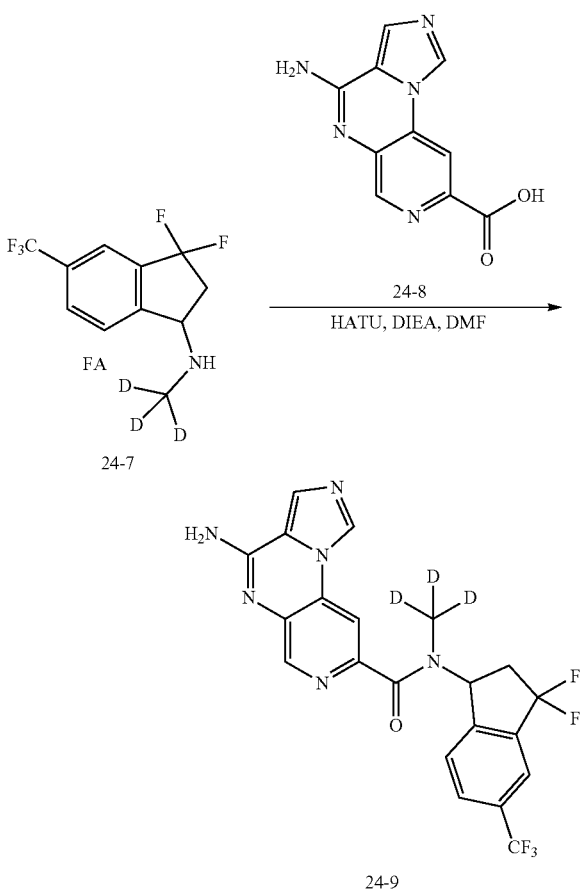

To a solution of compound 24-8 (120 mg, 524 μmol, 1.00 eq) in DMF (3.00 mL) was added HATU (239 mg, 628 μmol, 1.20 eq), DIEA (338 mg, 2.62 mmol, 456 μL, 5.00 eq), compound 24-7 (157 mg, 524 μmol, 1.00 eq, FA), the mixture was stirred at 25° C. for 1 hr. LC-MS showed there was desired mass. The mixture was filtered and filtrate was purified by prep-HPLC (FA condition; column: Waters Xbridge 150*25.0 mm*5.00 um; mobile phase: [water (FA)-ACN]; gradient: 35.0%-55.0% B over 10 min). Compound 24-9 (mixture of Compound 24 and 25) (80.0 mg, 156 μmol, 30.0% yield, FA) was obtained as a white solid.

Step 7: Separation of Compounds 24 and 25

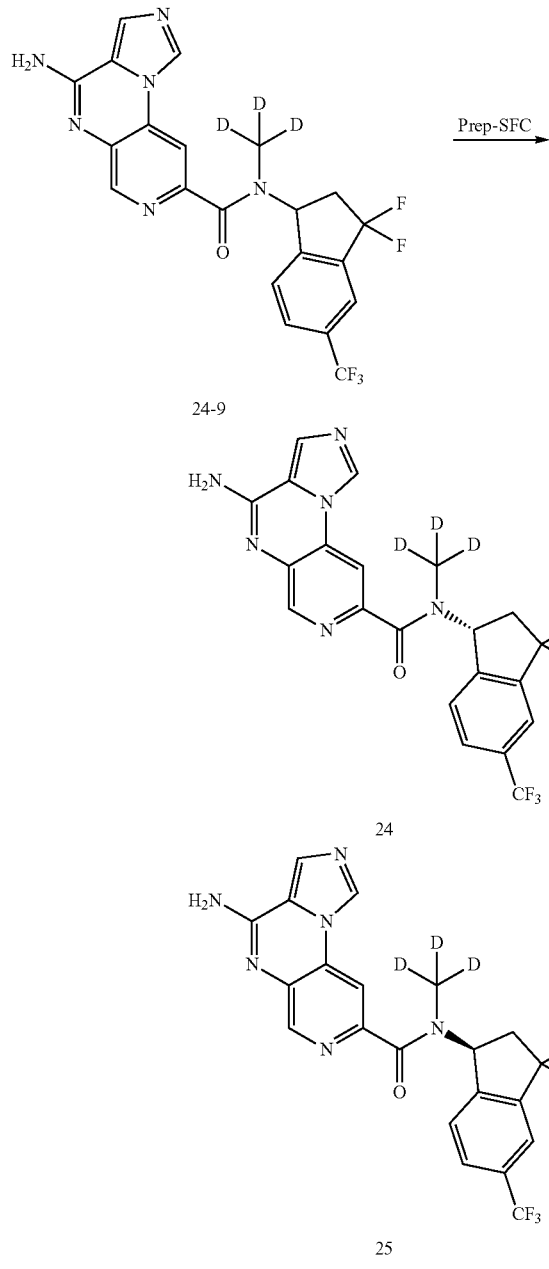

Compound 24-9 was separated by SFC (column: DAICEL CHIRALCEL OJ (250 mm*30 mm, 10 um); mobile phase: [$CO_2$-ACN/i-PrOH (0.1% $NH_3·H_2O$)]; B %: 25%, isocratic elution mode) to give Compound 24 (18.58 mg, 39.8 μmol, 25.5% yield, 99.8% purity) (Rt=1.645 min) and Compound 25 (22.50 mg, 47.5 μmol, 30.4% yield, 98.2% purity) (Rt=1.86 min). Compound 24 (18.58 mg, 39.8 μmol, 25.5% yield, 99.8% purity) was obtained. Compound 25 (22.50 mg, 47.5 μmol, 30.4% yield, 98.2% purity) was obtained.

H NMR of Compound 24 (400 MHz, DMSO-$d_6$) δ 9.31 (s, 1H), 8.68-8.65 (m, 1H), 8.57-8.55 (m, 1H), 8.09-8.05 (m, 2H), 7.99 (s, 1H), 7.87-7.67 (m, 3H), 6.31-6.02 (m, 1H), 3.21-3.08 (m, 1H), 2.93-2.82 (m, 1H).

H NMR of Compound 25 (400 MHz, DMSO-$d_6$) δ 9.31 (s, 1H), 8.68-8.65 (m, 1H), 8.57-8.55 (m, 1H), 8.09-8.05 (m, 2H), 7.99 (s, 1H), 7.87-7.67 (m, 3H), 6.31-6.01 (m, 1H), 3.22-3.07 (m, 1H), 2.92-2.84 (m, 1H).

Example 18: Synthesis of Compounds 26 and 27

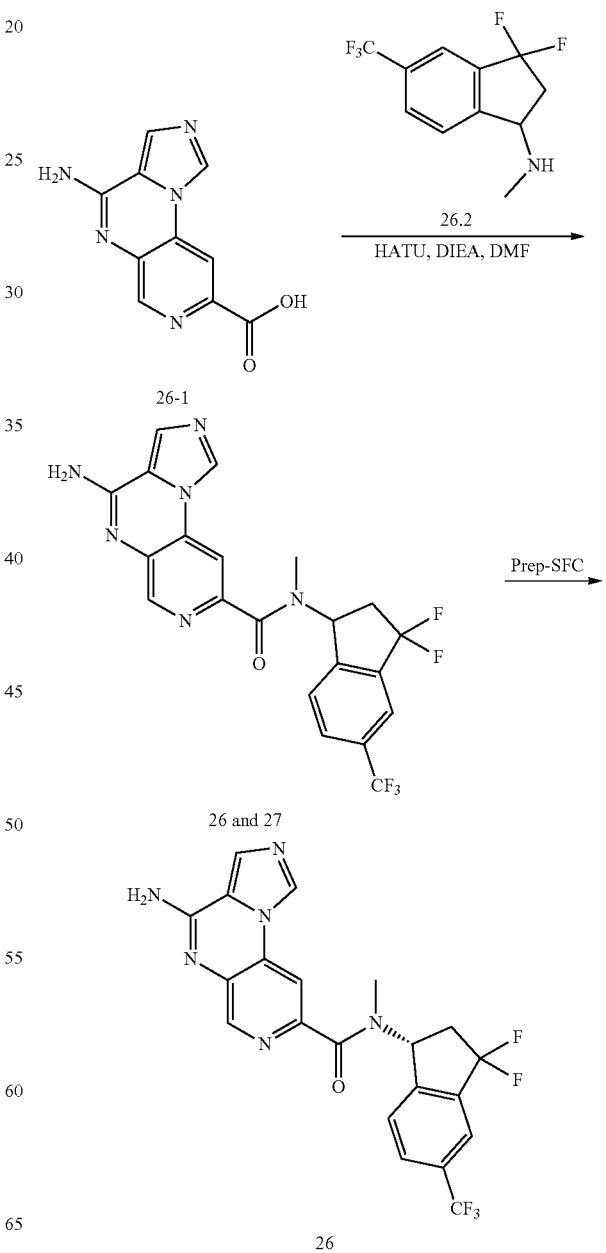

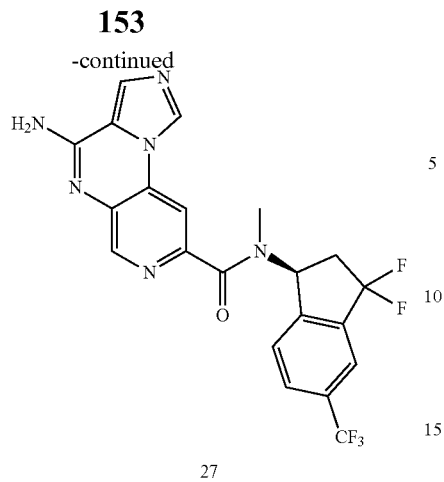

27

To a solution of compound 26-1 (0.12 g, 523.57 μmol, 1 eq) in DMF (4 mL) was added HATU (298.62 mg, 785.36 μmol, 1.5 eq) and DIEA (338.34 mg, 2.62 mmol, 455.98 μL, 5 eq) at 25° C., after stirring for 15 minutes, compound 26-2 (131.52 mg, 523.57 μmol, 1 eq) was added to the mixture, the reaction was stirred for 15 minutes. LCMS showed no starting material left and desired product was observed. The reaction was diluted with water (15 mL) and extracted with EA (10 mL×3), the combined organic layers were washed with sat. NaCl (10 mL×2), dried over $Na_2SO_4$, filtered and concentrated in vacuo. The residue was purified by Prep-HPLC (column: Waters Xbridge C18 150*50 mm*10 um; mobile phase: [water ($NH_4HCO_3$)-ACN]; gradient: 34%-54% B over 10 min) and SFC (column: DAICEL CHIRAL-CEL OJ (250 mm*30 mm, 10 um); mobile phase: [$CO_2$-i-PrOH (0.1% $NH_3H_2O$)]; B %: 35%, isocratic elution mode) to afford Compound 26 (0.025 g, 53.33 μmol, 10.19% yield, 98.63% purity) (Rt=1.642 min) which was confirmed by NMR, FNMR, LCMS, HPLC and SFC and Compound 27 (0.025 g, 54.07 μmol, 10.33% yield, 100% purity) (Rt=1.867 min) which was confirmed by NMR, FNMR, LCMS, HPLC and SFC.

H NMR of Compound 26 (400 MHz, DMSO-$d_6$) δ 9.30 (s, 1H), 8.66 (d, J=10.8 Hz, 1H), 8.55 (d, J=8.0 Hz, 1H), 8.11-8.02 (m, 2H), 7.99 (s, 1H), 7.89-7.61 (m, 3H), 6.39-5.79 (m, 1H), 3.10-2.58 (m, 5H)

LC-MS of Compound 26 (M+H)$^+$: 463.1

HPLC of Compound 26 98.63% purity (220 nm)

SFC of Compound 26 chiral purity: 100%.

H NMR of Compound 27 (400 MHz, DMSO-$d_6$) δ 9.30 (s, 1H), 8.66 (d, J=11.2 Hz, 1H), 8.55 (d, J=8.4 Hz, 1H), 8.13-8.02 (m, 2H), 7.99 (s, 1H), 7.88-7.64 (m, 3H), 6.37-5.87 (m, 1H), 3.05-2.65 (m, 5H)

LC-MS of Compound 27 (M+H)$^+$: 463.1

HPLC of Compound 27 100% purity (220 nm)

SFC of Compound 27 chiral purity: 98.56%.

Example 19: Synthesis of Compounds 28 and 29

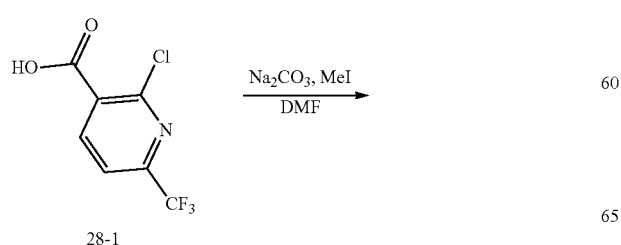

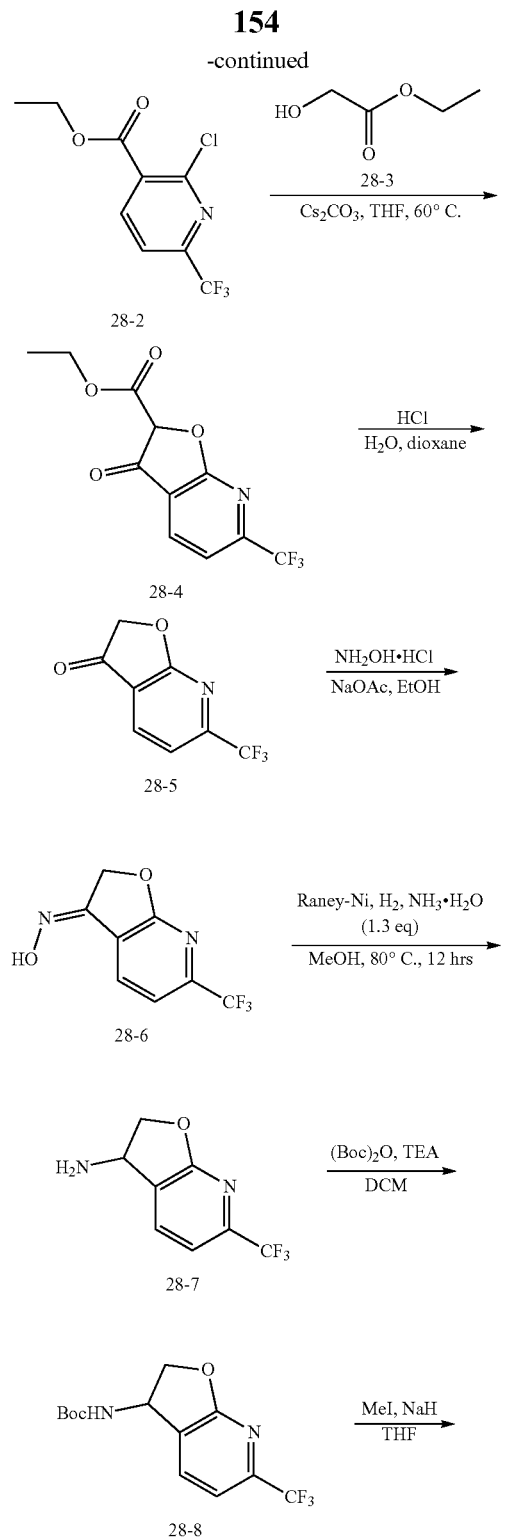

Step 1: Synthesis of Compound 28-2

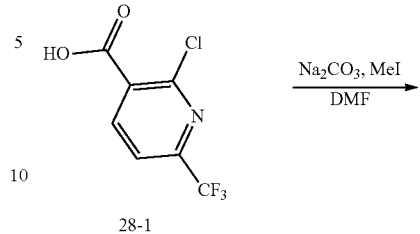

28-1

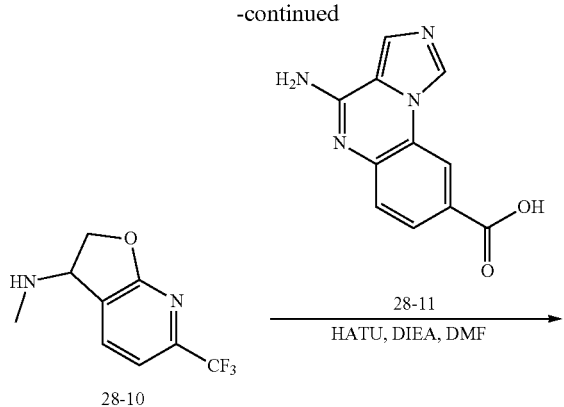

28-11
HATU, DIEA, DMF

28-2

To a solution of compound 28-1 (25 g, 110.84 mmol, 1 eq) in DMF (250 mL) was added Na₂CO₃ (23.50 g, 221.68 mmol, 2 eq) and MeI (47.20 g, 332.52 mmol, 20.70 mL, 3 eq). The mixture was stirred at 25° C. for 1 hrs. LC-MS showed reactant was consumed completely and one main peak with desired m/z was detected. The reaction mixture was quenched by NaHCO₃ (300 mL) and extracted with EA 600 mL (200 mL×3). The combined organic layers were washed with brine 600 mL (300 mL×2), dried over Na₂SO₄, filtered and concentrated under reduced pressure to give a residue. without further purification. Compound 28-2 (25 g, 104.35 mmol, 94.15% yield) was obtained as yellow oil.

H NMR: (400 MHz, CDCl3) δ 8.33 (d, J=8.0 Hz, 1H), 7.71 (d, J=8.0 Hz, 1H), 4.01 (s, 3H)

Step 2: Synthesis of Compound 28-4

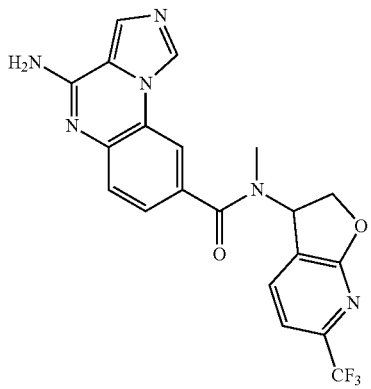

28

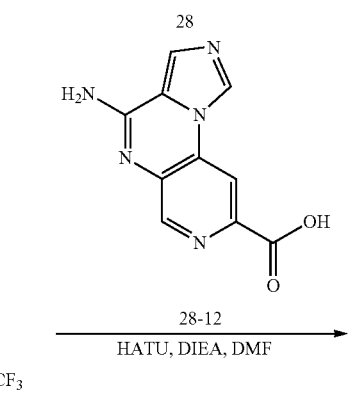

28-10

28-12
HATU, DIEA, DMF

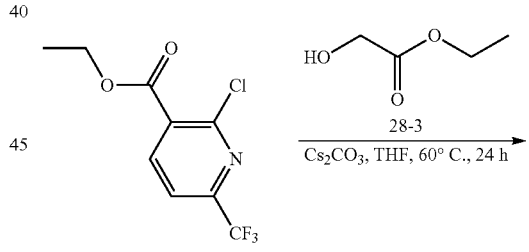

28-2 + 28-3

Cs₂CO₃, THF, 60° C., 24 h

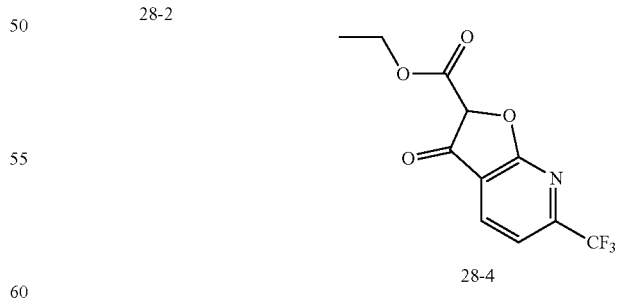

28-4

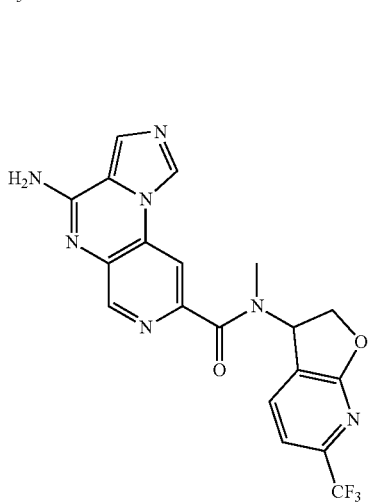

29

To a solution of compound 28-2 (6.75 g, 26.62 mmol, 1 eq) and compound 28-3 (6.93 g, 66.54 mmol, 6.41 mL, 2.5 eq) in THF (150 mL) was added CS₂CO₃ (21.68 g, 66.54 mmol, 2.5 eq) at 25° C., the reaction was stirred for 12 h at 65° C. LCMS showed no starting material left and desired product was observed. The reaction was diluted with water (150 mL) and extracted with EA (100 mL×3), the combined organic layers were washed with sat. NaCl (100 mL×2), dried over Na$_2$SO$_4$, filtered and concentrated in vacuo. The residue was purified by column chromatography (SiO$_2$, Petroleum ether:Ethyl acetate=5:1-0:1, then Dichloromethane:Methanol=10:1). To afford compound 28-4 (2.5 g, 9.08 mmol, 34.13% yield) as a yellow solid which was confirmed by NMR.

H NMR: (400 MHz, DMSO-d$_6$) δ 8.64 (d, J=8.4 Hz, 1H), 7.89 (d, J=8.0 Hz, 1H), 5.65-5.42 (m, 1H), 4.33 (q, J=7.2 Hz, 2H), 1.32 (t, J=6.8 Hz, 3H)

Step 3: Synthesis of Compound 28-5

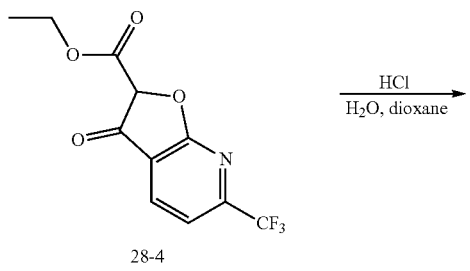

The mixture of compound 28-4 (2.5 g, 9.08 mmol, 1 eq) in H$_2$SO$_4$ (20 mL) was stirred for 1 h at 100° C. LCMS showed no starting material left and desired product was observed. The reaction cooled to rt and poured into ice-water (20 mL), then extracted with EA (15 mL×3), the combined organic layers were washed with sat. NaHCO$_3$ (15 mL×2), sat. NaCl (15 mL×2), dried over Na$_2$SO$_4$, filtered and concentrated in vacuo. The crude was used directly next step. To afford compound 28-5 (1.5 g, crude) as a red solid.

Step 4: Synthesis of Compound 28-6

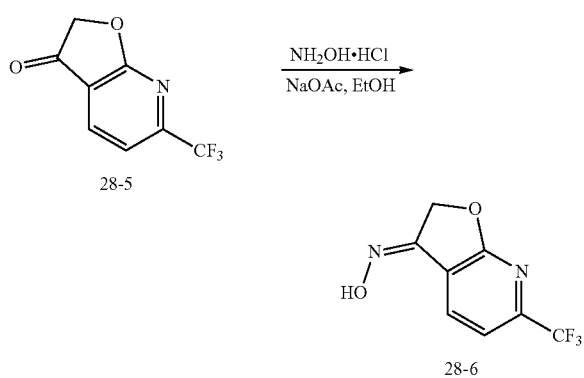

To a solution of compound 28-5 (1.5 g, 7.38 mmol, 1 eq) in EtOH (25 mL) was added NaOAc (1.82 g, 22.15 mmol, 3 eq) and NH$_2$OH·HCl (1.54 g, 22.15 mmol, 3 eq), the reaction was stirred for 1 h at 25° C. LCMS showed no starting material left and desired product was observed. The reaction was diluted with water (40 mL) and extracted with EA (25 mL×3), the combined organic layers were washed with sat. NaCl (20 mL×2), dried over Na$_2$SO$_4$, filtered and concentrated in vacuo. TLC (PE:EA=2:1) showed the main spot observed. The residue was purified by column chromatography (SiO$_2$, Petroleum ether:Ethyl acetate=5:1-2:1). To afford compound 28-6 (0.85 g, crude) as a red solid.

Step 5: Synthesis of Compound 28-7

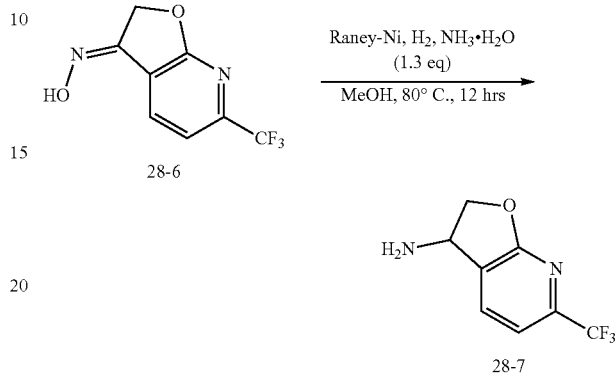

The mixture of compound 28-6 (0.85 g, 3.90 mmol, 1 eq) and Raney-Ni (0.5 g, 5.84 mmol, 1.50 eq) in MeOH (10 mL) and NH$_3$·H$_2$O (0.5 mL) was stirred for 12 h at 80° C. under H$_2$ atmosphere (50 psi). LCMS showed no starting material left and desired product was observed. The reaction was filtered through of the celite and the filtrate was concentrated in vacuo. The residue was purified by column chromatography (SiO$_2$, Petroleum ether:Ethyl acetate=3:1-0:1, then Dichloromethane:Methanol=10:1). To afford compound 28-7 (0.120 g, 587.81 µmol, 15.08% yield) as yellow oil.

Step 6: Synthesis of Compound 28-8

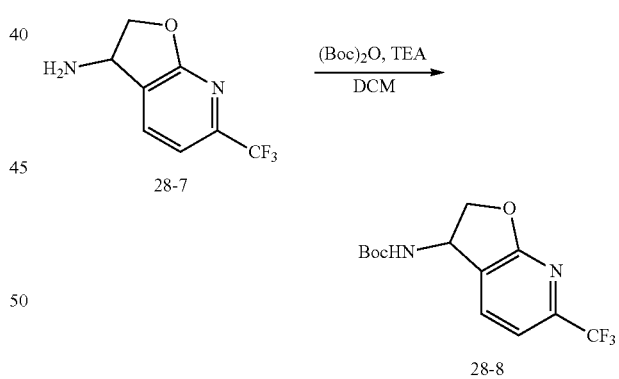

To a solution of compound 28-7 (0.120 g, 587.81 µmol, 1 eq) in DCM (10 mL) was added TEA (118.96 mg, 1.18 mmol, 163.63 µL, 2 eq) and (Boc)$_2$O (134.70 mg, 617.20 µmol, 141.79 µL, 1.05 eq) at 25° C., the reaction was stirred for 12 h. LCMS showed nearly no starting material left and desired product was observed. The reaction was diluted with water (15 mL) and extracted with DCM (10 mL×3), the combined organic layers were washed with sat. NaCl (10 mL×2), dried over Na$_2$SO$_4$, filtered and concentrated in vacuo. The residue was purified by Prep-TLC (PE:EA=3:1). To afford compound 28-8 (0.040 g, 131.46 µmol, 22.37% yield) as a yellow solid.

Step 7: Synthesis of Compound 28-9

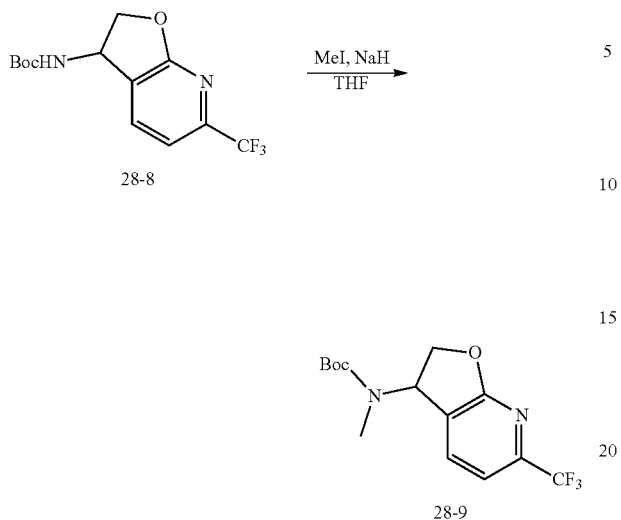

Step 9: Synthesis of Compound 28

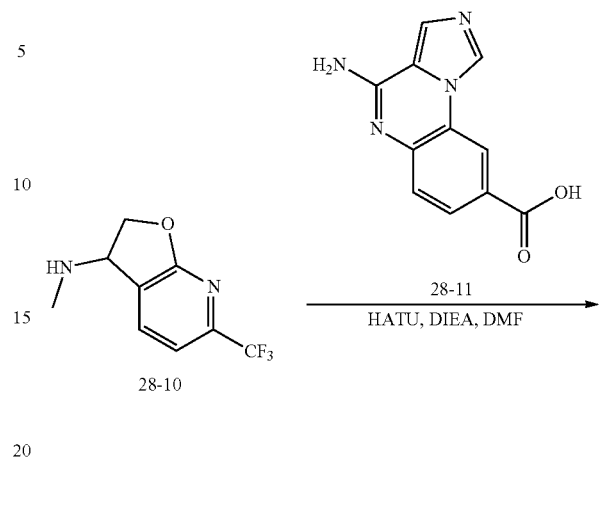

To a solution of compound 28-8 (0.040 g, 131.46 μmol, 1 eq) in THF (4 mL) was added NaH (13.15 mg, 328.66 μmol, 60% purity, 2.5 eq) at 0° C. under ice-bath, after stirring for 15 minutes, MeI (37.32 mg, 262.93 μmol, 16.37 μL, 2.0 eq) was added to the mixture, the reaction was stirred for 12 h at 25° C. LCMS showed no starting material left and desired product was observed. The reaction was quenched by addition of MeOH (5 mL) and concentrated in vacuo. The residue was purified by Prep-TLC (PE:EA=3:1). To afford compound 28-9 (0.025 g, 78.54 μmol, 59.75% yield) as colorless oil.

Step 8: Synthesis of Compound 28-10

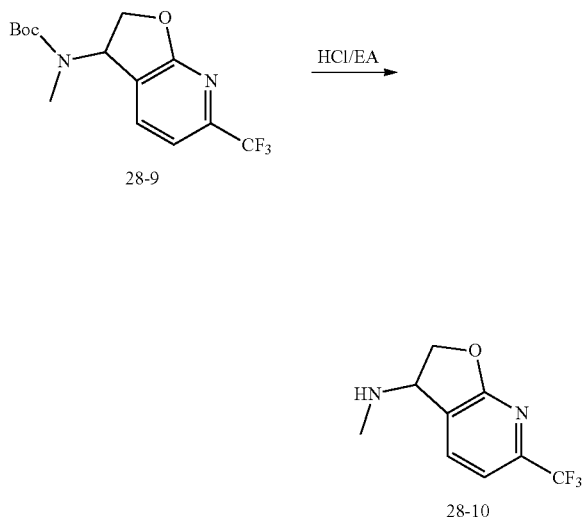

To a solution of compound 28-9 (0.025 g, 78.54 μmol, 1 eq) in EA (4 mL) was added HCl/dioxane (2 M, 4 mL, 101.85 eq), the reaction was stirred for 2 h at 25° C. LCMS showed no starting material left and desired product was observed. The reaction was concentrated in vacuo. The crude was used directly next step. To afford compound 28-10 (0.020 g, crude, HCl) as a yellow solid.

To a solution of compound 28-11 (0.020 g, 87.64 μmol, 1 eq), compound 28-10 (19.64 mg, 77.12 μmol, 0.88 eq, HCl) in DMF (2 mL) was added HATU (66.65 mg, 175.28 μmol, 2 eq) and DIEA (56.63 mg, 438.20 μmol, 76.32 μL, 5 eq), the reaction was stirred for 12 h at 25° C. LCMS showed no starting material left and desired product was observed. The reaction was diluted with water (10 mL) and extracted with EA (10 mL×3), the combined organic layers were washed with sat. NaCl (10 mL×3), dried over Na$_2$SO$_4$, filtered and concentrated in vacuo. The residue was purified by Prep-HPLC (column: Waters Xbridge 150*25 mm*5 um; mobile phase: [water (ammonia hydroxide v/v)-ACN]; gradient: 22%-52% B over 9 min) to afford Compound 28 (0.007 g, 16.14 μmol, 18.41% yield, 98.75% purity) which was confirmed by H NMR, F NMR, LCMS, HPLC and SFC.

H NMR: (400 MHz, DMSO-d$_6$) δ 9.16 (s, 1H), 8.32 (s, 1H), 8.12 (d, J=7.2 Hz, 1H), 7.92 (s, 1H), 7.59-7.42 (m, 5H), 6.54-5.92 (m, 1H), 5.04-4.80 (m, 1H), 4.78-4.62 (m, 1H), 2.77 (br s, 3H)

Step 10: Synthesis of Compound 29

Example 20: Synthesis of Compounds 30 and 31

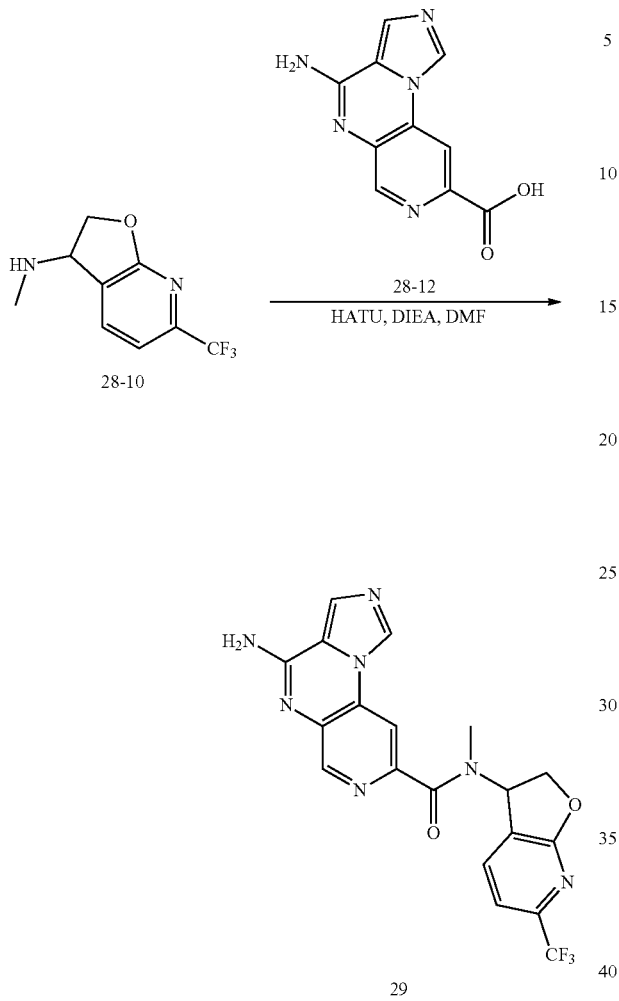

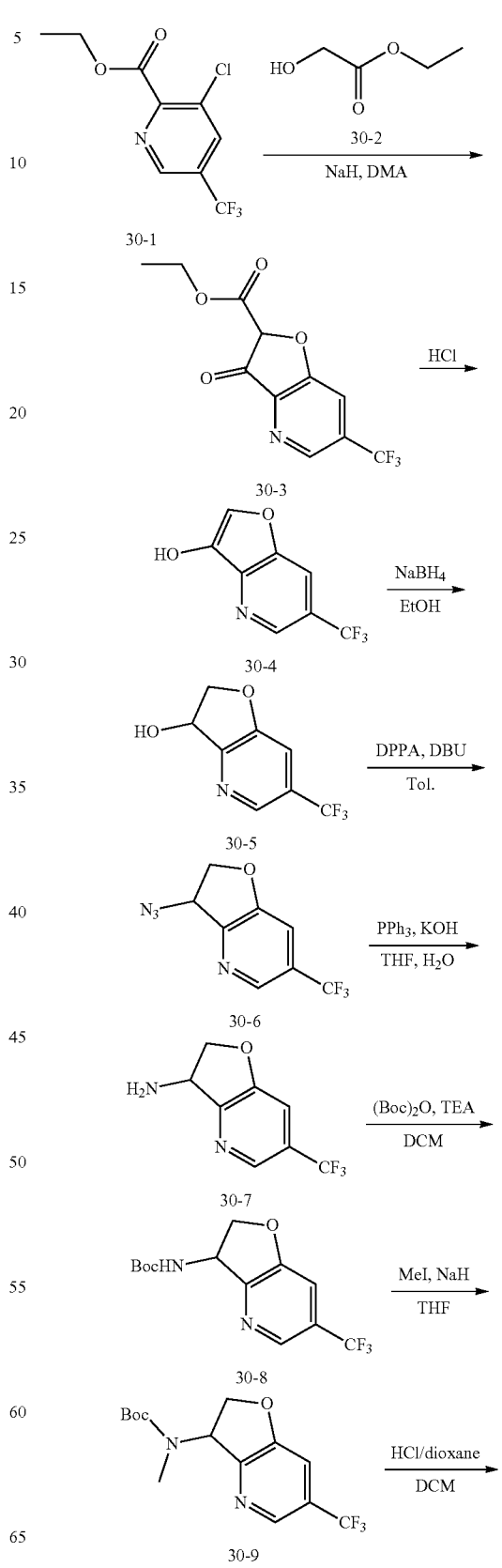

To a solution of compound 28-12 (0.04 g, 174.52 μmol, 1 eq) in DMF (2 mL) was added HATU (99.54 mg, 261.79 μmol, 1.5 eq) and DIEA (112.78 mg, 872.62 μmol, 151.99 μL, 5 eq), after stirring for 15 minutes, compound 28-10 (42.22 mg, 165.80 μmol, 0.95 eq, HCl) was added to the mixture, the reaction was stirred for 12 h at 25° C. LCMS showed no starting material left and desired product was observed. The reaction was diluted with water (15 mL) and extracted with EA (15 mL×3), the combined organic layers were washed with sat. NaCl (15 mL×2), dried over $Na_2SO_4$, filtered and concentrated in vacuo. The residue was purified by Prep-HPLC (column: Phenomenex Luna C18 150*25 mm*10 um; mobile phase: [water (HCl)-ACN]; gradient: 14%-44% B over 9 min) and (column: Waters Xbridge 150*25 mm*5 um; mobile phase: [water (ammonia hydroxide v/v)-ACN]; gradient: 10%-40% B over 9 min) to afford Compound 29 (0.011 g, 25.12 μmol, 14.39% yield, 98.03% purity) which was confirmed by NMR, FNMR, LCMS, HPLC and SFC.

H NMR: (400 MHz, DMSO-$d_6$) δ 9.39-9.27 (m, 1H), 8.73-8.64 (m, 1H), 8.59-8.47 (m, 1H), 8.22-7.94 (m, 2H), 7.82-7.69 (m, 2H), 7.51 (d, J=7.6 Hz, 1H), 6.37-6.01 (m, 1H), 5.01-4.66 (m, 2H), 2.97-2.71 (m, 3H)

Step 1: Synthesis of Compound 30-3

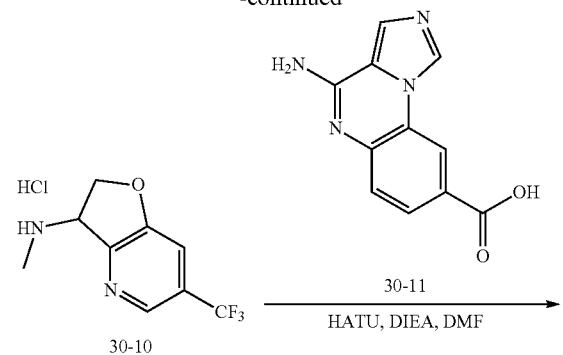

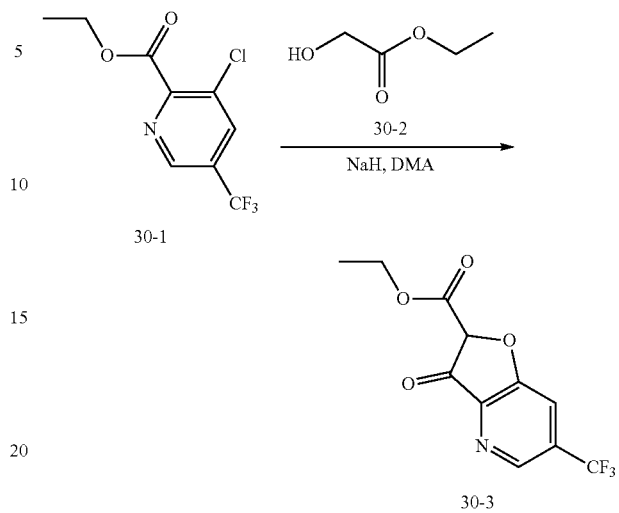

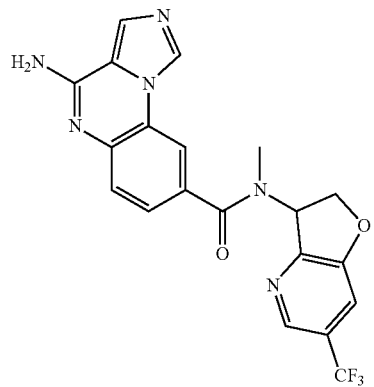

To a solution of compound 30-2 (4.93 g, 47.3 mmol, 4.56 mL, 1.20 eq) in DMA (100 mL) was added NaH (3.15 g, 78.9 mmol, 60.0% purity, 2.00 eq) at 0° C., the mixture was stirred at 0° C. for 0.5 hr, then compound 30-1 (10.0 g, 39.4 mmol, 1.00 eq) in DMA (20.0 mL) was added dropwise at 0° C., the mixture was stirred at 25° C. for 1 hr. LC-MS showed compound 30-1 was consumed and a peak with desired mass was detected. A solution of saturated NH₄Cl (150 mL) was added to the mixture at 0° C., then filtered, the filtrate cake was concentrated to give a residue. Compound 30-3 (5.50 g, 20.0 mmol, 50.7% yield) was obtained as yellow solid, confirmed by H NMR, F NMR.

H NMR: (400 MHz, DMSO-$d_6$) δ 8.70 (s, 1H), 8.24 (s, 1H), 4.19 (q, J=7.2 Hz, 2H), 1.26 (t, J=7.2 Hz, 3H).

Step 2: Synthesis of Compound 30-4

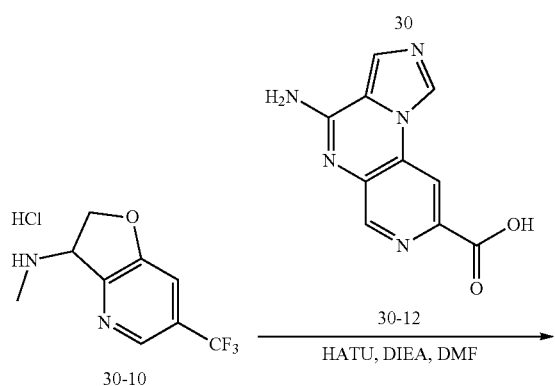

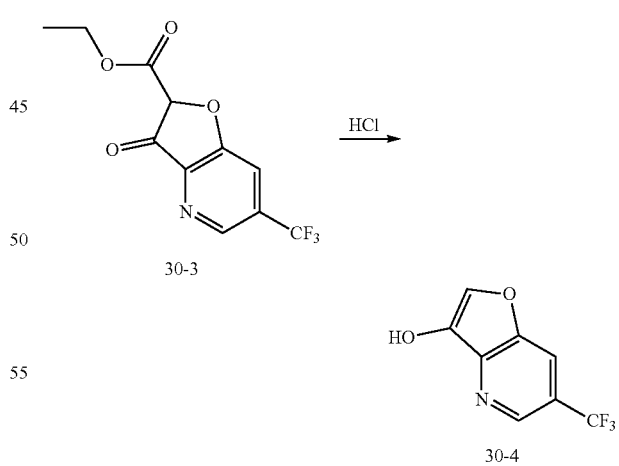

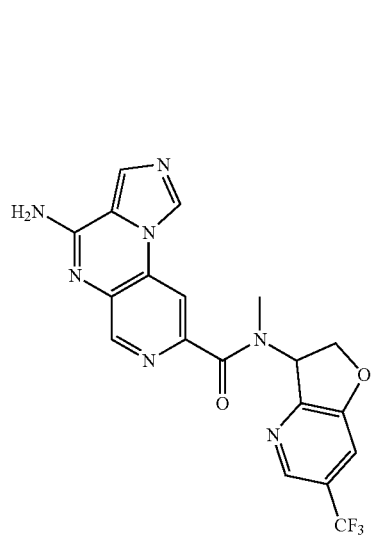

A mixture of compound 30-3 (5.50 g, 20.0 mmol, 1.00 eq) in HCl (12.0 M, 50.0 mL, 30.0 eq) was stirred at 100° C. for 2 hrs. LC-MS showed compound 30-3 was consumed and a peak with desired mass was detected. The mixture was diluted with H₂O (100 mL) and extracted with EtOAc (100 mL*3), the combined organic phase was washed with brine (100 mL*2), dried over Na₂SO₄ and concentrated to give a residue. Compound 30-4 (3.20 g, 15.8 mmol, 78.8% yield) was obtained as yellow solid, confirmed by H NMR, F NMR.

H NMR: (400 MHz, DMSO-d$_6$) δ 10.06 (s, 1H), 8.86 (s, 1H), 8.44 (s, 1H), 8.09 (s, 1H).

Step 3: Synthesis of Compound 30-5

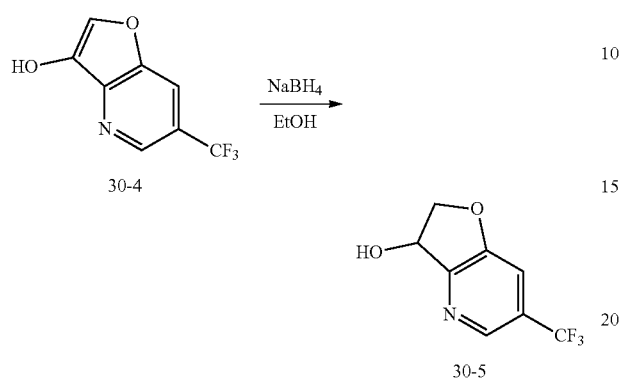

To a solution of compound 30-4 (2.00 g, 9.85 mmol, 1.00 eq) in EtOH (20.0 mL) was added NaBH$_4$ (745 mg, 19.7 mmol, 2.00 eq) at 0° C., then the mixture was stirred at 25° C. for 1 hr. LC-MS showed compound 30-4 was consumed and a peak with desired mass was detected. A solution of saturated NH$_4$Cl (30.0 mL) was added to the mixture at 0° C., then extracted with DCM (30.0 mL*3), the combined organic phase was dried over Na$_2$SO$_4$ and concentrated to give a residue. The residue was purified by column chromatography (SiO$_2$, Petroleum ether:Ethyl acetate=100:1 to 3:1). TLC (Petroleum ether:Ethyl acetate=3:1, R$_f$=0.30). Compound 30-5 (1.30 g, 6.34 mmol, 64.4% yield) was obtained as yellow solid, confirmed by H NMR, F NMR.

H NMR: (400 MHz, DMSO-d$_6$) δ 8.49 (s, 1H), 7.70 (d, J=0.8 Hz, 1H), 6.11 (d, J=6.0 Hz, 1H), 5.27-5.23 (m, 1H), 4.74 (dd, J$_1$=10.8 Hz, J$_2$=7.2 Hz, 1H), 4.42 (dd, J$_1$=10.8 Hz, J$_2$=3.2 Hz, 1H).

Step 4: Synthesis of Compound 30-6

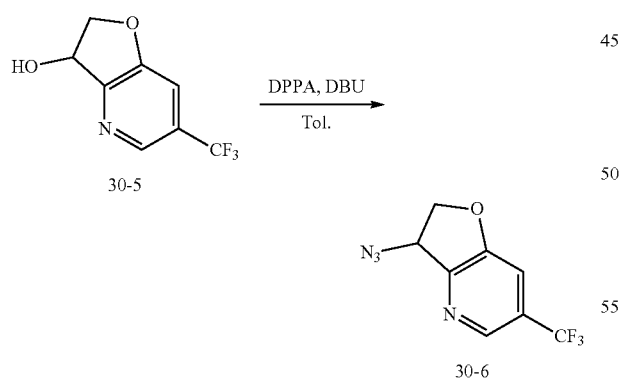

To a solution of compound 30-5 (500 mg, 2.44 mmol, 1.00 eq) in Tol. (10.0 mL) was added DPPA (805 mg, 2.92 mmol, 631 μL, 1.20 eq) and a solution of DBU (445 mg, 2.92 mmol, 441 μL, 1.20 eq) in Tol. (1.00 mL) at 0° C., then the mixture was stirred at 25° C. for 2 hrs. LC-MS showed compound 30-5 was consumed and a peak with desired mass was detected. A solution of saturated NH$_4$Cl (30.0 mL) was added to the mixture at 0° C., then extracted with DCM (30.0 mL*3), the combined organic phase was dried over Na$_2$SO$_4$ and concentrated to give a residue. The residue was purified by column chromatography (SiO$_2$, Petroleum ether:Ethyl acetate=100:1 to 5:1). TLC (Petroleum ether:Ethyl acetate=5:1, R$_f$=0.70). Compound 30-6 (500 mg, 2.17 mmol, 89.1% yield) was obtained as yellow oil, confirmed by H NMR, F NMR.

H NMR: (400 MHz, DMSO-d$_6$) δ 8.58 (s, 1H), 7.84 (d, J=1.2 Hz, 1H), 5.59 (dd, J=8.0 Hz, J$_2$=3.2 Hz, 1H), 4.83 (dd, J$_1$=10.8 Hz, J$_2$=8.0 Hz, 1H), 4.42 (dd, J$_1$=10.8 Hz, J$_2$=3.2 Hz, 1H).

Step 5: Synthesis of Compound 30-7

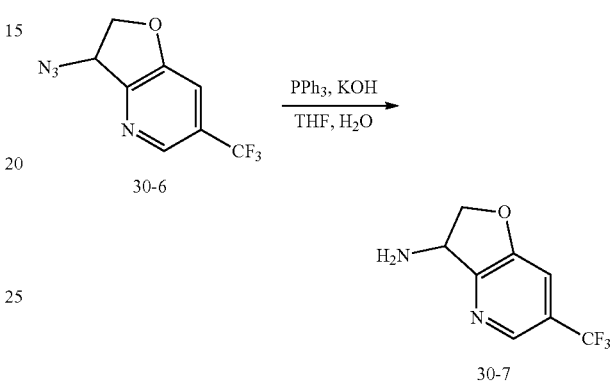

To a solution of compound 30-6 (450 mg, 1.96 mmol, 1.00 eq) in THF (2.00 mL) was added PPh$_3$ (769 mg, 2.93 mmol, 1.50 eq), the mixture was stirred at 25° C. for 1 hr, then KOH (274 mg, 4.89 mmol, 2.50 eq) in H$_2$O (1.00 mL) was added and the mixture was stirred at 25° C. for 12 hrs. LC-MS showed compound 30-6 was consumed and a peak with desired mass was detected. The mixture was diluted with H$_2$O (20.0 mL) and extracted with EtOAc (20.0 mL*3), the combined organic phase was dried over Na$_2$SO$_4$ and concentrated to give a residue. The residue was purified by column chromatography (SiO$_2$, Petroleum ether:Ethyl acetate=100:1 to 0:1). TLC (Petroleum ether:Ethyl acetate=0:1, R$_f$=0.20). Compound 30-7 (300 mg, 1.47 mmol, 75.2% yield) was obtained as yellow solid.

Step 6: Synthesis of Compound 30-8

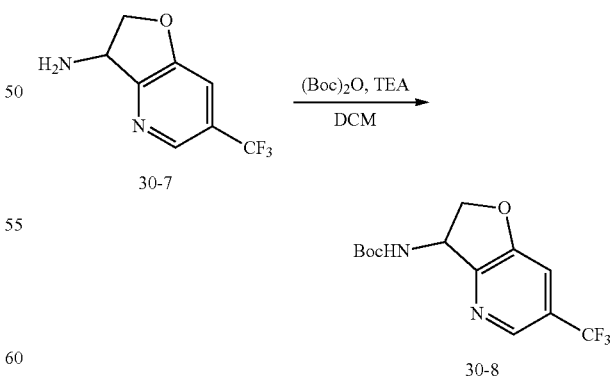

To a solution of compound 30-7 (300 mg, 1.47 mmol, 1.00 eq) in DCM (5.00 mL) was added TEA (446 mg, 4.41 mmol, 614 μL, 3.00 eq) and (Boc)$_2$O (641 mg, 2.94 mmol, 675 μL, 2.00 eq), then the mixture was stirred at 25° C. for 2 hrs. LC-MS showed compound 30-7 was consumed and a peak with desired mass was detected. The mixture was diluted with $H_2O$ (20.0 mL) and extracted with EtOAc (20.0 mL*3), the combined organic phase was dried over $Na_2SO_4$ and concentrated to give a residue. The residue was purified by column chromatography ($SiO_2$, Petroleum ether:Ethyl acetate=100:1 to 5:1). TLC (Petroleum ether:Ethyl acetate=3:1, $R_f$=0.60). Compound 30-8 (300 mg, 986 μmol, 67.1% yield) was obtained as yellow solid, confirmed by H NMR, F NMR.

H NMR: (400 MHz, DMSO-$d_6$) δ 8.45 (s, 1H), 7.63 (s, 2H), 5.35-5.30 (m, 1H), 4.88 (t, J=9.2 Hz, 1H), 4.36-4.32 (m, 1H), 1.39 (s, 9H).

Step 7: Synthesis of Compound 30-9

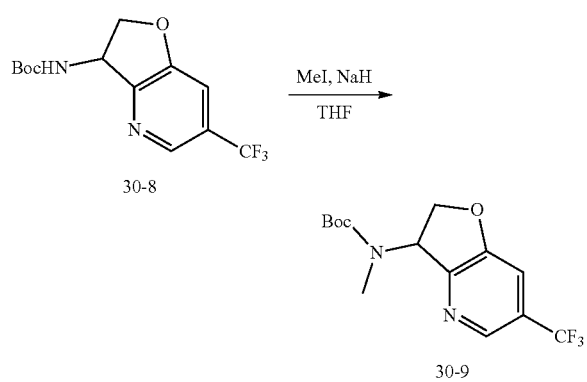

To a solution of compound 30-8 (300 mg, 986 μmol, 1.00 eq) in THF (5.00 mL) was added NaH (59.2 mg, 1.48 mmol, 60.0% purity, 1.50 eq) at 0° C., then $CH_3I$ (420 mg, 2.96 mmol, 184 μL, 3.00 eq) was added, the mixture was stirred at 25° C. for 2 hrs. LC-MS showed compound 30-8 was consumed and a peak with desired mass was detected. A solution of saturated $NH_4Cl$ (20.0 mL) was added to the mixture at 0° C., then extracted with EtOAc (20.0 mL*3), the combined organic phase was washed with brine (20.0 mL*2), dried over $Na_2SO_4$ and concentrated to give a residue. The residue was purified by Prep-HPLC (column: Waters Xbridge 150*25 mm*5 um; mobile phase: [water ($NH_4HCO_3$)-ACN]; gradient: 37%-57% B over 10 min). Compound 30-9 (200 mg, 628 μmol, 63.7% yield) was obtained as yellow solid, confirmed by H NMR, F NMR.

H NMR: (400 MHz, DMSO-$d_6$) δ 8.47 (s, 1H), 7.67 (s, 1H), 5.91-5.52 (m, 1H), 4.88 (t, J=9.6 Hz, 1H), 4.59 (dd, $J_1$=10.0 Hz, $J_2$=6.0 Hz, 1H), 2.54 (s, 3H), 1.41-1.21 (m, 9H).

Step 8: Synthesis of Compound 30-10

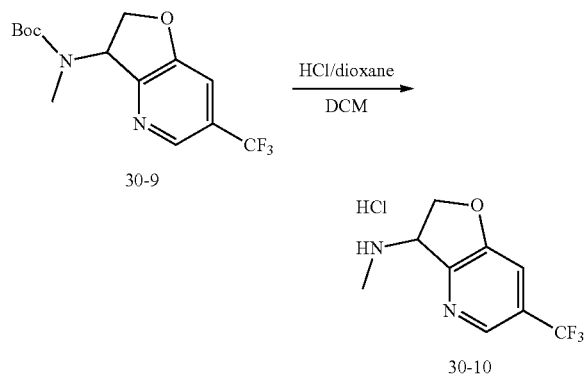

To a solution of compound 30-9 (200 mg, 628 μmol, 1.00 eq) in DCM (2.00 mL) was added HCl/dioxane (2 M, 4.00 mL, 12.7 eq) at 0° C., then the mixture was stirred at 25° C. for 1 hr. LC-MS showed compound 30-9 was consumed and a peak with desired mass was detected. The mixture was concentrated to give a residue. Compound 30-10 (160 mg, crude, HCl) was obtained as yellow solid.

Step 9: Synthesis of Compound 30

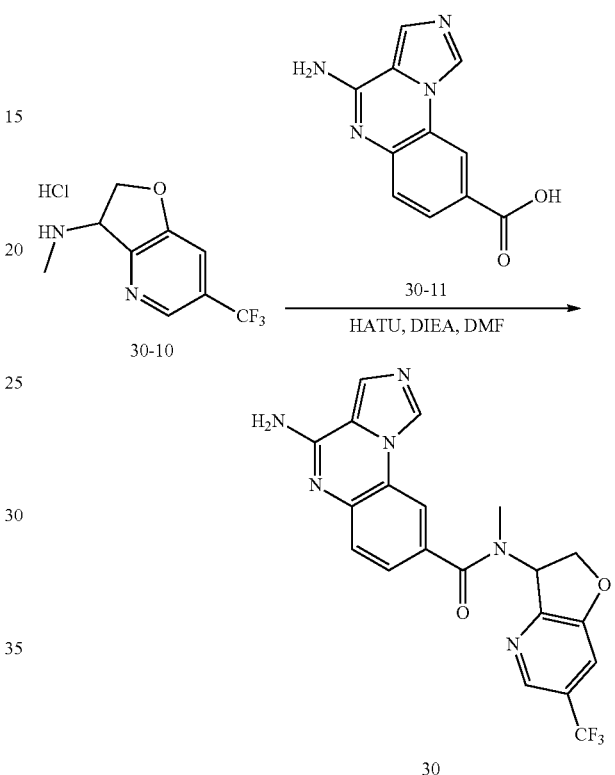

To a solution of compound 30-10 (30.0 mg, 118 μmol, 1.00 eq, HCl) and compound 30-11 (26.9 mg, 118 μmol, 1.00 eq) in DMF (1.00 mL) was added HATU (67.2 mg, 177 μmol, 1.50 eq) and DIEA (76.1 mg, 589 μmol, 103 μL, 5.00 eq), then the mixture was stirred at 25° C. for 2 hrs. LC-MS showed compound 30-10 was consumed and a peak with desired mass was detected. The mixture was diluted with $H_2O$ (20.0 mL) and extracted with EtOAc (20.0 mL*3), the combined organic phase was washed with brine (20.0 mL*2), dried over $Na_2SO_4$ and concentrated to give a residue. The residue was purified by Prep-HPLC (column: Waters Xbridge 150*25 mm*5 um; mobile phase: [water (ammonia hydroxide v/v)-ACN]; gradient: 22%-52% B over 9 min). Compound 30 (10.66 mg, 24.6 μmol, 20.9% yield, 99.0% purity) was obtained, confirmed by H NMR, F NMR, LC-MS, HPLC, SFC.

H NMR: (400 MHz, DMSO-$d_6$) δ 9.18-9.13 (m, 1H), 8.62-8.34 (m, 2H), 7.91 (s, 1H), 7.77 (s, 1H), 7.48-7.46 (m, 4H), 6.27-5.86 (m, 1H), 5.02-4.79 (m, 2H), 2.82-2.67 (m, 3H).

H NMR: (400 MHz, DMSO-$d_6$) δ 9.04 (s, 1H), 8.55 (s, 1H), 8.34 (s, 1H), 7.92 (s, 1H), 7.61 (s, 1H), 7.50 (s, 2H), 7.08 (s, 2H), 6.06-6.03 (m, 1H), 4.94 (t, J=9.6 Hz, 1H), 4.81 (dd, $J_1$=10.4 Hz, $J_2$=5.2 Hz, 1H), 2.80 (s, 3H).

Step 10: Synthesis of Compound 31

Example 21: Synthesis of Compounds 32 and 33

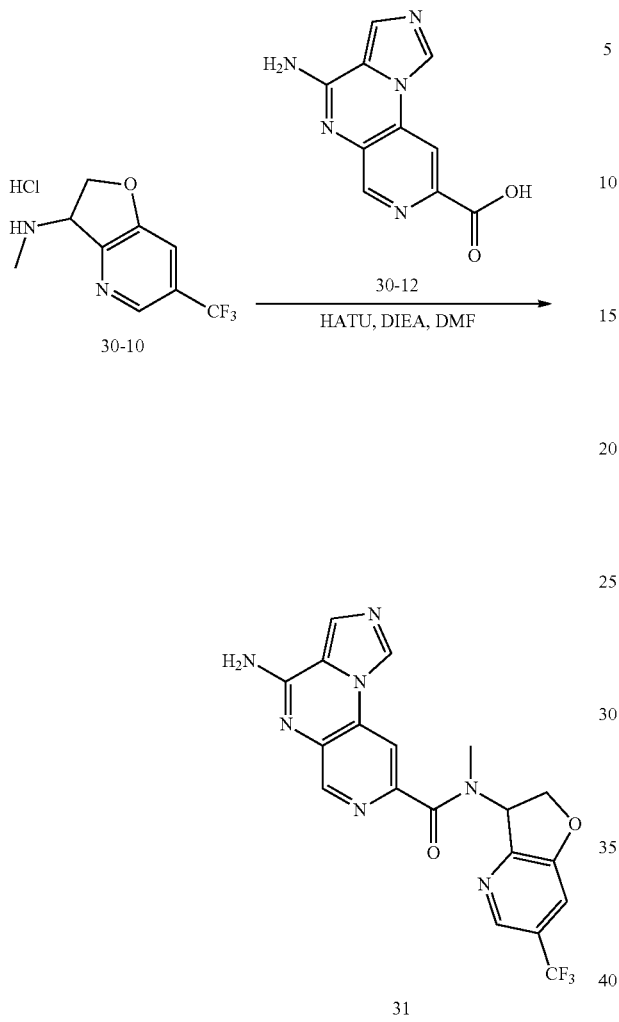

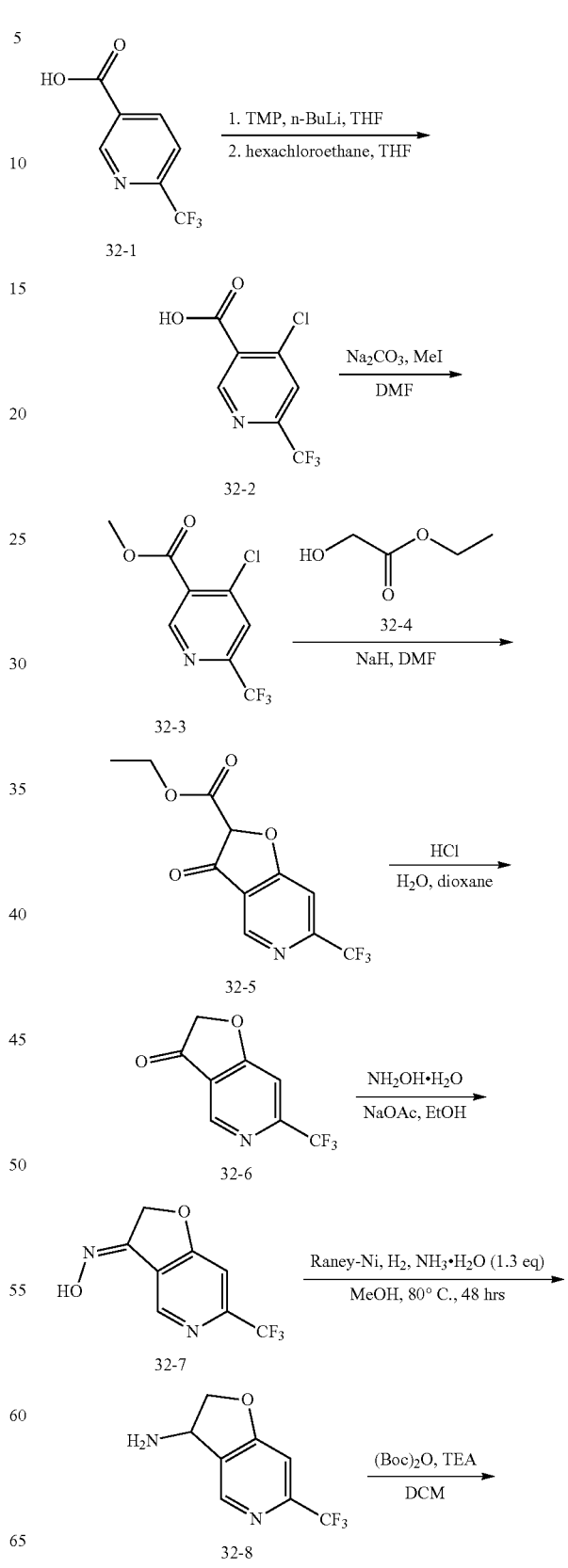

To a solution of compound 30-10 (30.0 mg, 118 μmol, 1.00 eq, HCl) and compound 12 (27.0 mg, 118 μmol, 1.00 eq) in DMF (1.00 mL) was added HATU (67.2 mg, 177 μmol, 1.50 eq) and DIEA (76.1 mg, 589 μmol, 103 μL, 5.00 eq), then the mixture was stirred at 25° C. for 2 hrs. LC-MS showed compound 30-12 was consumed and a peak with desired mass was detected. The mixture was diluted with H₂O (20.0 mL) and extracted with EtOAc (20.0 mL*3), the combined organic phase was washed with brine (20.0 mL*2), dried over Na₂SO₄ and concentrated to give a residue. The residue was purified by Prep-HPLC (column: Waters Xbridge 150*25 mm*5 um; mobile phase: [water (ammonia hydroxide v/v)-ACN]; gradient: 20%-50% B over 9 min). Compound 31 (8.52 mg, 18.8 μmol, 15.9% yield, 94.5% purity) was obtained, confirmed by H NMR, F NMR, LC-MS, HPLC, SFC.

H NMR: (400 MHz, DMSO-$d_6$) δ 9.32 (d, J=9.2 Hz, 1H), 8.66 (t, J=10.0 Hz, 1H), 8.60-8.50 (m, 2H), 7.98 (d, J=4.8 Hz, 1H), 7.75-7.32 (m, 3H), 6.26-6.08 (m, 1H), 5.05-5.00 (m, 1H), 4.90-4.75 (m, 1H), 2.91-2.71 (m, 3H).

H NMR: (400 MHz, DMSO-$d_6$) δ 9.18 (s, 1H), 8.67 (s, 1H), 8.47 (d, J=6.8 Hz, 2H), 7.99 (s, 1H), 7.58 (s, 1H), 7.34 (s, 2H), 6.21 (dd, $J_1$=9.6 Hz, $J_2$=5.6 Hz, 1H), 5.02 (t, J=10.0 Hz, 1H), 4.80 (dd, $J_1$=10.0 Hz, $J_2$=5.6 Hz, 1H), 2.87 (s, 3H).

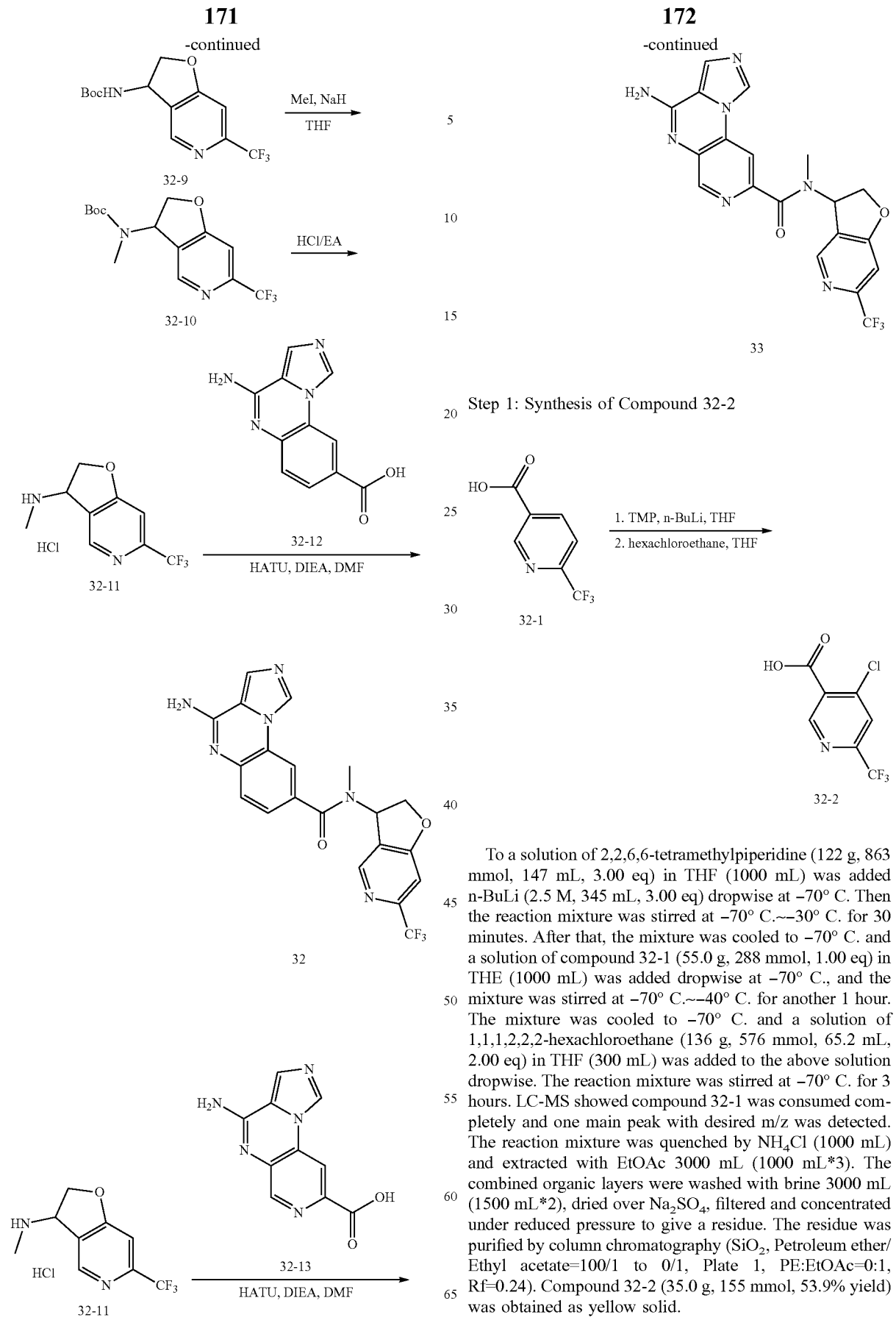

Step 1: Synthesis of Compound 32-2

To a solution of 2,2,6,6-tetramethylpiperidine (122 g, 863 mmol, 147 mL, 3.00 eq) in THF (1000 mL) was added n-BuLi (2.5 M, 345 mL, 3.00 eq) dropwise at −70° C. Then the reaction mixture was stirred at −70° C.~−30° C. for 30 minutes. After that, the mixture was cooled to −70° C. and a solution of compound 32-1 (55.0 g, 288 mmol, 1.00 eq) in THF (1000 mL) was added dropwise at −70° C., and the mixture was stirred at −70° C.~−40° C. for another 1 hour. The mixture was cooled to −70° C. and a solution of 1,1,1,2,2,2-hexachloroethane (136 g, 576 mmol, 65.2 mL, 2.00 eq) in THF (300 mL) was added to the above solution dropwise. The reaction mixture was stirred at −70° C. for 3 hours. LC-MS showed compound 32-1 was consumed completely and one main peak with desired m/z was detected. The reaction mixture was quenched by $NH_4Cl$ (1000 mL) and extracted with EtOAc 3000 mL (1000 mL*3). The combined organic layers were washed with brine 3000 mL (1500 mL*2), dried over $Na_2SO_4$, filtered and concentrated under reduced pressure to give a residue. The residue was purified by column chromatography ($SiO_2$, Petroleum ether/ Ethyl acetate=100/1 to 0/1, Plate 1, PE:EtOAc=0:1, Rf=0.24). Compound 32-2 (35.0 g, 155 mmol, 53.9% yield) was obtained as yellow solid.

H NMR: (400 MHz, $CD_3OD$) δ 9.10 (s, 1H), 8.03 (s, 1H).

Step 2: Synthesis of Compound 32-3

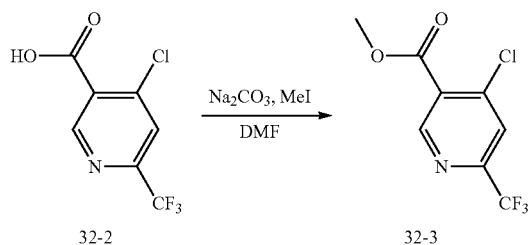

To a solution of compound 32-2 (10.0 g, 44.3 mmol, 1.00 eq) in DMF (100 mL) was added Na₂CO₃ (9.40 g, 88.7 mmol, 2.00 eq) and MeI (18.9 g, 133 mmol, 8.28 mL, 3.00 eq). The mixture was stirred at 25° C. for 2 hrs. LC-MS showed compound 32-2 was consumed completely and one main peak with desired m/z was detected. The reaction mixture was quenched by NaHCO₃ (100 mL) and extracted with EtOAc 300 mL (100 mL*3). The combined organic layers were washed with brine 300 mL (150 mL*2), dried over Na₂SO₄, filtered and concentrated under reduced pressure to give a residue. The residue was purified by prep-HPLC (FA condition; column: Phenomenex luna C18 150*25 mm*10 um; mobile phase: [water (FA)-ACN]; gradient: 42%-62% B over 10 min). Compound 32-3 (10.0 g, 41.7 mmol, 94.2% yield) was obtained as yellow oil.

H NMR: (400 MHz, CDCl₃) δ 9.12 (s, 1H), 7.80 (s, 1H), 4.02 (s, 3H).

Step 3: Synthesis of Compound 32-5

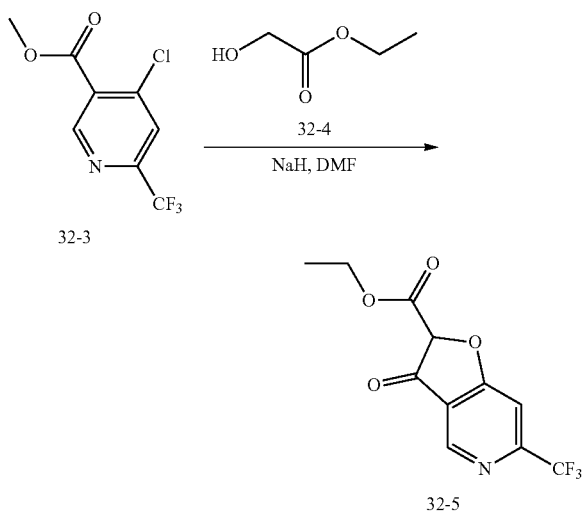

To a solution of compound 32-4 (4.69 g, 45.1 mmol, 1.00 eq) in DMF (20 mL) was added NaH (3.45 g, 90.2 mmol, 2.00 eq) dropwise at 0° C. and the mixture was stirred at 25° C. for 0.5 hrs. Then compound 32-3 (9.00 g 90.2 mmol, 1.00 eq). The resulting mixture was stirred at 25° C. for 2 hrs. LC-MS showed compound 32-3 was consumed completely and one main peak with desired m/z was detected. The reaction mixture was quenched by NH₄Cl (100 mL) and extracted with EA 300 mL (100 mL*3). The combined organic layers were washed with brine 300 mL (150 mL*2), dried over Na₂SO₄, filtered and concentrated under reduced pressure to give a residue. The residue was purified by column chromatography (SiO₂, Petroleum ether/Ethyl acetate=100/1 to 5/1, PE:EtOAc=1:1, Rf=0.40). Compound 32-5 (6.80 g, 24.7 mmol, 65.8% yield) was obtained as brown solid.

H NMR: (400 MHz, CDCl₃) δ 9.17 (s, 1H), 7.81 (s, 1H), 4.55-4.50 (m, 2H), 4.06 (s, 1H), 1.48 (d, J=7.2 Hz, 3H).

Step 4: Synthesis of Compound 32-6

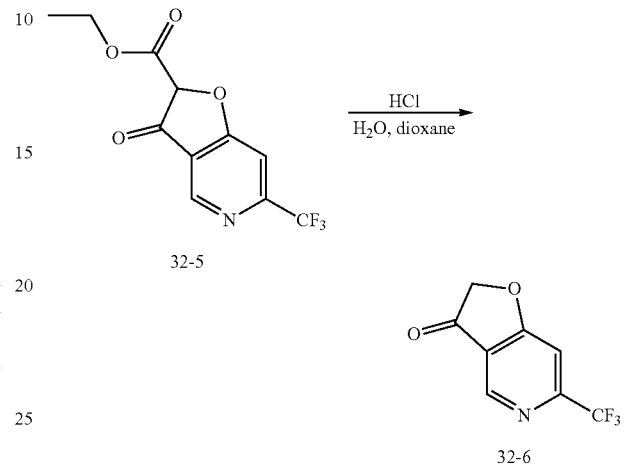

A solution of compound 32-5 (6.8 g, 24.7 mmol, 1.00 eq) in HCl (12 M, 20 mL, 10.0 eq) was stirred at 110° C. for 2 hrs. LC-MS showed compound 32-5 was consumed completely and one main peak with desired m/z was detected. The reaction mixture was diluted with (30.0 mL) and extracted with EtOAc 60.0 mL (20.0 mL*3). The combined organic layers were washed with brine 30.0 mL (15.0 mL*2), dried over Na₂SO₄, filtered and concentrated under reduced pressure to give a residue. Compound 32-6 (5.00 g, crude) was obtained as yellow solid.

Step 5: Synthesis of Compound 32-7

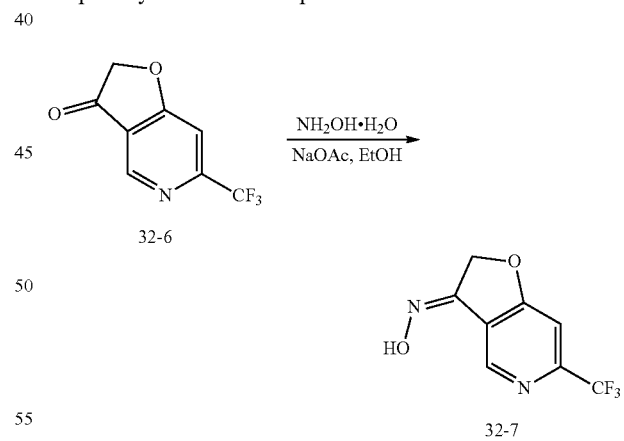

To a solution of compound 32-6 (5.00 g, crude, 1.00 eq) in EtOH (50.0 mL) was added NaOAc (4.85 g, 59.1 mmol, 3.00 eq) and hydroxylamine; hydrochloride (4.11 g, 59.08 mmol, 3.00 eq). The mixture was stirred at 25° C. for 1 hrs. LC-MS showed compound 32-6 was consumed completely and one main peak with desired m/z was detected. The reaction mixture was concentrated under reduced pressure to remove EtOH, then diluted with water 100 mL and extracted with EtOAc 300 mL (100 mL*3). The combined organic layers were washed with brine 300 mL (150 mL*2), dried over Na$_2$SO$_4$, filtered and concentrated under reduced pressure to give a residue. The residue was purified by column chromatography (SiO$_2$, Petroleum ether/Ethyl acetate=100/1 to 5/1, PE:EtOAc=1:1, Rf=0.40). Compound 32-7 (2.10 g, 9.34 mmol, 39% yield two steps) was obtained as yellow solid.

Step 6: Synthesis of Compound 32-8

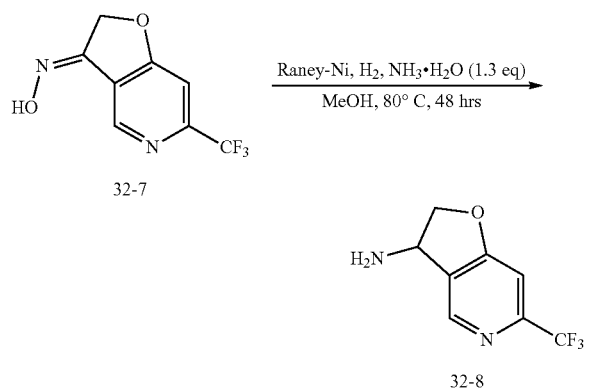

To a solution of compound 32-7 (2.00 g, 9.34 mmol, 1.00 eq) in MeOH (50.0 mL) was added Raney-Ni (50.0 mg, 5.84 mmol, 0.200 eq) and NH$_3$·H$_2$O (3.29 g, 23.50 mmol, 3.62 mL, 25% purity, 2.50 eq) under N$_2$. The suspension was degassed under vacuum and purged with H$_2$ several times. The mixture was stirred under H$_2$ (50 psi) at 80° C. for 16 hours. LC-MS showed compound 32-7 was consumed and one main peak with desired m/z was detected. The reaction mixture was filtered and the solid was collected then concentrated under reduced pressure to give a residue. The crude product compound 32-8 (2.0 g, crude) as brown oil was used into the next step without further purification.

Step 7: Synthesis of Compound 32-9

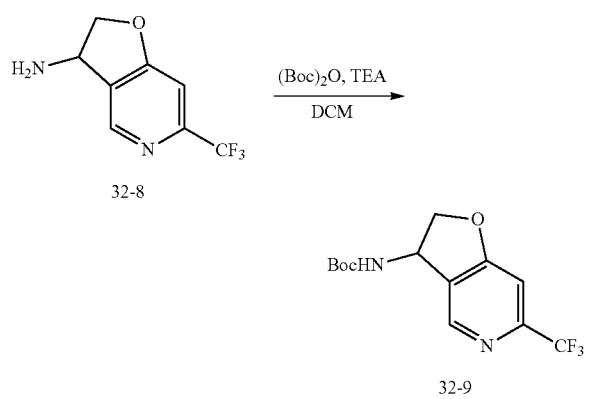

To a solution of compound 32-8 (2.00 g, crude, 1.00 eq) in DCM (20.0 mL) was added TEA (3.47 g, 34.29 mmol, 4.77 mL, 4.00 eq) and Boc$_2$O (4.12 g, 18.9 mmol, 4.33 mL, 2.00 eq). The mixture was stirred at 25° C. for 2 hrs. LC-MS showed compound 32-8 was consumed completely and one main peak with desired m/z was detected. The reaction mixture was diluted with water 10.0 mL and extracted with DCM 15.0 mL*3). The combined organic layers were washed with brine 30.0 mL (15.0 mL*2), dried over Na$_2$SO$_4$, filtered and concentrated under reduced pressure to give a residue. The residue was purified by prep-HPLC (FA condition; column: Phenomenex luna C18 (250*70 mm, 10 um); mobile phase: [water (FA)-ACN]; gradient: 35%-65% B over 22 min). Compound 32-9 (400 mg, 1.31 mmol, 14.3% yield two steps) was obtained as yellow oil.

H NMR: (400 MHz, CDCl$_3$) δ 8.62 (s, 1H), 7.18 (s, 1H), 5.51 (brs, 1H), 4.96-4.91 (m, 2H), 4.56-4.52 (m, 1H), 1.48 (s, 9H).

Step 8: Synthesis of Compound 32-10

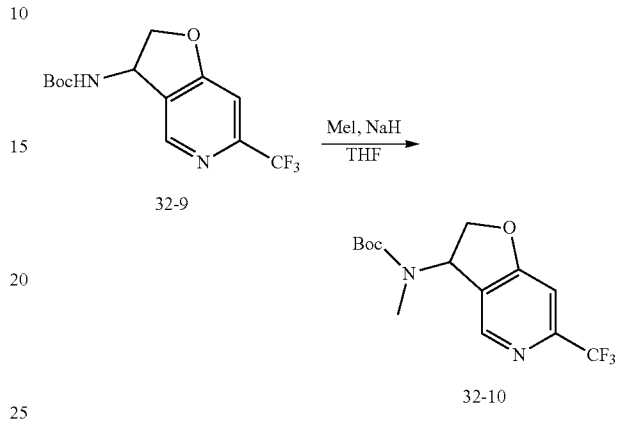

To a solution of compound 32-9 (400 mg, 1.31 mmol, 1.00 eq) in THF (5.00 mL) was added NaH (78.9 mg, 1.97 mmol, 60% purity, 1.50 eq) at 0° C., the mixture was stirred at 0° C. for 0.5 hr. Then MeI (187 mg, 1.31 mmol, 81.8 μL, 1.00 eq) was added to the mixture. The mixture was stirred at 20° C. for another 2 hrs. LC-MS showed compound 32-9 was consumed completely and one main peak with desired m/z was detected. The reaction mixture was diluted with water 100 mL and extracted with EA 300 mL (100 mL*3). The combined organic layers were washed with brine 300 mL (150 mL*2), dried over Na$_2$SO$_4$, filtered and concentrated under reduced pressure to give a residue. The residue was purified by column chromatography (SiO$_2$, Petroleum ether/Ethyl acetate=100/1 to 5/1, PE:EtOAc=5:1, Rf=0.40). Compound 32-10 (350 mg, 1.10 mmol, 83.64% yield) was obtained as yellow oil.

H NMR: (400 MHz, CDCl$_3$) δ 8.51 (s, 1H), 7.18 (s, 1H), 6.19-5.89 (m, 1H), 4.81-4.76 (m, 1H), 4.57-4.55 (m, 1H), 2.60 (brs, 3H), 1.50 (s, 9H).

Step 9: Synthesis of Compound 32-11

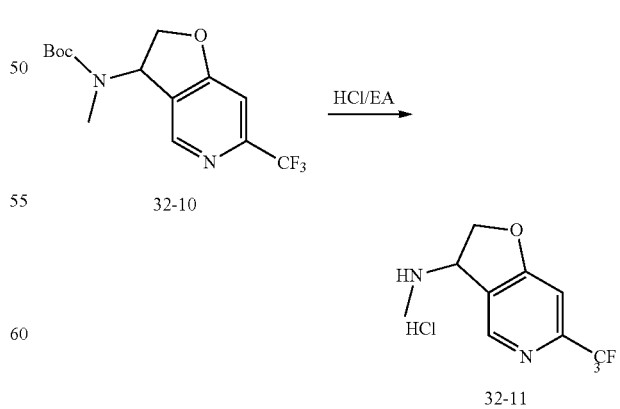

To a solution of compound 32-10 (350 mg, 1.10 mmol, 1.00 eq) in DCM (10.0 mL) was added HCl/dioxane (2 M, 10 mL, 18.19 eq) at 0° C. The mixture was stirred at 25° C.

for 12 hrs. LC-MS showed compound 32-10 was consumed completely and one main peak with desired m/z was detected. The reaction mixture was concentrated under reduced pressure to give a residue. Compound 32-11 (250 mg, 0.981 mmol, 89.3% yield, HCl) was obtained as yellow oil.

Step 10: Synthesis of Compound 32

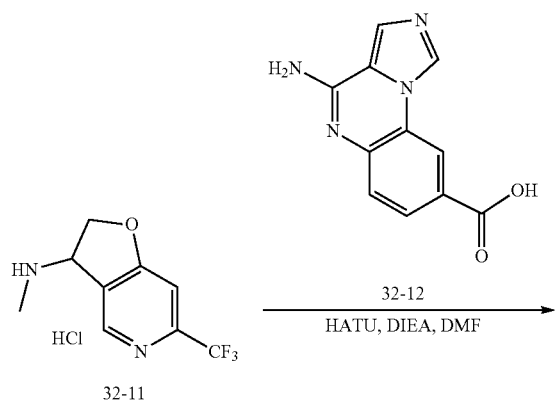

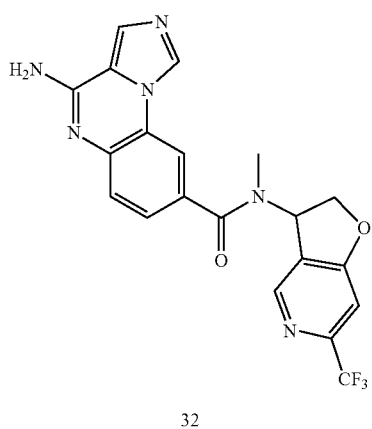

To a solution of compound 32-12 (40.0 mg, 175 μmol, 1.00 eq) and compound 32-11 (44.6 mg, 175 μmol, 1.00 eq, HCl) in DMF (2.00 mL) was added HATU (99.5 mg, 262 μmol, 1.50 eq) and DIEA (67.7 mg, 524 μmol, 5.00 eq). The mixture was stirred at 25° C. for 1 hr. LC-MS showed compound 32-12 was consumed and one peak with desired m/z was detected. The reaction mixture was concentrated under reduced pressure to give a residue. The residue was purified by prep-HPLC (neutral condition; column: Waters Xbridge C18 150*50 mm*10 um; mobile phase: [water (NH₄HCO₃)-ACN]; gradient: 20%-50% B over 10 min). Compound 32 (21.6 mg, 49.0 μmol, 28.0% yield, 97.18% purity) was obtained.

H NMR: (400 MHz, DMSO-d₆) δ 9.18 (s, 1H), 8.73 (s, 1H), 8.33 (s, 1H), 7.91 (s, 1H), 7.53-7.46 (m, 5H), 6.38-6.28 (m, 0.5H), 4.99-4.82 (m, 2H), 2.74 (s, 3H).

Step 11: Synthesis of Compound 33

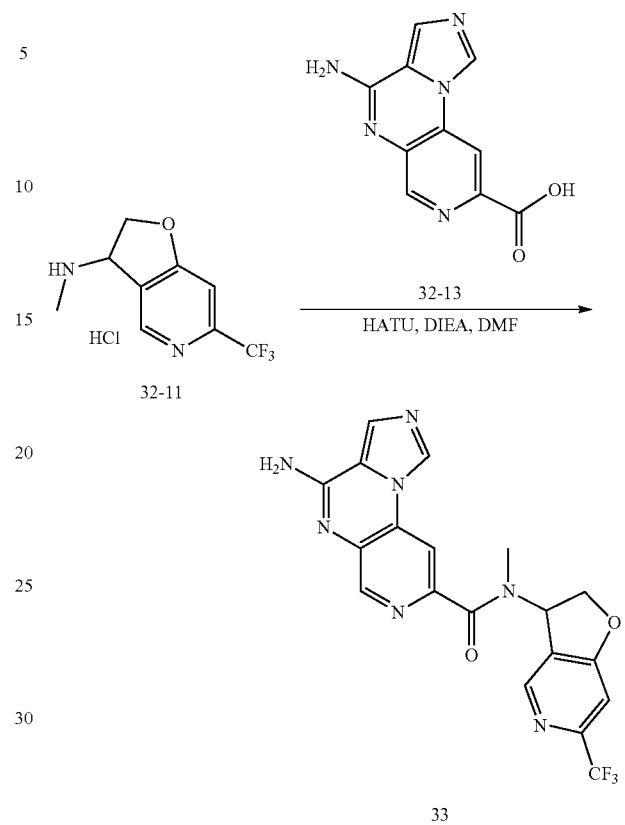

To a solution of compound 32-13 (40.0 mg, 175 μmol, 1.00 eq) and compound 32-11 (44.4 mg, 175 μmol, 1.00 eq, HCl) in DMF (2.00 mL) was added HATU (99.5 mg, 262 μmol, 1.50 eq) and DIEA (67.7 mg, 524 μmol, 5.00 eq). The mixture was stirred at 25° C. for 1 hr. LC-MS showed compound 32-13 was consumed and one peak with desired m/z was detected. The reaction mixture was concentrated under reduced pressure to give a residue. The residue was purified by prep-HPLC (neutral condition; column: Waters Xbridge C18 150*50 mm*10 um; mobile phase: [water (NH₄HCO₃)-ACN]; gradient: 21%-51% B over 10 min). Compound 33 (18.53 mg, 41.2 μmol, 23.6% yield, 95.44% purity) was obtained.

H NMR: (400 MHz, DMSO-d₆) δ 9.33-9.29 (m, 1H), 8.82-8.83 (m, 1H), 8.65-8.51 (m, 2H), 8.00-7.98 (m, 1H), 7.80-7.74 (m, 2H), 7.55-7.53 (m, 1H), 6.42-6.11 (m, 1H), 5.02-4.82 (m, 2H), 2.86-2.72 (m, 3H).

Example 22: Synthesis of Compounds 34

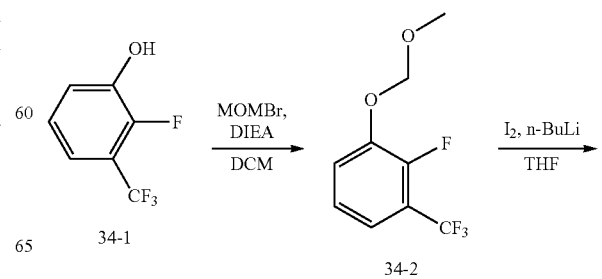

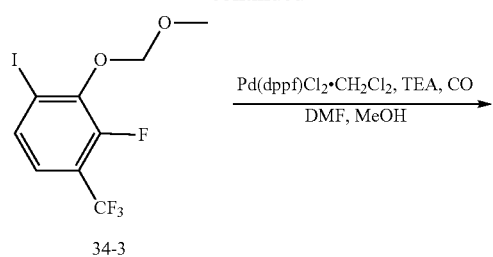
34-3
Pd(dppf)Cl$_2$·CH$_2$Cl$_2$, TEA, CO
DMF, MeOH
→
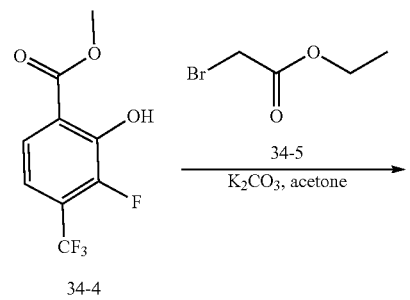
34-4
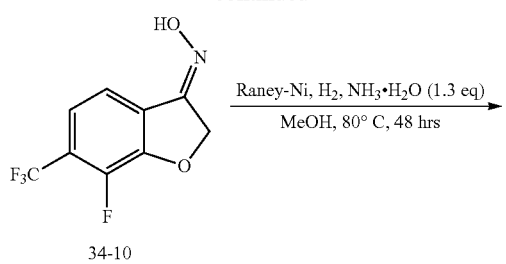
34-10
Raney-Ni, H$_2$, NH$_3$·H$_2$O (1.3 eq)
MeOH, 80° C, 48 hrs
→
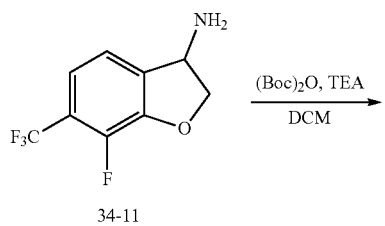
34-11
(Boc)$_2$O, TEA
DCM
→
Br—CH$_2$—C(=O)—O—Et
34-5
K$_2$CO$_3$, acetone
→
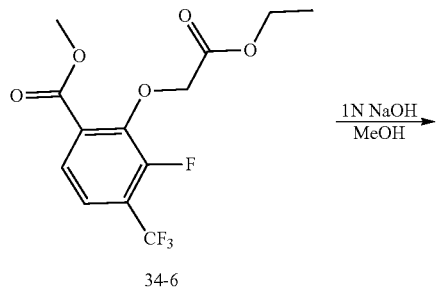
34-6
1N NaOH
MeOH
→
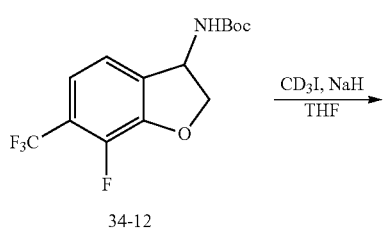
34-12
CD$_3$I, NaH
THF
→
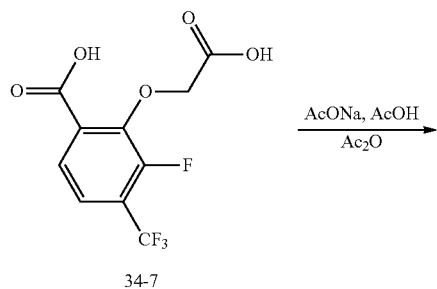
34-7
AcONa, AcOH
Ac$_2$O
→
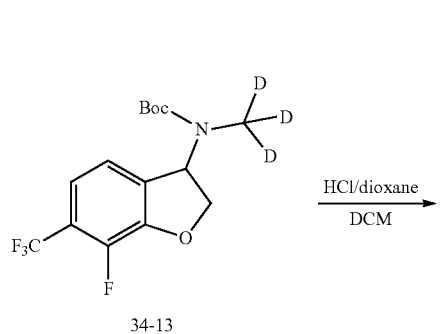
34-13
HCl/dioxane
DCM
→
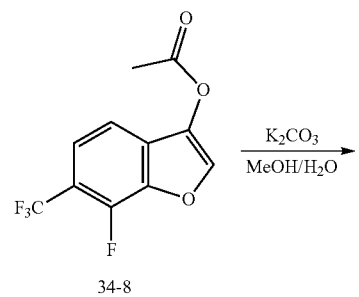
34-8
K$_2$CO$_3$
MeOH/H$_2$O
→
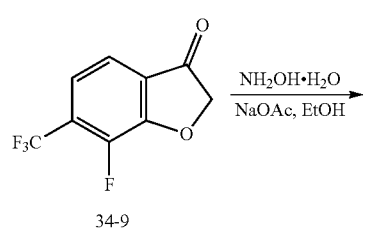
34-9
NH$_2$OH·H$_2$O
NaOAc, EtOH
→
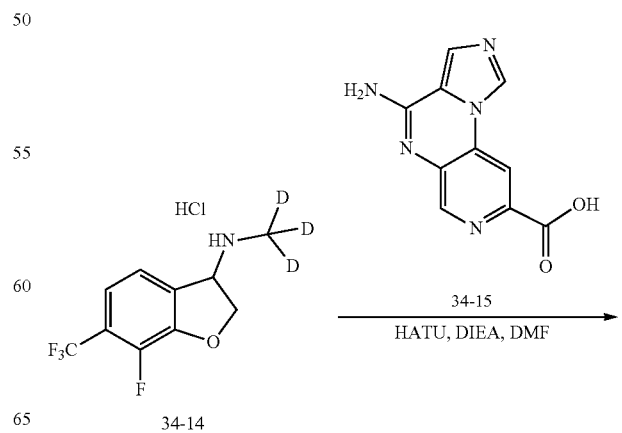
34-14
34-15
HATU, DIEA, DMF
→

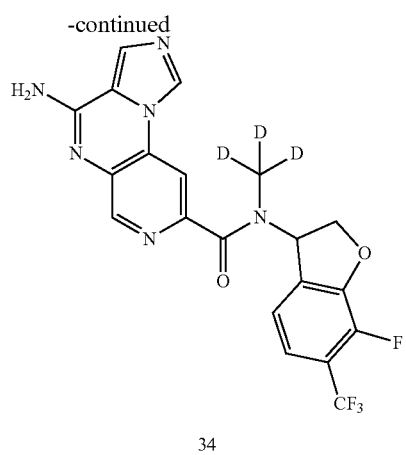

34

Step 1: Synthesis of Compound 34-2

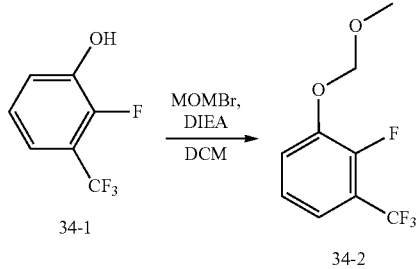

To a solution of compound 34-1 (7.00 g, 38.9 mmol, 4.89 mL, 1.00 eq) in DCM (70.0 mL) was added DIEA (10.1 g, 77.7 mmol, 13.5 mL, 2.00 eq) and MOMCl (5.10 g, 40.8 mmol, 3.33 mL, 1.05 eq) at 0° C., then the mixture was stirred at 25° C. for 2 hrs. TLC (Petroleum ether:Ethyl acetate=5:1) showed compound 34-1 was consumed and a new spot formed. The mixture was diluted with a solution of saturated NH$_4$Cl (100 mL), then extracted with DCM (100 mL*3), the combined organic phase was dried over Na$_2$SO$_4$ and concentrated to give a residue. The residue was purified by column chromatography (SiO$_2$, Petroleum ether:Ethyl acetate=1:0 to 10:1). Compound 34-2 (8.00 g, 35.7 mmol, 91.8% yield) was obtained as yellow liquid, confirmed by H NMR and F NMR.

H NMR: (400 MHz, DMSO-d$_6$) δ 7.62-7.58 (m, 1H), 7.38-7.34 (m, 2H), 5.33 (s, 2H), 3.42 (s, 3H).

Step 2: Synthesis of Compound 34-3

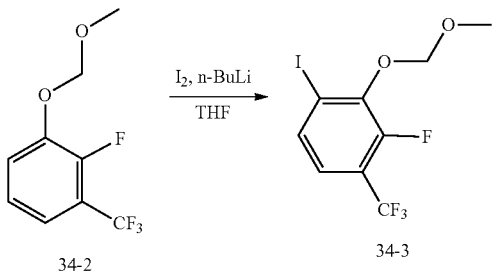 [SMILES: COCOc1cccc(C(F)(F)F)c1F ; COCOc1c(I)ccc(C(F)(F)F)c1F ; "THF"]

To a solution of compound 34-2 (8.00 g, 35.7 mmol, 1.00 eq) in THF (80.0 mL) was added dropwise n-BuLi (2.5 M, 17.1 mL, 1.20 eq) at −78° C., the mixture was stirred at −78° C. for 1 hr, then I$_2$ (10.9 g, 42.8 mmol, 8.63 mL, 1.20 eq) in THF (20.0 mL) was added dropwise, the mixture was stirred at 25° C. for 1 hr. TLC (Petroleum ether:Ethyl acetate=5:1) showed ~40% compound 34-2 remained and a new spot formed. The mixture was diluted with a solution of saturated NH$_4$Cl (200 mL) and extracted with Ethyl acetate (200 mL*3), the combined organic phase was washed with brine (200 mL*2), dried over Na$_2$SO$_4$ and concentrated to give a residue. The residue was purified by column chromatography (SiO$_2$, Petroleum ether:Ethyl acetate=1:0 to 10:1). Compound 34-3 (8.00 g, crude) was obtained as yellow liquid, confirmed by H NMR and F NMR.

H NMR: (400 MHz, DMSO-d$_6$) δ 7.90 (d, J=4.8 Hz, 1H), 7.30-7.28 (m, 1H), 5.23 (s, 2H), 3.55 (s, 3H).

Step 3: Synthesis of Compound 34-4

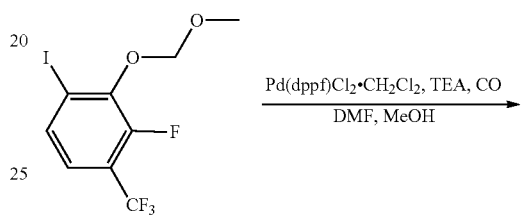

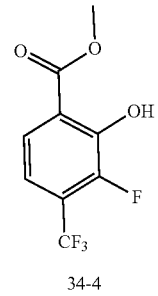

To a solution of compound 34-3 (8.00 g, 22.9 mmol, 1.00 eq) in DMF (50.0 mL) and MeOH (50.0 mL) was added TEA (11.6 g, 114 mmol, 15.9 mL, 5.00 eq), Pd(dppf)Cl$_2$·CH$_2$Cl$_2$ (1.87 g, 2.29 mmol, 0.100 eq) under N$_2$, the mixture was stirred at 80° C. for 12 hrs under CO (50 Psi) atmosphere. TLC (Petroleum ether:Ethyl acetate=10:1) showed compound 34-3 was consumed completely and a new spot formed. The mixture was concentrated to remove MeOH, then diluted with H$_2$O (50.0 mL) and extracted with Ethyl acetate (50.0 mL*3), the combined organic phase was washed with brine (50.0 mL*2), dried over Na$_2$SO$_4$ and concentrated to give a residue. The residue was purified by column chromatography (SiO$_2$, Petroleum ether:Ethyl acetate=1:0 to 10:1). Compound 34-4 (4.50 g, crude) was obtained as yellow solid, confirmed by H NMR and F NMR.

H NMR: (400 MHz, DMSO-d$_6$) δ 10.81 (br s, 1H), 7.70 (d, J=8.4 Hz, 1H), 7.28-7.27 (m, 1H), 3.91 (s, 3H).

Step 4: Synthesis of Compound 34-6

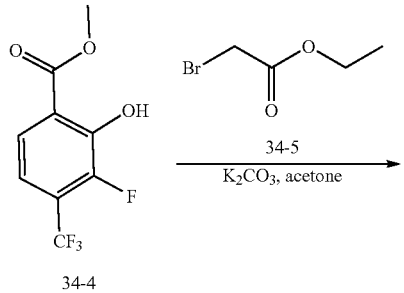

To a solution of compound 34-4 (2.00 g, 8.40 mmol, 1.00 eq) and compound 34-5 (1.68 g, 10.1 mmol, 1.12 mL, 1.20 eq) in acetone (25.0 mL) was added K₂CO₃ (5.80 g, 42.0 mmol, 5.00 eq), then the mixture was stirred at 60° C. for 12 hrs. LC-MS showed compound 34-4 was consumed and a peak with desired mass was detected. The mixture was filtered and the filtrate was concentrated to give a residue. The residue was purified by Prep-HPLC (column: Welch Ultimate XB-CN 250*50*10 um; mobile phase: [Hexane-EtOH]; B %: 0%, isocratic elution mode). Compound 34-6 (1.10 g, 3.39 mmol, 40.4% yield) was obtained as yellow liquid, confirmed by H NMR and F NMR.

H NMR: (400 MHz, DMSO-$d_6$) δ 7.69 (d, J=8.4 Hz, 1H), 7.63-7.60 (m, 1H), 4.84 (s, 2H), 4.17-4.15 (m, 2H), 3.96 (s, 3H), 1.21 (s, 3H).

Step 5: Synthesis of Compound 34-7

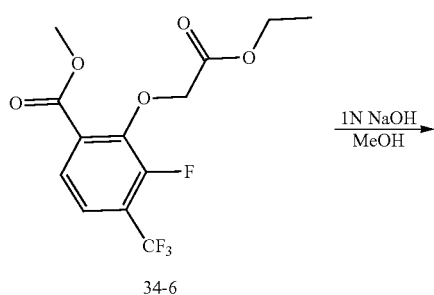

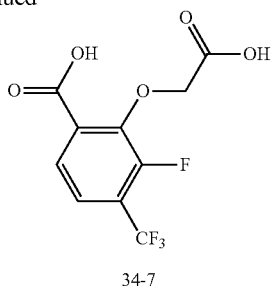

To a solution of compound 34-6 (1.10 g, 3.39 mmol, 1.00 eq) in MeOH (11.0 mL) was added NaOH (2.00 M, 5.09 mL, 3.00 eq), then the mixture was stirred at 25° C. for 3 hrs. LC-MS showed compound 34-6 was consumed and a peak was detected. The mixture was concentrated to give a residue, HCl (1M) was added to adjust pH to about 3 at 0° C., then diluted with H₂O (30.0 mL) and extracted with Ethyl acetate (30.0 mL*3), the combined organic phase was dried over Na₂SO₄ and concentrated to give a residue. Compound 34-7 (780 mg, 2.76 mmol, 81.5% yield) was obtained as yellow solid, confirmed by H NMR and F NMR.

LC-MS: (M+H)⁺: 283.0

H NMR: (400 MHz, DMSO-$d_6$) δ 7.65-7.63 (m, 1H), 7.57-7.54 (m, 1H), 4.74 (s, 2H).

Step 6: Synthesis of Compound 34-8

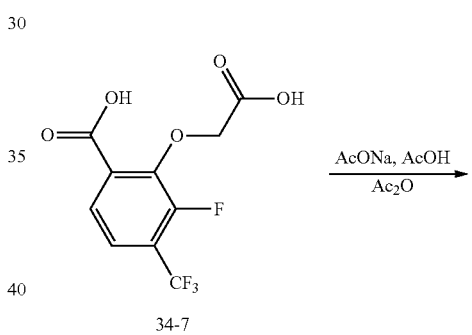

To a solution of compound 34-7 (780 mg, 2.76 mmol, 1.00 eq) in Ac₂O (8.00 mL) was added NaOAc (272 mg, 3.32 mmol, 1.20 eq) and AcOH (606 mg, 10.1 mmol, 578 μL, 3.65 eq), then the mixture was stirred at 140° C. for 2 hrs. LC-MS showed compound 34-7 was consumed and a peak with desired mass was detected. The mixture was diluted with H₂O (30.0 mL) and extracted with Ethyl acetate (30.0 mL*3), the combined organic phase was washed with brine (20.0 mL*2), dried over Na₂SO₄ and concentrated to give a residue. Compound 34-8 (650 mg, 2.48 mmol, 89.7% yield) was obtained as yellow solid, confirmed by H NMR and F NMR.

LC-MS: (M+H)⁺: 263.0

H NMR: (400 MHz, DMSO-d$_6$) δ 8.56 (s, 1H), 7.66-7.65 (m, 2H), 2.40 (s, 3H).

Step 7: Synthesis of Compound 34-9

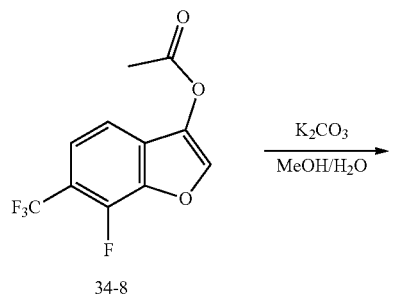

To a solution of compound 34-8 (650 mg, 2.48 mmol, 1.00 eq) in MeOH (10.0 mL) and H$_2$O (2.00 mL) was added K$_2$CO$_3$ (1.03 g, 7.44 mmol, 3.00 eq), then the mixture was stirred at 25° C. for 0.5 hr. LC-MS showed compound 34-8 was consumed and a peak with desired mass was detected. HCl (1.00 M) was added to adjust pH to about 5 at 0° C., then diluted with H$_2$O (20.0 mL) and extracted with DCM (20.0 mL*3), the combined organic phase was dried over Na$_2$SO$_4$ and concentrated to give a residue. Compound 34-9 (500 mg, crude) was obtained as yellow solid, confirmed by H NMR and F NMR.

H NMR: (400 MHz, DMSO-d$_6$) δ 7.67 (d, J=8.0 Hz, 1H), 7.50-7.47 (m, 1H), 5.03 (s, 2H).

Step 8: Synthesis of Compound 34-10

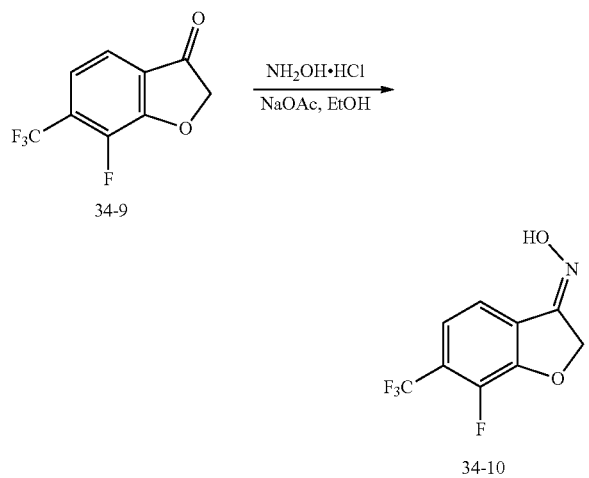

To a solution of compound 34-9 (500 mg, 2.27 mmol, 1.00 eq) in EtOH (10.0 mL) was added NaOAc (559 mg, 6.81 mmol, 3.00 eq) and NH$_2$OH·HCl (316 mg, 4.54 mmol, 2.00 eq), then the mixture was stirred at 25° C. for 2 hrs. LC-MS showed compound 34-9 was consumed and a peak with desired mass was detected. The mixture was diluted with H$_2$O (20.0 mL) and extracted with DCM (20.0 mL*3), the combined organic phase was dried over Na$_2$SO$_4$ and concentrated to give a residue. The residue was purified by column chromatography (SiO$_2$, Petroleum ether:Ethyl acetate=100:1 to 5:1). TLC (Petroleum ether:Ethyl acetate=5:1, R$_f$=0.60). Compound 34-10 (400 mg, crude) was obtained as yellow solid, confirmed by H NMR and F NMR.

LC-MS: (M+H)$^+$: 236.0

H NMR: (400 MHz, DMSO-d$_6$) δ 11.94 (s, 1H), 7.53 (d, J=8.0 Hz, 1H), 7.35 (dd, J$_1$=8.0 Hz, J$_2$=6.0 Hz, 1H), 5.37 (s, 2H).

Step 9: Synthesis of Compound 34-11

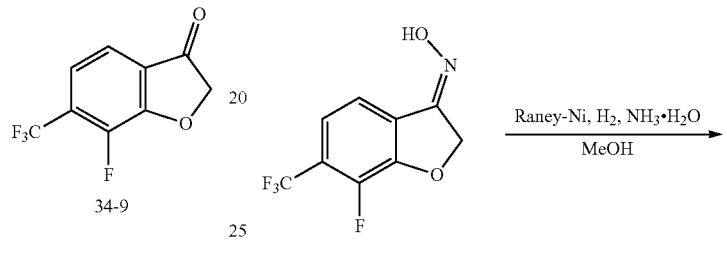

To a solution of compound 34-10 (400 mg, 1.70 mmol, 1.00 eq) in MeOH (10.0 mL) was added NH$_3$·H$_2$O (910 mg, 6.49 mmol, 1.00 mL, 25.0% purity, 3.82 eq) and Raney-Ni (100 mg) under N$_2$, then the mixture was stirred at 80° C. for 12 hrs under H$_2$ (50 Psi) atmosphere. LC-MS showed compound 34-10 was consumed and a peak with desired mass was detected. The mixture was filtered and the filtrate was concentrated to give a residue. Compound 34-11 (350 mg, crude) was obtained as yellow solid, confirmed by H NMR and F NMR.

H NMR: (400 MHz, DMSO-d$_6$) δ 7.37-7.35 (m, 1H), 7.27-7.24 (m, 1H), 6.99-6.76 (m, 1H), 4.82-4.74 (m, 1H), 4.35-4.25 (m, 1H).

Step 10: Synthesis of Compound 34-12

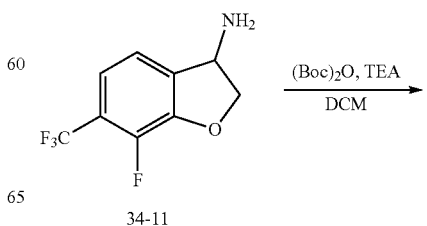

188

Step 12: Synthesis of Compound 34-14

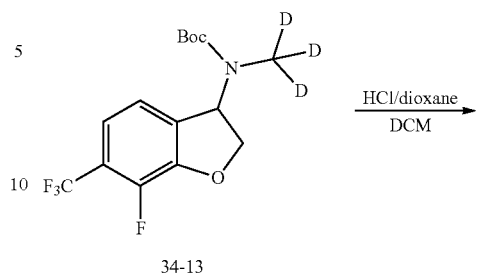

34-13

To a solution of compound 34-10 (350 mg, 1.58 mmol, 1.00 eq) in DCM (5.00 mL) was added TEA (480 mg, 4.75 mmol, 661 µL, 3.00 eq) and Boc₂O (691 mg, 3.17 mmol, 727 µL, 2.00), then the mixture was stirred at 25° C. for 1 hr. LC-MS showed compound 34-11 was consumed and a peak was detected. The mixture was diluted with H₂O (20.0 mL) and extracted with DCM (20.0 mL*3), the combined organic phase was dried over Na₂SO₄ and concentrated to give a residue. The residue was purified by column chromatography (SiO₂, Petroleum ether:Ethyl acetate=100:1 to 5:1). TLC (Petroleum ether:Ethyl acetate=5:1, R$_f$=0.50). Compound 34-12 (180 mg, 560 µmol, 35.4% yield) was obtained as yellow solid, confirmed by H NMR, F NMR.

H NMR: (400 MHz, DMSO-d₆) δ 7.72-7.67 (m, 1H), 7.30-7.24 (m, 2H), 5.42-5.38 (m, 1H), 4.85 (t, J=9.2 Hz, 1H), 4.44-4.40 (m, 1H), 1.40 (s, 9H).

Step 11: Synthesis of Compound 34-13

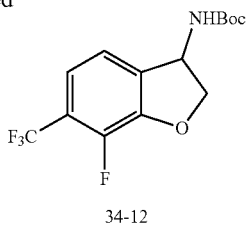

34-12

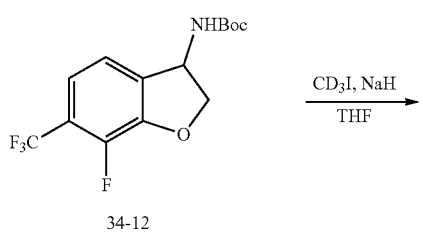

34-13

To a solution of compound 34-12 (180 mg, 560 µmol, 1.00 eq) in THF (5.00 mL) was added NaH (33.6 mg, 840 µmol, 60.0% purity, 1.50 eq) at 0° C., the mixture was stirred at 0° C. for 0.5 hr, then CD₃I (238 mg, 1.68 mmol, 102 µL, 3.00 eq) was added, the mixture was stirred at 25° C. for 4 hrs. LC-MS showed compound 34-12 was consumed and a peak was detected. A solution of saturated NH₄Cl (20.0 mL) was added to the mixture at 0° C., then extracted with Ethyl acetate (20.0 mL*3), the combined organic phase was washed with brine (20.0 mL*2), dried over Na₂SO₄ and concentrated to give a residue. The residue was purified by Prep-TLC (Petroleum ether:Ethyl acetate=5:1, R$_f$=0.60). Compound 34-13 (120 mg, 355 µmol, 63.3% yield) was obtained as yellow solid, confirmed by H NMR and F NMR.

H NMR: (400 MHz, DMSO-d₆) δ 7.31-7.28 (m, 2H), 6.04-5.68 (m, 1H), 4.83 (t, J=10.0 Hz, 1H), 4.65 (dd, J₁=10.0 Hz, J₂=4.4 Hz, 1H), 1.35 (s, 9H).

To a solution of compound 34-13 (120 mg, 355 µmol, 1.00 eq) in DCM (1.00 mL) was added HCl/dioxane (2.00 M, 2.00 mL, 11.3 eq) at 0° C., then the mixture was stirred at 25° C. for 2 hrs. LC-MS showed compound 34-13 was consumed and a new peak was detected. The mixture was concentrated to give a residue. Compound 34-14 (95.0 mg, crude, HCl) was obtained as yellow solid.

Step 12: Synthesis of Compound 34

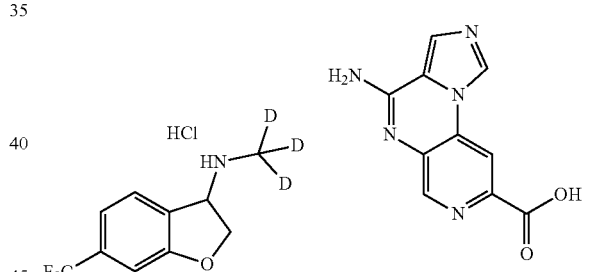

34

To a solution of compound 34-14 (95.0 mg, 346 µmol, 1.00 eq, HCl) and compound 34-15 (83.2 mg, 363 µmol, 1.05 eq) in DMF (2.00 mL) was added HATU (197 mg, 519 μmol, 1.50 eq) and DIEA (134 mg, 1.04 mmol, 181 L, 3.00 eq), then the mixture was stirred at 25° C. for 1 hr. LC-MS showed compound 34-14 was consumed and a new peak was detected. The mixture was diluted with H₂O (20.0 mL) and extracted with Ethyl acetate (20.0 mL*3), the combined organic phase was washed with brine (20.0 mL*2), dried over Na₂SO₄ and concentrated to give a residue. The residue was purified by Prep-HPLC (column: Waters Xbridge C18 150*50 mm*10 um; mobile phase: [water (NH₄HCO₃)-ACN]; gradient: 22%-52% B over 10 min). Compound 34 (21.11 mg, 47.0 μmol, 13.6% yield) was obtained as yellow solid, confirmed by H NMR, F NMR, LC-MS, HPLC, and SFC.

H NMR: (400 MHz, DMSO-d₆) δ 9.22 (s, 1H), 8.68 (s, 1H), 8.48 (s, 1H), 8.00 (s, 1H), 7.51-7.45 (m, 3H), 7.33-7.30 (m, 1H), 6.25 (br s, 1H), 4.92-4.80 (m, 2H).

LC-MS: (M+H)⁺: 450.2

HPLC: purity: 91.1% (220 nm)

Example 23: Synthesis of Compounds 35

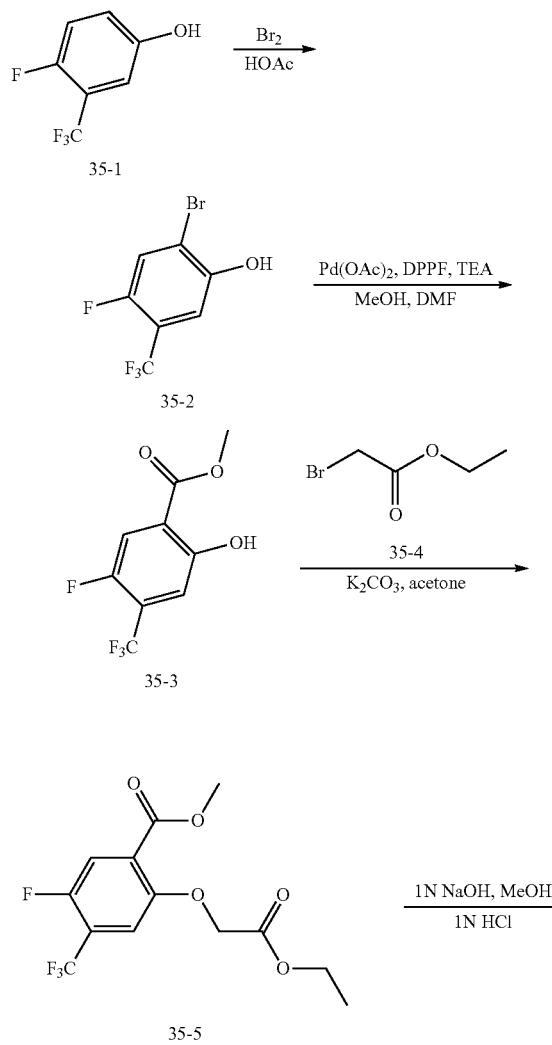

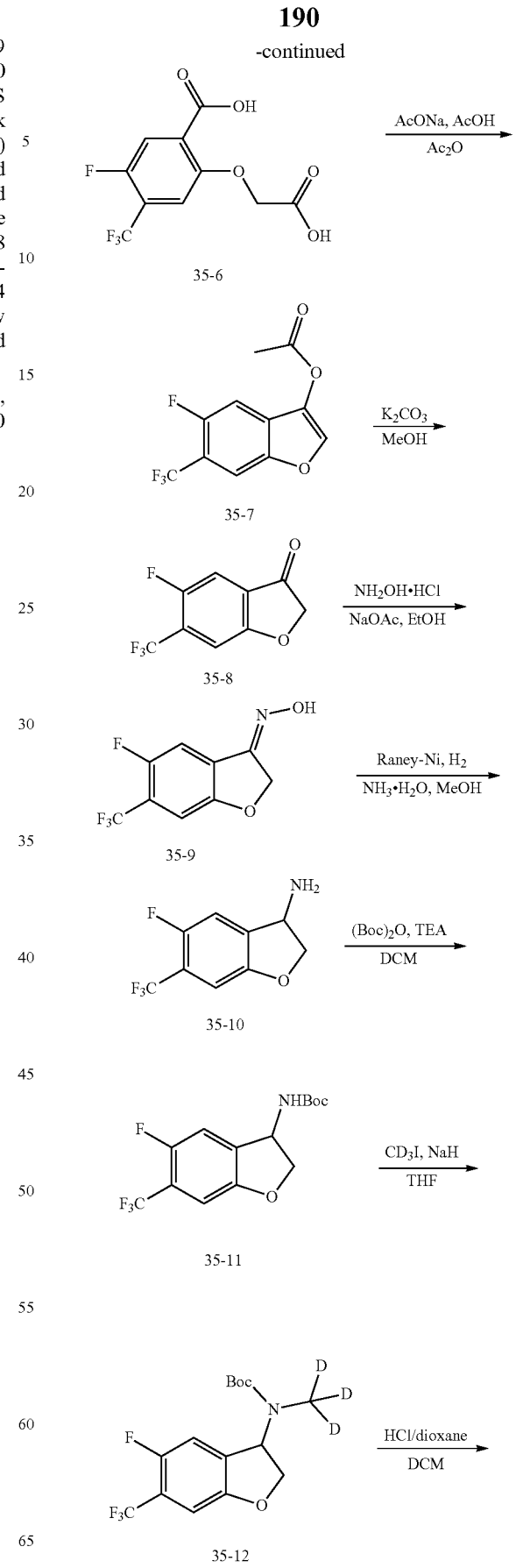

191

-continued

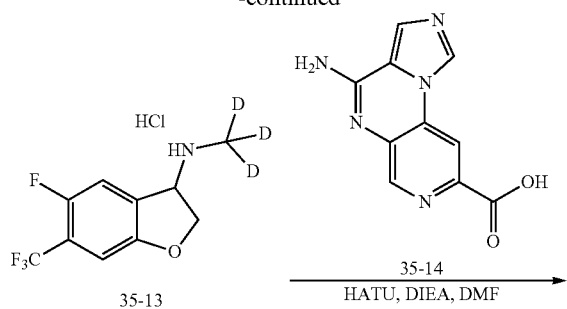

35-13

35-14
HATU, DIEA, DMF

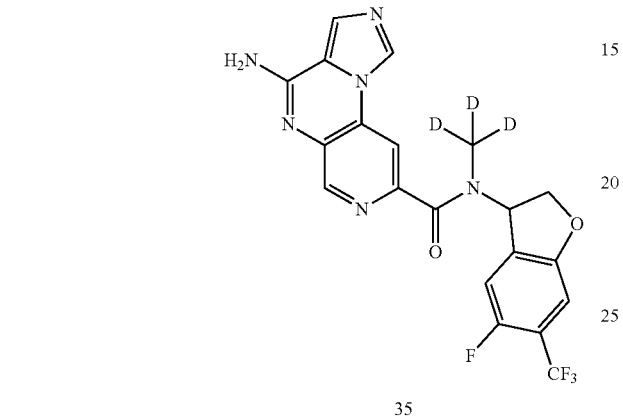

35

Step 1: Synthesis of Compound 35-2

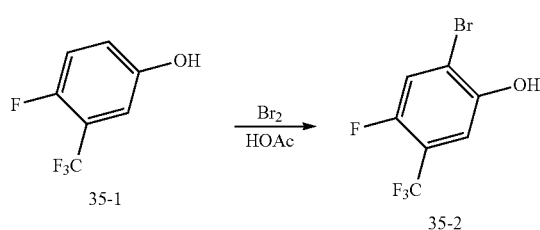 [SMILES: Oc1ccc(F)c(C(F)(F)F)c1 ; "Br2" ; Oc1cc(C(F)(F)F)c(F)cc1Br ; "HOAc"]

To a mixture of compound 35-1 (10.0 g, 55.5 mmol, 1.00 eq) in HOAc (50.0 mL) was added $Br_2$ (8.87 g, 55.5 mmol, 2.86 mL, 1.00 eq), then the mixture was stirred at 25° C. for 10 hrs. TLC (Plate 1: Petroleum ether:Ethyl acetate=5:1) indicated all of compound 35-1 was consumed, and one major new spot was detected. The mixture was diluted with DCM (150 mL) and washed with sat. $Na_2SO_3$ (100 mL*2), the organic layer was washed with sat. $NaHCO_3$ (100 mL*2), dried over $Na_2SO_4$, filtered and concentrated under reduced pressure.

The residue was purified by prep-HPLC (column: Welch Ultimate XB-SiOH 250*70*10 um; mobile phase: [Hexane-EtOH (0.1% $NH_3·H_2O$)]; gradient: 1%-5% B over 15 min). Compound 35-2 (5.50 g, 21.2 mmol, 38.3% yield) was obtained as yellow oil, confirmed by H NMR, F NMR, 2D NMR, and LC-MS.

H NMR: (400 MHz, $CDCl_3$) δ 10.93 (br s, 1H), 7.81 (d, J=10.0 Hz, 1H), 7.19 (d, J=6.4 Hz, 1H).

LC-MS: $(M-H)^+$=258.9

192

Step 2: Synthesis of Compound 35-3

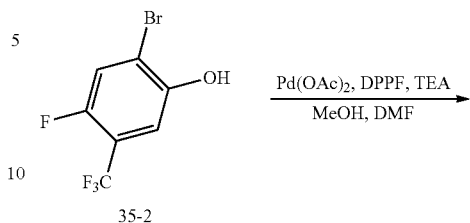

To a solution of compound 35-2 (5.00 g, 19.3 mmol, 1.00 eq) and TEA (5.86 g, 57.9 mmol, 8.06 mL, 3.00 eq) in DMF (15.0 mL) and MeOH (35.0 mL) was added Pd(dppf)$Cl_2·CH_2Cl_2$ (788 mg, 965 μmol, 0.05 eq) under $N_2$. The suspension was degassed under vacuum and purged with CO several times. The mixture was stirred under CO (50 psi) at 80° C. for 10 hrs. LC-MS showed all of compound 35-2 was consumed and a major new peak with desired mass was detected. The mixture was filtered and the filtrate was concentrated to remove MeOH. The residue was diluted with EtOAc (100 mL) and washed with $H_2O$ (100 mL*2) and brine (50.0 mL*1), the organic layer was dried over $Na_2SO_4$, filtered and concentrated under reduced pressure to give a residue. The residue was purified by column chromatography ($SiO_2$, Petroleum ether/Ethyl acetate=I/O to 10/1). Compound 35-3 (3.20 g, 13.4 mmol, 69.6% yield) was obtained as white solid, confirmed by H NMR and F NMR.

LC-MS: $(M+H)^+$=236.9

H NMR: (400 MHz, $CDCl_3$) δ 10.60 (br s, 1H), 7.65 (d, J=10.0 Hz, 1H), 7.24 (d, J=5.6 Hz, 1H), 4.01 (s, 3H).

Step 3: Synthesis of Compound 35-5

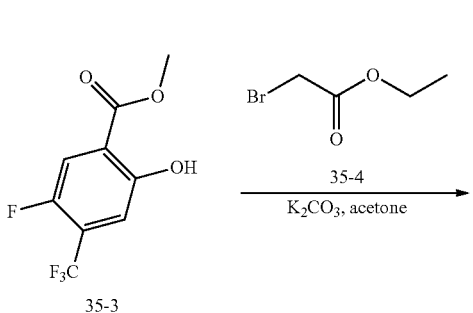

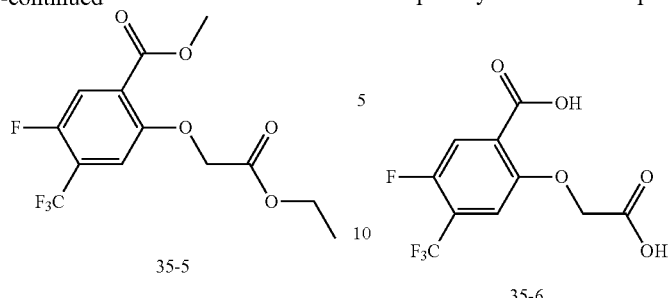

35-5

To a solution of compound 35-3 (3.20 g, 13.4 mmol, 1.00 eq) in acetone (30.0 mL) was added $K_2CO_3$ (2.79 g, 20.2 mmol, 1.50 eq) and compound 35-4 (3.37 g, 20.2 mmol, 2.23 mL, 1.50 eq). The mixture was stirred at 60° C. for 12 hrs. LC-MS showed all of compound 35-3 was consumed and ~63.3% of desired mass was detected. The mixture was concentrated under reduced pressure. The residue was purified by column chromatography ($SiO_2$, Petroleum ether/Ethyl acetate=I/O to 10/1). Compound 35-5 (3.00 g, 9.25 mmol, 68.9% yield) was obtained as colorless oil, confirmed by H NMR, F NMR and LC-MS.

LC-MS: $(M+H)^+=325.1$

H NMR: (400 MHz, $CDCl_3$) δ 7.65 (d, J=10.0 Hz, 1H), 7.14 (d, J=5.6 Hz, 1H), 4.72 (s, 2H), 4.28 (q, J=6.0 Hz, 2H), 3.94 (s, 3H), 1.31 (d, J=7.8 Hz, 1H).

Step 4: Synthesis of Compound 35-6

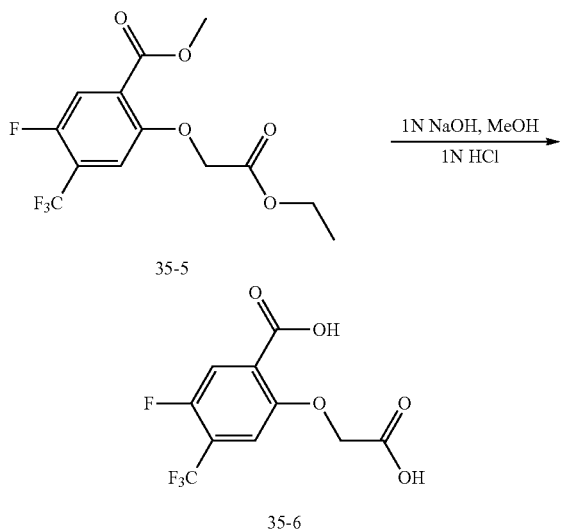

A mixture of compound 35-5 (3.50 g, 10.8 mmol, 1.00 eq), NaOH (2 M, 16.2 mL, 3.00 eq) in MeOH (30.0 mL) was stirred at 25° C. for 2 hrs under $N_2$ atmosphere. LC-MS showed all of compound 35-5 was consumed and a new peak was detected. The mixture was concentrated to remove MeOH, then the pH was adjusted to ~2 with HCl (1.00 M), the solid was filtered and concentrated under reduced. Compound 35-6 (2.60 g, 9.22 mmol, 85.4% yield) was obtained as a white solid, confirmed by H NMR and F NMR.

LC-MS: $(M+23)^+=305.0$

H NMR: (400 MHz, DMSO-$d_6$) δ 7.75 (d, J=6.4 Hz, 1H), 7.47 (d, J=10.4 Hz, 1H), 4.69 (s, 2H).

Step 5: Synthesis of Compound 35-7

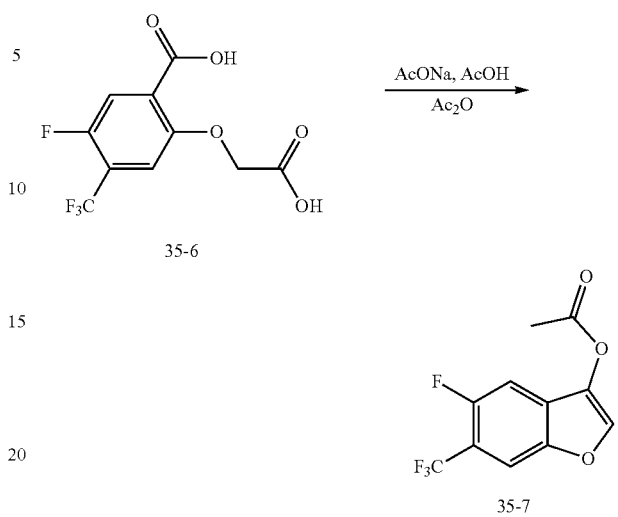

To a solution of compound 35-6 (1.60 g, 5.67 mmol, 1.00 eq) in $Ac_2O$ (8.00 mL) was added AcOH (1.24 g, 20.7 mmol, 1.18 mL, 3.65 eq) and NaOAc (521 mg, 6.35 mmol, 1.12 eq). The mixture was stirred at 140° C. for 6 hrs. LC-MS showed all of compound 35-6 was consumed and a new peak with desired mass was detected. The reaction mixture was diluted with water 50.0 mL and extracted with EtOAc (50.0 mL*3). The combined organic layers were washed with brine (50.0 mL*2), dried over $Na_2SO_4$, filtered and concentrated under reduced pressure to give a residue. Compound 35-7 (1.35 g, crude) was obtained as yellow solid, confirmed by H NMR and F NMR.

H NMR: (400 MHz, $CDCl_3$) δ 8.18 (s, 1H), 7.72 (d, J=4.2 Hz, 1H), 7.38 (d, J=9.6 Hz, 1H), 2.39 (s, 3H).

Step 6: Synthesis of Compound 35-8

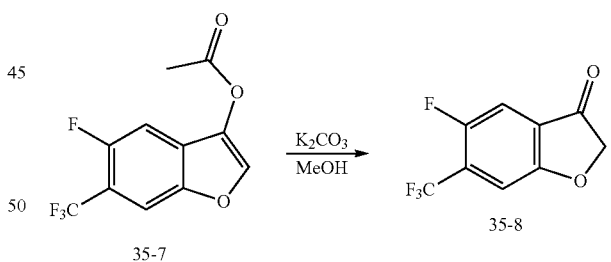

A solution of compound 35-7 (200 mg, 763 μmol, 1.00 eq) and $K_2CO_3$ (316 mg, 2.29 mmol, 3.00 eq) in MeOH (5.00 mL) and $H_2O$ (1.00 mL) was stirred at 25° C. for 0.5 hr. LC-MS showed all of compound 35-7 was consumed and a new peak with desired mass was detected. The mixture was diluted with $H_2O$ (20.0 mL) and adjusted pH to ~2 with HCl (1 M) at 0° C., then extracted with EtOAc (25.0 mL*3), the combined organic layers was washed with brine (20.0 mL*1), dried over $Na_2SO_4$, filtered and concentrated under reduced pressure. Compound 35-8 (150 mg, crude) was obtained as red solid, confirmed by H NMR and F NMR.

H NMR: (400 MHz, $CDCl_3$) δ 7.48 (d, J=8.0 Hz, 1H), 7.43 (d, J=4.8 Hz, 1H), 4.75 (s, 2H).

Step 7: Synthesis of Compound 35-9

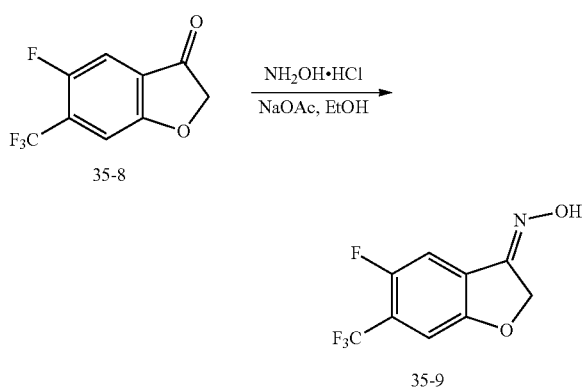

To a solution of compound 35-8 (500 mg, 2.27 mmol, 1.00 eq) in EtOH (10.0 mL) was added NaOAc (559 mg, 6.81 mmol, 3.00 eq) and NHOH·HCl (474 mg, 6.81 mmol, 3.00 eq). The mixture was stirred at 25° C. for 1 hr. LC-MS showed ~54.5% of desired mass was detected. The reaction mixture was concentrated under reduced pressure to remove EtOH, then diluted with water 20.0 mL and extracted with EtOAc (15.0 mL*2). The combined organic layers were washed with brine (15.0 mL*1), dried over $Na_2SO_4$, filtered and concentrated under reduced pressure to give a residue. The residue was purified by column chromatography ($SiO_2$, Petroleum ether/Ethyl acetate=I/O to 10/1). Compound 35-9 (300 mg, crude) was obtained as yellow solid, confirmed by H NMR and F NMR.

H NMR: (400 MHz, $CDCl_3$) δ 7.61 (s, 1H), 7.38 (d, J=7.2 Hz, 1H), 7.17 (d, J=5.2 Hz, 1H), 5.24 (s, 2H).

Step 8: Synthesis of Compound 35-10

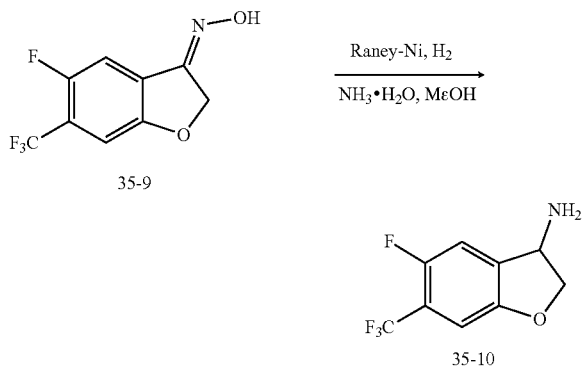

To a solution of compound 35-9 (300 mg, 1.28 mmol, 1.00 eq) and $NH_3 \cdot H_2O$ (910 mg, 6.49 mmol, 1.00 mL, 25% purity, 5.09 eq) in MeOH (10.0 mL) was added Raney-Ni (109 mg, 1.28 mmol, 1.00 eq) under $N_2$. The suspension was degassed under vacuum and purged with $H_2$ several times. The mixture was stirred under $H_2$ (50 psi) at 80° C. for 10 hrs. LC-MS showed all of compound 35-9 was consumed and anew peak was detected. The mixture was filtered and the filtrate was concentrated under reduced pressure. Compound 35-10 (250 mg, crude) was obtained as yellow solid.

Step 9: Synthesis of Compound 35-11

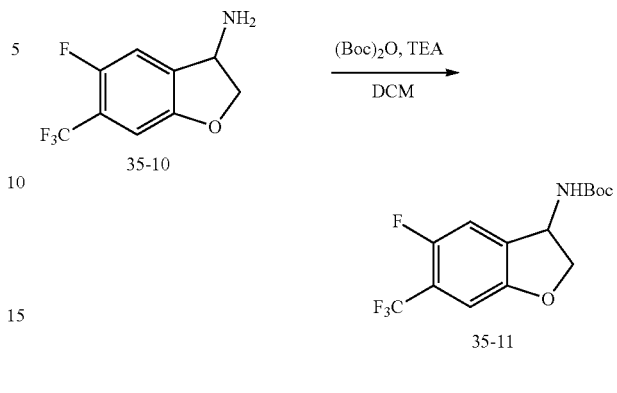

A solution of compound 35-10 (250 mg, 1.13 mmol, 1.00 eq), $Boc_2O$ (370 mg, 1.70 mmol, 390 μL, 1.50 eq) and TEA (343 mg, 3.39 mmol, 472 μL, 3.00 eq) in DCM (10.0 mL) was stirred at 25° C. for 1 hr. LC-MS showed all of compound 35-10 was consumed. The mixture was diluted with $H_2O$ (20.0 mL) and extracted with DCM (15.0 mL*2), the combined organic layers was washed with brine (15.0 mL*1), dried over $Na_2SO_4$, filtered and concentrated under reduced pressure. The residue was purified by column chromatography ($SiO_2$, Petroleum ether/Ethyl acetate=1/0 to 10/1). Compound 35-11 (170 mg, crude) was obtained as yellow solid, confirmed by H NMR and F NMR.

H NMR: (400 MHz, $CDCl_3$) δ 7.18 (d, J=10.0 Hz, 1H), 7.02 (d, J=5.2 Hz, 1H), 5.43 (s, 1H), 4.88 (s, 1H), 4.76 (s, 1H), 4.37 (dd, $J_1$=10.0 Hz, $J_2$=4.8 Hz, 1H), 1.47 (s, 9H).

Step 10: Synthesis of Compound 35-12

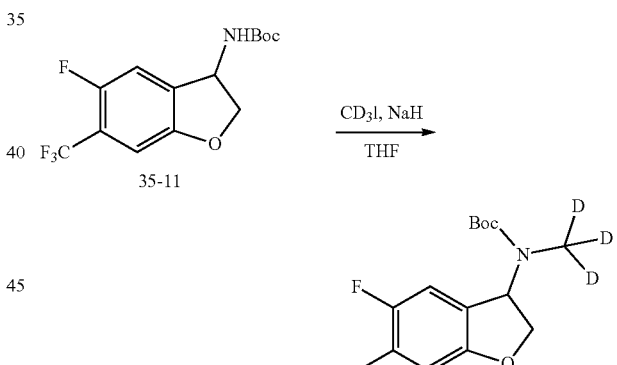

To a solution of compound 35-11 (70.0 mg, 218 μmol, 1.00 eq) in THE (5.00 mL) was added NaH (13.1 mg, 327 μmol, 60% purity, 1.50 eq) at 0° C., the mixture was stirred at 0° C. for 0.5 hr. Then trideuterio(iodo)methane (37.9 mg, 261 μmol, 16.3 μL, 1.20 eq) was added to the mixture. The mixture was stirred at 20° C. for another 10 hrs. LC-MS showed all of compound 35-11 was consumed and a new peak with desired mass was detected. The mixture was quenched with sat. $NH_4Cl$ (20.0 mL) and extracted with EtOAc (15.0 mL*2), the combined organic layers were washed with brine (15.0 mL*1), dried over $Na_2SO_4$, filtered and concentrated under reduced pressure. The residue was purified by prep-HPLC (column: Phenomenex luna C18 150*25 mm*10 um; mobile phase: [water (FA)-ACN]; gradient: 48%-78% B over 10 min). Compound 35-12 (30.0 mg, 88.7 μmol, 40.7% yield) was obtained as colorless oil, confirmed by H NMR and F NMR.

H NMR: (400 MHz, CDCl$_3$) δ 7.08 (d, J=8.8 Hz, 1H), 7.03 (d, J=5.6 Hz, 1H), 6.17 (s, 1H), 4.68 (t, J=5.6 Hz, 1H), 1.50 (s, 9H).

Step 11: Synthesis of Compound 35-13

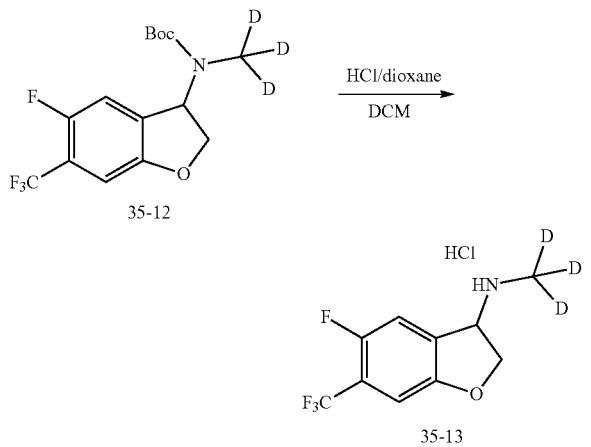

A mixture of compound 35-12 (70.0 mg, 207 μmol, 1.00 eq) and HCl/dioxane (2 M, 1.50 mL, 14.5 eq) in DCM (5.00 mL) was stirred at 20° C. for 10 hrs. LC-MS showed all of compound 35-12 was consumed and a major new peak with desired mass was detected. The mixture was concentrated under reduced pressure. Compound 35-13 (56.0 mg, 204 μmol, 98.5% yield, HCl) was obtained as off-white solid.

Step 12: Synthesis of Compound 35

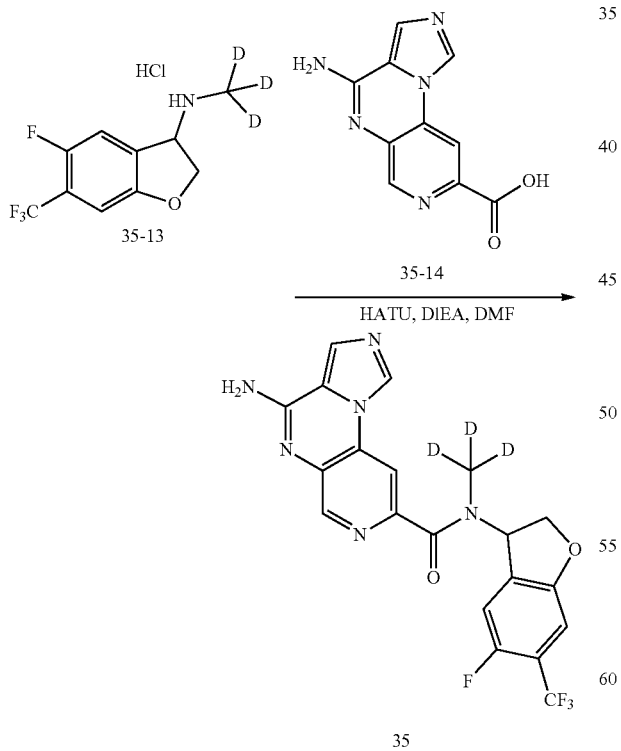

A solution of compound 35-14 (43.3 mg, 189 μmol, 1.00 eq), HATU (108 mg, 283 μmol, 1.50 eq) and DIEA (122 mg, 945 μmol, 165 μL, 5.00 eq) in DMF (2.00 mL) was stirred at 20° C. for 15 min, then compound 35-13 (45.0 mg, 189 μmol, 1.00 eq) was added. The mixture was stirred at 20° C. for 30 min. LC-MS showed all of compound 35-13 was consumed and a major new peak with desired mass was detected. The mixture was purified by prep-HPLC (column: Waters Xbridge C18 150*50 mm*10 um; mobile phase: [water (NH$_4$HCO$_3$)-ACN]; gradient: 22%-52% B over 10 min). Compound 35 (18.36 mg, 39.4 μmol, 20.9% yield, 96.5% purity) was obtained, confirmed by H NMR, F NMR, LC-MS, HPLC and SFC.

H NMR: (400 MHz, DMSO-d$_6$) δ 9.31-9.28 (m, 1H), 8.71-8.64 (m, 1H), 8.54-8.50 (m, 1H), 7.99 (s, 1H), 7.76-7.49 (m, 3H), 7.32-7.29 (m, 1H), 6.39-6.03 (m, 1H), 4.90-4.68 (m, 2H).

LC-MS: (M+H)$^+$=450.2

HPLC: 96.4% purity (220 nm)

Example 24: Synthesis of Compounds 36

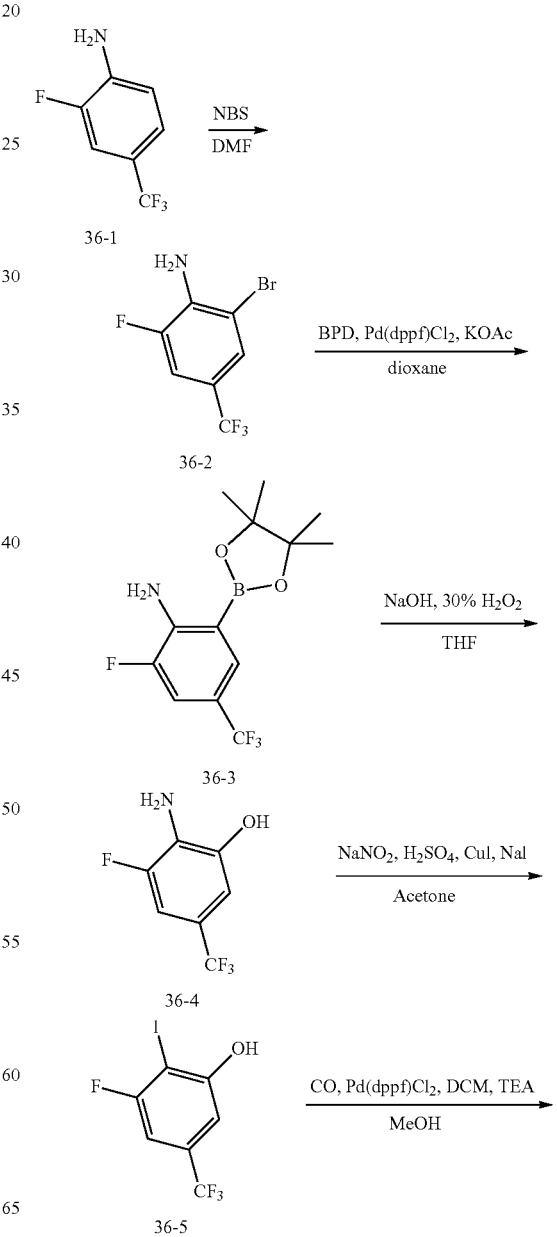

-continued
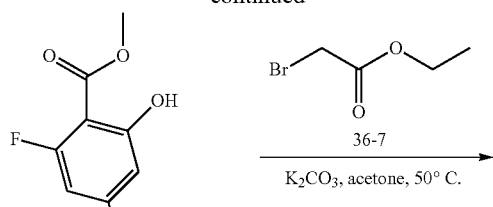
36-6
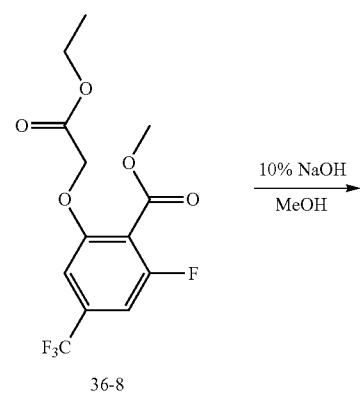
36-8
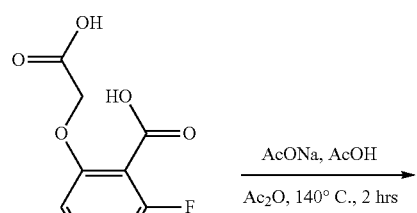
36-9
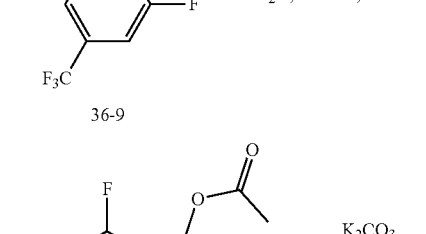
36-10
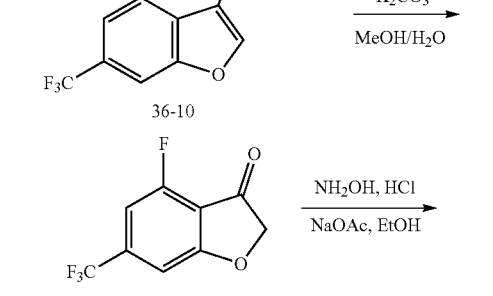
36-11
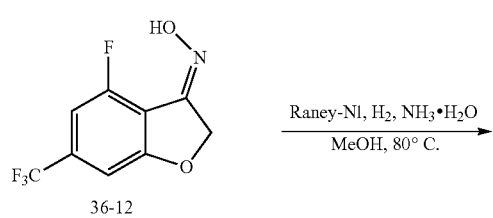
36-12
-continued
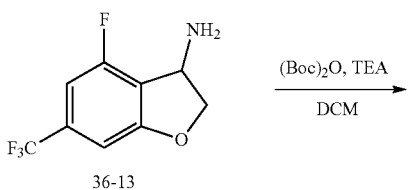
36-13
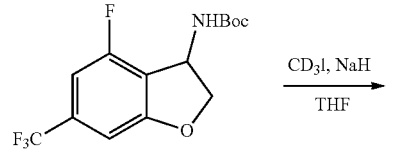
36-14
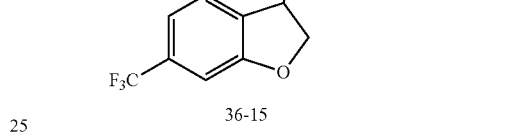
36-15
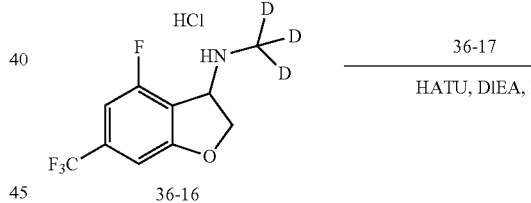
36-16
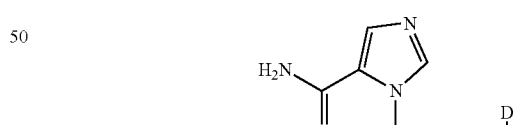
36

Step 1: Synthesis of Compound 36-2

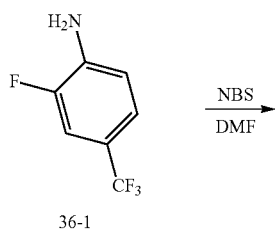

To a solution of compound 36-1 (20 g, 111.66 mmol, 1 eq) in DMF (250 mL) was added NBS (20.87 g, 117.24 mmol, 1.05 eq) at −10° C., the reaction was stirred for 1 h at 25° C., continually. LCMS showed no starting material left and desired product was observed. The reaction was diluted with water (300 mL) and extracted with EA (100 mL×2), the combined organic layers were washed with sat. NaCl (100 mL×3), dried over $Na_2SO_4$, filtered and concentrated in vacuo. The residue was purified by MPLC ($SiO_2$, Petroleum ether/Ethyl acetate=1:0-10:1). To afford compound 36-2 (32 g, crude) as yellow oil which was confirmed by H NMR.

LC-MS: $(M+H)^+$:258.0, 259.9

H NMR: (400 MHz, chloroform-d) δ 7.49 (s, 1H), 7.22 (d, J=10.4 Hz, 1H), 4.48 (br s, 2H)

Step 2: Synthesis of Compound 36-3

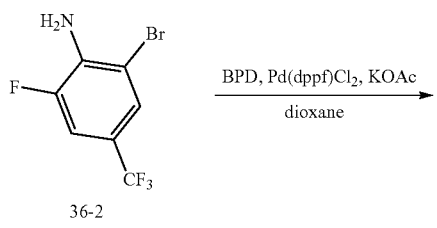

The mixture of compound 36-2 (21 g, 81.39 mmol, 1 eq), BPD (41.34 g, 162.78 mmol, 2 eq), KOAc (19.97 g, 203.48 mmol, 2.5 eq) and $Pd(dppf)Cl_2·CH_2Cl_2$ (3.32 g, 4.07 mmol, 0.05 eq) in dioxane (300 mL) was stirred for 3 h at 100° C. LCMS showed no starting material left and desired product was observed. The reaction was concentrated in vacuo. The residue was purified by column chromatography ($SiO_2$, Petroleum ether/Ethyl acetate=1:0-50:1). To afford compound 36-3 (35 g, crude) as yellow solid which was confirmed by H NMR.

H NMR: (400 MHz, chloroform-d) δ 7.65 (s, 1H), 7.25 (d, J=12.0 Hz, 1H), 5.17 (br s, 2H), 1.36 (s, 12H)

Step 3: Synthesis of Compound 36-4

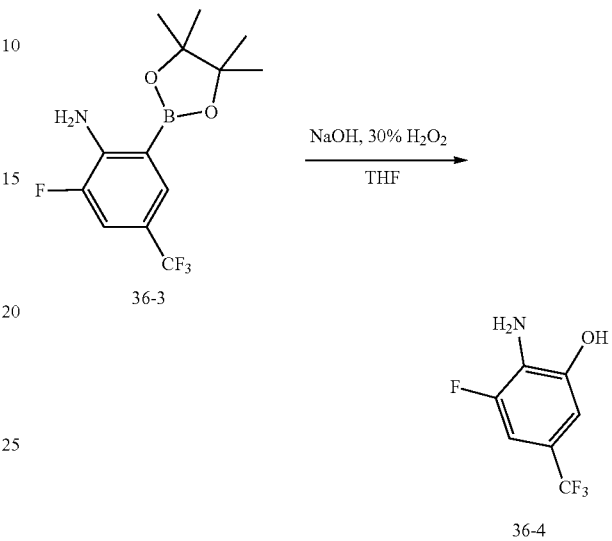

To a solution of compound 36-3 (20 g, 65.56 mmol, 1 eq) in THF (300 mL) was added NaOH (2 M, 98.34 mL, 3 eq) and $H_2O_2$ (41.30 g, 364.26 mmol, 35.00 mL, 30% purity, 5.56 eq) at 0° C., then the reaction was stirred for 2 h at 25° C. LCMS showed no starting material left and desired product was observed. The reaction was diluted with water (100 mL) and neutralized with HCl (2M) to pH=7, then extracted with EA (150 mL×3), the combined organic layers were washed with sat. $Na_2SO_3$ solution (150 mL×2), sat. NaCl solution (150 mL×2), dried over $Na_2SO_4$, filtered and concentrated in vacuo. The residue was purified by column chromatography ($SiO_2$, Petroleum ether/Ethyl acetate=5:1). To afford compound 36-4 (5.44 g, 27.88 mmol, 42.53% yield) as brown solid.

Step 4: Synthesis of Compound 36-5

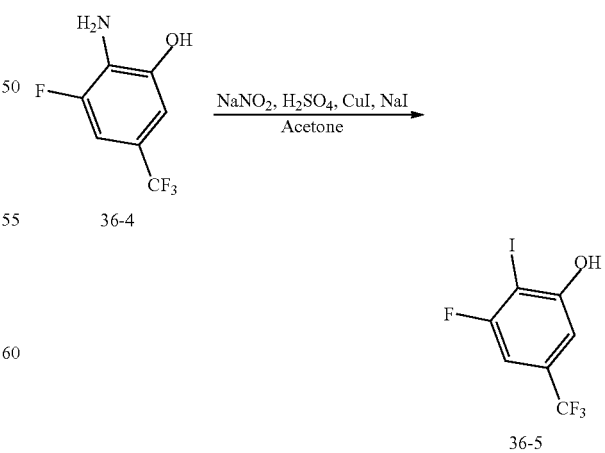

To a solution of compound 36-4 (3.33 g, 17.07 mmol, 1 eq) in $H_2O$ (60 mL) and acetone (15 mL) was added $H_2SO_4$ (12.00 g, 122.37 mmol, 6.52 mL, 7.17 eq) and NaNO$_2$ (2.36 g, 34.13 mmol, 2 eq) at 0° C. under ice-bath, after stirring for 30 minutes, CuI (8.13 g, 42.67 mmol, 2.5 eq) and NaI (6.40 g, 42.67 mmol, 2.5 eq) were added to the mixture, the reaction was stirred for 12 h at 25° C., continually. LCMS showed no starting material left and desired product was observed. The reaction was filtered and the cake was washed with EA, the filtrate was extracted with EA (30 mL×3), the combined organic layers were washed with sat. NaCl (30 mL×2), dried over Na$_2$SO$_4$, filtered and concentrated in vacuo. The residue was purified by column chromatography (SiO$_2$, Petroleum ether/Ethyl acetate=4:1). To afford compound 36-5 (7 g, crude) as red oil.

LC-MS: (M+Na)$^+$:329.0

Step 5: Synthesis of Compound 36-6

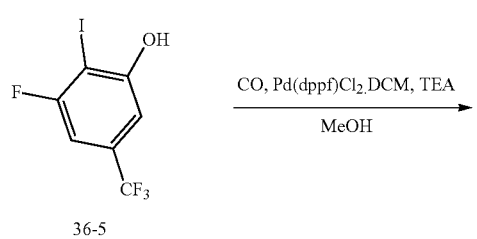

36-5

36-6

To a solution of compound 36-5 (7 g, 22.88 mmol, 1 eq) in MeOH (100 mL) was added TEA (6.94 g, 68.63 mmol, 9.55 mL, 3 eq) and Pd(dppf)Cl$_2$·CH$_2$Cl$_2$ (1.87 g, 2.29 mmol, 0.1 eq), the reaction was stirred for 12 h at 80° C. under CO atmosphere (50 psi). TLC (PE:EA=5:1) showed no starting material left and desired product was observed. The reaction was concentrated in vacuo. The residue was purified by column chromatography (SiO$_2$, Petroleum ether/Ethyl acetate=4:1). To afford compound 36-6 (2.10 g, 8.82 mmol, 38.55% yield) as red oil which was confirmed by NMR.

H NMR: (400 MHz, chloroform-d) δ 11.43 (s, 1H), 7.27 (s, 1H), 7.08 (s, 1H), 6.87 (dd, J=1.2, 10.8 Hz, 1H), 4.04 (s, 3H)

Step 6: Synthesis of Compound 36-8

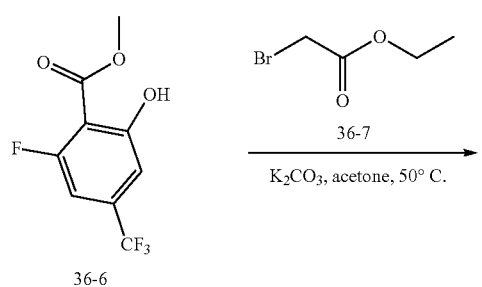

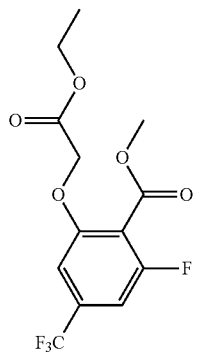

36-8

To a solution of compound 36-6 (2.1 g, 8.82 mmol, 1 eq) in acetone (25 mL) was added K$_2$CO$_3$ (1.83 g, 13.23 mmol, 1.5 eq) and compound 36-7 (1.84 g, 11.02 mmol, 1.22 mL, 1.25 eq), the reaction was stirred for 12 h at 50° C. LCMS showed no starting material left and desired product was observed. The reaction was concentrated in vacuo. The residue was purified by column chromatography (SiO$_2$, Petroleum ether/Ethyl acetate=1:0-5:1). To afford compound 36-8 (2.1 g, 6.48 mmol, 73.45% yield) as yellow oil which was confirmed by H NMR.

H NMR: (400 MHz, chloroform-d) δ 7.08 (d, J=8.8 Hz, 1H), 6.85 (s, 1H), 4.72 (s, 2H), 4.28 (q, J=7.2 Hz, 2H), 3.97 (s, 3H), 1.30 (t, J=7.2 Hz, 3H)

Step 7: Synthesis of Compound 36-9

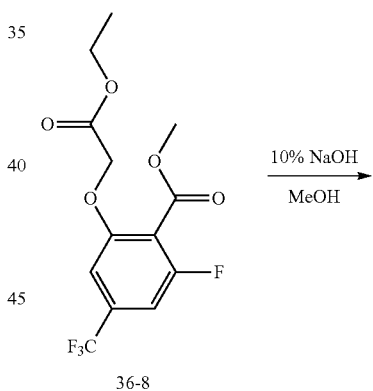

36-8

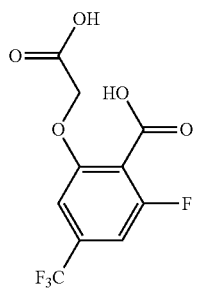

36-9

To a solution of compound 36-8 (2.9 g, 8.94 mmol, 1 eq) in MeOH (40 mL) was added NaOH (10.73 g, 26.83 mmol, 10% purity, 3 eq), the reaction was stirred for 12 h at 25° C. LCMS showed no starting material left and desired product was observed. The reaction was concentrated in vacuo and neutralized with HCl (2M) to pH=2, then extracted with EA (35 mL×3), the combined organic layers were washed with sat. NaCl (35 mL×2), dried over Na₂SO₄, filtered and concentrated in vacuo. The crude was used directly next step. To afford compound 36-9 (2.52 g, crude) as red solid.

LC-MS: (M+Na)⁺:305.0

Step 8: Synthesis of Compound 36-10

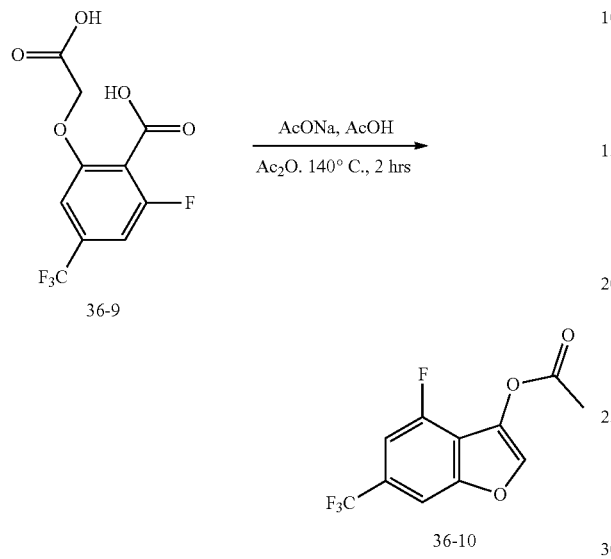

To a solution of compound 36-9 (2 g, 7.09 mmol, 1 eq) in Ac₂O (20 mL) was added HOAc (1.55 g, 25.87 mmol, 1.48 mL, 3.65 eq) and NaOAc (651.28 mg, 7.94 mmol, 1.12 eq), the reaction was stirred for 2 h at 140° C. LCMS showed no starting material left and desired product was observed. The reaction was diluted with water (15 mL) and extracted with EA (10 mL×3), the combined organic layers were washed with sat. NaCl (10 mL×2), dried over Na₂SO₄, filtered and concentrated in vacuo. The residue was purified by column chromatography (SiO₂, Petroleum ether/Ethyl acetate=5:1). To afford compound 36-10 (1.28 g, 4.88 mmol, 68.88% yield) as red oil which was confirmed by H NMR.

H NMR: (400 MHz, chloroform-d) δ 8.05 (s, 1H), 7.60 (s, 1H), 7.23 (d, J=9.6 Hz, 1H), 2.41 (s, 3H)

Step 9: Synthesis of Compound 36-11

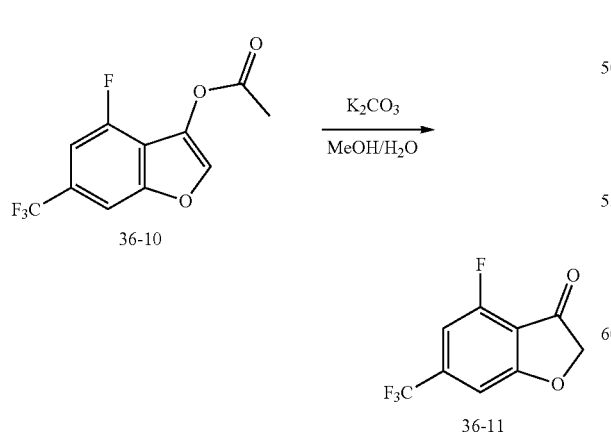

To a solution of compound 36-10 (0.5 g, 1.91 mmol, 1 eq) in MeOH (16 mL) and H₂O (2 mL) was added K₂CO₃ (790.78 mg, 5.72 mmol, 3 eq), the reaction was stirred for 30 minutes at 25° C. LCMS showed no starting material left and desired product was observed. The reaction was neutralized with HCl (2M) to pH=2 and extracted with EA (15 mL×3), the combined organic layers were washed with sat. NaCl (15 mL×2), dried over Na₂SO₄, filtered and concentrated in vacuo. The crude was used directly next step. To afford compound 36-11 (0.35 g, crude) as red oil which was confirmed by H NMR.

H NMR: (400 MHz, chloroform-d) δ 7.23 (s, 1H), 6.99 (d, J=8.0 Hz, 1H), 4.75 (s, 2H)

Step 10: Synthesis of Compound 36-12

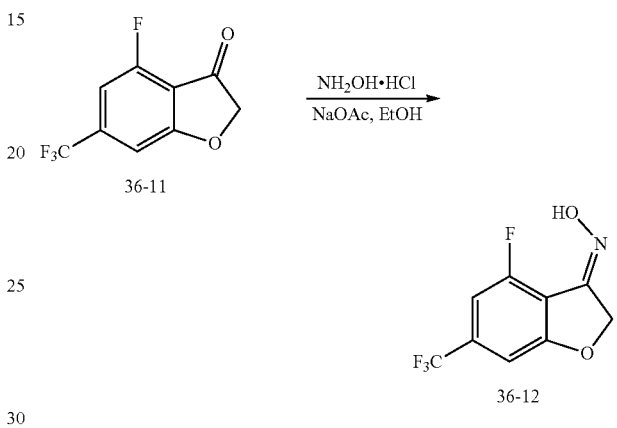

To a solution of compound 36-11 (0.350 g, 1.59 mmol, 1 eq) in EtOH (12 mL) was added NaOAc (391.31 mg, 4.77 mmol, 3 eq) and NH₂OH·HCl (331.48 mg, 4.77 mmol, 3 eq), the reaction was stirred for 12 h at 25° C. LCMS showed no starting material left and desired product was observed. The reaction was diluted with water (10 mL) and extracted with EA (10 mL×3), the combined organic layers were washed with sat. NaCl (10 mL×2), dried over Na₂SO₄, filtered and concentrated in vacuo. The residue was purified by column chromatography (SiO₂, Petroleum ether/Ethyl acetate=1:0~-3:1). To afford compound 36-12 (0.3 g, 1.28 mmol, 80.24% yield) as light yellow solid.

LC-MS: (M−H)⁺:234.1

Step 11: Synthesis of Compound 36-13

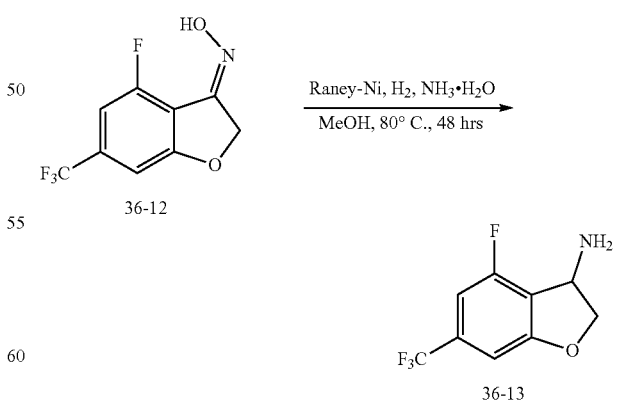

The mixture of compound 36-12 (0.3 g, 1.28 mmol, 1 eq) and Raney-Ni (0.030 g, 350.18 μmol, 2.74e-1 eq) in MeOH (10 mL), NH₃·H₂O (1 mL) was stirred for 12 h at 80° C. under H₂ atmosphere (50 PSI). LCMS showed no starting material left and desired product was observed. The reaction was filtered through of the celite and the filtrate was concentrated in vacuo. The residue was used directly next step. To afford compound 36-13 (0.308 g, crude) as yellow solid.

LC-MS: (M−NH$_2$)$^+$:205.1

Step 12: Synthesis of Compound 36-14

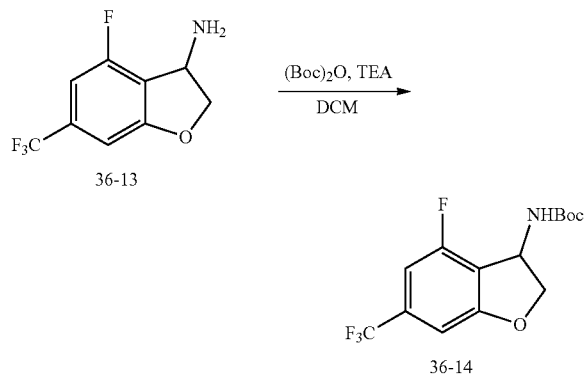

To a solution of compound 36-13 (0.308 g, 1.39 mmol, 1 eq) in DCM (15 mL) was added TEA (281.85 mg, 2.79 mmol, 387.69 μL, 2 eq) and (Boc)$_2$O (319.15 mg, 1.46 mmol, 335.95 μL, 1.05 eq) at 25° C., the reaction was stirred for 2 h, continually. LCMS showed no starting material left and desired product was observed. The reaction was concentrated in vacuo. The residue was purified by column chromatography (SiO$_2$, Petroleum ether/Ethyl acetate=1:0-5:1). To afford compound 36-14 (0.170 g, 529.16 μmol, 37.99% yield) as red solid which was confirmed by H NMR.

LC-MS: (M−55)$^+$:266.0

H NMR: (400 MHz, chloroform-d) δ 6.98-6.84 (m, 2H), 5.66-5.47 (m, 1H), 5.02-4.88 (m, 1H), 4.83-4.70 (m, 1H), 4.53-4.48 (m, 1H), 1.47 (s, 9H)

Step 13: Synthesis of Compound 36-15

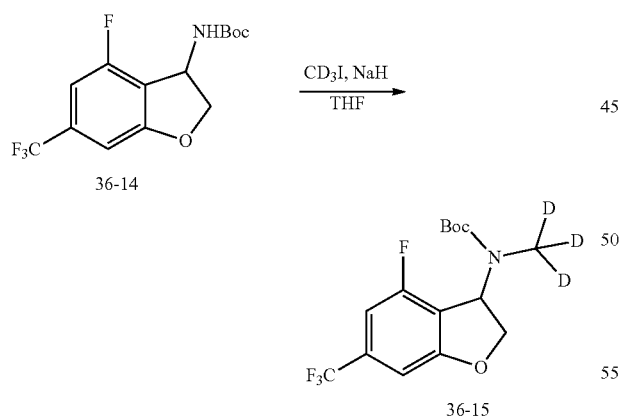

To a solution of compound 36-14 (0.170 g, 529.16 μmol, 1 eq) in THF (15 mL) was added NaH (52.92 mg, 1.32 mmol, 60% purity, 2.5 eq) at 0° C. under ice-bath, after stirring for 15 minutes, trideuterio(iodo)methane (153.41 mg, 1.06 mmol, 65.87 μL, 2.0 eq) was added to the mixture, the reaction was stirred for 12 h at 25° C. LCMS showed no starting material left and desired product was observed. The reaction was quenched by addition of MeOH (10 mL) under ice-bath, then concentrated in vacuo. The residue was purified by column chromatography (SiO$_2$, Petroleum ether/Ethyl acetate=1:0-5:1). To afford compound 36-15 (0.170 g, 502.49 μmol, 94.96% yield) as red solid which was confirmed by H NMR.

LC-MS: (M−55)$^+$:283.1

H NMR: (400 MHz, chloroform-d) δ 6.94-6.88 (m, 2H), 6.34-5.84 (m, 1H), 4.87-4.66 (m, 1H), 4.57-4.34 (m, 1H), 1.49 (s, 9H)

Step 14: Synthesis of Compound 36-16

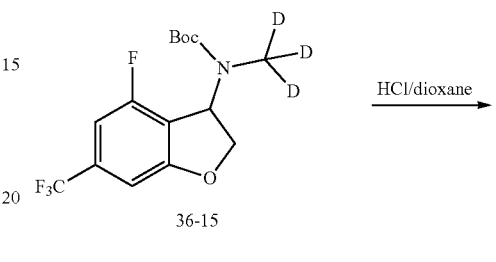

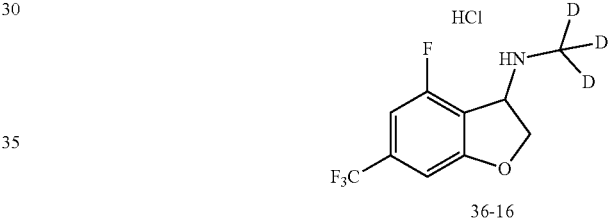

To a solution of compound 36-15 (0.170 g, 502.49 μmol, 1 eq) in EA (4 mL) was added HCl/dioxane (2 M, 17.00 mL), the reaction was stirred for 12 h at 25° C. LCMS showed no starting material left and desired product was observed. The reaction was concentrated in vacuo. To afford compound 36-16 (0.140 g, crude, HCl) as yellow solid.

LC-MS: (M+H)$^+$:239.1

Step 15: Synthesis of Compound 36

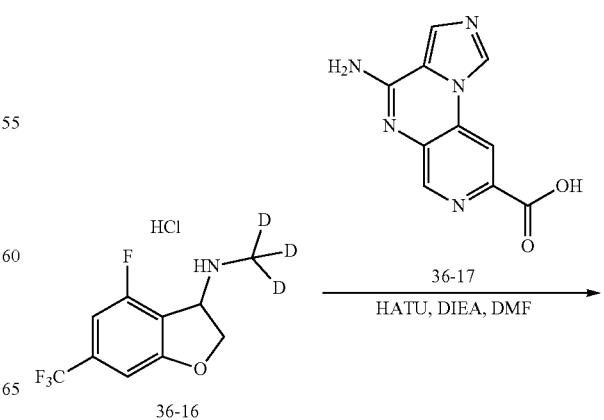

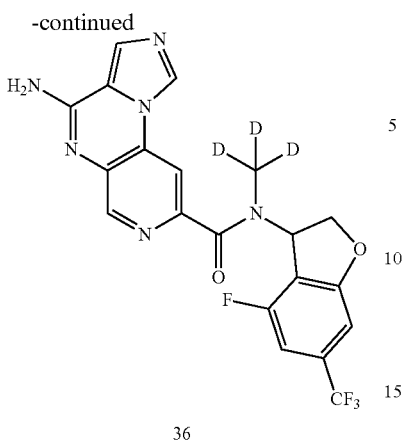

36

To a solution of compound 36-17 (0.070 g, 305.42 μmol, 1 eq) in DMF (2 mL) was added HATU (232.26 mg, 610.83 μmol, 2 eq) and DIEA (197.37 mg, 1.53 mmol, 265.99 μL, 5 eq), after stirring for 15 minutes, compound 36-16 (71.30 mg, 259.60 μmol, 0.85 eq, HCl) was added to the mixture, the reaction was stirred for 1 h at 25° C. LCMS showed no starting material left and desired product was observed. The reaction was diluted with water (15 L) and extracted with EA (10 mL×3), the combined organic layers were washed with sat. NaCl (10 mL×2), dried over $Na_2SO_4$, filtered and concentrated in vacuo. The residue was purified by Prep-HPLC (column: Waters Xbridge C18 150*50 mm*10 um; mobile phase: [water ($NH_4HCO_3$)-ACN]; gradient: 22%-52% B over 10 min). To afford Compound 36 (0.027 g, 59.52 μmol, 19.49% yield, 99.06% purity) which was confirmed by HNMR, FNMR, LCMS, HPLC, and SFC.

LC-MS: $(M+Na)^+$:472.1; $(M+H)^+$450.1

H NMR: (400 MHz, DMSO-$d_6$) δ 9.33 (d, J=14.4 Hz, 1H), 8.66 (d, J=10.4 Hz, 1H), 8.62-8.42 (m, 1H), 7.98 (d, J=5.2 Hz, 1H), 7.83-7.67 (m, 2H), 7.34-7.16 (m, 2H), 6.66-6.28 (m, 1H), 5.04-4.69 (m, 2H)

HPLC: 99.06% purity (220 nm)

Example 25: Synthesis of Compounds 37

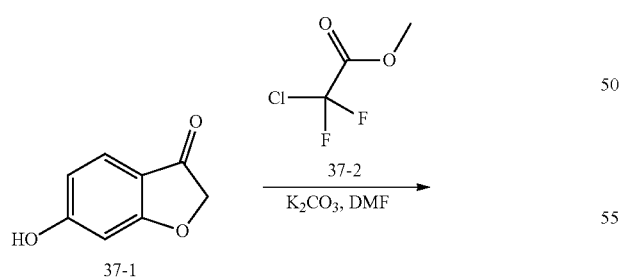

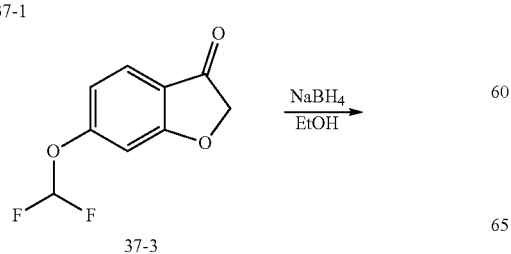

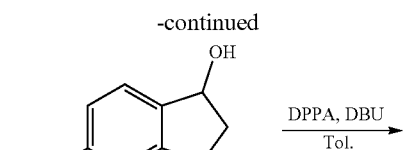

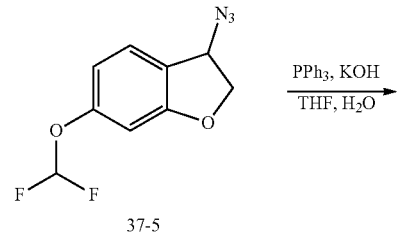

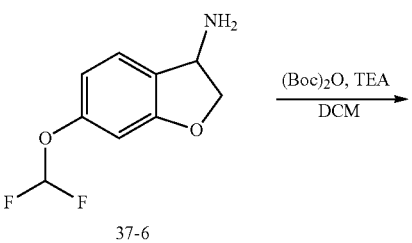

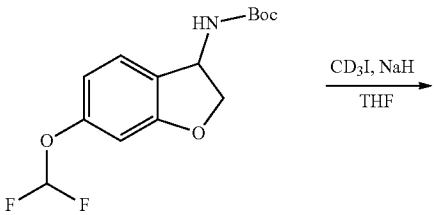

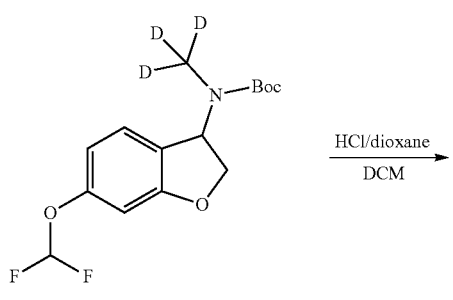

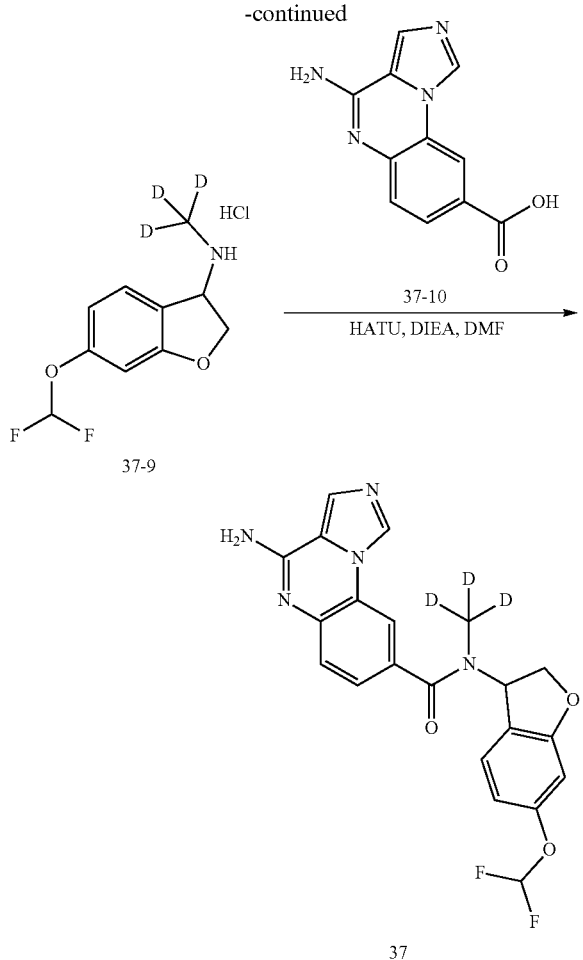

Step 1: Synthesis of Compound 37-2

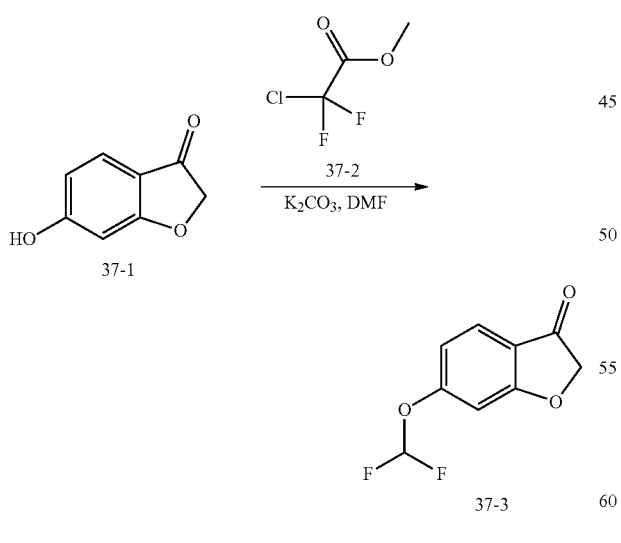

To a solution of compound 37-1 (10.0 g, 66.6 mmol, 1.00 eq) in DMF (100 mL) was added K₂CO₃ (9.21 g, 66.6 mmol, 1.00 eq) and compound 37-2 (14.4 g, 99.9 mmol, 1.50 eq), then the mixture was stirred at 75° C. for 2 hrs. LC-MS showed compound 37-1 was consumed and a peak with desired mass was detected. The mixture was diluted with H₂O (100 mL) and extracted with EtOAc (100 mL*3), the combined organic phase was washed with brine (100 mL*3), dried over Na₂SO₄ and concentrated to give a residue. The residue was purified by column chromatography (SiO₂, Petroleum ether:Ethyl acetate=100:1 to 3:1). TLC (Petroleum ether:Ethyl acetate=3:1, $R_f$=0.60). Compound 37-2 (3.00 g, 15.0 mmol, 22.5% yield) was obtained as yellow solid, confirmed by H NMR and F NMR.

H NMR: (400 MHz, DMSO-d₆) δ 7.70 (d, J=8.8 Hz, 1H), 7.46 (br t, J=72.8 Hz, 1H), 7.10 (d, J=2.0 Hz, 1H), 6.92 (dd, $J_1$=8.4 Hz, $J_1$=2.0 Hz, 1H), 4.85 (s, 2H).

Step 2: Synthesis of Compound 37-4

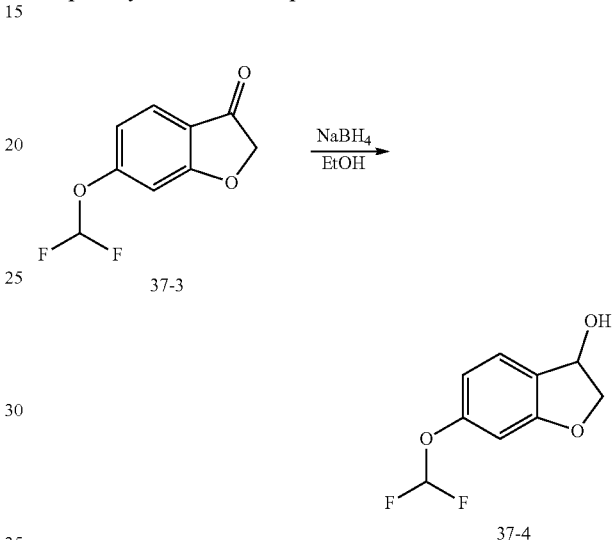

To a solution of compound 37-3 (1.00 g, 5.00 mmol, 1.00 eq) in EtOH (15.0 mL) was added NaBH₄ (378 mg, 9.99 mmol, 2.00 eq) at 0° C., then the mixture was stirred at 25° C. for 0.5 hr. LC-MS showed compound 37-3 was consumed and a peak with desired mass was detected. A solution of saturated NH₄Cl (30.0 mL) was added to the mixture at 0° C., then extracted with DCM (30.0 mL*3), the combined organic phase was washed with brine (30.0 mL*2), dried over Na₂SO₄ and concentrated to give a residue. Compound 37-4 (900 mg, 4.45 mmol, 89.1% yield) was obtained as yellow solid, confirmed by H NMR and F NMR.

H NMR: (400 MHz, DMSO-d₆) δ 7.39-7.36 (m, 1H), 7.20 (br t, J=74.4 Hz, 1H), 6.70-6.67 (m, 2H), 5.62 (d, J=5.6 Hz, 1H), 5.25-5.21 (m, 1H), 4.56 (dd, $J_1$=10.0 Hz, $J_1$=6.8 Hz, 1H), 4.27 (dd, $J_1$=10.4 Hz, $J_1$=3.2 Hz, 1H).

Step 3: Synthesis of Compound 37-5

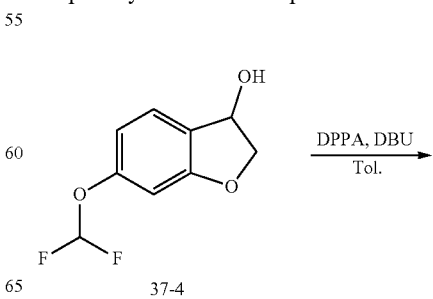

Step 5: Synthesis of Compound 37-7

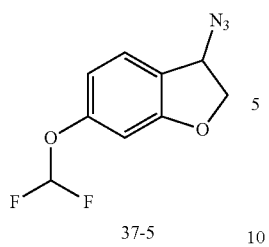
37-5

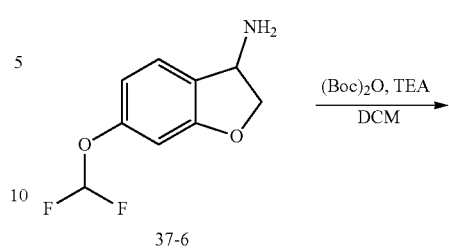
37-6

To a solution of compound 37-4 (300 mg, 1.48 mmol, 1.00 eq) in Tol. (5.00 mL) was added DPPA (613 mg, 2.23 mmol, 480 μL, 1.50 eq) and a solution of DBU (339 mg, 2.23 mmol, 336 μL, 1.50 eq) in Tol. (1.00 mL) at 0° C., then the mixture was stirred at 25° C. for 12 hrs. LC-MS showed compound 37-4 was consumed and a peak was detected. A solution of saturated NH$_4$Cl (20.0 mL) was added to the mixture at 0° C., then extracted with DCM (20.0 mL*3), the combined organic phase was dried over Na$_2$SO$_4$ and concentrated to give a residue. The residue was purified by column chromatography (SiO$_2$, Petroleum ether:Ethyl acetate=100:1 to 5:1). TLC (Petroleum ether:Ethyl acetate=5:1, R$_f$=0.50). Compound 37-5 (250 mg, 1.10 mmol, 74.2% yield) was obtained as yellow solid, confirmed by H NMR and F NMR.

H NMR: (400 MHz, DMSO-d$_6$) δ 7.54 (d, J=7.6 Hz, 1H), 7.47-7.46 (m, 1H), 6.79-6.76 (m, 2H), 5.34 (dd, J$_1$=6.8 Hz, J$_1$=2.0 Hz, 1H), 4.63 (dd, J$_1$=10.8 Hz, J$_1$=6.8 Hz, 1H), 4.53 (dd, J$_1$=10.8 Hz, J$_1$=2.0 Hz, 1H).

Step 4: Synthesis of Compound 37-6

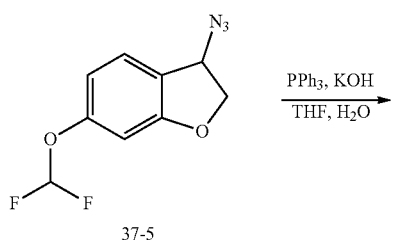
37-5

To a solution of compound 37-5 (250 mg, 1.10 mmol, 1.00 eq) in THF (3.00 mL) was added PPh$_3$ (433 mg, 1.65 mmol, 1.50 eq), the mixture was stirred at 25° C. for 1 hr, then KOH (154 mg, 2.75 mmol, 2.50 eq) in H$_2$O (1.00 mL) was added, the mixture was stirred at 25° C. for 12 hrs. LC-MS showed compound 37-5 was consumed and a peak with desired mass was detected. The mixture was diluted with H$_2$O (10.0 mL) and extracted with EtOAc (10.0 mL*3), the combined organic phase was dried over Na$_2$SO$_4$ and concentrated to give a residue. The residue was purified by column chromatography (SiO$_2$, Petroleum ether:Ethyl acetate=100:1 to 0:1). TLC (Petroleum ether:Ethyl acetate=0:1, R$_f$=0.20). Compound 37-6 (200 mg, 994 μmol, 90.3% yield) was obtained as yellow solid.

To a solution of compound 37-6 (200 mg, 994 μmol, 1.00 eq) in DCM (5.00 mL) was added TEA (302 mg, 2.98 mmol, 415 μL, 3.00 eq) and Boc$_2$O (434 mg, 1.99 mmol, 457 μL, 2.00 eq), then the mixture was stirred at 25° C. for 1 hr. LC-MS showed compound 37-6 was consumed and a peak was detected. The mixture was diluted with H$_2$O (20.0 mL) and extracted with DCM (20.0 mL*3), the combined organic phase was dried over Na$_2$SO$_4$ and concentrated to give a residue. The residue was purified by column chromatography (SiO$_2$, Petroleum ether:Ethyl acetate=100:1 to 5:1). TLC (Petroleum ether:Ethyl acetate=5:1, R$_f$=0.50). Compound 37-7 (100 mg, 332 μmol, 33.4% yield) was obtained as yellow solid, confirmed by H NMR and F NMR.

H NMR: (400 MHz, DMSO-d$_6$) δ 7.54 (d, J=7.6 Hz, 1H), 7.37-7.00 (m, 2H), 6.68-6.65 (m, 2H), 5.26-5.21 (m, 1H), 4.69 (t, J=9.2 Hz, 1H), 4.28-4.25 (m, 1H), 1.40 (s, 9H).

Step 6: Synthesis of Compound 37-8

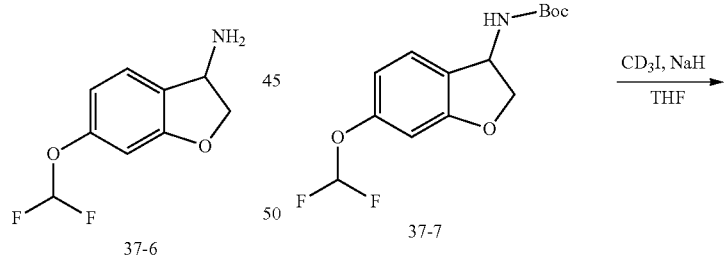
37-7

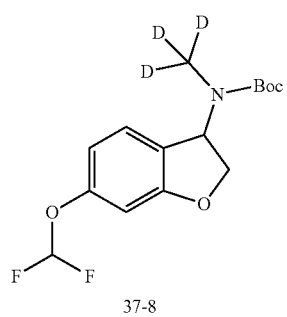
37-8

To a solution of compound 37-7 (100 mg, 332 μmol, 1.00 eq) in THF (3.00 mL) was added NaH (19.9 mg, 498 μmol, 60.0% purity, 1.50 eq) at 0° C., the mixture was stirred at 0°

C. for 0.5 hr, then CD$_3$I (141 mg, 996 μmol, 60.7 μL, 3.00 eq) was added, the mixture was stirred at 25° C. for 4 hrs. LC-MS showed compound 37-7 was consumed and a new peak was detected. A solution of saturated NH$_4$Cl (20.0 mL) was added to the mixture at 0° C., then extracted with EtOAc (20.0 mL*3), the combined organic phase was washed with brine (20.0 mL*2), dried over Na$_2$SO$_4$ and concentrated to give a residue. Compound 37-8 (100 mg, crude) was obtained as yellow solid, confirmed by H NMR and F NMR.

H NMR: (400 MHz, DMSO-d$_6$) δ 7.41-7.04 (m, 2H), 6.73-6.71 (m, 2H), 5.88-5.64 (m, 1H), 4.66 (t, J=10.0 Hz, 1H), 4.49-4.47 (m, 1H), 1.41 (s, 9H).

Step 7: Synthesis of Compound 37-9

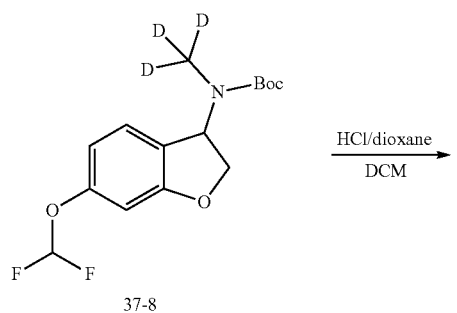

Step 8: Synthesis of Compound 37

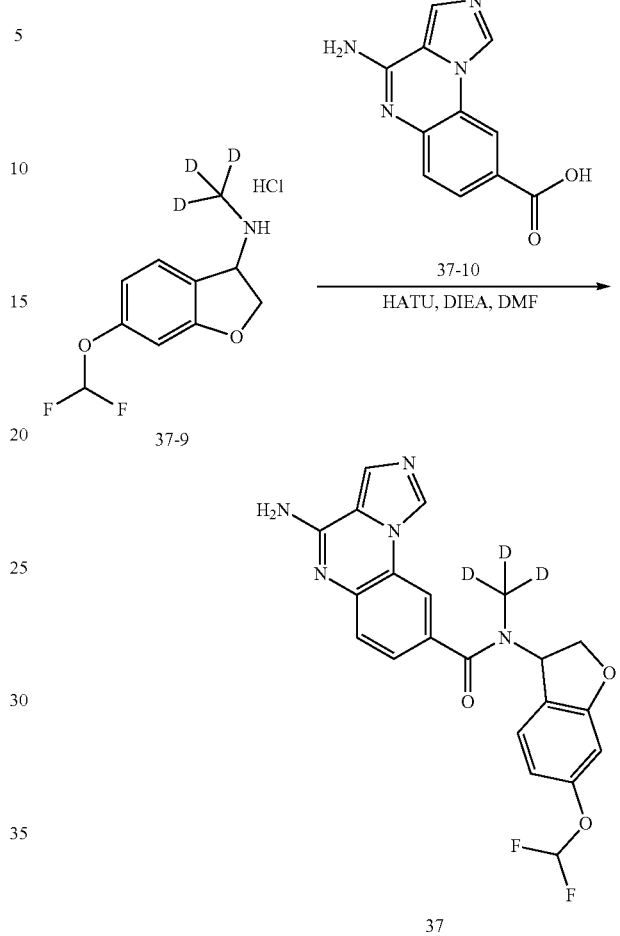

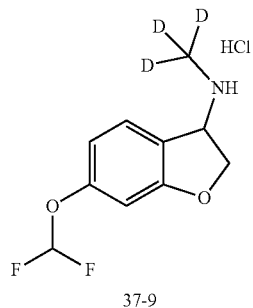

To a solution of compound 37-8 (100 mg, 314 μmol, 1.00 eq) in DCM (1.00 mL) was added HCl/dioxane (2 M, 2.00 mL, 12.7 eq) at 0° C., then the mixture was stirred at 25° C. for 4 hrs. LC-MS showed compound 37-8 was consumed and a new peak was detected. The mixture was concentrated to give a residue. Compound 37-9 (80.0 mg, crude, HCl) was obtained as yellow solid.

To a solution of compound 37-9 (80.0 mg, 314 μmol, 1.00 eq, HCl) and compound 37-10 (75.3 mg, 330 μmol, 1.05 eq) in DMF (1.00 mL) was added DIEA (122 mg, 942 μmol, 164 μL, 3.00 eq) and HATU (179 mg, 471 μmol, 1.50 eq), then the mixture was stirred at 25° C. for 1 hr. LC-MS showed compound 37-9 was consumed and a peak with desired mass was detected. The mixture was diluted with H$_2$O (20.0 mL) and extracted with EtOAc (20.0 mL*3), the combined organic phase was washed with brine (20.0 mL*2), dried over Na$_2$SO$_4$ and concentrated to give a residue. The residue was purified by Prep-HPLC (column: Waters Xbridge BEH C18 150*25 mm*5 um; mobile phase: [water (NH$_4$HCO$_3$)-ACN]; gradient: 18%-48% B over 10 min). Compound 37 (29.15 mg, 68.0 μmol, 21.7% yield) was obtained, confirmed by H NMR, F NMR, LC-MS, HPLC, and SFC.

H NMR: (400 MHz, DMSO-d$_6$) δ 9.18 (s, 1H), 8.31 (s, 1H), 7.91 (s, 1H), 7.48-7.07 (m, 6H), 6.78-6.72 (m, 2H), 6.31-4.65 (m, 2H).

LC-MS: (M+H)$^+$: 429.1

HPLC: purity: 98.1% (220 nm)

Example 26: MTase-Glo Methyl Transferase Assay

The PRMT5 inhibitory activity of test compounds was determined using the MTase-Glo™ assay (Promega), which monitors the product (S-adenosyl homocysteine or SAH) of methyltransferase reactions. The PRMT5 MTase-Glo assays were conducted in a 384-well white ProxiPlate (PerkinElmer, catalog no.: 6008280) in a total volume of 12 μL. The PRMT5 enzymatic reaction (in 4 μL) contained 50 nM PRMT5/MEP50 (Reaction Biology Corp, catalog no.: HMT-22-148), 25 μM S-adenosyl methionine (SAM, Promega), 5 μM Histone H4 peptide (1-21) (BPS Bioscience, catalog no.: 52018-2) and five-fold serially diluted compounds in a reaction buffer of 50 mM Tris (pH 8.0), 50 mM NaCl, 0.01% Tween 20, 0.01% BSA, and 1 mM DTT. The test compounds were pre-incubated with PRMT5/MEP50 and Histone H4 peptide for 20 minutes at room temperature before the addition of SAM to initiate the PRMT5 reaction. The reaction was allowed to proceed for 1 hour at 37° C. and was terminated by 2 μL of 3× MTase-Glo™ Reagent (Promega) and 150 μM EPZ015666 (Selleck, catalog no.: 1616391-65-1). After a 30-minute incubation at room temperature, 6 μL of MTase-Glo™ Detection Solution (Promega) was added and the plate was incubated at room temperature for an additional 30 minutes. The light signal corresponding to the amount of SAH produced by the PRMT5 reaction was subsequently measured using an Envision multimode reader (PerkinElmer). $IC_{50}$ and $K_i$ values were obtained by analyzing dose-response curves using GraphPad Prism.

Table 1 shows $IC_{50}$ data for exemplary compounds as described herein for PRMT5 inhibiting.

TABLE 1

$IC_{50}$ Data for PRMT5 Inhibiting of Exemplary Compounds

| Compound No. | $IC_{50}$ (nM) |
|---|---|
| 1 | 45 |
| 2 | 45 |
| 3 | 24 |
| 4 | 28 |
| 5 | 26 |
| 6 | 36 |
| 7 | 91 |
| 8 | 104 |
| 9 | 101 |
| 10 | 54 |
| 11 | 51 |
| 12 | 26 |
| 13 | 40 |
| 14 | 47 |
| 15 | 16 |
| 16 | 231 |
| 17 | 12 |
| 18 | 420 |
| 19 | 25 |
| 20 | 455 |
| 21 | 25 |
| 22 | 1152 |
| 23 | 31 |
| 24 | 14 |
| 25 | 167 |
| 26 | 34 |
| 27 | 1693 |
| 28 | 37 |
| 29 | 37 |
| 30 | 89 |
| 31 | 96 |
| 32 | 25 |
| 33 | 51 |
| 34 | 70 |
| 35 | 87 |
| 36 | 53 |
| 37 | 29 |

Example 27: PRMT5/MEP50 HotSpot Methyltransferase Assay

The assay used recombinant full-length histone H2A as the substrate of PRMT5. Enzymatic transfer of the tritiated methyl group from S-adenosyl-L-[methyl-3H]methionine (3H-SAM) to the histone H2A protein generated a radiolabeled histone H2A by measuring in a scintillation counter to determine the activity of PRMT5 enzyme in the presence and absence of compound. The assay reactions were conducted in the presence of 100 nM MTA. Briefly, compounds were solubilized in 100% DMSO at the highest concentration of 10 mM. For $IC_{50}$ determinations, the initial starting concentration for the serial dilutions of each compound is 50 μM. Control samples lacking compound, PRTM5/MEP50 complex or various reaction components also were prepared and processed in parallel with compound test samples. SAH was used as a positive control for assay validation. To measure PRMT5 inhibitory activity, 1 nM PRTM5/MEP50 complex was preincubated with test compound in assay buffer containing 5 μM full-length histone H2A for 15 minutes at room temperature. The enzymatic reaction was initiated by adding 1 μM $^3$H-SAM (final concentration) and the mixture was incubated at 30° C. for 1 hour. The reaction was stopped and transferred to filter paper for detection. The amount of tritiated H2A in each sample was determined using a scintillation counter. The $IC_{50}$ value for each compound was calculated from each 10-point dose-response curve for samples using GraphPad Prism software.

Table 2 shows $IC_{50}$ binding data for exemplary compounds as described herein for PRMT5/MEP50 HotSpot methyltransferase assay.

TABLE 2

| PRMT5/MEP50 HotSpot methyltransferase assay (with 100 nM MTA) | |
|---|---|
| Compound No. | $IC_{50}$ (nM) |
| 1 | 8 |
| 3 | 64 |
| 4 | 6 |
| 5 | 81 |
| 6 | 101 |
| 7 | 91 |
| 8 | 198 |
| 9 | 321 |
| 10 | 379 |

Example 28: HCT116 Cell Proliferation Assay

Proliferation assays were performed using HCT116 parental and HCT116 homozygous MTAP knockout cell lines to demonstrate increased potency of compounds of the present invention in the MTAP-deficient cells. Control samples were analyzed in parallel.

On Day 0, 150 HCT116 parental or HCT116 homozygous MTAP knockout cells were seeded in 96-well plates in McCoy's 5A medium containing 10% fetal bovine serum and pen/strep. And the cells were incubated overnight at 37° C. and 5% $CO_2$.

On Day 1, cells were treated with 9-point serial dilution of compound, using a top concentration of 50 μM, 1:5 serial dilution steps and, a DMSO-only control. And cells were incubated for 6 days.

On Day 7, cell viability was measured using a CTG assay Kit (Cell Titer-Glo; Promega, catalog no.: G7573) in accordance with the manufacturer's instructions. Assays plates were read on a EnVision™ Multilabel Reader using the Ultra-Sensitive luminescence model. The data were analyzed by GraphPad Prism 5.0 software, and the dose-effect curve was obtained by fitting the data using nonlinear S-curve regression, from which the $IC_{50}$ value was calculated.

Table 3 shows $IC_{50}$ data for exemplary compounds as described herein for HCT116 cell lines.

TABLE 3

$IC_{50}$ Data for HCT116 Cell Lines of Exemplary Compounds

| Compound No. | $IC_{50}$ (nM) | |
|---|---|---|
| | Wild Type | MTAP knockout |
| 1 | 4365 | 73 |
| 2 | 5718 | 158 |
| 3 | 16,020 | 156 |
| 4 | 105 | 12 |
| 5 | 1583 | 138 |
| 6 | 230 | 17 |
| 7 | 961 | 77 |
| 8 | 146 | 97 |
| 9 | 1161 | 72 |
| 10 | 495 | 33 |
| 11 | 7684 | 64 |
| 12 | 5161 | 43 |
| 13 | 4568 | 181 |
| 14 | 6269 | 70 |
| 15 | 5339 | 37 |
| 17 | 4079 | 32 |
| 19 | 3060 | 39 |
| 23 | 5347 | 40 |
| 24 | 3927 | 52 |
| 26 | 6586 | 64 |
| 28 | >50000 | 483 |
| 29 | 21880 | 377 |
| 30 | >50000 | 4017 |
| 31 | 9581 | 1499 |
| 32 | 8086 | 286 |
| 33 | 17964 | 980 |
| 34 | 14010 | 364 |
| 35 | 3206 | 70 |
| 36 | 9619 | 110 |
| 37 | 13801 | 234 |

Example 29: Hepatic Metabolic Stability Assay

Hepatic metabolic stability (TINMS) assay was performed on five types (H: human, R: rat, M: mouse, D: dog, C: cynomolgus monkey) of cryopreserved hepatocytes with 7-Ethoxycoumarin (Ref. 1) and 7-Hydroxycoumarin (Ref 2) as positive control.

Cryopreserved Hepatocytes Information:

| Species | Strain | Cell Viability | Vendor | Cat No. |
|---|---|---|---|---|
| Mouse | CD-1 | 77.0% | Milestone | CMH-100CD-SQ |
| Rat | SD | 72.4% | Milestone | CRH-100SD-SQ |
| Dog | Beagle | 93.8% | Bioreclamation IVT | M00205 |
| Monkey | Cynomolgus | 85.7% | RILD | HP-SXH-02M |
| Human | / | 87.9% | BioreclamationIVT | X008001 |

Buffer Solution Information:

Thawing Medium: Williams' Medium E containing 5% fetal bovine serum and 30% Percoll solution and other supplements.

Incubation Medium: Williams' Medium E (no phenol red) containing 2 mM L-Glutamine and 25 mM HEPES.

Stop Solution: Acetonitrile containing tolbutamide and labetalol as internal standards.

Dilution Solution: Ultra-pure water.

Experimental Procedure:

1) 10 mM test compounds were provided.
2) 30 mM positive control stock solutions: Dissolved accurate amount of positive control compounds in dimethyl sulfoxide (DMSO).
3) 1000× Stock Solution: Diluted 10 mM test compounds and 30 mM positive control compounds to 1 mM and 3 mM with DMSO in 96-well plates.
4) 100× Dosing Solution: Diluted 1 mM test compounds and 3 mM positive control compounds to 100 μM and 300 μM dosing solutions with ACN.
5) Preparation of 0.5×106/mL cells suspension: cryopreserved cells were thawed, isolated and suspended in Incubation Medium, then diluted with pre-warmed Incubation Medium to 0.5×106 cells/mL.
6) Add 198 μL of pre-warmed cell suspensions in 96-well plates.
7) Preparation of Quenching Plate: Transfer 125 μL of stop solution in a set of pre-labeled 96-well plates.
8) Spike 2 μL dosing solution to each well of 96-well plates in duplicate.
9) For T0 Samples, mix to achieve a homogenous suspension for about 1 min, then immediately transfer 25 μL of each sample into well containing 125 μL of ice-cold stop solution followed by mixing.
10) Incubate all plates at 37° C. in a 95% humidified incubator at 5% $CO_2$ to start the reactions with constant shaking.
11) At 15, 30, 60 and 90 min, mix samples and then transfer 25 μL of each sample at each time point to well containing 125 μL of ice-cold stop solution followed by mixing.
12) Medium Control (MC) sample plates (labeled as T0-MC and T90-MC) are prepared in the same way as cell incubation except that medium was used instead of cell suspension.
13) At each corresponding time point, stop the reactions by removing the plates from incubator and mixing with 125 μL of ice-cold stop solution.
14) Vortex the plates immediately on a plate shaker at 600 rpm for 10 minutes. Then, centrifuge all sample plates at 3220×g for 20 min at 4° C.
15) After centrifugation, 80 μL/well of supernatant in the sample plates are transferred to another set of pre-labeled 96-well plates which containing 240 μL of ultra pure water according to the plate map.
16) Analytical plates are sealed and store at 4° C. until LC-MS/MS analysis.

| The final concentration of each component in the incubation medium | |
|---|---|
| Component | Final Concentration |
| Hepatocyte | 0.5 × $10^6$ cells/mL |
| Test Compound | 1 μM |
| Positive Control | 3 μM |
| ACN | 0.90% |
| DMSO | 0.10% |

Data Analysis

The remaining percents of test articles after incubation were calculated by the follow equations:

% Remaining=(Peak area ratio of analyte to internal standard at each time point)/(Peak area ratio of analyte to internal standard at $t=0$)×100

Use the following equation of first order kinetics to calculate $T_{1/2}$ and $CL_{int}$.

$$C_t = C_0 \cdot e^{-k \cdot t}$$

when $C_t = 1/2 \cdot C_0$, $t_{1/2} = \ln 2/k = 0.693/k$.

$CL_{int\ (hep)} = k/$million cells per mL $CL_{int\ (liver)} = CL_{int\ (hep)} \cdot$liver weight (g/kg body weight)·hepatocellularity Tables 4 and 5 respectively show the half-life time ($T_{1/2}$) and $CL_{int}$ for positive control and exemplary compounds provided herein.

TABLE 4

Half-Life Time for Exemplary Compounds and positive controls

| Compound No. | $T_{1/2}$, min | | | | |
|---|---|---|---|---|---|
| | H | R | M | D | C |
| 12 | 110.2 | 135.5 | 111.5 | 127.1 | 66.8 |
| 17 | 191 | 130.3 | 89.8 | 203.4 | 80.5 |
| 19 | >216.8 | 146.6 | 141.0 | >216.8 | 213.1 |
| 21 | >216.8 | 179.0 | 154.9 | >216.8 | >216.8 |
| 24 | >216.8 | 107.8 | 76.1 | 214.6 | 131.6 |
| Ref. 1 | 19.2 | 35.3 | 2.1 | 2.7 | 9.0 |
| Ref. 2 | 3.0 | 2.0 | 2.3 | 2.9 | 2.1 |

TABLE 5

$CL_{int\ (hep)}$ (μL/min/$10^6$) and $CL_{int\ (liver)}$ (mL/min/kg) for Exemplary Compounds and positive controls

| Compound No. | H | | R | | M | | D | | C | |
|---|---|---|---|---|---|---|---|---|---|---|
| | $CL_{int\ (hep)}$ | $CL_{int\ (liver)}$ | $CL_{int\ (hep)}$ | $CL_{int\ (liver)}$ | $CL_{int\ (hep)}$ | $CL_{int\ (liver)}$ | $CL_{int\ (hep)}$ | $CL_{int\ (liver)}$ | $CL_{int\ (hep)}$ | $CL_{int\ (liver)}$ |
| 17 | 7.3 | 20.2 | 10.6 | 49.8 | 15.4 | 183.3 | 6.8 | 46.9 | 17.2 | 62.0 |
| 19 | <6.4 | <17.8 | 9.5 | 44.3 | 9.8 | 116.7 | <6.4 | <44 | 6.5 | 23.4 |
| 21 | <6.4 | <17.8 | 7.7 | 36.2 | 8.9 | 106.3 | <6.4 | <44 | <6.4 | <23 |
| 24 | <6.4 | <17.8 | 12.9 | 60.2 | 18.2 | 216.4 | 6.5 | 44.4 | 10.5 | 37.9 |
| Ref. 1 | 72.1 | 200.6 | 39.2 | 183.7 | 647.9 | 7697.0 | 521.1 | 3585.0 | 154.0 | 554.5 |
| Ref. 2 | 367.6 | 1021.8 | 678.0 | 3173.1 | 608.1 | 7223.9 | 475.1 | 3268.9 | 655.8 | 2360.7 |

Example 30: Liver Microsome Metabolic Stability Assay

Liver microsome metabolic stability (LMS) assay was performed on five types (H: human, R: rat, M: mouse, D: dog, C: cynomolgus monkey) of liver microsome, with Testosterone (Ref. 4), Diclofenac (Ref. 5), Propafenone (Ref. 6) as positive control.

Experimental Procedure:

1. Test Compound and Control Working Solution Preparation:
   1.1. Working solution: 5 μL of compound and control stock solution (10 mM in dimethyl sulfoxide (DMSO)) were diluted with 495 μL of acetonitrile (ACN)
2. NADPH Cofactor Preparation:
   2.1. Materials: NADPH powder: β-Nicotinamide adenine dinucleotide phosphate reduced form, tetrasodium salt; NADPH4Na (Vendor: BONTAC, Cat. No. BT04)
   2.2. Preparation Procedure: The appropriate amount of NADPH powder was weighed and diluted into a 10 mM MgCl2 solution (working solution concentration: 10 mM; final concentration in reaction system: 1 mM)
3. Liver Microsomes Preparation:
   3.1. Materials:

| Species | Product Information | Vendor |
|---|---|---|
| Human | Cat No. 452117 Lot No. 38298 | Corning |
| SD Rat | Cat No. WuXi-RLM Lot No. 20231106-A | ADME |
| Beagle Dog | Cat No. 0121C1.01 Lot No. 23D022 | IPHASE |
| Cyno Monkey | Cat No. LM-SXH-02M Lot No. LZML | RILD |

3.2. Preparation procedure:
   The appropriate concentrations of microsome working solutions were prepared in 100 mM potassium phosphate buffer.
4. Stop Solution Preparation:
   Cold (4° C.) acetonitrile (ACN) containing 250 nM tolbutamide and 250 nM labetalol as internal standards (IS) was used as the stop solution.
5. Assay Procedure:
   5.1. Pre-warm empty 'Incubation' plates T60 and NCF60 for 10 min minutes.
   5.2. Dilute liver microsomes to 0.56 mg/mL in 100 mM phosphate buffer.
   5.3. Transfer 445 uL microsome working solutions (0.56 mg/mL) into pre-warmed 'Incubation' plates T60 and NCF60, Then pre-incubate 'Incubation' plates T60 and NCF60 for 10 min at 37° C. with constant shaking. Transfer 54 μL liver microsomes to blank plate, then add 6 μL NAPDH cofactor to blank plate, and then add 180 μL quenching solution to blank plate.
   5.4 Add 5 μL compound working solution (100 μM) into 'incubation' plates (T60 and NCF60) containing microsomes and mix 3 times thoroughly.
   5.5. For the NCF60 plate, add 50 μL of buffer and mix 3 times thoroughly. Start timing; plate will be incubated at 37° C. for 60 min while shaking.
   5.6. In 'Quenching' plate TO, add 180 μL quenching solution and 6 μL NAPDH cofactor. Ensure the plate is chilled to prevent evaporation.
   5.7. For the T60 plate, mix 3 times thoroughly, and immediately remove 54 μL mixture for the 0-min time point to 'Quenching' plate. Then add 44 μL NAPDH cofactor to incubation plate (T60). Start timing; plate will be incubated at 37° C. for 60 min while shaking.

| Final Concentration of Each Component in Incubation Medium | |
| --- | --- |
| Component | Concentration |
| Microsome | 0.5 mg protein/mL |
| Test Compound | 1 µM |
| Control Compound | 1 µM |
| Acetonitrile | 0.99% |
| DMSO | 0.01% |

5.8. At 5, 15, 30, 45, and 60 min, add 180 µL quenching solution to 'Quenching' plates, mix once, and serially transfer 60 µL sample from T60 plate per time point to 'Quenching' plates.

5.9. For NCF60: mix once, and transfer 60 µL sample from the NCF60 incubation to 'Quenching' plate containing quenching solution at the 60-min time point.

5.10. All sampling plates are shaken for 10 min, then centrifuged at 4000 rpm for 20 minutes at 4° C.

5.11. Transfer 80 µL supernatant into 240 µL HPLC water, and mix by plate shaker for 10 min. 5.12. Each bioanalysis plate was sealed and shaken for 10 minutes prior to LC-MS/MS analysis.

5.12. Each bioanalysis plate was sealed and shaken for 10 minutes prior to LC-MS/MS analysis 6. Data Analysis The following equation of first order kinetics was used to calculate $T_{1/2}$ and $CL_{int(mic)}$ (µL/min/mg):

$$C_t = C_0 \cdot e^{-k_e \cdot t} \text{ when } C_t = \frac{1}{2} C_0$$

$$T_{1/2} = \frac{Ln2}{k_e} = \frac{0.693}{k_e}$$

$$CL_{int(mic)} = \frac{0.693}{\text{In vitro } T_{1/2}} \cdot \frac{1}{\text{mg/mL microsomal protein in reaction system}}$$

$$CL_{int(liver)} = CL_{int(mic)} \cdot \frac{\text{mg microsomes}}{\text{g liver}} \cdot \frac{\text{g liver}}{\text{kg body weight}}$$

Tables 6 and 7 respectively shows half-life time $T_{1/2}$ and $CL_{int}$ for positive control and exemplary compounds provided herein.

TABLE 6

Half-Life Time of LMS for Exemplary Compounds and positive controls

| Compound No. | $T_{1/2}$, min | | | | |
| --- | --- | --- | --- | --- | --- |
| | H | R | M | D | C |
| 12 | >145 | >145 | 68.2 | >145 | 56.1 |
| 14 | >145 | | 132 | | |
| 17 | >145 | >145 | 96.4 | >145 | 64.2 |
| 19 | >145 | >145 | 120 | >145 | >145 |
| 21 | >145 | >145 | 109 | >145 | >145 |
| 24 | >145 | >145 | >145 | >145 | 140.3 |
| 26 | 139 | | 119 | | |
| Ref. 4 | 17.6 | 0.7 | | 34.0 | 9.1 |
| Ref. 5 | 6.7 | 10.7 | | >145 | >145 |
| Ref. 6 | 5.1 | 1.4 | | 4.5 | 1.3 |

TABLE 7

$CL_{int\ (mic)}$ (µL/min/mg) and $CL_{int\ (liver)}$ (mL/min/kg) for Exemplary Compounds and positive controls

| Compound No. | H | | R | | D | | C | |
| --- | --- | --- | --- | --- | --- | --- | --- | --- |
| | $CL_{int\ (mic)}$ | $CL_{int\ (liver)}$ | $CL_{int\ (mic)}$ | $CL_{int\ (liver)}$ | $CL_{int\ (mic)}$ | $CL_{int\ (liver)}$ | $CL_{int\ (mic)}$ | $CL_{int\ (liver)}$ |
| 19 | <9.6 | <8.6 | <9.6 | <17.3 | <9.6 | <13.8 | <9.6 | <13.0 |
| 21 | <9.6 | <8.6 | <9.6 | <17.3 | <9.6 | <13.8 | <9.6 | <13.0 |
| 24 | <9.6 | <8.6 | <9.6 | <17.3 | <9.6 | <13.8 | 9.9 | 13.3 |
| Ref. 4 | 79.0 | 71.1 | 2101.3 | 3782.4 | 40.8 | 58.7 | 152.3 | 205.6 |
| Ref. 5 | 205.9 | 185.3 | 129.5 | 233.1 | <9.6 | <13.8 | <9.6 | <13.0 |
| Ref. 6 | 273.1 | 245.8 | 1018.9 | 1834.0 | 305.7 | 440.2 | 1066.7 | 1440.1 |

Example 31: Caco-2 Cell Monolayer Model Assay

Caco-2 cell model was used to assess the permeability of the compounds disclosed herein. Caco-2 cell was obtained from the CO-BIOR and the CO-BIOR Number is CBP60025. The cell generation used in the experiment was P9.

1. Preparation of Monolayer
   1) 25 mL of cell culture medium was added to each well of the Transwell reservoir, respectively. And then the PET transwell plates were incubated at 37° C., 5% $CO_2$ for 1 hour before cell seeding.
   2) Caco-2 cells were diluted to $3.43 \times 10^5$ cells/mL with culture medium and 100 µL of cell suspension were dispensed into the filter well of the 96-well PET Transwell plate. Cells were cultivated for 14-18 days in a cell culture incubator at 37° C., 5% $CO_2$, 95% relative humidity. Cell culture medium was replaced every other day, beginning no later than 24 hours after initial plating.
   3) Measure the electrical resistance across the monolayer by using Millicell Epithelial Volt-Ohm measuring system. Record the electrical resistance for each well. Once all wells have been measured, return the plate(s) to the incubator.
   4) TEER of each well is calculated by the equation below. The TEER value of each well should be greater than 230 ohms·cm².

TEER value (ohm·cm²)=TEER measurement (ohms)×Area of membrane (cm²)

2. Procedures of Transport Assay
   1) Remove the Caco-2 plate(s) from the incubator. Wash the monolayer twice with pre-warmed HBSS (10 mM HEPES, pH 7.4). Then incubate the plate(s) at 37° C. for 30 minutes.
   2) Prepare stock solutions of control compounds in DMSO at 5 mM and dilute with HBSS (10 mM HEPES, pH 7.4) to get 5 µM working solutions. Prepare stock solutions of test compounds in DMSO at 1 mM and dilute with HBSS (10 mM HEPES, pH 7.4) to get 1 µM working solutions. Digoxin is used as the reference substrate of Pgp. Atenolol is used as the low permeability marker, minoxidil is used as the high permeability marker.
   3) To determine the rate of drug transport in the apical to basolateral direction, add 100 µL of the working donor solutions (without inhibitor) to the Transwell insert (apical compartment). Fill the wells in the receiver plate (basolateral compartment) with 300 µL of transport buffer. To determine the rate of drug transport in the basolateral to apical direction, add 300 µL of the working donor solutions (without inhibitor) to the receiver plate wells (basolateral compartment). Fill the Transwell insert (apical compartment) with 100 µL of transport buffer.
   4) Transfer 50 µL samples from the working solutions to 300 µL of cold MeOH:acetonitrile=1:1 with IS (50 ng/mL Labetalol, 50 ng/mL Tolbutamide) to prepare the time 0 samples. Incubate the Transwell plate at 37° C., 5% $CO_2$ with shaking at 60 rpm on a rotary shaker for 2 hours.
   5) At the end of the transport period, transfer 50 µL of samples from apical and basolateral wells to a new 96-well plate. Add 300 µL of quenching solution (MeOH:acetonitrile=1:1 with IS (50 ng/mL Labetalol, 50 ng/mL Tolbutamide)) into each well of the plate(s). Vortex for 10 minutes. Samples are centrifuged at 4000 rpm g for 30 minutes. An aliquot of 100 µL of the supernatant is mixed with an appropriate volume of ultra-pure water (depends on the LC-MS/MS signal response and peak shape) before LC-MS/MS analysis.
   6) To determine the Lucifer Yellow leakage after 2-hour transport period, prepare stock solutions of Lucifer yellow in DMSO and dilute with HBSS (10 mM HEPES, pH 7.4) to reach the final concentration of 100 µM. Add 100 µL of the Lucifer yellow solution to the apical compartment. Fill the basolateral compartment with 300 µL of HBSS (10 mM HEPES, pH 7.4). Incubate the plate(s) at 37° C. for 30 minutes and remove 80 µL directly from the apical and basolateral wells and transfer to new 96 wells plates. Measure Lucifer Yellow fluorescence (to monitor monolayer integrity) in a fluorescence plate reader at 485 nM excitation and 530 nM emission.
   7) Discard the remaining solution in the cell plate, Add 300 µL of quenching solution (MeOH:acetonitrile=1:1 with IS (50 ng/mL Labetalol, 50 ng/mL Tolbutamide)) into each well of the plate(s), blow up and down and mix well for 5 times. Transfer 50 µL of lysate to a new 96-well plate. Add 300 µL of quenching solution (MeOH:acetonitrile=1:1 with IS (50 ng/mL Labetalol, 50 ng/mL Tolbutamide)) into each well of the plate(s). Vortex for 10 minutes. Samples are centrifuged at 4000 rpm g for 10 minutes. An aliquot of 100 µL of the supernatant is mixed with an appropriate volume of ultra-pure water (depends on the LC-MS/MS signal response and peak shape) before LC-MS/MS analysis.

3. Data Analysis

All calculations are carried out using Microsoft Excel. Percent parent compounds remaining at each time point are estimated by determining the peak area ratios from extracted ion chromatograms.

The apparent permeability coefficient ($P_{app}$), in units of centimeter per second, can be calculated for Caco-2 drug transport assays using the following equation:

$$P_{app} = (V_A \times [drug]_{acceptor})/(Area \times Time \times [drug]_{initial,\ donor})$$

where $V_A$ is the volume (in mL) in the acceptor well, Area is the surface area of the membrane (0.143 cm² for Transwell-96 Well Permeable Supports), and time is the total transport time in seconds.

The efflux ratio will be determined using the following equation:

$$\text{Efflux Ratio} = P_{app(B-A)}/P_{app(A-B)}$$

where $P_{app\ (B-A)}$ indicates the apparent permeability coefficient in basolateral to apical direction, and $P_{app\ (A-B)}$ indicates the apparent permeability coefficient in apical to basolateral direction.

The recovery can be determined using the following equation:

$$\text{Recovery \%} = (V_A \times [drug]_{acceptor} + V_D \times [drug]_{donor})/(V_D \times [drug]_{initial, donor})$$

where $V_A$ is the volume (in mL) in the acceptor well (0.3 mL for Ap→Bl flux, and 0.1 mL for Bl→Ap), $V_D$ is the volume (in mL) in the donor well (0.1 mL for Ap→Bl flux, and 0.3 mL for Bl→Ap)

The leakage of Lucifer Yellow, in unit of percentage (%), can be calculated using the following equation:

$$\text{\% LY leakage} = 100 \times V_A \times [LY]_{acceptor}/([LY]_{donor} \times V_D + [LY]_{acceptor} \times V_A)$$

LY leakage of <1.5% is acceptable to indicate the well-qualified Caco-2 monolayer.

Table 8 shows data for exemplary compounds as described herein measured in Caco-2 cell assay.

TABLE 8

Data of Caco-2 for Exemplary Compounds

| Compound No. | Conc. μM | $P_{app\,(A-B)}$ $10^{-6}$ cm/s | $P_{app\,(B-A)}$ $10^{-6}$ cm/s | Efflux Ratio | Recovery AP – BL | Recovery BL – AP |
|---|---|---|---|---|---|---|
| 12 | 1 | 6.07 | 12.0 | 1.98 | | |
| 17 | 1 | 6.70 | 11.8 | 1.76 | 81.0% | 85.6% |

Example 32: hERG Potassium Ion Channel Inhibition Assay

Drug-hERG interaction was measured by automated patch-clamp methods, with cisapride as positive control.

Experimental Procedure

1. Cell Preparation 1.1 CHO-hERG cells were cultured in 175 cm² culture bottle. After the cell density grew to 6080, the culture medium was removed, washed with 7 mL of phosphate buffered saline (PBS), and then digested with 3 mL Detachin.

1.2 After the digestion was complete, 7 mL culture solution was added for neutralization, and then centrifuged, the clear solution was sucked, and 5 mL culture solution was added for re-suspension to ensure the cell density was 2-5×10⁶/mL.

2. Solution Preparation

Composition of Extracellular Fluid and Intracellular Fluid

| Reagent | Extracellular Fluid/mM | Intracellular Fluid/mM |
|---|---|---|
| $CaCl_2$ | 1 | 1 |
| $MgCl_2$ | 1.25 | 1 |
| KCl | 5 | 140 |
| NaCl | 140 | 0 |
| Glucoses | 10 | 0 |
| HEPES | 10 | 10 |
| EGTA | 0 | 10 |
| pH | 7.40 (adjusted with NaOH), Osmolarity~305 mOsm | 7.20 (adjusted with KOH), Osmolarity~290 mOsm |

3. Electrophysiological Recording

The process of single-cell high-impedance sealing and whole-cell pattern formation was all automatically completed by Qpatch instrument. After obtaining whole-cell recording mode, the cell was pinching at −80 millivolts. Before giving a 5-second +40 millivolt depolarization stimulus, a 50-millisecond pre-voltage of −50 millivolts was given first, and then repolarized to −50 millivolts for 5 seconds. Go back to −80 millivolts. This voltage stimulation was applied every 15 seconds, recorded for 2 minutes, then extracellular fluid was given and recorded for 5 minutes, and then the administration process began. The concentration of test compound was given from the lowest test concentration for 2.5 minutes per test concentration. After continuous administration of all concentrations, the positive control 3 μM cisapride was given. At least 2 cells were tested for each concentration (n≥2).

4. Test Compound Preparation 4.1 The compound mother liquor was diluted with DMSO, and 10 μL compound stock solution was added to 20 μL DMSO solution, which was continuously 3-fold diluted to 6 DMSO-concentrations.

4.2 4 μL of test compounds in 6 DMSO-concentrations were added to 396 μL extracellular solution and were 100-fold diluted to 6 intermediate concentrations. Then, 80 μL of test compounds in 6 intermediate concentrations were added to 320 μL extracellular solution and were 5-fold diluted to the final concentration to be tested.

4.3 The highest test concentration was 40.00 μM, and six test concentrations were 40.00, 13.33, 4.44, 1.48, 0.49, 0.16 μM, respectively.

4.4 The DMSO content in the final test concentration did not exceed 0.2%, and this concentration of DMSO had no effect on the hERG potassium channel.

4.5 Entire dilution process for test compound preparation was performed by Bravo instrument.

5. Data Analysis

The experimental data were analyzed by GraphPad Prism 5.0 software.

Table 9 shows $IC_{50}$ of exemplary compounds as described herein for hERG inhibition.

TABLE 9

$IC_{50}$ of Exemplary Compounds for hERG inhibition

| Compound No. | $IC_{50}$/μM |
|---|---|
| 12 | 5.38 |
| 14 | 17.91 |
| 15 | 5.58 |
| 17 | 12.83 |
| 19 | 13.5 |
| 21 | 13.63 |
| 24 | 24.8 |
| 26 | 13.56 |

It can be seen that the exemplary compounds provided herein do not show hERG liability, indicating a much improved safety margin of the compounds.

Example 33: In Vivo Pharmacokinetics Assay

Pharmacokinetics assay for test compounds was performed in mice via IV and PO.

1. Test Compound Preparation

Test compound solution was prepared on the day of administration.

Solvent: IV+PO: 5% DMSO+10% Soultol+85% $H_2O$ or saline

2. Experimental Animal

Species: ICR mice; SPF level.

Source: Beijing Vital River Laboratory Animal Technology Co., Ltd.

Animal selection: Males. No random grouping

3. Experiments Design

| Group | Number of Animal Male | Dose mg/kg | Conc. mg/mL | Administration volume mL/kg | Administration Route | Sample Collection |
|---|---|---|---|---|---|---|
| 1 | 3 | 1 | 0.2 | 5 | IV, single | Plasma |
| 2 | 3 | 10 | 1.0 | 10 | PO1*, single | Plasma |

-continued

| Group | Number of Animal Male | Dose mg/kg | Conc. mg/mL | Administration volume mL/kg | Administration Route | Sample Collection |
|---|---|---|---|---|---|---|
| 3 | 3 | 30 | 3.0 | 10 | PO2*, single | Plasma |
| 4 | 6 | 30 | 3.0 | 10 | PO*, single | Plasma&brain |

*animals in the oral administration group fasted overnight (10-14 hours) before administration, and were given food 4 hours after administration.

4. Administration Route

Weighed before dosing, calculated dosage according to body weight. For Groups 1-3, the drug was administered intravenously or intragastrically. For Group 4, the drug administered intragastrically.

5. Time Point of Sample Collection

For Groups 1-3, at 0.083 h, 0.25 h, 0.5 h, 1 h, 2 h, 4 h, 6 h, 8 h, 24 h, after administration. For Group 4, at 2 h and 4 h after administration.

Blood was collected through the cheeks. For each sample, about 0.05 mL of blood was collected and was added heparin sodium or EDTA-2K as anticoagulant, and was placed on wet ice.

6. Plasma Sample Processing

The blood samples were collected and placed on ice and was centrifuged within 1 hour (centrifugation: 6000 g, 3 minutes, 2-8° C.) to separate plasma. Plasma samples were stored in a −80° C. refrigerator prior to analysis.

7. Result Analysis

The pharmacokinetic parameters were calculated using Phoenix WinNonlin8.2.0 based on the blood concentration data at different time points, and $AUC_{0-t}$, $AUC_{0-\infty}$, $MRT_{0-\infty}$, $C_{max}$, $T_{max}$, and $T_{1/2}$ and mean values and standard deviations thereof were provided.

Tables 10 and 11 show in vivo PK data of exemplary compounds as described herein.

TABLE 10

PK data of Exemplary Compounds

Administration via PO

| Compound No. | Dose (mg/kg) | $C_{max}$ (ng/mL) | $C_{8h}$ (ng/mL) | $C_{24h}$ (ng/mL) | $T_{1/2}$ (h) | $AUC_{0-t}$ (h × ng/mL) |
|---|---|---|---|---|---|---|
| 14 | 30 | 7503 | 3833 | 574 | 5.96 | 81054 |
|  | 50 | 9920 | 6927 | 615 | 5 | 122981 |
| 17 | 10 | 4627 | 2287 | 257 | 5.07 | 50800 |
|  | 30 | 16233 | 8260 | 860 | 4.87 | 174589 |
| 19 | 10 | 2620 | 1833 | 178 | 4.88 | 32782 |
|  | 30 | 8117 | 4817 | 540 | 5.26 | 94249 |
| 21 | 10 | 2820 | 2537 | 415 | 6.67 | 43397 |
|  | 30 | 8710 | 6880 | 1257 | 6.45 | 124997 |
| 24 | 10 | 3355 | 2598 | 186 | 4.41 | 44942 |
|  | 50 | 15733 | 4983 | 178 | 3.23 | 130284 |

Administration via IV

| Compound No. | Dose (mg/kg) | $C_{max}$ (ng/mL) | Cl (mL/kg/min) | $T_{1/2}$ (h) | $AUC_{0-t}$ (h × ng/mL) |
|---|---|---|---|---|---|
| 12 | 1.0 |  | 3.48 |  |  |
| 14 | 1.0 |  | 7.62 |  |  |
| 17 | 1.0 | 965 | 3.10 | 5.05 | 5219 |
| 19 | 1.0 |  | 4.38 |  |  |
| 21 | 1.0 |  | 3.94 |  |  |
| 24 | 1.0 |  | 2.41 |  |  |
| 26 | 1.0 |  | 10.5 |  |  |

TABLE 11

PK data of Exemplary Compounds

| Compound No. | Time (h) | Mean Concentration In plasma (ng/mL) | Mean Concentration In brain (ng/g) | B/P ratio |
|---|---|---|---|---|
| 17 | 2 | 14843 ± 4945 | 3308 ± 1056 | 21% |
|  | 4 | 13667 ± 1365 | 2668 ± 224 |  |
| 24 | 2 | 6327 ± 2604 | 3132 ± 1647 | 51% |
|  | 4 | 5983 ± 361 | 3084 ± 145 |  |

Example 34: CYP Isoforms Inhibitory Assay

CYP isoforms inhibitory activities of test compounds were measured in human liver microsome.

Study Design

1. Equipment, Materials and Reagents 1.1. Phosphate Buffer (100 mmol/L, pH 7.4)

9.24291 g $K_2HPO_4 \cdot 3H_2O$, 1.29286 g $KH_2PO_4$, and 808.047 mg EDTA dipotassium were weighed and dissolved in 500 mL pure water to form a PB buffer, which was stored in a 4° C. freezer.

1.2. 12 mmol/L $MgCl_2$ Solution 123.21 mg magnesium chloride hexahydrate (mV=203.3, 99%) solid was weighed and dissolved in 50 mL phosphate solution to prepare magnesium chloride stock solution with a concentration of 12 mM.

1.3. NADPH Regenerant 6.803 mg of NADPH (MV=833.35, 98%) powder was weighed and added 800 μL PB, to prepare a 10 mM NADPH solution.

390 μL of 10 mM NADPH solution was taken, added 3900 μL of 12 mM magnesium chloride stock solution followed by 3510 μL of phosphate buffer to form a NADPH regeneration solution containing 2 mM NADPH and 6 mM magnesium chloride.

1.4. Substrates

Preparation details of these substrates are given in below table. The substrate stock solution was stored in a −20° C. freezer. Prior to use, the substrate stock solution was removed from the freezer and allowed to rise to room temperature. Then the substrate stock solution was mixed on a whirly mixer for 30 seconds.

| CYP Isoform | Substrate | MW(g/mol) | Stock solution Conc. (mM) | Final Conc. (μM) |
|---|---|---|---|---|
| 1A2 | phenacetin | 179.2 | 75 (in MeOH) | 75 |
| 2C9 | diclofenac | 318.13 | 10 (in MeOH) | 10 |
| 2C19 | s-mephenytoin | 218.25 | 20 (in MeOH) | 20 |
| 2D6 | dextromethorphan | 370.3 | 10 (in MeOH) | 10 |
| 3A4 | midazolam | 325.77 | 2 (in MeOH) | 2 |
|  | testosterone | 412.6 | 40 (in DMSO) | 40 |

1.5. Human Liver Microsome (HLM)

HLMs were stored in a −80° C. freezer. Prior to use, the pooled HLM was removed from the freezer and allowed to thaw in a 37° C. water bath and then stored on wet ice.

1.6. Inhibitors

The positive control inhibitors and their concentrations used by each isozyme are summarized below.

| CYP Isoform | Inhibitor | Final Conc. (μM) |
|---|---|---|
| 1A2 | α-Naphthoflavone | 0.0001, 0.0003, 0.001, 0.003, 0.01, 0.03, 0.1, 0.3 |
| 2C9 | Sulfaphpenazole | 0.01, 0.03, 0.1, 0.3, 1, 3, 10, 30 |
| 2C19 | N-3-benzylnirvanol | 0.003, 0.01, 0.03, 0.1, 0.3, 1, 3, 10 |
| 2D6 | Quinidine | 0.003, 0.01, 0.03, 0.1, 0.3, 1, 3, 10 |
| 3A4 | Ketoconazole | 0.0003, 0.001, 0.003, 0.01, 0.03, 0.1, 0.3, 1 |

The stock solution of inhibitors was stored at −20° C. Prior to use, working solution was removed from the freezer and allowed to rise to room temperature. Then the standard inhibitors stock solution was mixed on a whirly mixer for 30 seconds.

1.7. Stop Solution (50 ng/mL Tolbutamide in 50% ACN/MeOH (v:v))

6.006 mg of tolbutamide was weighed and added 30 mL of acetonitrile to make 200 μg/mL tolbutamide stock solution.

250 μL of 200 μg/mL tolbutamide stock solution was taken and added 250 mL acetonitrile and 250 mL methanol.

2. Assay Procedure

2.1. Preparation of Human Liver Microsome Working Solution

The human liver microsome working solution was prepared according to below table to obtain the substrate and HLM mixture.

| Buffer | Stock Concentration | Volume | Final Concentration |
|---|---|---|---|
| Microsomes | 20 mg/mL | 80 μL | 0.2 mg/mL |
| Phosphate buffer | 100 mM | 7.904 mL | 100 mM |
| Substrate | — | 16 μL | — |

2.2. Compound Dilution

The working solution of the test compound was configured according to the final concentration of 30, 10, 3, 1, 0.3, 0.1, 0.03 and 0.01 μM, and the appropriate solvent (DMSO or 30% DMSO/ACN) was selected according to the solubility of the compound.

2.3. Incubation

All samples were incubated in a 37° C. water bath, with three parallels for each concentration of the test compound and two parallels for each concentration of the positive control inhibitor. 100 μL of microsome working solution was taken and added 2 μL of the test product or positive inhibitor working solution. 2 μL solvents was added to the solvent control, and put in a water bath to pre-incubate for 10 min. After pre-incubation, 98 μL of NADPH regeneration solution was added to all samples to start the reaction. Then the mixture was put back in the water bath and incubated for a certain period of time. The experiments of each isozyme are summarized in the following table.

| CYP Isoform | Substrate | Protein Conc. | Incubation time(min) | metabolite |
|---|---|---|---|---|
| 1A2 | phenacetin | 0.100 mg/mL | 10 | paracetamol |
| 2C9 | diclofenac |  | 10 | 4'-hydroxydiclofenac |
| 2C19 | s-mephenytoin |  | 20 | 4-hydroxymephenytoin |
| 2D6 | dextromethorphan |  | 20 | dextrorphan |
| 3A4 | testosterone |  | 10 | 6β-hydroxytesterone |
|  | midazolam |  | 3 | 1-hydroxymidazolam |

2.4. Reaction Quenching

The reaction was quenched by 200 μL stop solution. The plate was centrifuged at 3,220 g for 10 minutes. Appropriate volume of supernatant was transferred, added water and mix well to the analysis plate for LC-MS/MS analysis.

| CYP Isoform | Supernatant Volume(μL) | Water (μL) |
|---|---|---|
| 1A2 | 100 | 100 |
| 2C9 | 100 | 100 |
| 2C19 | 100 | 100 |
| 2D6 | 50 | 150 |
| 3A4 | 100 | 100 |

3. Data Processing

The automatic peak integration areas are checked for all of the samples. The Analyte Peak Area and Internal Standard Peak Area are exported into excel spreadsheet.

The inhibition of each $P_{450}$ enzyme in human liver microsomes is measured as the percentage decrease in activity of marker metabolite formation compared to non-inhibited DMSO controls (=100% activity). Calculate $IC_{50}$ value (test compound concentration which produces 50% inhibition) by using GraphPad Prism 7. $IC_{50}$ values were determined using 3- or 4-parameter logistic equation. $IC_{50}$ values were reported as ">30 μM" when % inhibition at the highest concentration (30 μM) is less than 50%.

Calculate the percentage of remaining activity as follows:

Area Ratio=Peak Area Analyte/Peak Area Internal Standard

Remaining Activity (%)=Area $\text{Ratio}_{test\ compound}$/Area $\text{Ratio}_{vehicle}$*100%

Table 12 shows $IC_{50}$ of exemplary compounds as described herein for inhibiting CYP isoforms.

TABLE 12

$IC_{50}$ of Exemplary Compounds for CYP inhibition

| Compound No. | $IC_{50}$ (μM) | | | | | |
|---|---|---|---|---|---|---|
|  | CYP1A2 | CYP2C9 | CYP2C19 | CYP2D6 | CYP3A4 (midazolam) | CYP3A4 (testosterone) |
| α-Naphthoflavone | 0.00865 | / | / | / | / | / |
| Sulfaphenazole | / | 0.599 | / | / | / | / |
| N-3-benzylnirvanol | / | / | 0.333 | / | / | / |

TABLE 12-continued

IC$_{50}$ of Exemplary Compounds for CYP inhibition

| Compound No. | CYP1A2 | CYP2C9 | CYP2C19 | CYP2D6 | CYP3A4 (midazolam) | CYP3A4 (testosterone) |
|---|---|---|---|---|---|---|
| Quinidine | / | / | / | 0.108 | / | / |
| Ketoconazole (midazolam) | / | / | / | / | 0.0241 | / |
| Ketoconazole (testosterone) | / | / | / | / | / | 0.0407 |
| 17 | >30 | >30 | 15.1 | >30 | >30 | 27.3 |

Example 35: In Vivo Efficacy Assay

The antitumor effect or MTAP/MTA selectivity of the compounds provided herein in the subcutaneously transplanted Balb/C nude female mouse model of human colon cancer cell line HCT 116 (WT and MTAP KO) was tested.

Procedure

1. Tumor Inoculation

Cell viability and cell count were determined. Cell count of the suspension was adjusted to 1×10$^8$ cells/mL and mixed with Matrigel in a 1:1 volume. Each mouse for this study were inoculated subcutaneously in the right front flank region with 5×10$^6$ tumor cells (0.1 mL) for tumor development.

2. Randomization

The randomization started when the mean tumor size reaches approximately 100-150 mm$^3$. Mice inoculated with HCT 116 WT cells were randomized on day 7. Mice inoculated with HCT 116 MTAP KO cells were randomized on day 8. All animals were randomly allocated to 5 study groups, each group consisted of 8 animals. Randomization was performed based on randomized block design.

Cell number: 5 × 10$^6$
Tumor volume: 100-150 mm$^3$
Dosing formulation: 5% DMSO + 10% Solutol + 85% H$_2$O

| Group | Size | Treatment | Dose (mg/kg) | Route/ Frequency | Treatment time |
|---|---|---|---|---|---|
| 1 | 8 | Vehicle | — | PO/QD | 21 days |
| 2 | 8 | 17 | 15 | PO/QD | 21 days |
| 3 | 8 | 19 | 15 | PO/QD | 21 days |
| 4 | 8 | 21 | 15 | PO/QD | 21 days |
| 5 | 8 | 24 | 15 | PO/QD | 21 days |

3. Observation and Data Collection

Tumor volume was measured twice per week in two dimensions using a caliper, and the volume was expressed in mm$^3$ using the formula: "V=(L×W×W)/2", where V is tumor volume, L is tumor length (the longest tumor dimension) and W is tumor width (the longest tumor dimension perpendicular to L).

Figure 1B:
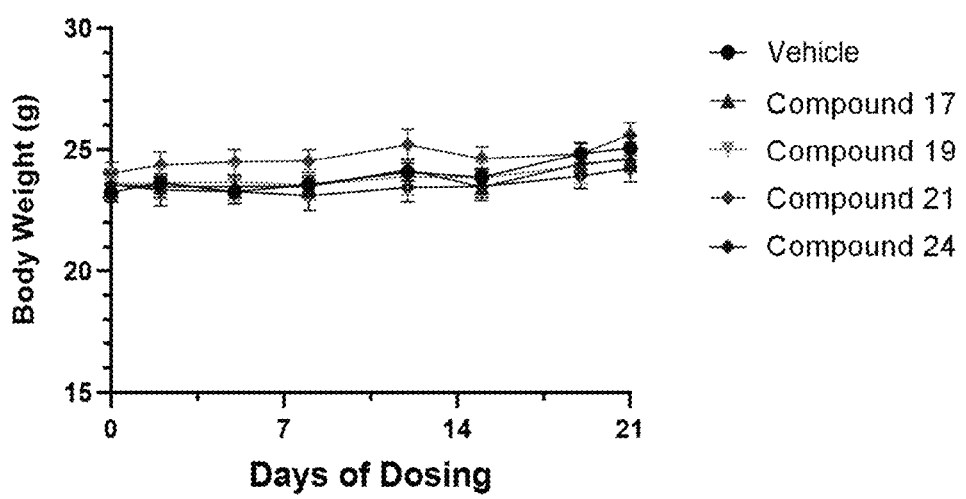
Figure 2A:
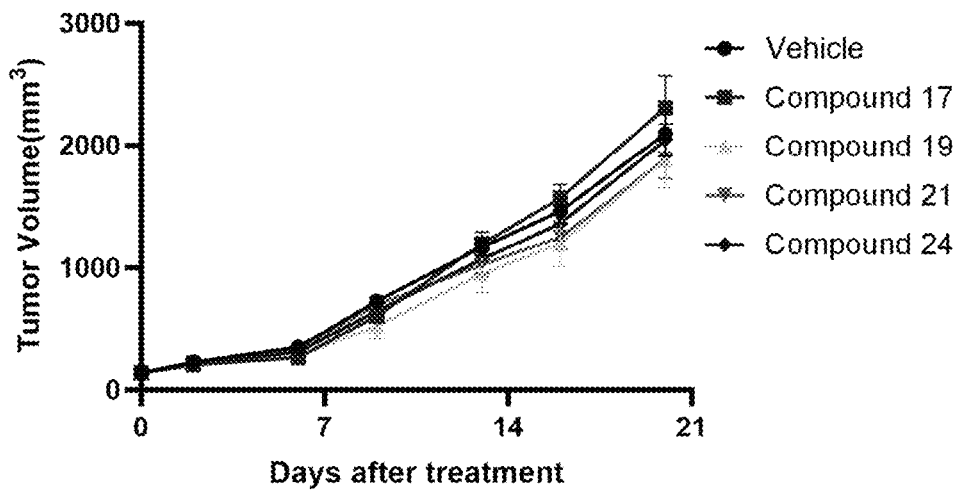
FIGS. 2A and 2B show the in vivo efficacy of exemplary compounds in human colon cancer cell line HCT 116 (WT).
Figure 2B:
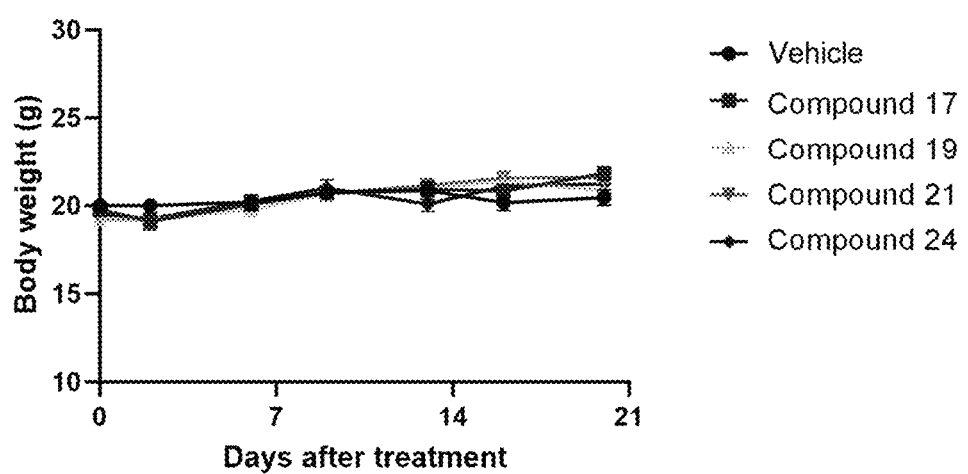

Table 13 and FIGS. 1 and 2 show the results of in vivo efficacy of exemplary compounds as described herein.

TABLE 13

In vivo efficacy of Exemplary Compounds

| | | Compound No. | | | |
|---|---|---|---|---|---|
| | | 17 | 19 | 21 | 24 |
| Tumor growth inhibition (TGI) | HCT 116 WT | 66% | 74% | 59% | 62% |
| | HCT 116 MTAP KO | −11% | 11% | 11% | 3% |

It can be seen that the compounds provided herein demonstrate potent in vivo efficacy with excellent MTAP/MTA selectivity and good tolerability.

The foregoing description is considered as illustrative only of the principles of the present disclosure. Further, since numerous modifications and changes will be readily apparent to those skilled in the art, it is not desired to limit the invention to the exact construction and process shown as described above. Accordingly, all suitable modifications and equivalents maybe considered to fall within the scope of the invention as defined by the claims that follow.

The words "comprise", "comprising", "include", "including" and "includes" when used in this specification and in the following claims are intended to specify the presence of stated features, integers, components, or steps, but they do not preclude the presence or addition of one or more other features, integers, components, steps, or groups thereof.

What claimed is:

1. A compound having a structure of:

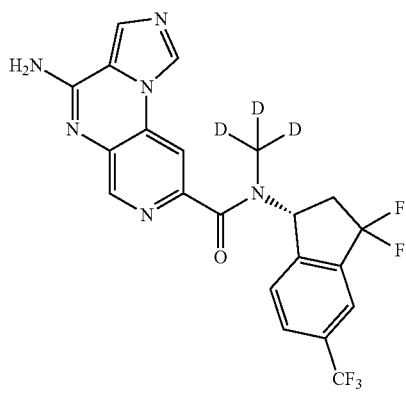 [SMILES: [2H]C([2H])([2H])N(C(=O)c1cc2c(cn1)nc(N)c1cncn12)[C@@H]1CC(F)(F)c2cc(C(F)(F)F)ccc21]

or a pharmaceutically acceptable salt thereof.

2. The compound of claim 1, wherein the compound has a structure of:
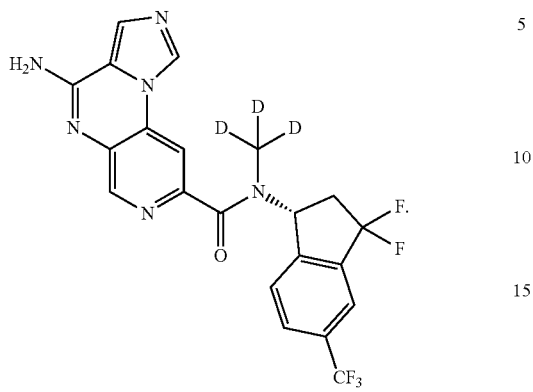
3. A pharmaceutical composition, comprising a therapeutically effective amount of the compound of claim 1 or a pharmaceutically acceptable salt thereof, and a pharmaceutically acceptable excipient.
* * * * *